United States Patent
Voronenko et al.

(10) Patent No.: US 12,115,386 B2
(45) Date of Patent: Oct. 15, 2024

(54) MULTI-TARGET TREATMENT PLANNING AND DELIVERY AND VIRTUAL LOCALIZATION FOR RADIATION THERAPY

(71) Applicant: RefleXion Medical, Inc., Hayward, CA (US)

(72) Inventors: Yevgen Voronenko, San Jose, CA (US); Debashish Pal, Sunnyvale, CA (US); David Quentin Larkin, Menlo Park, CA (US); George Zdasiuk, Portola Valley, CA (US); Jayakrishnan Janardhanan, Union City, CA (US); Michael Kirk Owens, North Easton, MA (US); Peter Demetri Olcott, Los Gatos, CA (US)

(73) Assignee: RefleXion Medical, Inc., Hayward, CA (US)

(*) Notice: Subject to any disclaimer, the term of this patent is extended or adjusted under 35 U.S.C. 154(b) by 250 days.

(21) Appl. No.: 17/571,273

(22) Filed: Jan. 7, 2022

(65) Prior Publication Data
US 2022/0126117 A1    Apr. 28, 2022

Related U.S. Application Data

(63) Continuation of application No. PCT/US2020/040774, filed on Jul. 2, 2020.
(Continued)

(51) Int. Cl.
*A61N 5/10*    (2006.01)

(52) U.S. Cl.
CPC ......... *A61N 5/1031* (2013.01); *A61N 5/1039* (2013.01); *A61N 5/1043* (2013.01); *A61N 5/1045* (2013.01); *A61N 5/1084* (2013.01)

(58) Field of Classification Search
CPC .. A61N 5/1031; A61N 5/1039; A61N 5/1043; A61N 5/1045; A61N 5/1084; A61B 6/032; A61B 6/037
See application file for complete search history.

(56) References Cited

U.S. PATENT DOCUMENTS

| | | | |
|---|---|---|---|
| 3,794,840 A | 2/1974 | Scott | |
| 5,647,663 A | 7/1997 | Holmes | |

(Continued)

FOREIGN PATENT DOCUMENTS

| | | |
|---|---|---|
| CN | 1824342 A | 8/2006 |
| CN | 101267767 A | 9/2008 |

(Continued)

OTHER PUBLICATIONS

Corrected Notice of Allowability mailed on Mar. 13, 2023, for U.S. Appl. No. 17/235,812, filed Apr. 20, 2021, 4 pages.
(Continued)

*Primary Examiner* — Keith M Raymond
*Assistant Examiner* — Patrick M Mehl
(74) *Attorney, Agent, or Firm* — Cooley LLP

(57) ABSTRACT

Disclosed herein are methods for patient setup and patient target region localization for the irradiation of multiple patient target regions in a single treatment session. Virtual localization is a method that can be used to register a patient target region without requiring that the patient is physically moved using the patient platform. Instead, the planned fluence is updated to reflect the current location of the patient target region by selecting a localization reference in the localization image, calculating a localization function based on the localization reference point, and calculating the delivery fluence by convolving the localization function with a shift-invariant firing filter. Mosaic multi-target localization partitions a planned fluence map for multiple patient (Continued)

target regions into sub-regions that can be individually localized. De-coupled multi-target localization involves generating a separate planned fluence map for each target but constraining a cumulative fluence map to ensure dosimetric goals are met.

43 Claims, 78 Drawing Sheets

Related U.S. Application Data

(60) Provisional application No. 62/873,742, filed on Jul. 12, 2019.

(56) References Cited

U.S. PATENT DOCUMENTS

| | | |
|---|---|---|
| 6,385,286 B1 | 5/2002 | Fitchard et al. |
| 6,438,202 B1 | 8/2002 | Olivera et al. |
| 6,618,467 B1 | 9/2003 | Ruchala et al. |
| 6,714,620 B2 | 3/2004 | Caflisch et al. |
| 6,810,108 B2 | 10/2004 | Clark et al. |
| 7,265,356 B2 | 9/2007 | Pelizzari et al. |
| 7,280,633 B2 | 10/2007 | Cheng et al. |
| 7,302,033 B2 | 11/2007 | Carrano et al. |
| 7,302,038 B2 | 11/2007 | Mackie et al. |
| 7,379,531 B2 | 5/2008 | Esham et al. |
| 7,412,029 B2 | 8/2008 | Myles |
| 7,412,280 B2 | 8/2008 | Hertel et al. |
| 7,446,328 B2 | 11/2008 | Rigney et al. |
| 7,469,035 B2 | 12/2008 | Keall et al. |
| 7,522,779 B2 | 4/2009 | Fu et al. |
| 7,623,623 B2 | 11/2009 | Raanes et al. |
| 7,639,853 B2 | 12/2009 | Olivera et al. |
| 7,839,972 B2 | 11/2010 | Ruchala et al. |
| 7,906,770 B2 | 3/2011 | Otto |
| 7,945,021 B2 | 5/2011 | Shapiro et al. |
| 7,983,380 B2 | 7/2011 | Guertin et al. |
| 8,019,042 B2 | 9/2011 | Shukla et al. |
| 8,063,376 B2 | 11/2011 | Manlawski et al. |
| 8,086,004 B2 | 12/2011 | Kuduvalli et al. |
| 8,090,074 B2 | 1/2012 | Filiberti et al. |
| 8,107,589 B2 | 1/2012 | Sakural et al. |
| 8,144,962 B2 | 3/2012 | Busch et al. |
| 8,149,991 B2 | 4/2012 | Moreau |
| 8,269,195 B2 | 9/2012 | Rigney et al. |
| 8,278,633 B2 | 10/2012 | Nord et al. |
| 8,295,430 B2 | 10/2012 | Zhu et al. |
| 8,331,532 B2 | 12/2012 | Nord et al. |
| 8,442,287 B2 | 5/2013 | Fordyce et al. |
| 8,457,372 B2 | 6/2013 | Fu et al. |
| 8,467,497 B2 | 6/2013 | Lu et al. |
| 8,483,803 B2 | 7/2013 | Partain et al. |
| 8,509,383 B2 | 8/2013 | et al. |
| 8,536,547 B2 | 9/2013 | Maurer, Jr. et al. |
| 8,559,596 B2 | 10/2013 | Thomson et al. |
| 8,588,367 B2 | 11/2013 | Busch et al. |
| 8,605,857 B1 | 12/2013 | Renner |
| 8,681,938 B2 | 3/2014 | Myles |
| 8,767,917 B2 | 7/2014 | Ruchala et al. |
| 8,816,307 B2 | 8/2014 | Kuusela et al. |
| 8,824,630 B2 | 9/2014 | Maurer, Jr. et al. |
| 8,831,706 B2 | 9/2014 | Fu et al. |
| 8,836,697 B2 | 9/2014 | Nord et al. |
| 8,861,672 B2 | 10/2014 | Maltz et al. |
| 8,874,187 B2 | 10/2014 | Thomson et al. |
| 8,917,813 B2 | 12/2014 | Maurer, Jr. et al. |
| 9,019,307 B1 | 4/2015 | Grimm |
| 9,061,142 B2 | 6/2015 | Vilsmeier |
| 9,155,909 B2 | 10/2015 | Ishikawa |
| 9,437,340 B2 | 9/2016 | Echner et al. |
| 9,498,167 B2 | 11/2016 | Mostafavi et al. |
| 9,616,251 B2 | 4/2017 | Filiberti et al. |
| 9,849,308 B2 | 12/2017 | Berlinger et al. |
| 9,956,428 B2 | 5/2018 | Kelly |
| 9,956,429 B2 | 5/2018 | Holmes et al. |
| 9,974,494 B2 | 5/2018 | Mostafavi et al. |
| 9,990,711 B2 | 6/2018 | Lugosi et al. |
| 10,022,559 B2 | 7/2018 | Vilsmeier |
| 10,065,049 B2 | 9/2018 | Lugosi et al. |
| 10,279,196 B2 | 5/2019 | West et al. |
| 10,350,436 B2 | 7/2019 | Kelly |
| 10,449,389 B2 | 10/2019 | Ollila et al. |
| 10,456,600 B2 | 10/2019 | Owens et al. |
| 10,674,983 B2 | 6/2020 | Black |
| 10,688,320 B2 | 6/2020 | Voronenko et al. |
| 10,695,586 B2 | 6/2020 | Harper et al. |
| 10,737,118 B2 | 8/2020 | Mostafavi |
| 10,799,716 B2 | 10/2020 | Morgas et al. |
| 10,806,368 B2 | 10/2020 | Hebert |
| 10,835,761 B2 | 11/2020 | Beriault et al. |
| 10,918,884 B2 | 2/2021 | O'Connor et al. |
| 10,918,885 B2 | 2/2021 | Haas et al. |
| 11,033,757 B2 | 6/2021 | Voronenko et al. |
| 11,083,913 B2 | 8/2021 | Achaine et al. |
| 11,154,269 B2 | 10/2021 | Shea et al. |
| 11,173,324 B2 | 11/2021 | Paysan et al. |
| 11,278,737 B2 | 3/2022 | Peltola et al. |
| 11,291,858 B2 | 4/2022 | MacDonald et al. |
| 11,358,008 B2 | 6/2022 | Voronenko et al. |
| 11,369,805 B2 | 6/2022 | Maltz |
| 11,369,806 B2 | 6/2022 | Laurence, Jr. et al. |
| 11,478,662 B2 | 10/2022 | Sayeh et al. |
| 11,504,548 B2 | 11/2022 | Fong de los Santos et al. |
| 11,504,550 B2 | 11/2022 | Maolinbay |
| 11,596,807 B2 | 3/2023 | Maurer et al. |
| 11,617,903 B2 | 4/2023 | Lamb et al. |
| 11,633,626 B2 | 4/2023 | Voronenko et al. |
| 11,648,418 B2 | 5/2023 | Owens et al. |
| 11,684,801 B2 | 6/2023 | Schadewaldt et al. |
| 2002/0137991 A1 | 9/2002 | Scarantino et al. |
| 2004/0079899 A1 | 4/2004 | Ma |
| 2004/0122308 A1 | 6/2004 | Ding |
| 2005/0207531 A1 | 9/2005 | Dempsey et al. |
| 2006/0058637 A1 | 3/2006 | Sommer |
| 2006/0159220 A1 | 7/2006 | Heuscher |
| 2006/0173294 A1 | 8/2006 | Ein-Gal et al. |
| 2007/0025524 A1* | 2/2007 | Yue ............... A61N 5/1049 378/205 |
| 2008/0071131 A1 | 3/2008 | Rietzel |
| 2008/0226030 A1 | 9/2008 | Otto |
| 2009/0116616 A1 | 5/2009 | Lu et al. |
| 2009/0117044 A1 | 5/2009 | Hengerer et al. |
| 2010/0054411 A1 | 3/2010 | Nord et al. |
| 2010/0086183 A1 | 4/2010 | Vik et al. |
| 2010/0150309 A1 | 6/2010 | Nord et al. |
| 2011/0049377 A1 | 3/2011 | Morf et al. |
| 2011/0122997 A1 | 5/2011 | Lu et al. |
| 2011/0163238 A1 | 7/2011 | Teshigawara et al. |
| 2011/0200170 A1 | 8/2011 | Nord et al. |
| 2011/0291015 A1 | 12/2011 | Mazin |
| 2012/0053961 A1* | 3/2012 | Wang ............... G16H 70/20 705/2 |
| 2012/0230464 A1 | 9/2012 | Ling et al. |
| 2012/0250971 A1 | 10/2012 | Holmes et al. |
| 2012/0292534 A1 | 11/2012 | Geneser et al. |
| 2013/0083004 A1 | 4/2013 | Nord et al. |
| 2013/0102830 A1 | 4/2013 | Otto |
| 2013/0188856 A1 | 7/2013 | Adler, Jr. et al. |
| 2014/0005464 A1 | 1/2014 | Bharat et al. |
| 2014/0126700 A1 | 5/2014 | Gertner et al. |
| 2014/0252227 A1 | 9/2014 | Sasai et al. |
| 2014/0270053 A1 | 9/2014 | Larson |
| 2014/0275704 A1 | 9/2014 | Zhang et al. |
| 2015/0043709 A1 | 2/2015 | Shapiro et al. |
| 2015/0161338 A1 | 6/2015 | Scherrer et al. |
| 2015/0224342 A1 | 8/2015 | Baltes et al. |
| 2015/0251017 A1 | 9/2015 | De Crevoisier et al. |
| 2015/0360056 A1 | 12/2015 | Xing et al. |
| 2015/0367143 A1 | 12/2015 | Muraki et al. |
| 2016/0023019 A1 | 1/2016 | Filiberti et al. |
| 2016/0038767 A1 | 2/2016 | Wiersma et al. |
| 2016/0074541 A1 | 3/2016 | Zalutsky et al. |

(56) References Cited

U.S. PATENT DOCUMENTS

| | | | |
|---|---|---|---|
| 2016/0140300 A1 | 5/2016 | Purdie et al. | |
| 2016/0193480 A1 | 7/2016 | Ribbing et al. | |
| 2016/0361566 A1 | 12/2016 | Larkin et al. | |
| 2016/0361568 A1 | 12/2016 | Chappelow et al. | |
| 2017/0014642 A1 | 1/2017 | An et al. | |
| 2017/0023494 A1 | 1/2017 | Yu et al. | |
| 2017/0028220 A1 | 2/2017 | Schulte et al. | |
| 2017/0087385 A1 | 3/2017 | Miettinen et al. | |
| 2017/0095678 A1 | 4/2017 | Oster et al. | |
| 2017/0209715 A1* | 7/2017 | Ruebel | A61N 5/1067 |
| 2018/0133518 A1 | 5/2018 | Harper et al. | |
| 2018/0154179 A1 | 6/2018 | Ollila et al. | |
| 2018/0345042 A1* | 12/2018 | Voronenko | A61N 5/1039 |
| 2018/0369611 A1 | 12/2018 | Owens et al. | |
| 2019/0001152 A1 | 1/2019 | O'Connor et al. | |
| 2019/0054315 A1* | 2/2019 | Isola | A61N 5/1039 |
| 2019/0070436 A1* | 3/2019 | Willcut | A61N 5/1077 |
| 2020/0121953 A1 | 4/2020 | Fredriksson | |
| 2020/0346033 A1 | 11/2020 | MacDonald et al. | |
| 2021/0236854 A1 | 8/2021 | Voronenko et al. | |
| 2021/0339047 A1 | 11/2021 | Janardhanan et al. | |
| 2022/0001209 A1 | 1/2022 | Owens et al. | |
| 2023/0356003 A1 | 11/2023 | Voronenko et al. | |
| 2023/0390580 A1 | 12/2023 | Owens et al. | |

FOREIGN PATENT DOCUMENTS

| | | |
|---|---|---|
| CN | 101489477 A | 7/2009 |
| CN | 101496018 A | 7/2009 |
| CN | 102068763 A | 5/2011 |
| CN | 102641561 A | 8/2012 |
| CN | 103180014 A | 6/2013 |
| CN | 103209736 A | 7/2013 |
| CN | 103845068 A | 6/2014 |
| CN | 104284697 A | 1/2015 |
| CN | 104866928 A | 8/2015 |
| CN | 104994909 A | 10/2015 |
| CN | 105658279 A | 6/2016 |
| CN | 106563211 A | 4/2017 |
| CN | 107072595 A | 8/2017 |
| CN | 107072628 A | 8/2017 |
| EP | 2 072 081 A1 | 6/2009 |
| EP | 1 501 604 B1 | 12/2009 |
| EP | 1 898 234 B1 | 4/2010 |
| EP | 2 904 974 A1 | 8/2015 |
| EP | 2 990 078 A1 | 3/2016 |
| EP | 2 874 702 B1 | 9/2016 |
| EP | 3 169 402 B1 | 9/2020 |
| EP | 3 706 865 A1 | 9/2020 |
| JP | 2002-522128 A | 7/2002 |
| JP | 2005-261941 A | 9/2005 |
| JP | 2009-160308 A | 7/2009 |
| JP | 2009-538195 A | 11/2009 |
| JP | 2012-035072 A | 2/2012 |
| JP | 2012-506734 A | 3/2012 |
| JP | 2013-059576 A | 4/2013 |
| JP | 2014-023741 A | 2/2014 |
| JP | 2014-503315 A | 2/2014 |
| JP | 2016-055161 A | 4/2016 |
| JP | 2016-168077 A | 9/2016 |
| WO | WO-00/59576 A1 | 10/2000 |
| WO | WO-2007/082126 A2 | 7/2007 |
| WO | WO-2007/082126 A3 | 7/2007 |
| WO | WO-2008/011725 A1 | 1/2008 |
| WO | WO-2008/013598 A2 | 1/2008 |
| WO | WO-2008/013598 A3 | 1/2008 |
| WO | WO-2013/024380 A1 | 2/2013 |
| WO | WO-2013/054788 A1 | 4/2013 |
| WO | WO-2013/093852 A1 | 6/2013 |
| WO | WO-2015/168431 A1 | 11/2015 |
| WO | WO-2016/023786 A1 | 2/2016 |
| WO | WO-2016/064750 A1 | 4/2016 |
| WO | WO-2017/081768 A1 | 5/2017 |
| WO | WO-2018/183748 A1 | 10/2018 |
| WO | WO-2018/237328 A1 | 12/2018 |
| WO | WO-2019/090429 A1 | 5/2019 |

OTHER PUBLICATIONS

Extended European Search Report mailed on Jun. 23, 2023, for EP Application No. 20 840 804.7, filed on Jul. 2, 2020, 7 pages.

Final Office Action mailed on Sep. 15, 2022, for U.S. Appl. No. 16/582,308, filed Sep. 25, 2019, 10 pages.

Final Office Action mailed on Oct. 4, 2023, for U.S. Appl. No. 17/479,873, filed Sep. 20, 2021, 10 pages.

Fontenla, D.P. et al. (2008). "IMRT treatment plans: Dosimetry measurements & monitor units validation," North Shore LIJ, Presentation, 133 total pages.

Guohua H. et al. (Nov. 2002). "Chapter 8: Radionuclide diagnosis and treatment," in *Bladder Tumor*, Shanghai: Tongji University Press, first edition, first printing, p. 41 (with English Translation).

Hongsheng, S. (Aug. 2015). "Chapter 8: Nuclear medicine imaging," in *Practical Imaging Diagnosis*, Xi'an Jiaotong University Press, first edition, first printing, p. 167 (with English Translation).

Langen, K.M. et al. (2010). "QA for helical tomotherapy: Report of the AAPM task group 148," Med. Phys. 37:4817-4853.

Non-Final Office Action mailed on Aug. 30, 2022, for U.S. Appl. No. 17/235,812, filed Apr. 20, 2021, 8 pages.

Non-Final Office Action mailed on Nov. 21, 2022, for U.S. Appl. No. 16/016,272, filed Jun. 22, 2018, 27 pages.

Non-Final Office Action mailed on Jun. 29, 2023, for U.S. Appl. No. 17/479,873, filed Sep. 20, 2021, 10 pages.

Non-Final Office Action mailed on Mar. 5, 2024, for U.S. Appl. No. 17/479,873, filed Sep. 20, 2021, 11 pages.

Notice of Allowance mailed on Feb. 1, 2023, for U.S. Appl. No. 17/235,812, filed Apr. 20, 2021, 7 pages.

Notice of Allowance mailed on Mar. 9, 2023, for U.S. Appl. No. 16/016,272, filed Jun. 22, 2018, 8 pages.

Notice of Allowance mailed on Dec. 13, 2023, for U.S. Appl. No. 17/375,586, filed Jul. 14, 2021, 12 pages.

Parodi, K. (2015). "Vision 20/20: Positron emission tomography in radiation therapy planning, delivery, and monitoring," Am. Assoc. Phys. Med. 42:7153-7168.

Peng, C. et al. (Jun. 2016). "Chapter 15: Clinical radiotherapy technique," in *Clinical Diagnosis and Treatment of Oncological Diseases*, published by Jilin Science and Technology Press, first edition, first printing, p. 276 (with English translation).

Shiying, Y. (Jul. 2009). "Chapter 4: Design of radiotherapy plan," in *Guidelines for Standardized Diagnosis and Treatment of Tumors*, published by Huazhong University of Science and Technology Press, first edition, first printing, p. 106 (with English translation).

Xuening, Z. (Dec. 2010). "Chapter 2: Principles and Stereotactic Techniques of LEKSELL Gamma Knife," in *Gamma Knife Surgery for Intracranial Disease-Clinical Imaging*, published by Tianjin Science and Technology Press, first edition, first printing, pp. 29-30 (with English Translation).

Zhiliao, Z. et al. (Mar. 2002). "Progress in Physics of Tumor Radiotherapy," Beijing Medical University and China Union Medical University Joint Publishing House, first edition, first printing, pp. 163-164 (with English translation).

Adaptive Radiation Therapy: ISBN:9781439816356. 2011. CRC Press. X Allen Li (Ed.): 426 pages (cover only); URL https://www.google.com/books/edition/Adaptive_Radiation_Therapy/9hEPvAlgPfMC.

Akpati, H.C. et al. (2008). "Unified dosimetry index (UDI): A figure of merit for ranking treatment plans," J Appl Clin Med Phys. 9:99-108.

Alrowaili, Z.A. et al. (2015). "2D mapping of the MV photon fluence and 3D dose reconstruction in real time for quality assurance during radiotherapy treatment," J. Instrumentation IOP Science 10:P09019. 17 total pages.

ArcCHECK® & 3DVH (2016). Sun Nuclear, located at https://www.sunnuclear.com/solutions/patientqa/arccheck3dvh, retrieved on Jul. 31, 2019, 12 total pages.

(56) References Cited

OTHER PUBLICATIONS

Chang, J.Y. et al. (2008). "Image-guided radiation therapy for non-small cell lung cancer," J. Thorac Oncol. 3:177-186 (Abstract Only).
Chen, Q. et al. (2016). "SU-D-201-03: During-Treatment Delivery Monitoring System for TomoTherapy," Med. Phys. 43:3334, 1 total page.
Chen, Q. (2016) "During treatment delivery monitoring system for tomotherapy," Presentation, University of Virginia Health System, 16 total pages.
Chen, X. et al. (2012). "Smoothing proximal gradient method for general structured sparse regression," The Annals of Applied Statistics 6:719-752.
Croteau, E. et al. (2016). "PET Metabolic Biomarkers for Cancer," Biomark Cancer. 8(Suppl 2):61-69.
Dieterich, S. et al. (2003). "Skin respiratory motion tracking for stereotactic radiosurgery using the CyberKnife," *Elsevier Int'l Congress Series* 1256:130-136.
ECN Magazine (2016). "Magic plate radiation detector helps improve cancer radiotherapy," located at https://www.ecnmag.com/news/2016/03/magic-plate-radiation-detector-helps-improve-cancer-radiotherapy, retrieved on Jul. 31, 2019, 5 total pages.
Extended European Search Report mailed on Feb. 3, 2021, for EP Application No. 18 810 297.4, filed on May 30, 2018, 4 pages.
Extended European Search Report mailed on Oct. 15, 2019, for European Application No. 17 764 132.1, filed on Mar. 9, 2017, 4 pages.
Extended European Search Report mailed on Mar. 15, 2021, for EP Application No. 18 837 615.6, filed on Jul. 26, 2018, 8 pages.
Extended European Search Report mailed on Jun. 14, 2021, for EP Application No. 18 821 003.3, filed on Jun. 22, 2018, 5 pages.
Fan, Q. et al. (2013). "Toward a Planning Scheme for Emission Guided Radiation Therapy (EGRT): FDG Based Tumor Tracking in a Metastatic Breast Cancer Patient," *Med. Phys.* 40(8): 12 pages.
Fan, Q. et al. (2012). "Emission Guided Radiation Therapy for Lung and Prostrate Cancers: A Feasibility Study on a Digital Patient," *Med. Phys.* 39(11):7140-7152.
Final Office Action mailed on Jul. 14, 2021, for U.S. Appl. No. 16/582,308, filed Sep. 25, 2019, 8 pages.
Final Office Action mailed on May 18, 2022, for U.S. Appl. No. 16/016,272, filed Jun. 22, 2018, 31 pages.
Fredriksson (2013). "Robust optimization of radiation therapy accounting for geometric uncertainty," KTH Engin. Sciences, pp. 8-14.
Gibbons, J.P. (2004). "Dose calculation and verification for tomotherapy," 2004 ACMP Meeting, Scottsdale, AZ., 71 total pages.
Handsfield, L.L. et al. (2014). "Phantomless patient-specific TomoTherapy QA via delivery performance monitoring and a secondary Monte Carlo dose calculation," *Med. Phys.* 41:101703-1-101703-9.
Hoeben, B.A.W. et al. (2013). "Molecular PET imaging for biology-guided adaptive radiotherapy of head and neck cancer." Acta Oncologica 52:1257-1271.
Hunt, M.A. et al. (2003). "Treatment Planning Considerations using IMRT," pp. 103-121.
International Search Report mailed on Nov. 16, 2018, for PCT Application No. PCT/US2018/039104, filed on Jun. 22, 2018, 4 pages.
International Search Report mailed on Oct. 3, 2018, for PCT Application No. PCT/US2018/035188, filed on May 30, 2018, 4 pages.
International Search Report mailed on Oct. 3, 2018, for PCT Application No. PCT/US2018/043954, filed on Jul. 26, 2018, 3 pages,.
International Search Report mailed on Apr. 23, 2020, for PCT Application No. PCT/US2020/013927, filed on Jan. 16, 2020, 3 pages.
International Search Report mailed on Dec. 1, 2020, for PCT Application No. PCT/US2020/040774, filed on Jul. 2, 2020, 4 pages.
International Search Report mailed on Jun. 27, 2017, for PCT Patent Application No. PCT/US2017/021647, filed on Mar. 9, 2017, 3 pages.
Kak, A. et al. (1988). "Aliasing artifacts and noise in CT images," Principles of computerized tomographic imaging, pp. 177-201.
Kapatoes, J.M. et al. (2001). "A feasible method for clinical delivery verification and dose reconstruction in tomotherapy," *Med. Phys.* 28:528-542.
Kapatoes, J. M. (2001). "On the accuracy and effectiveness of dose reconstruction for tomotherapy," Physics in Med. Biol. 46:943-966.
Keall, P.J. et al. (2001). "Motion adaptive x-ray therapy: a feasibility study," *Physics in Med. Biol.* 46:1-10.
Kim et al. "18F-FDG PET/CT of Advanced Gastric Carcinoma and Association of H ER2 Expression with Standardized Uptake Value." Asia Oceania J Nucl Med Biol, 2014; 2(1): 12-18.
Kong et al. "Effect of Midtreatment PET/CT-Adapted Radiation Therapy with Concurrent Chemotherapy in Patients with Locally Advanced Non-Small-Cell Lung Cancer." JAMA Oncol. Oct. 2017: 3(10): 1358-1365.
Lu, W. (2008). "Real-time motion-adaptive delivery (MAD) using binary MLC: I. Static beam (topotherapy) delivery," Phys. Med. Biol. 53:6491-6511.
Lu, W. (2009). "Real-time motion-adaptive-optimization (MAO) in tomotherapy," Phys. Med. Biol. 54:4373-4398.
Mackie, T.R. et al. (1993). "Tomotherapy: A new concept for the delivery of dynamic conformal radiotherapy," Med. Phys. 20:1709-1719.
Mazin, S.R. et al. (2010). "Emission-guided radiation therapy: Biologic targeting and adaptive treatment," Am. College of Radiology, pp. 989-990.
McMahon, R. et al. (2008). "A real-time dynamic-MLC control algorithm for delivering IMRT to targets lundergoing 2D rigid motion in the beam's eye view," Med. Phys. 35:3875-3888.
Non-Final Office Action mailed on Dec. 6, 2019, for U.S. Appl. No. 15/993,325, filed May 30, 2018, 8 pages.
Non-Final Office Action mailed on Jun. 26, 2020, for U.S. Appl. No. 16/122,735, filed Sep. 5, 2018, 16 pages.
Non-Final Office Action mailed on Dec. 22, 2020, for U.S. Appl. No. 16/554,258, filed Aug. 28, 2019, 11 pages.
Non-Final Office Action mailed on Feb. 11, 2021, for U.S. Appl. No. 16/582,308, filed Sep. 25, 2019, 9 pages.
Non-Final Office Action malled on Sep. 21, 2021, for U.S. Appl. No. 16/016,272, filed Jun. 22, 2018, 34 pages.
Non-Final Office Action mailed on Jun. 8, 2022, for U.S. Appl. No. 16/582,308, filed Sep. 25, 2019, 9 pages.
Notice of Allowance mailed on Jul. 25, 2019, for U.S. Appl. No. 16/046,746, filed Jul. 26, 2018, 8 pages.
Notice of Allowance mailed on Aug. 15, 2019, for U.S. Appl. No. 16/046,746, filed Jul. 26, 2018, 7 pages.
Notice of Allowance mailed on Apr. 20, 2020, for U.S. Appl. No. 15/993,325, filed May 30, 2018, 7 pages.
Notice of Allowance mailed on Dec. 11, 2020, for U.S. Appl. No. 16/122,735, filed Sep. 5, 2018, 10 pages.
Olivera, G.H. et al. (2000). "Modifying a plan delivery without re-optimization to account for patient offset in tomotherapy," Proceedings of the 22$^{nd}$ Annual EMBS International Conference, Jul. 23-28, 2000, Chicago, IL, pp. 441-444.
Papanikolaou, N. et al. (2010). "MU-Tomo: Independent dose validation software for helical tomo therapy," *J. Cancer Sci. Ther.* 2:145-152.
Pyakuryal, A. et al. (2010). "A computational tool for the efficient analysis of dose-volume histograms for radiation therapy treatment plans," J Appl. Clin. Med. Phys. 11:137-157.
Rahmim, A. et al. (2009). "Four-dimensional (4d) image reconstruction strategies in dynamic pet: beyond conventional independent frame reconstruction," Medical physics 36:3654-3670.
Reader, A.J. et al. (2007). "Advances in pet image reconstruction," PET clinics 2:173-190.
Riederer, S.J. et al. (1978). "The noise power spectrum in computed x-ray tomography," Physics in medicine and biology 23:446.
ScandiDos (2019). Delta4$^4$ located at https://delta4family.com/products, retrieved on Jul. 31, 2019, 5 total pages.

(56) References Cited

OTHER PUBLICATIONS

Seppenwoolde, Y. et al. (2002). "Precise and real-time measurement of 3d tumor motion in lung due to breathing and heartbeat, measured during radiotherapy," International Journal of Radiation Oncology Biology Physics 53:822-834.

Thorek, D. "Positron lymphography: multimodal, high-resolution, dynamic mapping and resection of lymph nodes after X Intradermal injection of 18F-FDG." J Nucl Med. Sep. 2012;53(9):1438-45.

Thorwarth, D. et al. (2010). "Physical radiotherapy treatment planning based on functional PET/CT data," Radiotherapy Oncology, pp. 317-324.

Tuncel. N. (2021). "Adaptive radiotherapy from past to future frontiers." International Journal of Radiology & Radiation Therapy 8:81-84.

Varian Medical Systems (2019). MOBIUS3D, Varian oncology software products, located at https://www.varian.com/oncology/products/software/mobius3d, retrieved on Jul. 31, 2019, 3 total pages.

Written Opinion of the International Searching Authority mailed on Nov. 16, 2018, for PCT Application No. PCT/US2018/039104, filed on Jun. 22, 2018, 6 pages.

Written Opinion of the International Searching Authority mailed on Oct. 3, 2018, for PCT Application No. PCT/US2018/035188, filed on May 30, 2018, 28 pages.

Written Opinion of the International Searching Authority mailed on Oct. 3, 2018, for PCT Application No. PCT/US2018/043954, filed on Jul. 26, 2018, 5 pages.

Written Opinion of the International Searching Authority mailed on Apr. 23, 2020, for PCT Application No. PCT/US2020/013927, filed on Jan. 16, 2020, 4 pages.

Written Opinion of the International Searching Authority mailed on Dec. 1, 2020, for PCT Application No. PCT/US2020/040774, filed on Jul. 2, 2020, 8 pages.

Written Opinion of the International Searching Authority mailed on Jun. 27, 2017, for PCT Patent Application No. PCT/US2017/021647, filed on Mar. 9, 2017, 5 pages.

Yan, D. et al. (1997). "Adaptive radiation therapy." *Physics Med. Biol.* 42:123-132.

Zhang, H. et al. (2002). Progress in the Physics of Tumor Radiation Therapy, Beijing Medical University, China Union Medical University Joint Press, p. 164 (with English translation).

Zhao, H. et al. (2015). Practical Imaging Diagnosis, University Press, Aug. 2015, p. 167 (with English translation).

* cited by examiner

220

| Acquire one or more planning images of one or more patient target regions | 222 |

↓

| Define the contours of the one or more patient target regions and/or organs at risk (OARs) and corresponding dose constraints | 224 |

↓

| (Optional) For each patient target region: (a) Select SBRT/IMRT delivery or BgRT delivery, and if BgRT, (b) Define the contours of a spatial filter, e.g., biological firing zone | 226 |

↓

| Select a planned localization reference point for each of the one or more patient target regions and/or OARs | 228 |

↓

| For each patient target region and/or OAR, calculate a set of shift-invariant firing filters based on the planned localization reference point | 230 |

↓

| (Optional) Determine a set of therapeutic radiation source firing positions and calculate projections of the firing filters to each firing position | 232 |

↓

| Generate a treatment plan fluence map based on the firing filters and the one or more planning images | 234 |

↓

| Define perimeters around each patient target region that comprise regions of low fluence values in the treatment plan fluence map | 236 |

↓

| Calculate bounded dose-volume histogram curves for each patient target region and/or OAR | 238 |

↓

| Display bounded dose-volume histogram curves and/or dose calculation data for each patient target region and/or OAR to a display device | 240 |

| 352 | Acquire one or more planning images of one or more patient target regions |

↓

| 354 | Define the contours of the one or more patient target regions and/or organs at risk (OARs) and corresponding dose constraints |

↓

| 356 | For each patient target region: (a) Select SBRT/IMRT delivery or BgRT delivery, and if BgRT, (b) Define the contours of a spatial filter, e.g., region of interest |

↓

| 358 | Select a planned localization reference point for each of the one or more patient target regions |

↓

| 360 | For each patient target region, calculate a set of shift-invariant firing filters that is independent of the dose constraints of the other patient target regions and based on the planned localization reference point |

↓

| 362 | Generate a fluence map for each patient target region based on the firing filters and the one or more planning images |

↓

| 364 | Combine all of the patient target region fluence maps into a cumulative treatment plan fluence map |

↓

| 366 | Iteratively modify the cumulative treatment plan fluence map based on one or more dose constraints, for example, one or more of (a) high-fluence areas are kept separate from each other, (b) OAR constraints are met, (c) original dose constraints/objectives are fulfilled |

| 822 | Acquire one or more localization images of one or more patient target regions |

↓

| 824 | Partition a treatment plan fluence map into one or more fluence map sub-regions according to perimeters around each patient target region defined during treatment planning |

↓

| 826 | Calculate patient platform position-shift vectors for each fluence map sub-region based on the localization images and the treatment planning images |

↓

| 828 | For each patient platform position, shift each of the fluence map sub-regions such that a high-fluence region is co-localized with its corresponding patient target region |

↓

| 830 | Calculate fluence to each patient target region at each patient platform position-shift vector |

↓

| 832 | Calculate dose for each of the patient target regions based on the shifted fluence map sub-regions and patient platform positions, compare with a bounded dose-volume histogram curves calculated during treatment planning, and/or display bounded dose-volume histogram curves and/or dose calculation data for each patient target region and/or OAR to a display device |

↓

| 834 | Proceed with radiation delivery: Move the patient platform to each position specified by the platform position-shift vectors and emit the shifted fluence map sub-regions to each patient target region |

FIG. 8B

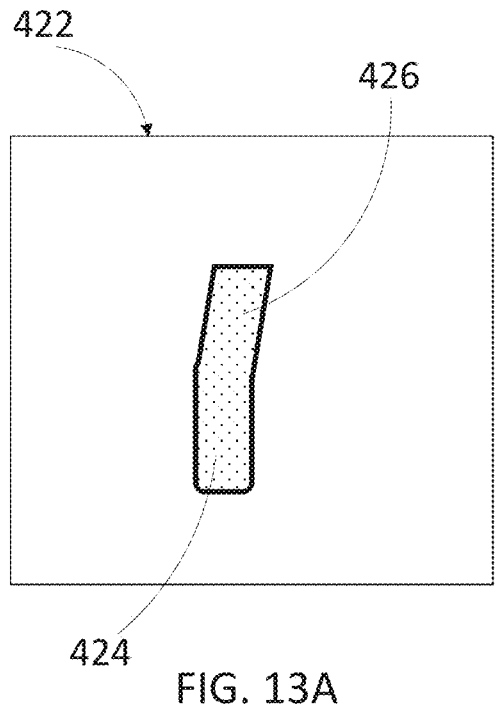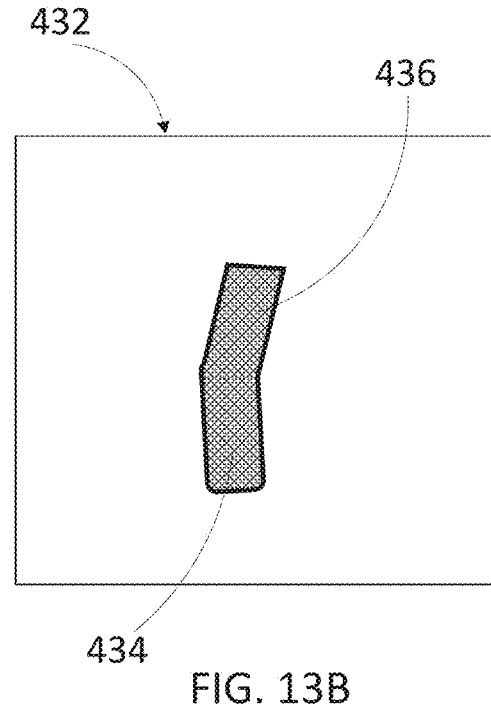
FIG. 13A    FIG. 13B
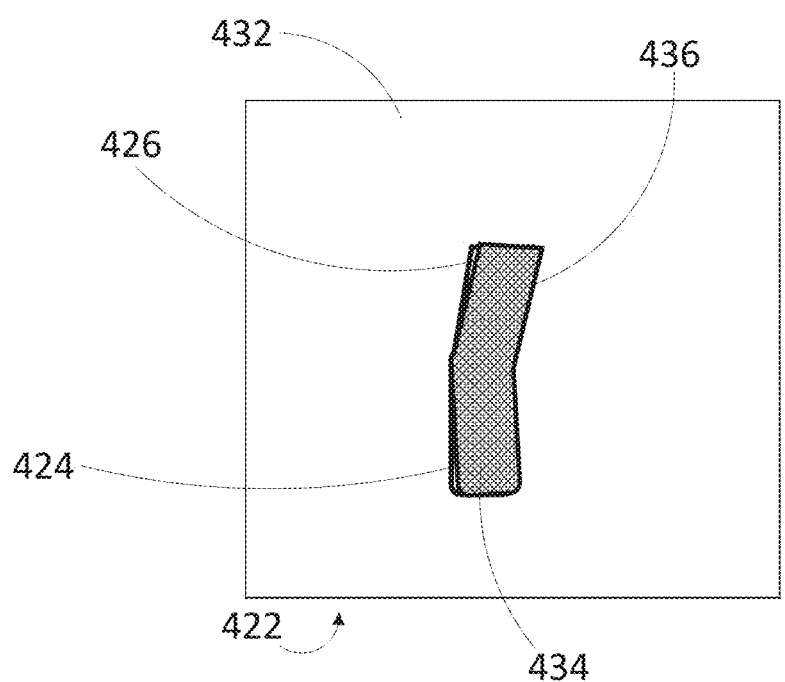
FIG. 13C

3D Dose - Nominal
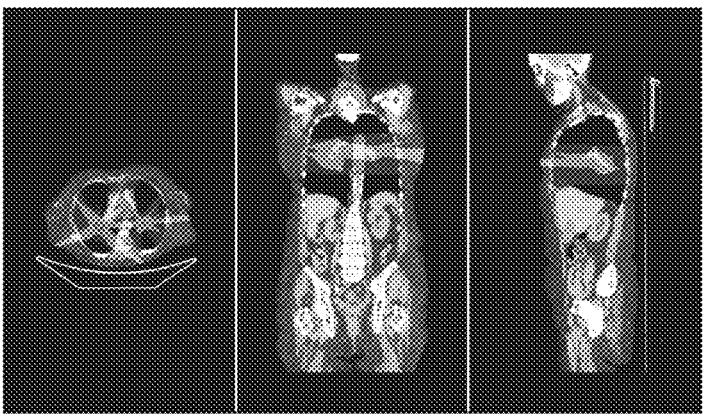
5D Dose with Dose Difference Probability Map
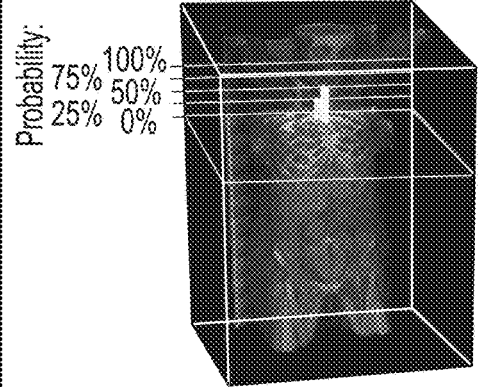
3D Dose - Minimum
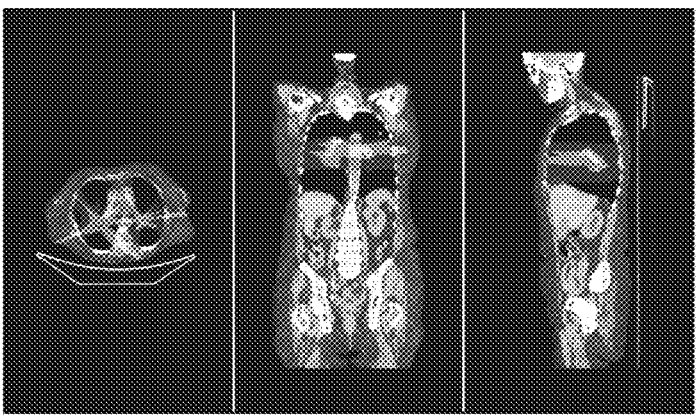
3D Dose - Maximum
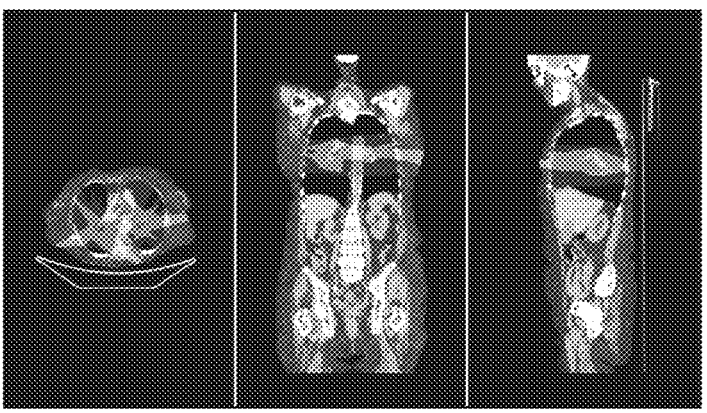
FIG. 15B

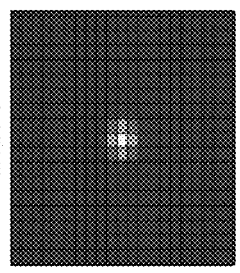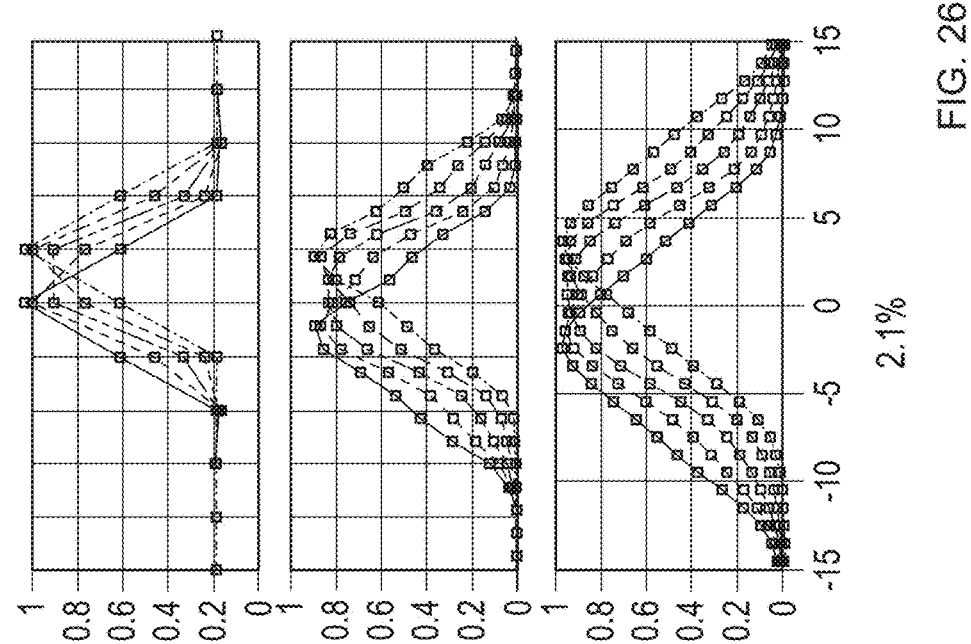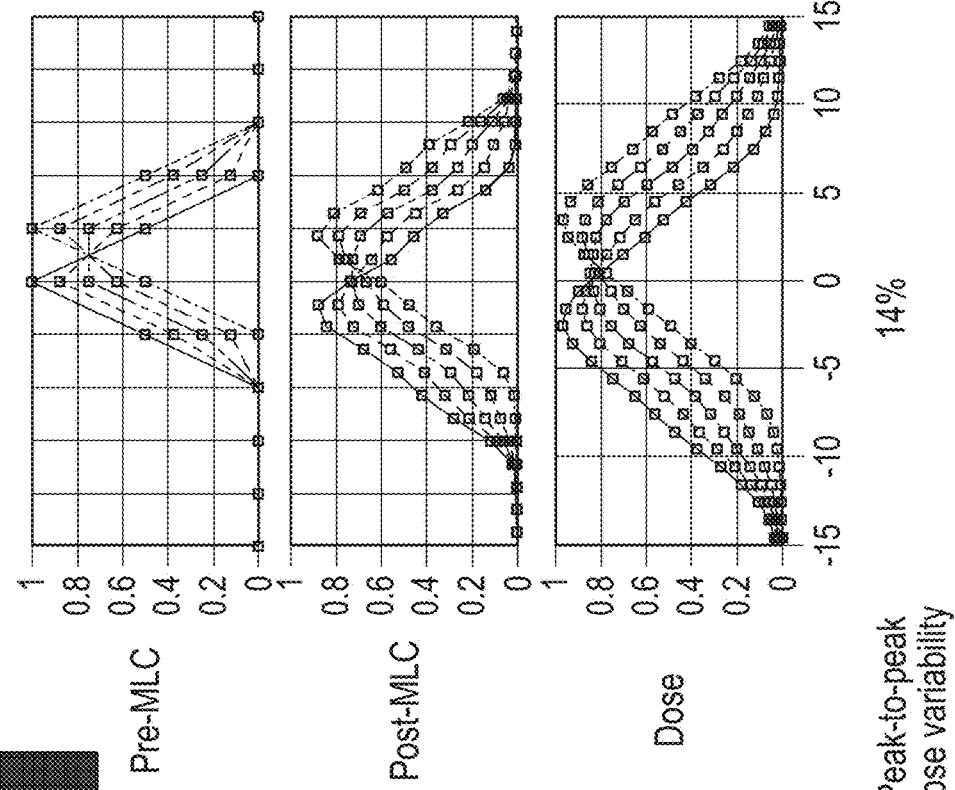
FIG. 26

Virtual Fluence rotation at target: Analysis of leaf shift

Fan beam, exact solution $$\Delta r_\theta = FP(\delta_{LOC}, \theta) \otimes FP(ROT(\delta_{LOC}, \varphi), \theta)^T$$

Approximate parallel beam solution:

$$\Delta x = x(1 - \cos \varphi) + y \sin \varphi$$
$$\Delta y = y(1 - \cos \varphi) + x \sin \varphi$$
$$\Delta r_\theta \approx (\Delta x \cos \theta + \Delta y \sin \theta)/\Delta w$$

$\Delta r$ is approximate, because this correction assumes a linear fan beam $$\Delta w = w \frac{D_t}{D_{iso}}$$ Leaf spacing at target point

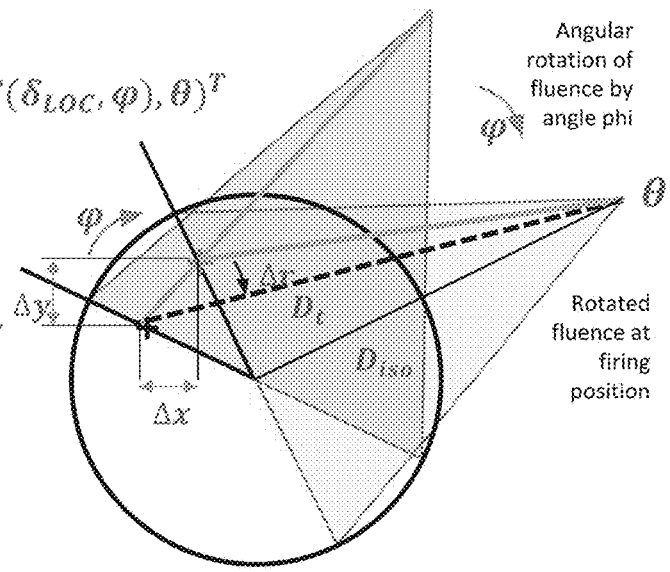

Angular rotation of fluence by angle phi

Rotated fluence at firing position

Rotated target without leaf shift

Original target

FIG. 33

BgRT Virtual Shift and Rotation

Filters $p$, are circularly convolved with roll $$p' = \delta(\varphi_{roll}) \otimes p$$

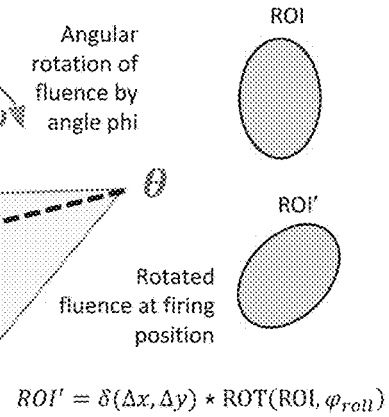

Angular rotation of fluence by angle phi

Rotated fluence at firing position

ROI: Spatial filter shifted by offset and rotated in place $$ROI' = \delta(\Delta x, \Delta y) * ROT(ROI, \varphi_{roll})$$

FIG. 34

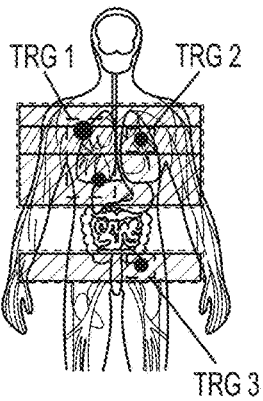
2 Patient Setups
3 Treatment Areas
3 Target Region Groups
3 Localization CTs
Up to 3 Physical Localizations
Up to 3 Virtual Locatization

FIG. 35A

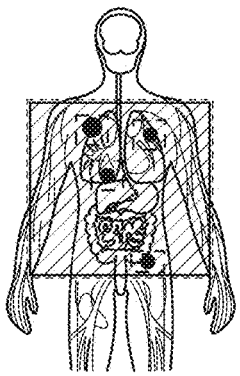
1 Patient Setups
1 Treatment Areas
4 Target Region Groups
1 Localization CTs
Up to 1 Physical Localizations
Up to 4 Virtual Locatization

FIG. 35B

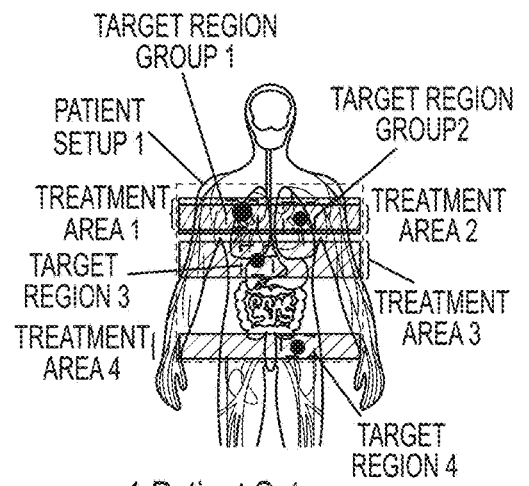
1 Patient Setups
4 Treatment Areas
4 Target Region Groups
4 Localization CTs
Up to 4 Physical Localizations
Up to 4 Virtual Locatizations

FIG. 35C

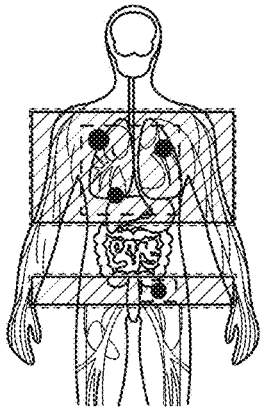
2 Patient Setups
2 Treatment Areas
2 Target Region Groups
2 Localization CTs
Up to 2 Physical Localizations
Up to 2 Virtual Locatization

FIG. 36A

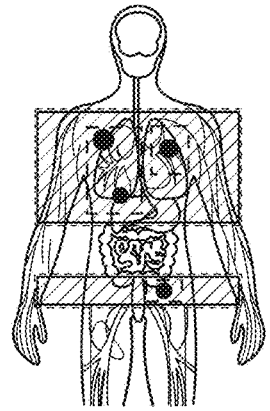
2 Patient Setups
2 Treatment Areas
3 Target Region Groups
2 Localization CTs
Up to 2 Physical Localizations
Up to 3 Virtual Locatizations

MULTI-TARGET TREATMENT PLANNING AND DELIVERY AND VIRTUAL LOCALIZATION FOR RADIATION THERAPY

CROSS-REFERENCE TO RELATED APPLICATIONS

This application is a continuation of International Patent Application No. PCT/US2020/040774, filed Jul. 2, 2020, which claims priority to U.S. Provisional Patent Application No. 62/873,742, filed Jul. 12, 2019, each of which is hereby incorporated by reference in its entirety.

BACKGROUND

Radiation therapy involves acquiring planning images of the patient and the one or more tumor regions and designing a treatment plan that provides a prescribed dose of radiation to the tumor regions. In addition to identifying the tumor regions to be irradiated, radiation therapy also seeks to limit the irradiation of healthy tissue. This may include identifying radiation-sensitive or radiation-avoidance regions (e.g., organs-at-risk or OARs) and designing a treatment plan that does not irradiate these radiation-avoidance regions beyond a prescribed. In most instances, a treatment plan assumes that the absolute and/or relative positions of the one or more tumor regions, OARs, and healthy tissue regions at the time of treatment matches (or nearly matches) their absolute and/or relative positions at the time the planning images were acquired. Once a treatment plan has been designed that meets the dosimetric goals for the tumor region(s) and for the OARs, a patient may be positioned on a patient platform or couch of a radiotherapy system so that the patient is reasonably comfortable on the couch and is in a suitable position for radiation delivery. One or more localization images may be acquired (e.g., a fan-beam CT scan, a cone-beam CT scan, and/or PET scan) of the patient on the couch. The location of each of the one or more tumor regions, OARs, and/or other anatomical structures may be determined using the localization image(s), and their absolute position relative to a therapeutic radiation source and/or their relative positions to each other may be compared to their locations from the treatment planning images. If any of the tumor regions and/or OARs have shifted, the radiotherapy system may calculate how the patient ought to be shifted to match their location during treatment planning, and to the extent possible, the couch may be adjusted to enact that shift.

However, patient setup and localization of the tumor regions and/or OARs with respect to the coordinates of a radiation therapy system can be time-consuming, particularly because the tumor region(s) and/or OARs can change in size, shape, and/or location between the time of acquisition of the planning images and the treatment session, and in some instances, may continue to change during a treatment session. Additionally, patient setup and localization are typically optimized for the treatment of a single target region and may not easily accommodate the treatment of multiple target regions. For example, one patient setup arrangement and localization may be suitable for one tumor region, but might not allow for the delivery of the prescribed dose for another tumor region, and/or may result in unwanted irradiation of an OAR. Accurately registering a patient to a plan designed to treat multiple targets simultaneously, involves somehow mapping the new, actual locations of multiple targets in the patient at the time of delivery to the original locations of multiple targets in the treatment plan. Since the tumors may shift one with respect to another, there may not be a single translation and orientation shift of the patient that can align all tumors to the plan. That is, adjustments, shifts and rotations of the patient that align one tumor with the expected position in the plan may cause the other tumors to fall out of alignment.

One approach to delivering radiation to a plurality of patient target regions involves performing a series of patent setup and localizations. For example, for a first patient target region, the couch may be adjusted to position the patient to a setup position that is suitable for radiation delivery to the first target region, a localization image may be acquired to locate the first target region, and then radiation is delivered to that first target region. These steps are then repeated for each target region, which can be time-consuming (especially if patient setup involves opening the bunker door so that a clinician or technician may enter to adjust the patient on the couch) and because each iteration is treated individually, may result in over-dosing OARs and/or healthy tissue, and/or under-dosing target regions (e.g., in an effort not to over-dose the OARs). Thus, improved radiation treatment planning, patient setup and registration, and localization methods are desirable, especially for the irradiation of multiple target regions.

SUMMARY

Disclosed herein are methods for treatment planning, patient setup, localization and radiation delivery for the irradiation of multiple patient target regions in a single treatment session or fraction.

Methods of treatment planning for the irradiation of multiple target regions may comprise selecting a planned localization reference point for each target region, and calculating shift-invariant firing filters for each target region based on the selected planned localization reference point. A treatment plan fluence map that specifies the radiation fluence delivered to the multiple target regions, as well as the radiation levels to OARs and healthy tissue, may be calculated based on the shift-invariant firing filters and the planned localization reference point of each target region.

Additionally or alternatively, the shift-invariant firing filters may be represented as functional shift and orientation operators of the radiation fluence delivered to multiple target regions based on the planned localization reference point of each target region. For example, a functional shift operator may comprise a function that interpolates a two-dimensional or three-dimensional map with a shift. A functional orientation operator may, for example, comprise a function that interpolates a two-dimensional or three-dimensional map using a rotation along an axis in the two-dimensional or three-dimensional space. For example, a functional orientation operator may be used to interpolate (e.g., transform) a two-dimensional (or three-dimensional) fluence map for delivery based on the location of the localization reference point on the day of treatment. This may comprise calculating translations of a fluence map in (x,y) coordinates, and/or scaling the fluence map in (x,y,z) and/or rotation of the fluence map along an axis in (θ, φ, ρ). In some variations, treatment planning methods may comprise defining perimeters in the treatment plan fluence map around each patient target region that comprise regions of low-fluence values. Treatment planning methods for multiple target regions may comprise calculating an individual treatment plan comprising an individual fluence map for each target region, combining the individual fluence maps into a cumulative treatment plan fluence map, and iteratively modifying the cumulative treatment plan fluence map based on one or more constraints (e.g., dose constraints such as keeping high-fluence areas separate from each other, meeting OAR fluence limits, meeting dose objectives for each target region). After the cumulative treatment plan fluence map has been iteratively modified per desired constraints, a treatment planning method may comprise defining perimeters in the treatment plan fluence map around each patient target region that comprise regions of low-fluence values, and may optionally comprise separating the iteratively modified cumulative treatment plan fluence map into individual fluence maps for each patient target region along the defined perimeters. In some variations, one or more of a functional shift operator and orientation operator may be used during treatment planning optimization to calculate a fluence map that is based on a planned localization reference point of each target region.

Optionally, in biologically-guided radiation therapy (BgRT) where positron annihilation emission path data is acquired during a treatment session and used to calculate the delivery fluence, a treatment planning method may comprise defining a first region of interest (ROI) or radiation firing zone that surrounds a first patient target region and a second ROI or radiation firing zone that surrounds a second patient target region for a predetermined range of location shifts of the first and second patient target regions. The output of the treatment planning methods described herein may comprise a treatment plan fluence map that defines the fluence to be delivered to each patient target region and the level of radiation exposure of OARs and healthy tissue, as well as a set of shift-invariant firing filters for each planned localization reference point associated with each patient target region. Alternatively or additionally, in treatment planning for BgRT, the treatment planning methods may output a set of shift-invariant firing filters associated with a ROI (e.g., a biological firing zone (BFZ)) defined around each patient target region. Additionally or alternatively, a set of shift-invariant firing filters may comprise a functional shift operator and/or orientation operator. Optionally, the output of a treatment planning method may comprise a set of radiotherapy machine instructions for execution by the radiotherapy system after patient setup and patient target region localization.

In some variations, a method for virtual target region localization and radiation delivery may comprise acquiring an image of a patient in a treatment position and identifying in the acquired image a patient target region, selecting a localization reference point within the acquired image, where the localization reference point corresponds with a planned localization reference point, calculating a spatial offset based on a shift between the localization reference point and the planned localization reference point, shifting a boundary of a planned region of interest based on the spatial offset, where the boundary of the planned region of interest surrounds the patient target region, acquiring imaging data that has been spatially filtered by the shifted region of interest, calculating a fluence for delivery to the patient target region at each firing position of a therapeutic radiation source by convolving a set of firing filters with the acquired imaging data, and emitting, using the therapeutic radiation source, the calculated fluence to the patient target region.

In some variations, the boundary of the planned region of interest may comprise a spatial filter. In some variations, shifting the boundary of the planned region of interest may comprise applying a rotation and a shift to the planned region of interest by a roll correction factor $\varphi$ that represents a rotational translation of the localization reference point relative to the planned localization reference point. Calculating the fluence for delivery may comprise circularly convolving the set of firing filters with the roll correction factor $\varphi$.

In some variations, a method of treatment planning for radiation delivery to multiple patient target regions may comprise identifying a first location of a first patient target region and a second location of a second patient target region in a patient planning image, defining a first region of interest having a boundary that surrounds the first patient target region, defining a second region of interest having a boundary that surrounds the second patient target region. The boundary of the second region of interest may be selected to surround the second patient target region for a predetermined range of location shifts of the first and second patient target regions. The first and second region of interest may represent spatial filters configured to select imaging data acquired during a treatment session. The method may further comprise calculating a treatment planning fluence map for the first patient target region and the second patient target region that designates the fluence to be delivered if the selected imaging data indicates that first patient target region is within the boundaries of the first region of interest and the second patient target region is within the boundaries of the second region of interest.

In some variations, the first patient target region may be in closer proximity to a planning structure. In some variations, the first region of interest may be smaller than the second firing zone. In some variations, the planning structure may be an organ-at-risk (OAR). In some variations, the first patient target region may be in closer proximity to two or more planning structures than the second patient target region. In some variations, the method may further comprise designating a treatment planning reference point within the first region of interest as a localization reference point to position a patient at the start of the treatment session. In some variations, selected imaging data may be used to guide radiation delivery during the treatment session. In some variations, the treatment planning reference point may be a center point in the first patient target region.

In some variations, the imaging data may comprise positron annihilation emission path data. In some variations, a positron annihilation emission path may be selected if it intersects at least one of the first and second firing zones. In some variations, the second region of interest may be sized to include a range of locations of the second patient target region. In some variations, the imaging data may comprise one or more of a positron emission tomography (PET) imaging data, computed tomography (CT) imaging data, and magnetic resonance imaging (MRI) imaging data.

Also disclosed herein are methods for patient setup and patient target region localization for the irradiation of multiple target tissue regions. Methods for patient setup and target registration/localization may comprise positioning a patient on a patient platform or couch of a radiotherapy system, acquiring one or more localization images of the patient, including the one or more target regions and/or OARs, and selecting a localization reference point within the one or more acquired localization images. The selected localization reference point may correspond with a planned localization reference point of a particular patient target region, and may represent the updated location of the patient target region. The fluence map for delivery for the particular patient target region may be calculated by calculating a localization function based on the selected localization reference point and applying the localization function with a shift-invariant firing filter derived based on the planned localization reference point. Alternatively or additionally, the shift-invariant firing filter may be derived from other planning parameters. For example, the fluence map for delivery to a patient target region may be calculated by calculating a delta function (e.g., a 3-D discrete delta function) based on the selected localization reference point and convolving the delta function with a shift-invariant firing filter derived based on the planned localization reference point and/or other planning parameters. In another example, the fluence map for delivery to a patient target region may be calculated by interpolating the fluence map with a shift or rotation based on the selected localization reference point. In such fashion, the fluence map for delivery may be updated with the current location of the patient target region and may not require adjusting the patient's position using the couch. Localization of a patient target region by calculating the fluence map based on a localization function based on a selected localization reference point (e.g., a delta function or Gaussian-type function centered over the selected localization reference point) and a set of shift-invariant firing filters may be referred to as "virtual localization". In some variations, the patient may be setup on the couch once, while the acquisition of localization images, selection of a localization reference point, and calculation of the fluence map for delivery may be performed for each patient target region (e.g., one physical localization/setup, multiple localization image scans, multiple virtual localizations corresponding to the multiple patient target regions). Alternatively, localization images may be acquired once (e.g., at the time the patient is initially positioned in the radiation therapy system) and the selection of a localization reference point and calculation of delivery fluence map may be performed for each patient target region (e.g., one physical setup, one localization image scan, multiple virtual localizations corresponding to the multiple patient target regions) using the initially-acquired localization images.

By contrast, conventional treatment delivery methods include the steps of acquiring a localization image (e.g., localization CT image) to physically position a patient and a patient target region on a patient platform to match the location of the patient target region determined at the time of treatment planning. To treat multiple patient target regions in a single treatment session, the patient may need to be physically re-positioned prior to irradiating each patient target region, since a particular physical location of the patient that might be appropriate for the irradiation of one patient target region may not be appropriate for irradiating another patient target region. For each re-positioning, an additional localization image is acquired. In some variations, the positioning and re-positioning of the patient may be provided by a patient platform. Furthermore, some treatment planning systems may be configured to output machine instructions (e.g., leaf patterns), which may then be shifted according to the localization image. However, the treatment planning systems and methods described herein are configured to output a fluence map and/or firing filters for a delivery system to convolve with an image and/or localization function of a localization reference point to generate a delivery fluence map. This may allow for the treatment of multiple patient target regions without needing to re-position the patient for each target region. The delivery fluence map may be segmented by the delivery system into machine instructions just prior to dose delivery. Thus, virtual localization may eliminate or reduce the number of times localization images are acquired and a patient is physically positioned (and/or re-positioned) for the treatment of multiple patient target regions.

Alternatively or additionally to virtual localizations, methods for patient setup may comprise acquiring an image of a first patient target region and a second patient target region. A first set of patient position-shift vectors may be calculated based on the acquired image and a treatment planning image of the first patient target region. A second set of patient position-shift vectors may be calculated based on the acquired image, a treatment planning image of the second patient target region, and the first set of patient position-shift vectors. The patient may be positioned according to the first set of patient position-shift vectors to a first location and/or position. The patient may be positioned at a second location and positioned according to the second set of patient position-shift vectors. Positioning the patient according to the first set of patient position-shift vectors may comprise moving a radiation therapy patient platform and/or a therapeutic radiation source according to the first set of patient position-shift vectors. The patient may be positioned at a second location and adjusted according to the second set of patient position-shift vectors. Positioning the patient according to a second set of patient position-shift vectors may comprise moving a radiation therapy patient platform and/or a therapeutic radiation source according to the second set of patient position-shift vectors. Moving the radiation therapy patient platform may comprise moving the platform along its X-axis, and/or Y-axis, and/or Z-axis. Moving the radiation therapy patient platform may comprise adjusting the yaw and/or pitch and/or roll of the platform and moving the therapeutic radiation source may comprise adjusting the yaw/pitch/roll of a gantry to which the therapeutic radiation source is coupled. The first treatment planning image and the second treatment planning image may be the same treatment planning image. The acquired image may be a PET (Positron Emission Tomography) image. The acquired image may be a CT (Computed Tomography) image. The acquired image may be an MRI (Magnetic Resonance Imaging) image. In some embodiments, calculating the first and second sets of patient position-shift vectors may occur before a therapeutic radiation source is activated. In some embodiments, a first location difference may be calculated by comparing a location of the first patient target region in the acquired image with a location of the first patient target region in the first treatment planning image. A second location difference may be calculated by comparing a location of the second patient target region in the acquired image with a location of the second patient target region in the second treatment planning image. A notification may be generated if the first location difference or the second location difference exceeds a location difference threshold. The first patient target region and the second patient target region may comprise one or more tumor regions. The first patient target region may comprise a first portion of a tumor and the second patient target region may comprise a second portion of the tumor. The first and second sets of position-shift vectors may comprise distance and direction translations. The direction translations may comprise tilt angles.

Methods for delivering radiation fluence to multiple patient regions may comprise transforming (a.k.a. segmenting) the delivery fluence map into radiotherapy system machine instructions (e.g., therapeutic radiation source radiation emission parameters, multi-leaf collimator configurations for each firing position about the patient platform, etc.), and then executing the machine instructions by emitting the radiation fluence from the therapeutic radiation source to the patient. The delivery fluence map for multiple patient target regions may be a combination of the individual fluence maps calculated during virtual localization for each of the patient target regions, and the machine instructions for delivering to two or more of the patient target regions (e.g., all of the patient target regions) may be segmented at the same time. Alternatively or additionally, the individual fluence maps for each of the patient target regions may be segmented separately (e.g., sequentially). Optionally, in BgRT where positron annihilation emission path data is acquired during a treatment session and used to calculate the delivery fluence, the delivery fluence map may be segmented into radiotherapy system machine instructions in real-time, e.g., 500 ms or less between the acquisition of emission path data and the delivery of a therapeutic radiation beam. The delivery fluence map may be the fluence map calculated from the emission path data, and the virtual localization may be achieved by shifting or rotating the ROI.

A method for virtual target region localization and radiation delivery may comprise acquiring an image of a patient in a treatment position and identifying a patient target region in the acquired image, selecting a localization reference point within the acquired image, where the localization reference point corresponds with a planned localization reference point, calculating a fluence for delivery to the patient target region at each firing position of a therapeutic radiation source by calculating a localization function based on the localization reference point, and applying the localization function to a shift-invariant firing filter derived based on the planned localization reference point, and emitting, using the therapeutic radiation source, the delivery fluence to the patient target region. The localization function may be a delta function and applying the localization function to the shift-invariant firing filter may comprise convolving the delta function with the shift-invariant firing filter. Additionally or alternatively, the shift-invariant firing filters may comprise one or more functional shift operators and orientation operators of the radiation fluence delivered to multiple target regions based on planned localization reference point of each target region. For example, as described above, a functional shift operator may comprise a function that interpolates a two-dimensional or three-dimensional map with a shift. An orientation operator may comprise a function that interpolates a two-dimensional or three-dimensional map using a rotation. For example, an interpolation may comprise one or more of a linear interpolation, nearest neighbor interpolation, bi-cubic interpolation, spline interpolation, or Fourier shift interpolation. The localization reference point may be a user-selected location within the acquired image and/or may correspond to a treatment plan isocenter defined relative to the patient target region during treatment planning. The first patient target region may be in a first treatment area of a patient defined during treatment planning and the second target region may be in a second treatment area of the patient defined during treatment planning. The first treatment area may comprise a first set of axial planes and may have an axial length of about 8 cm or less, and the second treatment area may not overlap with the first treatment area and may have an axial length of about 8 cm or less and may comprise a second set of axial planes. A center of the first treatment area and a center of the second treatment area may be collinear, e.g., along an IEC-Y axis and/or coplanar with the IEC-Y axis. In some variations, the first treatment area may overlap with the second treatment area.

The firing positions of a therapeutic radiation source comprise locations of the therapeutic radiation source relative to a patient platform location. The therapeutic radiation source may be mounted on a gantry rotatable about a longitudinal axis, and the locations of the therapeutic radiation source may be designated by gantry angles about the longitudinal axis. The patient platform may be movable to different locations along the longitudinal axis.

In some variations, a therapeutic radiation source may be mounted on a gantry such that radiation may be delivered to the patient in discrete continuous arcs (e.g., non-coplanar VMAT, 4-pi VMAT). In some of these variations, these radiation delivery arcs may not be co-planar to each other (e.g., perpendicular to the longitudinal axis). The firing positions may be specified as discrete positions along each arc and may be indexed by arc. The patient platform may be configured to reposition to a predetermined position and orientation between each arc.

In some variations, a therapeutic radiation source may be mounted on a gantry such that radiation may be delivered at fixed points around a 4-pi or 2-pi hemispherical envelope. In some of these variations, a set of firing positions may be specified as discrete positions based on a two-dimensional fluence map. The patient platform may be configured to move the patient to a predetermined set of positions and/or orientations between each fixed point.

A method may further comprise identifying a second patient target region in the acquired image, selecting a second localization reference point for the second patient target region within the acquired image, where the second localization reference point corresponds with a second planned localization reference point, calculating a second delivery fluence at each firing position of the therapeutic radiation source by calculating a second localization function based on the second localization reference point, and applying the second localization function to a second shift-invariant firing filter based on the second planned localization reference point, and emitting, using the therapeutic radiation source, the second delivery fluence to the second patient target region. Methods may optionally comprise identifying a second patient target region in the acquired image, selecting a second localization reference point for the second patient target region within the acquired image, where the second localization reference point corresponds with a second planned localization reference point, calculating a second delivery fluence at each firing position of the therapeutic radiation source by calculating a second delta function based on the second localization reference point, and convolving the second delta function with a second shift-invariant firing filter based on the second planned localization reference point, and emitting, using the therapeutic radiation source, the second delivery fluence to the second patient target region. Emitting the first delivery fluence to the first patient target region and emitting the second delivery fluence to the second patient target region may occur concurrently, and/or may occur sequentially.

In some variations, a method for virtual target region localization and radiation delivery may include the steps of acquiring an image of a patient in a treatment position and identifying a patient target region in the acquired image, selecting a localization reference point within the acquired image, wherein the localization reference point corresponds with a planned localization reference point, calculating a fluence for delivery to the patient target region at each firing position of a therapeutic radiation source by calculating a localization function based on the localization reference point, and applying the localization function to a shift-invariant firing filter derived based on the planned localization reference point, and emitting, using the therapeutic radiation source, the delivery fluence to the patient target region.

In some variations, applying the localization function to the shift-invariant firing filter may comprise convolving the localization function with the shift-invariant firing filter. In some variations, the localization function may be one of a delta function, Gaussian function, circular function, and interpolation. In some variations, the Gaussian function may be a truncated Gaussian function. In some variations, the interpolation may be one of a linear, bi-cubic, spline, or Fourier shift. In some variations, the acquired image may comprise one or more of a positron emission tomography (PET) image, X-ray projection image or images, computed tomography (CT) image, and magnetic resonance imaging (MRI) image.

In some variations, the method may further comprise identifying a second patient target region in the acquired image, and selecting a second localization reference point for the second patient target region within the acquired image. The second localization reference point may correspond with a second planned localization reference point. The method may further comprise calculating a second delivery fluence at each firing position of the therapeutic radiation source by calculating a second localization function based on the second localization reference point, and applying the second localization function to a second shift-invariant firing filter based on the second planned localization reference point, and emitting, using the therapeutic radiation source, the second delivery fluence to the second patient target region.

In some variations, the method may further comprise identifying a second patient target region in the acquired image, and selecting a second localization reference point for the second patient target region within the acquired image. The second localization reference point may correspond with a second planned localization reference point. The method may further comprise calculating a second delivery fluence at each firing position of the therapeutic radiation source by calculating a second delta function based on the second localization reference point, and convolving the second delta function with a second shift-invariant firing filter based on the second planned localization reference point, and emitting, using the therapeutic radiation source, the second delivery fluence to the second patient target region. In some variations, emitting the first delivery fluence to the first patient target region and emitting the second delivery fluence to the second patient target region occur concurrently. In some variations, emitting the first delivery fluence to the first patient target region and emitting the second delivery fluence to the second patient target region occur sequentially.

In some variations, the localization function is a first localization function ($\delta$). The first shift-invariant firing filter may comprise a first set of fluence map filters ($p_1, p_2, \ldots p_i$) calculated during treatment planning for each firing position (i) of a therapeutic radiation source. The method may comprise calculating a first set of projections of the localization function ($\delta_i$) to each firing position (i), $\delta_i = \text{proj}_i(\delta)$. Each projection ($\delta_i$) may be a 2-D fluence distribution. Calculating the first fluence for delivery may comprise calculating a first delivery fluence map ($f_i$) for each firing position (i) of the therapeutic radiation source by convolving each projection in the first set of projections of the first localization function ($\delta_i$) with the corresponding fluence map filter ($p_i$), $f_i = p_i * \delta_i$, and delivering the first fluence may comprise moving the therapeutic radiation source to each firing position (i) and emitting radiation according to the first delivery fluence map ($f_i$) to the first patient target region. In some variations, each projection ($\delta_i$) may be a m×n matrix, where m is a number of multi-leaf collimator leaves and n is a number selected during treatment planning. In some variations, n is the number of beam stations selected during the treatment planning. In some variations, the first localization function may be one of a delta function, Gaussian function, circular function, and interpolation. In some variations, the Gaussian function may be a truncated Gaussian function. In some variations, the interpolation may be one of a linear, bi-cubic, spline, and Fourier shift.

In some variations, the second shift-invariant firing filter may comprise a second set of fluence map filters ($p\_2_1, p\_2_2, \ldots, p\_2_i$) calculated during treatment planning for each firing position (i). The method may comprise calculating a second set of projections of the second localization function ($\delta\_2_i$) to each firing position (i), $\delta\_2_i = \text{proj}_i(\delta\_2)$, where each projection ($\delta\_2_i$) is a 2-D fluence distribution. Calculating the second fluence for delivery may comprise calculating a second delivery fluence map ($f\_2_i$) for each firing position (i) by convolving each projection in the second set of projections of the second localization function ($\delta\_2_i$) with the corresponding fluence map filter ($p\_2_i$), $f\_2_i = p\_2_i * \delta\_2_i$. Delivering the second calculated fluence may comprise moving the therapeutic radiation source to each firing position (i) and emitting radiation according to the second delivery fluence map ($f\_2_i$) to the second patient target region. In some variations, each projection ($\delta\_2_i$) may be a m×n matrix. In some variations, m is a number of multi-leaf collimator leaves and n is a number selected during treatment planning. In some variations, n is the number of beam stations selected during the treatment planning. In some variations, the second localization function may be one of a delta function, Gaussian function, circular function, and interpolation. In some variations, the Gaussian function may be a truncated Gaussian function. In some variations, the interpolation may be one of a linear, bi-cubic, spline, and Fourier shift. In some variations, delivering the calculated fluence may comprise segmenting the delivery fluence map ($f_i$, $f\_2_i$) into a plurality of radiation therapy system machine instructions for each firing position.

In some variations, delivering the calculated fluence may comprise segmenting the calculated fluence into a plurality of radiation therapy system machine instructions for each firing position. In some variations, delivering the second calculated fluence may comprise segmenting the second calculated fluence into a plurality of radiation therapy system machine instructions for each firing position.

In some variations, the plurality of radiation therapy system machine instructions may comprise one or more multi-leaf collimator configurations for each firing position. Emitting radiation fluence may further comprise moving leaves of a multi-leaf collimator to the multi-leaf collimator configuration that corresponds to the firing position location of the therapeutic radiation source, and emitting a pulse of radiation.

In some variations, the plurality of radiation therapy system machine instructions may further comprise therapeutic radiation source emission (e.g., pulse) parameters for each firing position. Emitting the pulse of radiation may comprise emitting radiation having the therapeutic radiation source pulse parameters that correspond to the firing position location of the therapeutic radiation source. In some variations, calculating the delivery fluence map ($f_i$, $f\_2_i$) may further comprise convolving each projection in the first or second set of projections with the corresponding shift-invariant fluence map filter, and applying a virtual flattening filter correction factor (FF):

$$(f_i)=FF \cdot (p_i * \delta_i); (f\_2i)=FF \cdot (p\_2_i * \delta\_2_i).$$

In some variations, the virtual flattening filter correction factor (FF) is a m×n matrix and is an inverse of flatness profile of a radiation beam emitted by the therapeutic radiation source.

In some variations, calculating the delivery fluence map ($f_i$, $f\_2_i$) may further comprise convolving each projection in the set of projections with the shift-invariant fluence map filter, applying the virtual flattening filter correction factor (FF), and a distance compensation factor $$\left(\frac{d'_i}{d_i}\right)^2 : (f_i) = \left(\frac{d'_i}{d_i}\right)^2 \cdot FF \cdot (p_i \star \delta_i); (f\_2_i) = \left(\frac{d'_i}{d_i}\right)^2 \cdot FF \cdot (p\_2_i \star \delta\_2_i).$$

In some variations, $d_i$ represents a distance from firing position i to a center of the patient target region defined during treatment planning, and $d_i'$ represents a distance from firing position i to a center of the patient target region determined at radiation delivery.

In some variations, the localization reference point may be a user-selected location within the acquired image. In some variations, the localization reference point may correspond to a treatment plan isocenter defined relative to the patient target region during treatment planning. In some variations, the first patient target region may be in a first treatment area of a patient defined during treatment planning and the second target region may be in a second treatment area of the patient defined during treatment planning. In some variations, the first treatment area has an axial length of about 8 cm or less and comprises a first set of axial planes, and the second treatment area has an axial length of about 8 cm or less and does not overlap with the first treatment area. The second treatment area may comprise a second set of axial planes. In some variations, a center of the first treatment area and a center of the second treatment area may be collinear along an IEC-Y axis and/or co-planar with the IEC-Y axis. In some variations, the first treatment area and the second treatment area may overlap. In some variations, the firing positions of a therapeutic radiation source may comprise locations of the therapeutic radiation source relative to a patient platform location. In some variations, the therapeutic radiation source may be mounted on a gantry rotatable about a longitudinal axis, and the locations of the therapeutic radiation source may be designated by gantry angles about the longitudinal axis. In some variations, the patient platform may be movable to different locations along the longitudinal axis.

In some variations, calculating the delivery fluence map ($f_i$, $f\_2_i$) may further comprise convolving each projection in the set of projections with the shift-invariant fluence map filter p', p_2' with a delta function $\delta_i$, $\delta\_2_i$ that have been circularly convolved with a delta function with an angular shift ($\varphi$, $\varphi\_2$) where the patient target region is located off isocenter at a location $\delta_{LOC}$ and $\delta\_2_{LOC}$, $$\delta_i = proj_i(\delta) * \delta_{i,roll}$$

$$p' = \delta(\varphi_{roll}) \otimes p$$

$$\delta_{i,roll} = proj_i(\delta_{LOC}) \otimes proj_i(ROT(\delta_{LOC}, \varphi_{roll}))^{-1}$$

$$(f_i) = (p_i' * \delta_i)$$

$$\delta\_2_i = proj_i(\delta\_2) * \delta\_2_{i,roll}$$

$$p\_2' = \delta(\Phi\_2_{roll}) \otimes p\_2$$

$$\delta\_2_{i,roll} = proj_i(\delta\_2_{LOC}) \otimes proj_i(ROT(\delta\_2_{LOC}, \varphi\_2_{roll}))^{-1}$$

$$(f\_2_i) = (p\_2_i' * \delta\_2_i)$$

A method for delivering radiation to multiple patient target regions may comprise acquiring a localization image at the beginning of a treatment session, identifying a first target region and a second target region in the localization image, shifting a first fluence map sub-region of a treatment plan fluence map such that a non-zero high-fluence region of the first fluence map sub-region is co-localized with the first target region in the localization image, shifting a second fluence map sub-region of the treatment plan fluence map such that a non-zero high-fluence region of the second fluence map sub-region is co-localized with the second target region in the localization image, delivering the shifted first fluence map sub-region to the first target region, and delivering the shifted second fluence map sub-region to the second target region.

The treatment plan fluence map may be partitioned into the first and second fluence map sub-regions by defining boundaries of each sub-region along non-zero low-dose regions of the treatment plan fluence map. Delivering the first and second shifted fluence map sub-regions may comprise segmenting the shifted first and second fluence map sub-regions into a plurality of radiation therapy system machine instructions for each firing position of a therapeutic radiation source. Radiation therapy system machine instructions may comprise one or more multi-leaf collimator configurations and therapeutic radiation source control parameters for each firing position. Methods may optionally comprise acquiring imaging data during the treatment session and modifying the shifted first fluence map sub-region according to the acquired imaging data before delivering fluence to the first target region. Alternatively or additionally, methods may comprise acquiring imaging data during the treatment session and modifying the shifted second fluence map sub-region according to the acquired imaging data before delivering fluence to the second target region.

Delivering the shifted first fluence map sub-region and delivering the shifted second fluence map sub-region may occur simultaneously and/or may occur sequentially. In some variations, delivering the shifted first fluence map sub-region and delivering the shifted second fluence map sub-region may occur sequentially. The localization image may comprise a CT image and/or a PET image and/or an MRI image. Methods may optionally comprise comparing the high-fluence region of the first fluence map sub-region with a location of the first target region to define a first localization correction, comparing the high-fluence region of the second fluence map sub-region with a location of the second target region to define a second localization correction, and adjusting a patient platform according to the first localization correction before delivering fluence to the first target region. After delivering fluence to the first target region, methods may comprise adjusting the patient platform according to the second localization correction before delivering the fluence to the second target region.

In some variations, delivering the shifted first fluence map sub-region to the first target region may comprise selecting a localization reference point that represents a location within the localization image, applying a localization function calculated from the localization reference point to a first shift-invariant firing filter calculated during treatment planning for the first target region to update the first fluence map sub-region, segmenting the updated first fluence map sub-region into a plurality of radiation therapy system instructions, and emitting radiation fluence to the first target region according to the first plurality of radiation therapy system instructions.

Applying the localization function may comprise convolving a first localization function (e.g., a first delta function or a first gaussian function such as a truncated gaussian function) calculated from the localization reference point with the first shift-invariant firing filter. Delivering the shifted second fluence map sub-region to the second target region may comprise acquiring imaging data of the second target region, convolving the imaging data with a second shift-invariant firing filter calculated during treatment planning for the second target region to update the second fluence map sub-region, segmenting the updated second fluence map sub-region into a second plurality of radiation therapy system instructions, and emitting radiation fluence to the second target region according to the second plurality of radiation therapy system instructions.

In some variations, the acquired imaging data may be PET imaging data. Delivering the shifted second fluence map sub-region to the second target region may comprise selecting a second localization reference point that is located within the second target region, calculating the second fluence map sub-region by applying a second localization function calculated from the second localization reference point to a second shift-invariant firing filter, segmenting the calculated second fluence map sub-region into a second plurality of radiation therapy system instructions, and emitting radiation fluence to the first target region according to the second plurality of radiation therapy system instructions. Alternatively or additionally, delivering the shifted second fluence map sub-region to the second target region may comprise selecting a second localization reference point that is located within the second target region, calculating the second fluence map sub-region by convolving a second localization function (e.g., a first delta function or a first gaussian function such as a truncated gaussian function) calculated from the second localization reference point with a second shift-invariant firing filter, segmenting the calculated second fluence map sub-region into a second plurality of radiation therapy system instructions, and emitting radiation fluence to the second target region according to the second plurality of radiation therapy system instructions. In some variations, the method may comprise adjusting a deliverable radiation dose to meet one or more dose constraints. In some variations, the one or more dose constraints may comprise one or more cost functions. In some variations, one or more cost functions may comprise a cumulative cost function with a weighting factor for each cost function given by:

$$C=\Sigma w_i C_i(x)+\Sigma w_k C_k(Ax)+\Sigma w_m C_m(Ax_{cumulative})+\Sigma w_n C_n(x_{cumulative})$$

Where x is a fluence to the patient target region, A is a dose calculation matrix for the patient target region, $Ax_{cumulative}$ is a cumulative planned dose and $x_{cumulative}$ is a cumulative planned fluence.

A method of treatment planning for radiation delivery to multiple patient target regions may comprise identifying a first location of a first patient target region and a second location of a second patient target region in a patient planning image, defining a first region of interest (ROI) (which may be a first firing zone) having a boundary that surrounds the first patient target region, defining a second ROI (which may be a second firing zone) having a boundary that surrounds the second patient target region, and calculating a treatment planning fluence map for the first patient target region and the second patient target region that designates the fluence to be delivered if the selected imaging data indicates that first patient target region is within the boundaries of the first region of interest and the second patient target region is within the boundaries of the second region of interest. The boundary of the second region of interest may be selected to surround the second patient target region for a predetermined range of location shifts of the first and second patient target regions, and the first and second region of interests may represent spatial filters configured to select imaging data acquired during a treatment session. The first patient target region may be in closer proximity to a planning structure. The first region of interest may be smaller than the second region of interest. In some variations, the planning structure may be an organ-at-risk (OAR). The first patient target region may be in closer proximity to two or more planning structures than the second patient target region. Some methods may further comprise designating a treatment planning reference point within the first region of interest as a localization reference point to position a patient at the start of the treatment session. The selected imaging data may be used to guide radiation delivery during the treatment session. The treatment planning reference point may be a center point in the first region of interest, and may, in some example, be a center point in the first patient target region. The imaging data may comprise positron annihilation emission path data (e.g., PET data), CT imaging data, and/or MRI imaging data. A positron annihilation emission path may be selected if it intersects at least one of the first and second region of interests. The second region of interest may be sized to include a range of locations of the second patient target region.

In some variations, a method for patient localization and radiation delivery may comprise acquiring an image that includes a first patient target region and a second patient target region, and aligning the first patient target region within a first region of interest defined during treatment planning. If the second patient target region is located within a second region of interest defined during treatment planning, the method may comprise acquiring positron annihilation emission data comprising a plurality of lines-of-response (LORs) using an array of positron emission detectors. If a LOR intersects either the first region of interest and the second region of interest, the method may comprise calculating a delivery fluence by convolving the LOR with a shift-invariant firing filter defined during treatment planning for the corresponding region of interest. Methods may further comprise emitting the delivery fluence using a therapeutic radiation source, where emitting the delivery fluence comprises segmenting the delivery fluence into a plurality of radiation therapy system machine instructions for each firing position of the therapeutic radiation source. Radiation therapy system machine instructions may comprise one or more multi-leaf collimator configurations and therapeutic radiation source emission (e.g., pulse) parameters for each firing position. In some variations, the image may comprise one or more of a positron emission tomography (PET) image, computed tomography (CT) image, and magnetic resonance imaging (MRI) image.

A method for positioning and registering a patient for a radiation therapy treatment session may comprise positioning a patient on a radiotherapy system platform such that a first patient target region is aligned with a location of the therapeutic radiation source and located within a first predetermined region of interest, and determining whether a location of a second patient target region is within a second predetermined region of interest. If the location of the second patient target region is within the second predetermined region of interest, the method may comprise proceeding with radiation delivery to the first patient target region. If the location of the second patient target region is not within the second predetermined region of interest, the method may comprise generating a visual and/or audio notification. The first and second predetermined region of interests may be calculated during treatment planning, and a position of the second predetermined radiation region of interest is defined relative to a position of the first predetermined region of interest.

Optionally, some methods may comprise acquiring imaging data before radiation delivery to the second patient target region, where the first and second region of interests are spatial masks that are configured to suppress imaging data with spatial characteristics that do not co-localize with either the first or second radiation region of interests. In some variations, methods may comprise determining based on the acquired imaging data whether the second target region is located within the second region of interest, and if the second target region is located within the second region of interest, proceeding with radiation delivery to the second target region. The acquired imaging data may be positron annihilation emission path data (e.g., PET imaging data), CT imaging data, and/or MRI imaging data. Delivering radiation may comprise segmenting the delivery fluence into a plurality of radiation therapy system machine instructions for each firing position of the therapeutic radiation source. Radiation therapy system machine instructions may comprise one or more multi-leaf collimator configurations and therapeutic radiation source emission (e.g., pulse) parameters for each firing position.

In some variations, the method may further comprise adjusting the patient's position when the location of the second patient target region is not within the second predetermined region of interest. In some variations, the method may further comprise adjusting the radiotherapy system platform to move the location of the second patient target region to be within the second predetermined region of interest. In some variations, the method may further comprise shifting a planned fluence for the second patient target region according to the location of a second patient target region. In some variations, the method may further comprise delivering radiation comprises segmenting the delivery fluence into a plurality of radiation therapy system machine instructions for each firing position of the therapeutic radiation source. In some variations, the method may further comprise radiation therapy system machine instructions comprise one or more multi-leaf collimator configurations and therapeutic radiation source pulse parameters for each firing position.

A method for radiation therapy may comprise acquiring an image that includes a first patient target region and a second patient target region, partitioning a planned fluence map into a first fluence sub-map that delivers a first prescribed dose to the first patient target region, and a second fluence sub-map that delivers a second prescribed dose to the second patient target region, shifting the first fluence sub-map to align with the first patient target region of the acquired image, shifting the second fluence sub-map to align with the second patient target region of the acquired image, calculating a delivery fluence map by combining the shifted first fluence sub-map and the shifted second fluence sub-map, and delivering radiation to the first patient target region if a high-fluence region of the shifted first sub-fluence map and a high-fluence region of the shifted second fluence sub-map do not co-localize with each other in the delivery fluence map. In some variations, the planned fluence map may be generated by identifying the first and second patient target regions in a treatment planning image, calculating a first fluence map to deliver the first prescribed dose to the first patient target region, calculating a second fluence map to deliver the second prescribed dose to the second patient target region, and calculating the planned fluence map by combining the first and second fluence maps and adjusting the combined fluence map such that high-fluence regions of the first and second fluence maps do not co-localize with each other, and the first and second patient target regions each receive the corresponding first and second prescribed doses. In some variations, the first fluence sub-map may include the first fluence map and the second fluence sub-map may include the second fluence map. In some variations, calculating the planned fluence map may comprise adjusting the combined fluence map based on one or more tuning constraints such that the first and second fluence maps do not exceed a predetermined dose limit. In some variations, the method may comprise identifying an organ-at-risk in the treatment planning image. Calculating the planned fluence map may further comprise adjusting the combined fluence map such that fluence to the organ-at-risk does not exceed a predetermined dose limit. In some variations, delivering radiation may comprise segmenting the delivery fluence into a plurality of radiation therapy system machine instructions for each firing position of the therapeutic radiation source. In some variations, radiation therapy system machine instructions may comprise one or more multi-leaf collimator configurations and therapeutic radiation source emission parameters for each firing position. In some variations, the method may comprise determining whether the delivery fluence map includes a fluence level to an organ-at-risk that exceeds a predetermined dose limit, and delivering radiation to the first patient target region if the fluence to the organ-at-risk does not exceed the predetermined dose limit. In some variations, the planned fluence map may be generated by identifying the first and second patient target regions in a treatment planning image, calculating a first fluence map to deliver the first prescribed dose to the first patient target region, calculating a second fluence map to deliver the second prescribed dose to the second patient target region, and calculating the planned fluence map by combining the first and second fluence maps and iteratively adjusting the combined fluence map to meet a joint set of constraints while maintaining the first and second fluence maps as separate fluence maps. In some variations, the acquired image may comprise one or more of a positron emission tomography (PET) image, computed tomography (CT) image, and magnetic resonance imaging (MRI) image.

The planned fluence map may be generated by identifying the first and second patient target regions in a treatment planning image, calculating a first fluence map to deliver the first prescribed dose to the first patient target region, calculating a second fluence map to deliver the second prescribed dose to the second patient target region, and calculating the planned fluence map by combining the first and second fluence maps and adjusting the combined fluence map such that high-fluence regions of the first and second fluence maps do not co-localize with each other, and the first and second patient target regions each receive the corresponding first and second prescribed doses. The first fluence sub-map may include the first fluence map and the second fluence sub-map may include the second fluence map. The planned fluence map may be re-optimized using, for example, a joint set of constraints while keeping the first sub-fluence map and the second fluence sub-map as separate fluence maps. Methods may further comprise identifying an organ-at-risk in the treatment planning image, and calculating the planned fluence map may further comprise adjusting the combined fluence map such that fluence to the organ-at-risk does not exceed a predetermined dose limit. Delivering radiation may comprise segmenting the delivery fluence into a plurality of radiation therapy system machine instructions for each firing position of the therapeutic radiation source. Radiation therapy system machine instructions may comprise one or more multi-leaf collimator configurations and therapeutic radiation source emission parameters for each firing position. Optionally, methods may comprise determining whether the delivery fluence map includes a fluence level to an organ-at-risk that exceed a predetermined dose limit, and delivering radiation to the first patient target region if the fluence to the organ-at-risk does not exceed the predetermined dose limit.

In some variations, separate treatment plans may be generated for each patient target region. Each of these plans may be individually optimized, summed, and then re-optimized based on a joint set of constraints while maintaining the treatment plans as separate entities. Separate fluence maps may be generated based on each treatment plan and summed as a combined fluence map. During a treatment session, each separate fluence map may be moved independently, and their summed dose volume histogram (DVH) may be confirmed prior to dose delivery.

Additionally or alternatively, one or more tuning constraints (e.g., artificial constraints in addition to tissue constraints, such as tuning structures) may be applied in addition to a predetermined set of constraints to ensure that a dose does not exceed a predetermined threshold in a given zone (e.g., region). For example, one or more predetermined dose-constrained zones may be added during treatment planning to maintained a zone as a "low dose valley" that may be useful for reducing the likelihood of dose "hot spots" that may arise when fluence maps of each patient target region are independently shifted during a treatment session. In some variations, one or more tuning constraints may help promote the decoupling of radiation delivery between two or more targets. Some variations of tuning constraints may limit dose delivery angles.

Disclosed herein are also methods for generating a visualization graphic representation of radiation dose. One variation of a method for generating a visualization graphic may comprise generating a treatment plan for irradiating one or more patient target regions, where the treatment plan comprises at least one or more a treatment plan fluence map, one or more planning images for each patient target region, and a corresponding nominal dose image, calculating, for each patient target region, a plurality of uncertainty data inputs that represent treatment session uncertainties, calculating, for each uncertainty data input, an expected dose to be delivered to each patient target region in the presence of the uncertainty data input, to derive a plurality of dose images, combining the plurality of dose images into a visualization graphic comprising a composite volume with each dose image representing a frame in the composite volume, and displaying the visualization graphic to a display device.

In some variations, the treatment plan may further comprise one or more shift-invariant firing filters. The plurality of data inputs may comprise one or more scalar values, vector values, and/or volumetric values. In some variations, the composite volume may be a 4-D volume. The plurality of dose images may comprise 2-D dose image slices of each of the one or more patient target regions. The composite volume may comprise 3-D dose volumes of each of the patient target regions, and each 3-D dose volume may comprise 2-D dose image slices of each of the patient target regions. In some variations, the method may comprise iterating through the dose values at each point in each dose image, comparing the dose values to a first matching point in a minimum dose volume and a second matching point in a maximum dose volume to update the first and second matching points, iterating through each point in the minimum dose volume, calculating a difference between the values of the minimum dose volume and nominal dose volume, storing the difference and a frequency of the difference in two frames of a delta dose volume, iterating through each point in the maximum dose volume, calculating a difference between the values of the maximum dose volume and nominal dose volume, storing the difference and a frequency of the difference in another two frames of the delta dose volume, and rendering a surface map for each four-frame slice of the delta dose volume with the frequency of maximum values extruding along a +Z from a 3-D plane, a frequency of minimum values extruding along a −Z from the 3-D plane, and the value at a point in the surface map being represented by a color.

One variation of a method for generating a visualization graphic may comprise generating a treatment plan for irradiating one or more patient target regions, where the treatment plan may comprise at least one or more of a treatment plan fluence map, one or more planning images for each patient target region, and a corresponding nominal dose image, calculating, for each patient target region, a plurality of uncertainty data inputs that represent treatment session uncertainties, calculating, for each uncertainty data input, an expected dose to be delivered to each patient target region in the presence of the uncertainty data input, to derive a plurality of dose images, combining the plurality of dose images into a visualization graphic comprising a composite volume with each dose image representing a frame in the composite volume, and displaying the visualization graphic to a display device. In some variations, the treatment plan may further comprise one or more shift-invariant firing filters. The plurality of data inputs may comprise one or more scalar values, vector values, and/or volumetric values. The composite volume may be a 4-D volume. The plurality of dose images may comprise 2-D dose image slices of each of the one or more patient target regions. The composite volume may comprise 3-D dose volumes of each of the patient target regions, and each 3-D dose volume may comprise 2-D dose image slices of each of the patient target regions. Optionally, methods may comprise iterating through the dose values at each point in each dose image, comparing the dose values to a first matching point in a minimum dose volume and a second matching point in a maximum dose volume to update the first and second matching points, iterating through each point in the minimum dose volume, calculating a difference between the values of the minimum dose volume and nominal dose volume, storing the difference and a frequency of the difference in two frames of a delta dose volume, iterating through each point in the maximum dose volume, calculating a difference between the values of the maximum dose volume and nominal dose volume, storing the difference and a frequency of the difference in another two frames of the delta dose volume, and rendering a surface map for each four-frame slice of the delta dose volume with the frequency of maximum values extruding along a +Z axis from a 3-D plane, a frequency of minimum values extruding along a −Z axis from the 3-D plane, and the value at a point in the surface map being represented by a color.

Described herein are visualization graphic representations of radiation dose. One variation of visual graphic representation may comprise a 3-D volume representing a patient's anatomy, where the 3-D volume comprises a stack of 2-D patient anatomy images, and a 3-D dose surface map corresponding to a dose distribution for each 2-D patient anatomy image. A height of the 3-D dose surface map may represent a dose level according to a treatment plan for the patient and a color value across the surface map may represent a probability value of the dose level at a treatment session.

In some variations, a graphical user interface for multi-target treatment planning may comprise a first graphical representation of multiple treatment areas that each contain one or more patient target regions. Each treatment area may span a different region of a patient and represent a different patient localization, and a second graphical representation of dosimetric characteristics for each treatment area. The first and second graphical representations may be configured to be simultaneously output to a display device.

In some variations, the dosimetric characteristics of all the multiple treatment areas may be visualized simultaneously on the display device. In some variations, the dosimetric characteristics of each treatment area may be visualized individually. In some variations, dosimetric characteristics of each treatment area may comprise one or more of dosimetric objectives, dose-volume histograms, dose statistics, and objective performance. In some variations, a third graphical representation may comprise a view of all patient target regions across the multiple treatment areas and visual indicia that represents relative spatial relationships between one or more of the patient target regions. In some variations, the graphical user interface may further comprise a third graphical representation that comprises a view of multiple organs-at-risk (OARs) across the multiple treatment areas, and visual indicia that represents each OAR's relative spatial relationship to one or more treatment areas. In some variations, the graphical user interface may further comprise a third graphical representation that comprises a view of all patient target regions across the multiple treatment areas and a first visual indicia that represents relative spatial relationships between one or more of the patient target regions, and a fourth graphical representation that comprises a view of multiple organs-at-risk (OARs) across the multiple treatment areas, and a second visual indicia that represents each OAR's relative spatial relationship to one or more treatment areas. In some variations, the graphical user interface may comprise a 3-D visualization representing the patient's anatomy. In some variations, the first graphical representation may be layered onto the anatomical 3-D visualization. In some variations, the first graphical representation may comprise a band for each of the multiple treatment areas. Each band may have an extent that represents a dimension of its corresponding treatment area. In some variations, the graphical user interface may comprise a first viewing mode that depicts a subset of the multiple treatment areas and a second viewing mode that depicts all the multiple treatment areas. In some variations, the subset of the multiple treatment areas may comprise user-selected treatment areas.

BRIEF DESCRIPTION OF THE DRAWINGS

The present application can be understood by reference to the following description taking in conjunction with the accompanying figures.

FIG. 2 is a flow chart representation of one variation of a method for treatment planning for mosaic multi-target localization.

FIGS. 3A-3B depict a flow chart representation of one variation of a method for treatment planning for de-coupled multi-target localization.

FIG. 8B is a flow chart representation of one variation of a method for mosaic multi-target localization.

FIGS. 13A-13F illustrate one variation of a procedure by which the position of a patient may be adjusted.

FIG. 15B depicts one variation of visualization graphics that represent 3-D dose distribution(s) (nominal, minimum, maximum dose levels).

FIG. 26 depicts fluence shifts of a truncated Gaussian function over MLC leaf indices for a set of firing angles.

FIG. 33 is a schematic diagram that depicts virtual localization with roll correction.

FIG. 34 is a schematic diagram that depicts virtual localization with roll correction for BgRT.

FIGS. 35A-35C are diagrams that depict three different patient treatment plan variations.

FIGS. 36A-36B are diagrams that depict examples of treatment plans.

FIG. 38A-38E depict graphical user interfaces for multi-target treatment area definitions.

DETAILED DESCRIPTION

Figure 1A:
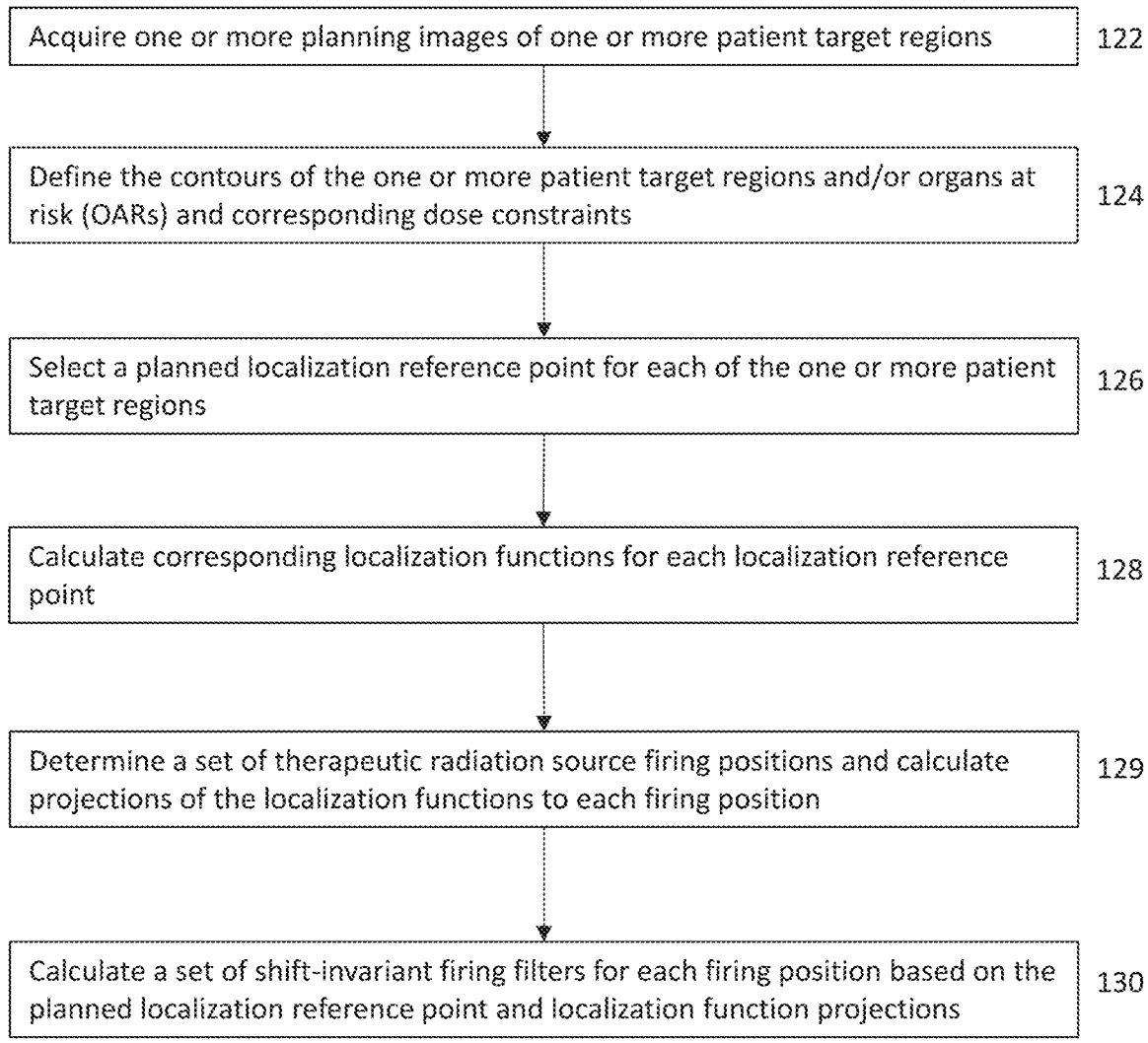
FIG. 1A is a flow chart representation of one variation of a method for treatment planning for virtual localization for SBRT.

Disclosed herein are methods for treatment planning, patient setup, localization and radiation delivery for the irradiation of multiple patient target regions in a single treatment session or fraction. Treatment planning methods may comprise selecting a planned localization reference point for each target region, and calculating shift-invariant firing filters for each target region based on the selected planned localization reference point. For the irradiation of multiple target regions, a treatment planning system that performs the methods described herein may generate a set of shift-invariant firing filters associated with a planned localization reference point for each patient target region. Optionally, a treatment planning system may generate a planned fluence map that represents the radiation fluence across the one or more patient target regions, one or more OARs, and/or healthy tissue. In some variations, the treatment planning system does not generate a set of radiotherapy machine instructions for execution by the radiotherapy system after patient setup and patient target region localization, and instead, the segmentation of a delivery fluence map may occur in "real-time", e.g., during the treatment session, within about 2 hours, within about 1 hour, within about 30 minutes, within about 10 minutes, within about 5 minutes, within about 1 minute, within about 30 seconds, within about 1 second, within about 0.5 second or less, etc. of calculating the delivery fluence map. By deferring machine instruction segmentation until the treatment session, the planned fluence map may be updated with the most up-to-date location data of the patient target regions (e.g., calculate the delivery fluence map) before calculating the machine instructions. Shifting a fluence map (e.g., linear shifts, rigid shifts) may be readily calculated, whereas "shifting" machine instructions may result in non-linear effects that affect the delivered dose. Furthermore, deferring machine instruction segmentation at least until after patient target region localization allows for "virtual localization," where the fluence maps generated by the treatment planning system are adjusted based on up-to-date location data. In some variations, virtual localization may comprise updating the planned fluence map by convolving the shift-invariant firing filters with a localization function derived from the up-to-date location data (e.g., the current location of the planned localization reference point). By updating the localization reference point during a treatment session and calculating a delivery fluence map based on a delta function (for example) centered over the localization reference point and a set of shift-invariant firing filters for that target region, the planned fluence map can "follow" a patient target region instead of physically adjusting the patient position (e.g., using the patient platform) to match a planned fluence map. Segmenting a fluence map that best reflects the actual location of a patient target region may facilitate radiation delivery with better accuracy than delivering radiation based on a fluence map that has not been updated to reflect the actual location of the patient target region. Virtual localization methods, in combination with BgRT methods (where the delivery fluence is further updated with in-session acquired imaging data, such as positron annihilation emission path data) may help to improve the accuracy of dose delivery to multiple patient target regions. With the virtual localization methods described herein, the patient may be physically setup and localized once (e.g., for one patient target region) but radiation may be applied to multiple patient target regions that are virtually localized.

Radiation delivery to multiple patient target regions and/or irregularly-shaped target regions poses challenges to localization/registration and radiation delivery. For example, multiple tumors may have changed in different ways (e.g., location, shape, and/or size) between the time the treatment planning image was acquired and when the patient has arrived for treatment. Some tumors may grow while others may shrink; some tumors may shift to the right while others shift to the left, etc. Tumor location relative to healthy tissue or bony landmarks may change if a patient has lost or gained weight (e.g., due to swelling). In addition, when treating multiple target regions in a single treatment session or fraction, target regions treated at a later portion of the treatment session may have moved from their location at an earlier portion (e.g., the beginning, during patient set up and localization) of the treatment session. The motion may be periodic (e.g. due to respiration) or static (e.g. during the serial treatment of multiple target regions, the localization of the last target to be treated is less likely to be valid, since the patient may have shifted position at some point during the delivery). Addressing changes in the patient and/or target regions between planning and treatment, as well as changes that may occur during a treatment session has an additional layer of complexity because of the highly-coupled nature of dose delivery to the patient. Radiation applied to one target region may create scattered dose for other target regions, and in some cases, a radiation beam may intersect two target regions (or a target region and an OAR) and will deliver dose directly to both regions. If these target regions move with respect to one another, the treatment plan fluence map may no longer deliver the prescribed dose. Thus, aligning the entirety of a target region or a collection of target regions associated with one or more tumors with a radiation therapy system for an intended (i.e., future) radiation treatment session, such as when a care provider is attempting to localize a single target or multiple targets at the start of a treatment session, can be challenging and may result in inaccurate dose delivery.

The treatment planning, localization and radiation delivery methods described herein may help to mitigate some of the dose delivery uncertainties associated with the treatment of multiple patient target regions in a single treatment session. One variation of a method for radiation delivery to multiple patient target regions may comprise localizing (e.g., virtually localizing and/or physically localizing) each patient target region individually (e.g., independently from the other patient target regions) to derive a delivery fluence map for each patient target region, and then delivering radiation to each patient target region according its corresponding delivery fluence map. Localizing each patient target region may comprise partitioning a planned fluence map along low-fluence areas into fluence map sub-regions for each target region (either by the treatment planning system during treatment planning or by the radiotherapy system at the start of a treatment session), and deriving a delivery fluence map by shifting the fluence map sub-regions, for example, by using virtual localization methods that shift the planned fluence map. Alternatively or additionally, methods for radiation delivery to multiple patient target regions may comprise generating a planned fluence map for each patient target region individually, localizing each patient target region individually (e.g., independently from the other patient target regions) to derive a delivery fluence map for each patient target region, combining the individual delivery fluence map and confirming that the cumulative fluence map meets the prescribed dose objectives are met, and if the dose objectives are met (i.e., prescribed minimum does to target regions, maximum does to OARs not exceeded, etc.), delivering radiation to each patient target region according to its individual corresponding delivery fluence map. BgRT methods for radiation delivery to multiple patient target regions may comprise designating one of the multiple patient target regions as a registration target region, defining a region of interest (ROI) (e.g., biological firing zones (BFZ)) around the other patient target regions that are large enough to encompass a range of location shifts of those patient target regions, localizing the registration target region, and delivering radiation to each patient target region according to imaging data that spatially co-localizes with the ROI of each patient target region. The ROI around the registration target region may be smaller than the ROIs around the other patient target regions.

Optionally, at one or more stages during treatment planning and/or radiation delivery, the system controller of the treatment planning system and/or radiotherapy system may generate and display one or more visualization graphics that indicate the deposition of dose over patient anatomical structures. Additional changes to radiation delivery may be included in response to the visualization graphic(s), as may be desirable by the clinician or technician. Providing visualization graphics that depict the distribution of dose over patient anatomical structures, especially as part of or after localization/registration procedures, may help the clinician or technician evaluate the interaction of the fluences calculated for each patient target region and determine whether these cumulative levels of fluence are acceptable. For example, if the scattered dose from one target region into another target region is relatively low, or is spatially uniform, it may be possible to ignore the impact of spatial changes between the planned fluence map and the delivery fluence map. Visualization graphics may help a clinician or technician to identify hot spots, and/or cold spots, and/or dose-coupling effects (e.g., when a radiation beam intersects two or more target regions and/or OARs) that may result from the delivery of radiation to multiple target regions. Identifying these unwanted dose interactions before radiation delivery and providing spatial information about the dose distribution as feedback to the treatment planning and optimization process may help further refine the planned fluence maps and/or firing filters.

Alternatively or additionally, patient setup and target region localization/registration methods may comprise acquiring images of one or more tumors during an image-guided localization procedure, which reflect current information regarding tumor location, size, and shape prior to applying radiation. The user may compare the acquired images to treatment planning images acquired and/or prepared in advance of the procedure. The user and/or the radiation therapy system may then make adjustments to the radiation treatment session (i.e., perform setup corrections to the positioning and orientation of the patient) based on the acquired images such that the applied radiation may more effectively target the current shape, size, and location of the one or more tumors. For example, the user may define one or more treatment areas (also referred to herein as "zones" and/or "treatment fields") in an image of one or more tumors for image-guided localization. An image match or position correction may then be defined for each treatment area or region of interest. A radiation therapy system may automate the application of each position correction as the radiation therapy system progresses with irradiation of a target region (e.g., a tumor or a portion of a tumor) or multiple target regions. The radiation therapy system may provide instructions to a user indicating position correction or adjustment instructions corresponding to position correction actions to be performed by the user (e.g., move a patient's arm or leg, or tilt and/or rotate a surface on which the patient is disposed). After the position corrections are made, the radiation therapy system may apply radiation to the real-time or updated location of a tumor or a portion of a tumor in each region of interest. Further, the tumor or tumor portions may be more accurately targeted in each region of interest by using the most effective positioning of the patient relative to the therapeutic radiation source for each region of interest, rather than keeping the patient in a position that allows for higher-quality conformal dose delivery for some tumor regions at the expense of lower-quality conformal dose delivery for other tumor regions. This may have the benefit of providing better treatment outcomes and overall conformality to treatment plans. Additionally, the time duration of radiation treatment sessions may be reduced because multiple targets may be treated during a single radiation treatment session. The reduced time may allow a care facility to treat more patients in a day. Further, the reduced time duration needed for the treatment of multiple tumors or multiple tumor portions also improves the patient experience.

A method for setting up a patient for radiation therapy may comprise acquiring an image of a first patient target region and a second patient target region. A first set of patient position-shift vectors may be calculated based on the acquired image and a treatment planning image of the first patient target region. A second set of patient position-shift vectors may be calculated based on the acquired image, a treatment planning image of the second patient target region, and the first set of patient position-shift vectors. The patient may be positioned according to the first set of patient position-shift vectors to a first location. The patient may be moved to a second location and positioned according to the second set of patient position-shift vectors.

It should be noted that the methods for patient setup, patient target region localization/registration, and radiation delivery for the irradiation of multiple patient target regions in a single treatment session described herein may be used, alone or in combination, in intensity-modulated radiation therapy (IMRT), and/or stereotactic body radiation therapy (SBRT), and/or BgRT. For example, a clinician may determine that all of the patient target regions are to be treated using IMRT/SBRT, or all of the patient target regions are to be treated using BgRT, or that some of the patient target regions are to be treated using SBRT/IMRT and others are to be treated using BgRT. Some treatment planning systems and/or radiotherapy systems may have two modes of operation, where a first mode is SBRT/IMRT planning and radiation delivery and a second mode is BgRT planning and radiation delivery. A single treatment session may comprise radiation delivery using SBRT/IMRT methods for some patient target regions and radiation delivery using BgRT methods for other patient target regions, as may be desirable.

Overview of Methods
Virtual Localization

Virtual localization of a patient target region comprises modifying (e.g. shifting) a planned fluence map for a particular patient target region to reflect the current/real-time location of that patient target region. A planned fluence map comprises a set of radiation beamlets and beamlet intensities to be applied to a patient as calculated by a treatment planning system based on one or more planning images. Conceptually, this may be thought of as adjusting the fluence map as if the localization image was the planning image. In contrast to physical patient setup where the position of the patient is physically adjusted by the patient platform such that the patient target region location at the time of treatment matches the location of the patient target region during treatment planning, virtual localization may require little if any patient platform adjustments. Physical patient setup typically comprises acquiring a localization image (e.g., a localization CT image, MRI image), comparing the localization image with the planning image to calculate an offset that represents a change in patient target region location, and enacting a patient platform adjustment and/or otherwise moving the patient based on the calculated offset so that the current location of the patient target region is aligned with its location in the planning image. In virtual localization, instead of adjusting the patient platform, the planned fluence map is adjusted (e.g., shifted or rolled) by the calculated offset, i.e. conceptually akin to moving the planning image to align with the localization image. Other fluence modifications may also be included to help ensure that the resulting dose distribution received by the patient shifts to the proper location in the localization image, without significant distortion, due to, for example, the fan-beam nature of the radiation beam and increased radiation fluence closer to radiation source.

Virtual localization methods aim to shift the dose received by the patient by modifying the fluence map delivered by the therapeutic radiation source of a radiotherapy system, after localization and prior to or during patient treatment. This is done by calculating, during treatment planning, a shift-invariant representation of the treatment plan (e.g., a shift-invariant firing filter) and choosing an appropriate localization reference point. The shift-invariant treatment plan (e.g., the shift-invariant firing filter) may be applied to an actual reference point location derived from the localization image to shift the dose received by the patient (and derive the delivery fluence map which may direct radiation to the current location of the patient target region). One example of a shift-invariant treatment plan representation may comprise a set of firing filters $p_i$ for every firing position i, for each patient target region where each firing filter is a 2D fluence map image in the radiation source beams-eye-view coordinate frame (i.e., for a case with three patient target regions and one hundred firing positions, a treatment plan would calculate three sets of firing filters, with each set designating 100 firing filters, one for each firing position). The firing filters $p_i$ may be calculated based on a planned localization reference point that is associated with the patient target region and may be, in some variations, selected by the user. Firing filters $p_i$ may be calculated by solving for the set of filters that when convolved with the 2-D projection of a discrete 3-D delta function δ centered over the planned localization reference point in the patient coordinate frame to the 2-D beams-eye-view at each firing position, results in the fluence $f_i$ for each firing position i.

$$f_i = p_i * \delta_i$$

where $$\delta_i = proj_i(\delta)$$

The projection $\delta_i$ may be a 2-D discrete delta function (i.e. an all zero image, except for a single pixel which value is 1), and hence the operation $p_i * \delta_i$ may be a 2-D shift of firing filter $p_i$, which can be thought of as a location-independent fluence map. The fluence $f_i$ may be determined based on the dose constraints and objectives, specified by a clinician for each patient target region, using standard radiotherapy dose optimization techniques, that for example, minimize a cost function on patient dose, using gradient descent methods. Any such $f_i$ can be decomposed into a convolution $p_i * \delta_i$ by selecting the desired plan localization reference point (e.g., a point in the center of a target region, a point in a treatment area that includes the target region), creating a Si that represents a shift to that reference point, and applying an inverse shift to $f_i$ to obtain $p_i = f_i * \delta_i^{-1}$. The planned localization reference point may be located in the tumor of the patient target region (e.g., a center-of-mass or central portion of a tumor) or may be in an anatomical structure located outside of the tumor (e.g., a nearby bony structure).

Figure 22A:
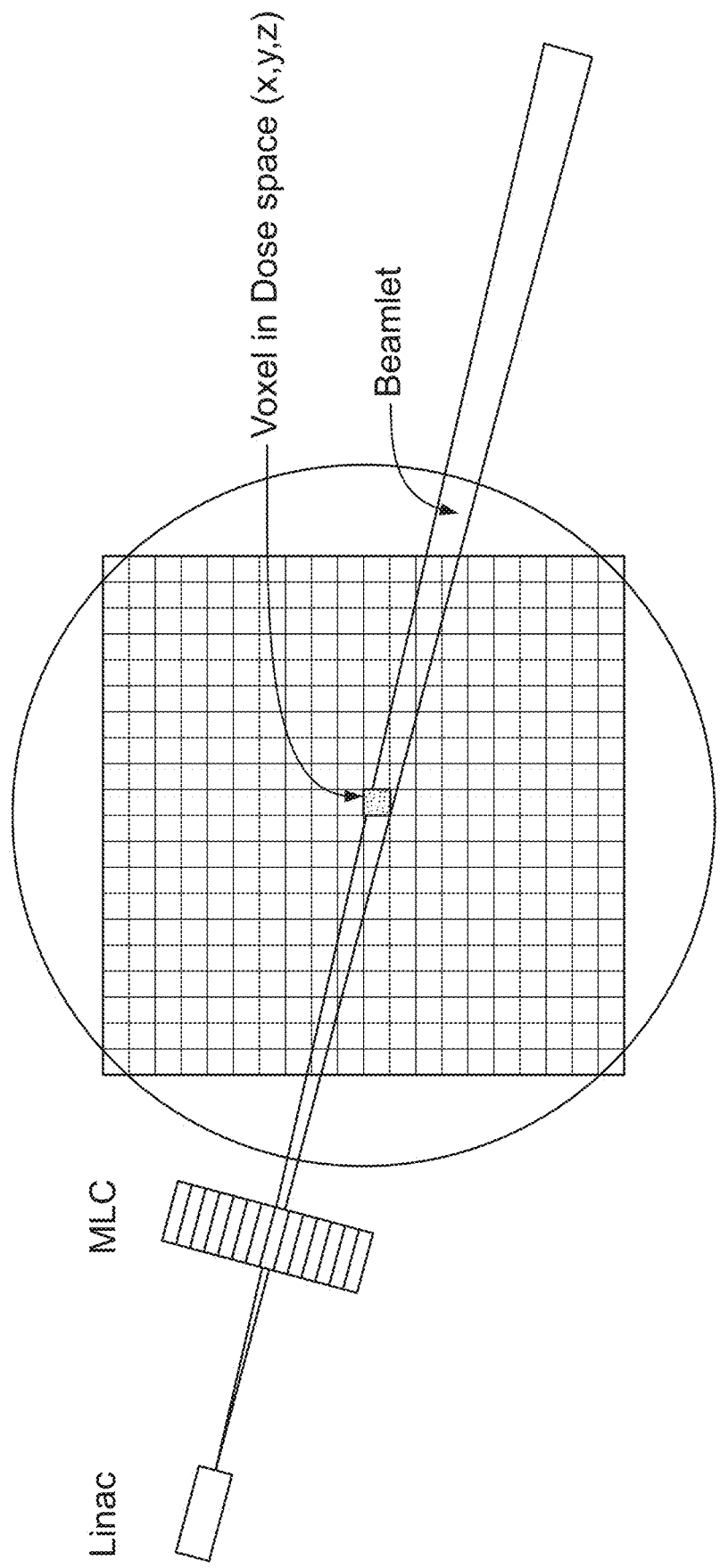
FIG. 22A is a schematic representation of a delta function based on a voxel in space.

A delta function $\delta$ centered over the localization reference point may represent a location of the patient target region and as such, may be used to calculate a shifted fluence map that directs radiation to the current location of the patient target region. Conceptually, delta function $\delta$ may be thought of as encoding a position of a patient target region designated in 3-D coordinates. A delta function $\delta$ may comprise an all zero 3-D image with a single unity voxel of infinitely narrow dimensions centered over the planned localization reference point, but its projection $\delta_i$ onto a firing position (e.g., "beams-eye-view" of the therapeutic radiation source, or multi-leaf collimator space), may be defined by the width of each multi-leaf collimator (MLC) leaf and/or beam station spacing (i.e., spacing between discrete patient platform locations where the platform is stopped during the delivery of therapeutic radiation), and may contain one or more non-zero voxels. The projection $\delta_i$ may be a matrix (or image) having dimensions that match the number of MLC leaves in the MLC of the radiotherapy system and the number of patient platform beam stations. A schematic representation of a delta function based on a voxel in space and its projection to a firing position is depicted in FIG. 22A. Alternatively, a delta function $\delta$ may have a finite size that is set during treatment planning.

Figure 24:
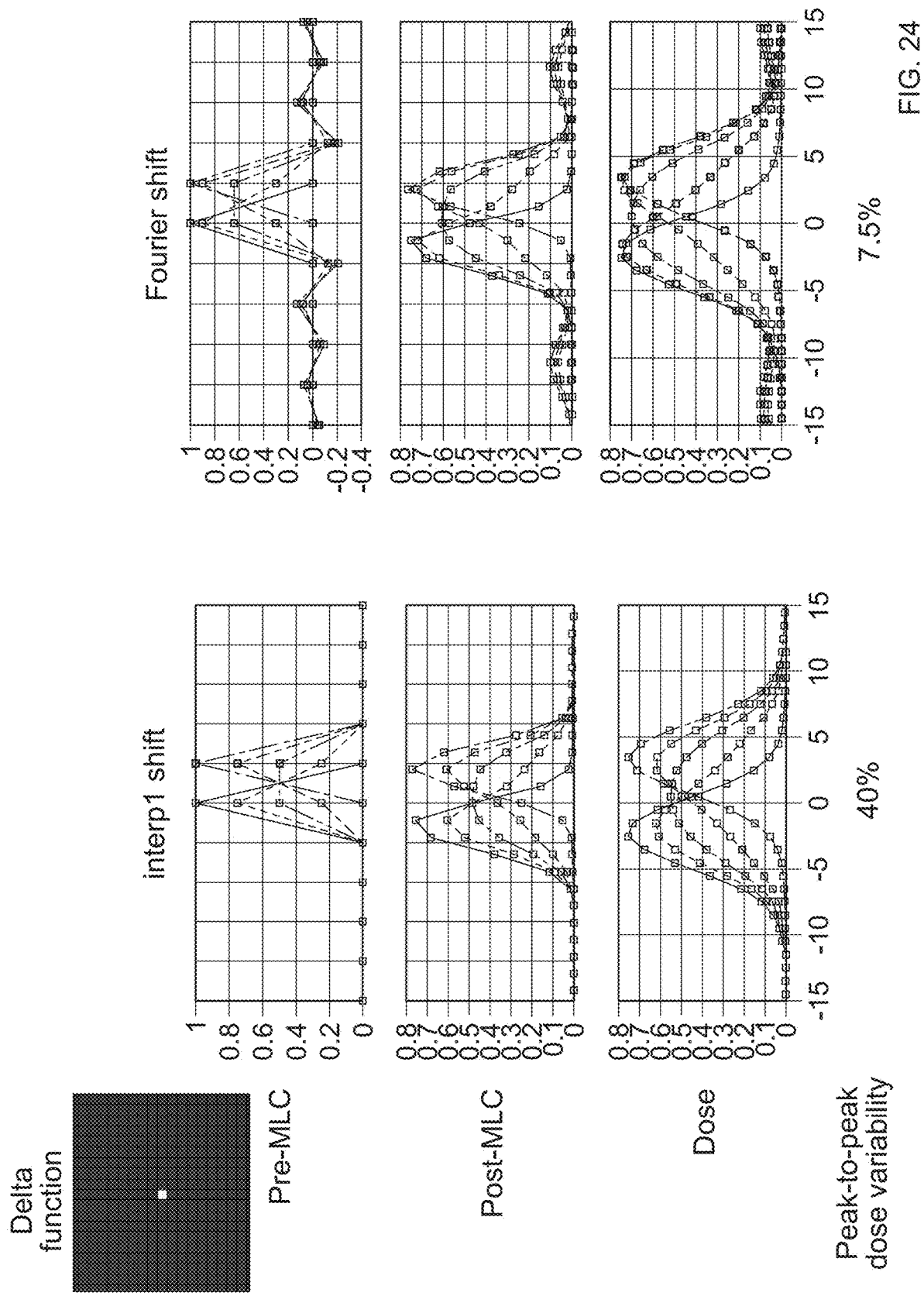
FIG. 24 depicts fluence shifts of a delta function over MLC leaf indices for a set of firing angles.
Figure 25:
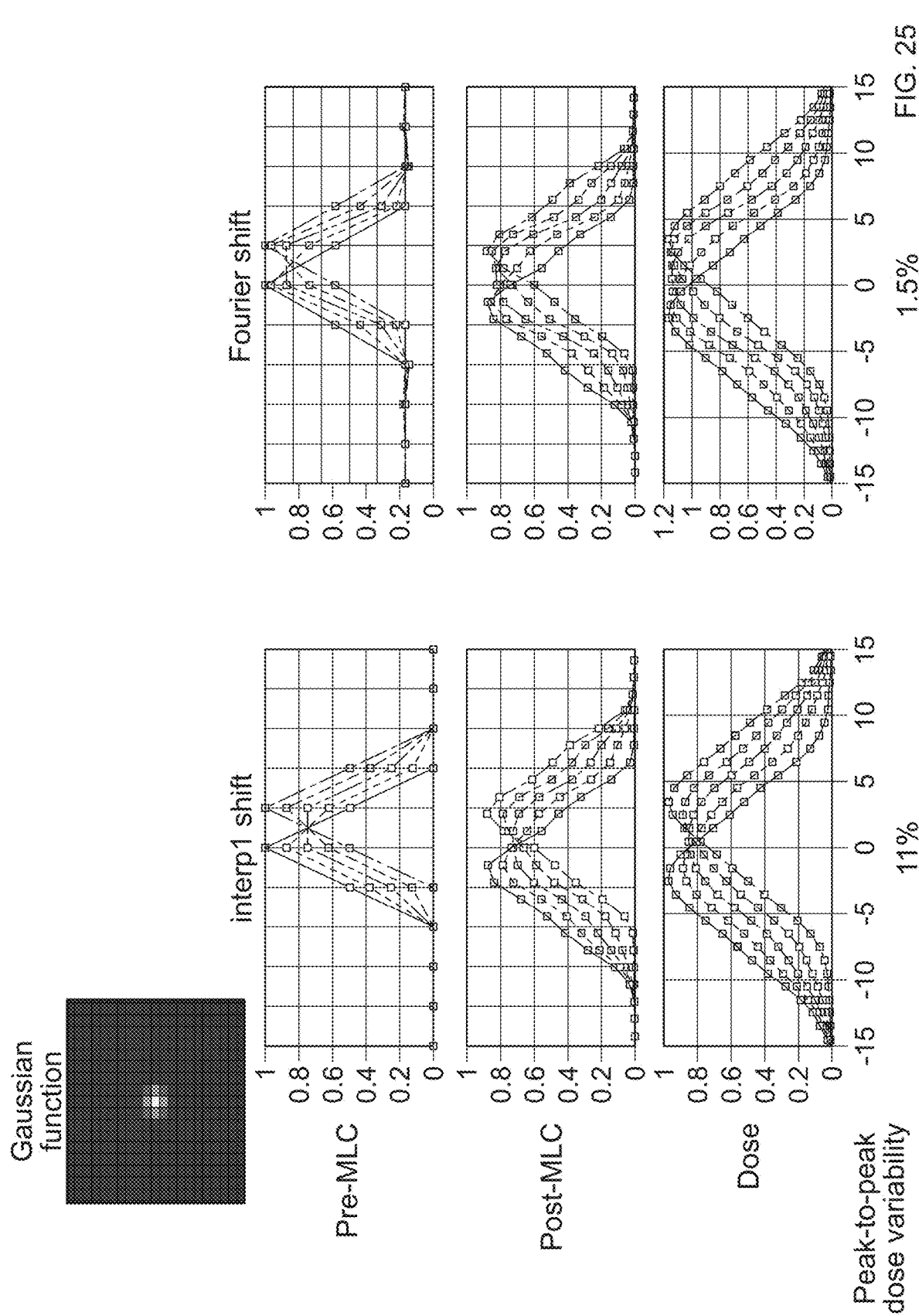
FIG. 25 depicts fluence shifts of a Gaussian function over MLC leaf indices for a set of firing angles.

In some variations, virtual localization may include convolving a set of filters with a localization function, which may include a delta function, Gaussian function, and truncated Gaussian function that are centered over a localization reference point. FIGS. 24-26 depict examples of localization functions that may be used in any of the virtual localization treatment planning and delivery methods described herein and their corresponding values across a set of MLC leaf indices for multiple firing angles or positions. FIG. 24 depicts the values of a delta function and dose profile, FIG. 25 depicts the values of a Gaussian function and dose profile, and FIG. 26 depicts the values of a truncated Gaussian function and dose profile. In FIGS. 24-26, the X-axis corresponds to an MLC leaf index and the Y-axis is a value or magnitude of the localization function projection of a one-dimensional interpolation shift (e.g., interp1 shift, set of plots on the left side) and a Fourier shift (set of plots on the right side). Each line represents the localization function values for a different firing angle and/or position. For each of the dose plots, the X-axis corresponds to distance in millimeters and the Y-axis corresponds to fluence (e.g., dose). Peak-to-peak dose variability is measured from the highest peak in the family of curves to the lowest peak in the family of curves.

FIG. 24 depicts the value or magnitude of a localization delta function projection over four firing angles and/or positions and their corresponding dose (or fluence) profile. The peak-to-peak dose variability for a one-dimensional interpolation shift is about 40% and the peak-to-peak dose variability for a Fourier shift is about 7.5%. FIG. 25 depicts the value or magnitude of a localization Gaussian function projection over four firing angles and/or positions and their corresponding dose (or fluence) profile while FIG. 26 depicts the value or magnitude of a localization truncated Gaussian function projection over four firing angles and/or positions and their corresponding dose (or fluence) profile. As shown in FIGS. 25 and 26, a Gaussian function and a truncated Gaussian function may have better peak-to-peak characteristics relative to the delta function shown in FIG. 24. The peak-to-peak dose variabilities for a Gaussian function are 11% and 1.5% and the peak-to-peak dose variabilities for a truncated Gaussian function are 14% and 2.1% (for linear interpolation and Fourier shift correspondingly). However, the Gaussian function and truncated Gaussian function have curves that are wider than the delta function curves. Wider curves corresponds to more MLC leaves that must be open to deliver the fluence. That is, for a particular firing angle or position, the values of the localization function span across more MLC leaves for a Gaussian or truncated Gaussian function than for a delta function. The truncated Gaussian function of FIG. 26 provides improved peak-to-peak characteristics over the delta function with narrower curves than the Gaussian function. Low peak-to-peak variability is desired so that shifting a fluence does not result in significant dose difference. A treatment planning method that incorporates virtual localization may comprise selecting the specific localization function that provides a dose distribution that meets prescribed objectives for each patient target region and/or OAR.

Figures 27, 28, 29:
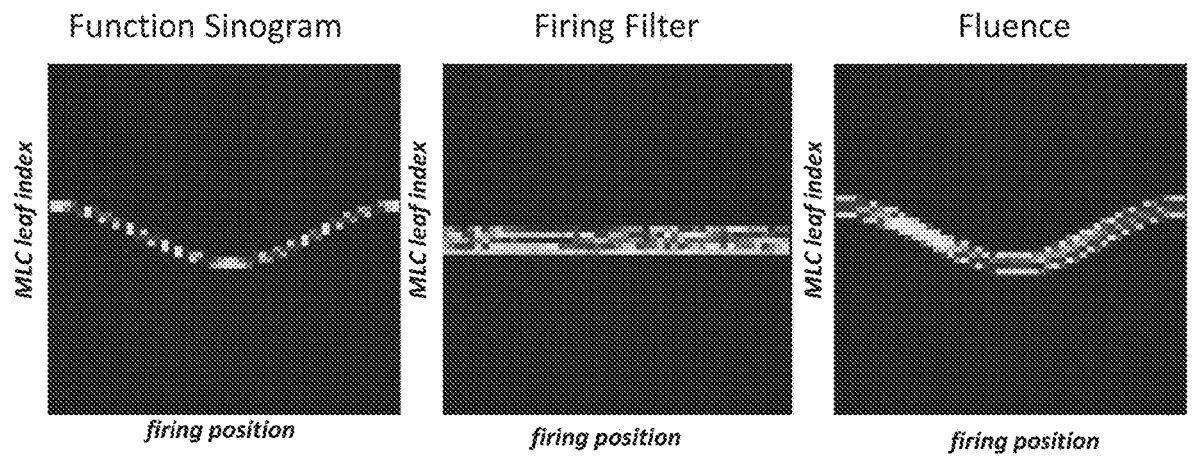
FIGS. 27-29 depict simulation color-intensity plots for a localization function that is a truncated Gaussian with a σ-value of 2 mm.
Figures 30, 31, 32:
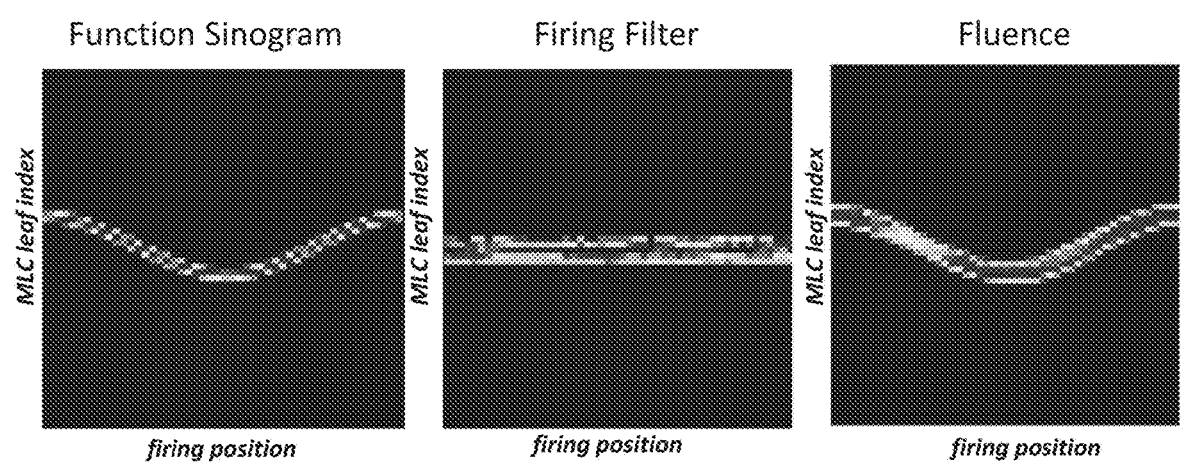
FIGS. 30-32 depict simulation plots for a localization function that is a truncated Gaussian with a σ-value of 4 mm.

In addition to selecting a specific localization function during treatment planning, some variations of a treatment planning method may also comprise selecting parameters (e.g., characteristics, constants, etc.) of a localization function. For example, a treatment planning method may comprise selecting a truncated Gaussian function as the localization function and selecting the σ-value (e.g., width) of the truncated Gaussian function. The y-value (e.g., average value or center) of the truncated Gaussian function may be the planned localization reference point. Localization functions with different σ-values may result in a delivery fluence with different conformality and/or distortion characteristics. For example, selecting a localization truncated Gaussian function with a lower σ-value may result in a shifted dose or fluence with better conformality as compared to a similar function with a higher σ-value. FIGS. 27-29 depict simulation color-intensity plots for a localization function that is a truncated Gaussian with a σ-value of 2 mm. FIGS. 30-32 depict simulation plots for a localization function that is a truncated Gaussian with a σ-value of 4 mm. The X-axis for the plots of FIGS. 27-32 is firing position/angle while the Y-axis is MLC leaf index. FIGS. 27 and 30 depict the projections of the localization function to every firing position for a 2 mm and a 4 mm truncated Gaussian function, respectively. FIGS. 28 and 31 depict the firing filter values for every firing position for a 2 mm and a 4 mm truncated Gaussian function, respectively. FIGS. 29 and 32 depict the fluence values for every firing position for a 2 mm and a 4 mm truncated Gaussian function, respectively. The projections of the localization function in FIG. 30 (σ-value of 4 mm) are somewhat wider (i.e., spans more MLC leaves) than the localization function in FIG. 27 (σ-value of 2 mm). This may result in a fluence profile for the 4 mm σ-value localization function (FIG. 32) that is more blurred than the fluence profile for the 2 mm σ-value localization function (FIG. 29). However, the fluence peaks across multiple firing positions may be more uniform (less distortion) for the 4 mm σ-value localization function than for the 2 mm σ-value localization function (more distortion). These different fluence characteristics may be adjusted during treatment planning based on the clinical and/or prescription objectives for each patient target region and/or OAR. For example, as depicted in FIGS. 27-32, a treatment planning system may balance the trade-offs between fluence conformality and uniformity or distortion by iterating through and evaluating different σ-values for the localization function.

In some variations, a convolution of a three-dimensional image or two-dimensional image with a localization function (e.g., delta function, Gaussian function, truncated Gaussian function) may be equivalently represented as an operation on the three-dimensional image or two-dimensional image followed by shift by an interpolation operator. A shift with a delta function may be implemented as linear, Fourier, bi-cubic interpolation of a 2-D or 3-D image. The operations on the three-dimensional image or two-dimensional image may be filtering by a Gaussian filter or a truncated Gaussian filter.

It should be understood that while the examples and variations of methods described herein may refer to the use of a delta function, any of the functions described above, e.g., Gaussian function, truncated Gaussian function, may instead be used.

While the delta function described above may encode a position of a patient target region via the localization reference point (i.e., the delta function is a function of the 3-D coordinates of the localization reference point), optionally, virtual localization methods may comprise a second rotational transform function that encodes an orientation of the patient target region. For example, the rotational function R may be a localization function of the pitch, yaw, and roll of the patient platform, which may represent the orientation of a patient target region in the patient. That is, a virtual localization method may comprise two localization functions: a first delta function that represents a reference position of the patient target region and a second rotational transform function that represents an orientation of the patient target region. That is, $$\delta = \delta_{x_{ref}, y_{ref}, z_{ref}}$$

$$R = R_{\varphi_{pitch}, \varphi_{yaw}, \varphi_{roll}}$$

Just as shifts may be projected to each firing angle, the fluence map rotation operations may also be projected to each firing angle. A 3-D rotation operation may become a 2-D affine transformation of fluence maps (i.e., rotate the fluence map in 3-D, then project to same 2-D beams-eye-view space). A 3-D rotation operation that implements pitch and yaw correction may be denoted as $R_i = R_{i, \theta_{pitch}, \theta_{yaw}}$ below. The real-time delivery fluence map used by radiotherapy system may be:

$$f_i = R_i(\delta_i * p_i)$$

For ring-gantry radiotherapy systems, one example of roll correction may be implemented by adding a single offset to the gantry encoder position to roll the plan to the patient. For multiple targets, there may not a single roll offset that can be implemented that can individually roll each of the individual firing filters. One example of virtual roll correction that can be implemented for a ring-gantry system with a set of firing filters $p_i$, where i is the index representing the firing position around the gantry, is by interpolating the filters across the firing angles. One example for a radiotherapy system with $N_{fp}$ firing positions and a rotation angle $\varphi_{roll}$ is negative with respect to the z-axis and $|\varphi_{roll}| < 360°/N_{fp}$ then the new firing filter $p'_i$ for each patient target region may be:

$$\alpha = |\varphi_{roll}| \frac{N_{fp}}{360°}$$

$$p'_i = \alpha p_{mod(i-1, N_{fp})} + (1 - \alpha) p_i$$

where the modulus function mod returns a firing position around the ring gantry. If the rotation angle $\varphi_{roll}$ is positive with respect to the z-axis and $|\varphi_{roll}| < 360°/N_{fp}$ then $$p'_i = \alpha p_i + (1 - \alpha) p_{mod(i+1, N_{fp})}$$

It is understood that if the $|\varphi| > 360°/N_{fp}$ then other interpolation algorithms may be used to rotate the filters to their new positions. In some variations, interpolation algorithms may comprise one or more Fourier, bi-cubic, and spline based interpolation algorithms. The above method is one example of a method that implements the rotation of the firing filters in the projection space, where the set of p' over the firing position angles θ can be described using circular convolution with a delta function angular roll φ where:

$$p' = \delta(\varphi_{roll}) \otimes p$$

After rotation by the angle $\varphi_{roll}$, the new firing filters p' may be used in place of the previous filters p. This may impart an order of operations that matches applying an offset to the gantry position encoder to implement roll correction. The advantage of calculating a new set of filters in this way is that any fluence that is calculated may be summed together. The fluences for all the patient target regions may be summed because they are on the same rotational grid.

In some ring gantry radiotherapy systems, patient target regions that are not at isocenter may undergo a virtual rotation of the patient target region, a rotation of the reference frame, and a virtual shift of the fluence. FIG. 33 depicts a virtual roll correction of an IMRT/SBRT treatment delivery system. Let δ be located at the virtual center-of-rotation for the patient target region.

$$\delta = \delta_{x_{ref}, y_{ref}, z_{ref}}$$

$$R = R_{\varphi_{roll}}$$

$\varphi_{roll}$ corresponds to an amount of roll at the target offset from the isocenter. In some variations, virtual roll correction may comprise rotating the entire reference frame by $\varphi_{roll}$ such that the patient target region may rotate and move based on the location of the patient target region as depicted in FIG. 33. Δx and Δy may correspond to a difference between the original location of the target, x y, and a new location after a rotation of the reference frame after a rotation of angle $\varphi_{roll}$.

$$\Delta x = x(1 - \cos \varphi) + y \sin \varphi$$

$$\Delta y = y(1 - \cos \varphi) + x \sin \varphi$$

$\Delta r_\theta$ corresponds to an amount of leaf offset at each therapeutic radiation source (e.g., linac) position to shift the fluence to center on the new location. For a fan-beam therapeutic radiation source, Δw may correspond to a spacing between leaves at the target and is based on the ratio of the distance to the target $D_t$ divided by a distance between the source of the linac and the isocenter of the system $D_{iso}$, where θ corresponds to an angle between firing positions around the ring gantry.

$$\Delta r_\theta \approx (\Delta x \cos\theta + \Delta y \sin\theta)/\Delta w$$

$$\Delta w = w \frac{D_t}{D_{iso}}$$

In some variations, the leaf offset may be approximately related to amount the patient target region has moved in both Δx and Δy in the rotation plane of the radiotherapy system. Patient target regions that are farther from the source may have larger leaf shifts. In some variations, a more accurate solution for $\Delta r_\theta$ may be obtained using convolution operations to calculate a leaf offset.

$$\delta_i(\Delta r) = \text{proj}_i(\delta_{LOC}) \otimes \text{proj}_i(\text{ROT}(\delta_{LOC}, \varphi))^{-1}$$

In this formulation, the location of the patient target region may be projected into fan-beam projection space. The location of the patient target region $\delta_{LOC}$ after it has been rotated by angle V may be projected into fan-beam projection space at a given firing position i. By inverting the projection of the delta function and convolving it with the location of the patient target region, this operation may shift the fluence. Inversion of a projected delta function is may be implemented as transposing a discrete representation of the delta function. Alternatively, inversion of a delta function may represent a negation of the shift of the delta function. This shift with the rotation implements virtual rotation of the planned fluence around an arbitrary patient target region location.

Where the localization reference point is selected at the treatment session having 3-D coordinates (x, y, z), and the pitch, yaw, roll, and x-, y-, z-positions reflect the orientation of the patient platform/couch at patient setup (which may correspond with the predetermined orientation of the patient platform during treatment planning). Localizing the patient target region both in position and orientation may shift the delivery fluence for firing position i accordingly:

$$f_{delivery,i} = \delta_{delivery,i} * p'_i$$

Where $\delta_{delivery,i}$ is the projection of $\delta_{delivery}$ on the firing position i, and $p'_i$ is the projection of the firing filters p' on the firing position i.

FIG. 34 depicts a schematic diagram of virtual roll correction for a BgRT treatment delivery system. For virtual roll at a patient target region, the fluence at each firing position i, may be a combination of the roll combined with a shift of the delivery fluence.

$$p' = \delta(\varphi_{roll}) \otimes p$$

$$\delta'_{delivery,i} = \delta_{delivery,i} * \delta_i(\Delta r)$$

$$f_{delivery,i} = \delta'_{delivery,i} * p'_i$$

With the shift-invariant firing filters $p_i$ calculated by the treatment planning system for a particular patient target region based on a planned localization reference point, virtual localization of that patient target region at the time of treatment may comprise acquiring a localization image of a patient in a treatment position (e.g., positioned or setup on the patient platform), identifying a patient target region in the image, selecting a localization reference point that corresponds with the planned localization reference point, and calculating the fluence for delivery f_delivery$_i$ at each firing position by calculating a delta function $\delta_{local}$ based on the localization reference point, and convolving the delta function with the shift-invariant firing filters $p_i$:

$$f\_delivery_i = p_i * \delta\_local_i$$

where $$\delta\_local_i = \text{proj}_i(\delta_{local})$$

Convolving the firing filters with the delta function centered over the localization reference point has the effect of moving (e.g., shifting) the planned fluence map to reflect the current location of the patient target region. After calculating the delivery fluence, the radiotherapy system controller may then segment the delivery fluence into machine instructions (e.g., MLC configurations, therapeutic radiation source parameters, etc.) that may then execute to deliver the prescribed fluence. Virtual localization and machine instruction segmentation may occur during the treatment session and preferably, in real-time. This is in contrast to other treatment planning and radiotherapy systems where the machine instructions are calculated during the treatment planning phase, not during the treatment session, which results in a set of machine instructions that deliver radiation to the location of the patient target region in the planning image, and not to the current location of the patient target region. In the case of SBRT/IMRT radiation delivery, after virtual localization and segmentation, the radiotherapy system may then proceed to deliver the prescribed fluence to the patient target region by following the newly-segmented machine instructions. In the case of BgRT radiation delivery, the region of interest or ROI (e.g., biological-firing zone or BFZ) may be adjusted (e.g., shifted) using virtual localization, and the delivery fluence map may not be segmented into machine instructions until after the delivery fluence map has been further updated with imaging data (e.g., positron annihilation emission path data) acquired during the treatment session. For example, about 500 ms before the delivery of a therapeutic radiation beam, the radiotherapy system may update the delivery fluence with imaging data acquired in the 500 ms window and then segment the delivery fluence just prior to delivery. In cases where multiple patient target regions are to be irradiated in a single session, virtual localization of each patient target region may be performed in a single batch at the beginning of the treatment session and/or sequentially throughout the treatment session (e.g., localize a first patient target region, segment delivery fluence into machine instructions, and irradiate the first patient target region, localize a second patient target region, segment delivery fluence into machine instructions, and irradiate the second patient target region, and so on).

When moving a fluence map to reflect the current location of a patient target region, some localization methods may consider and compensate for one or more physical effects of shifting a fluence map. Examples include the MLC leaf tongue-and-groove (T&G) effect, non-flat therapy beam effect, as well as the effect of the therapy beam intensity fall-off as the inverse square of distance from the therapeutic radiation source. Optionally, to calculate a delivery fluence map that accounts for one or more these effects, the convolution of the localization function (e.g., delta function, Gaussian-type function) with the firing filters may be convolved with additional factors. To compensate for a non-flat therapy beam (i.e., the beam intensity varying across the irradiation field in the IEC-X and IEC-Y directions, where the central portion of the field has a greater beam intensity than the edges of the field), a virtual flattening filter correction factor (FF) may be applied to each projection, where the virtual flattening filter correction factor is matrix that is an inverse of the beam intensity flatness profile of the therapeutic radiation source beam along the MLC leaf dimension:

$$(f_i) = FF \cdot (p_i * \delta_i)$$

Figure 22B:
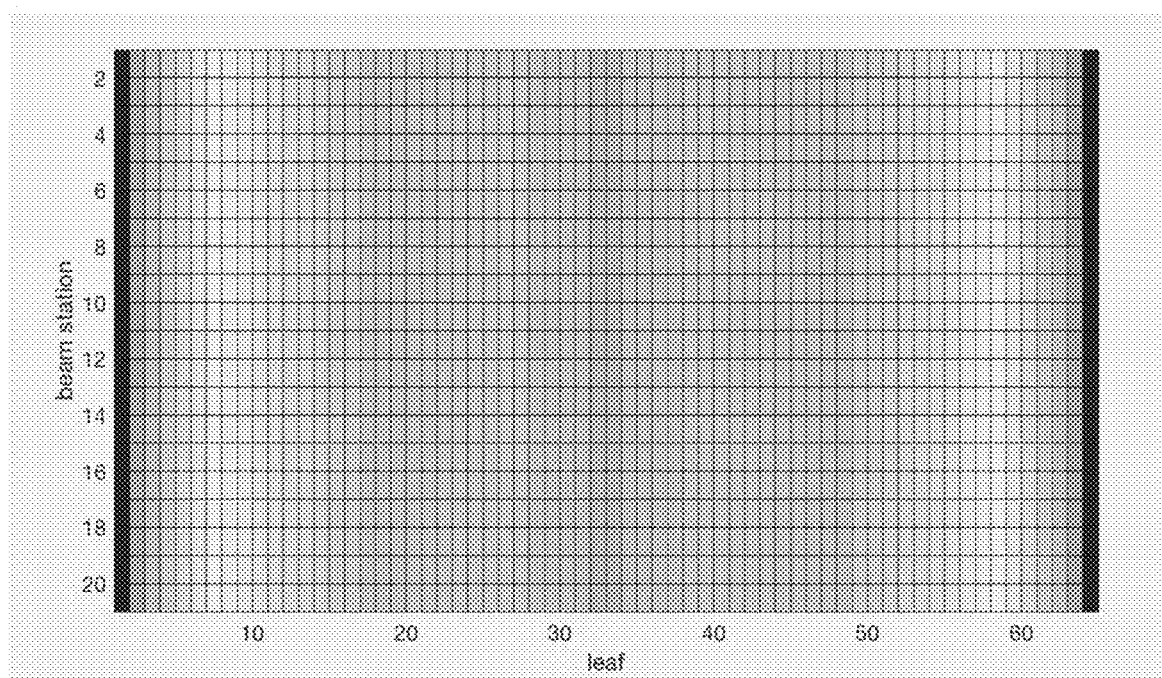
FIG. 22B is one example of a virtual flattening filter correction factor (FF) for a radiotherapy system having 64 MLC leaves and 20 patient platform beam stations.

The virtual flattening filter correction factor (FF) matrix may be a two-dimensional matrix, with the number of rows matching the number of MLC leaves and the number of columns matching the number of patient platform beam stations. FIG. 22B depicts one example of a virtual flattening filter correction factor (FF) for a radiotherapy system having 64 MLC leaves and 20 patient platform beam stations.

Calculating a delivery fluence map to compensate for inverse-square beam intensity reduction over distance from the therapeutic radiation source may comprise applying a distance compensation scaling factor $$\left(\frac{d_i'}{d_i}\right)^2$$

in the delivery fluence calculation:

$$(f_i) = \left(\frac{d_i'}{d_i}\right)^2 \cdot (p_i \star \delta_i)$$

where $d_i$ represents a distance from a firing position i to a center of the patient target region (e.g., target region centroid) determined during treatment planning, and $d_i'$ represents a distance from the firing position i to a center of the patient target region (e.g., target region centroid) determined at radiation delivery based on the localization image(s).

A delivery fluence map that accounts for both the non-flat therapy beam and the inverse-square beam intensity reduction may be calculated as follows:

$$(f_i) = \left(\frac{d_i'}{d_i}\right)^2 \cdot FF \cdot (p_i \star \delta_i)$$

The virtual localization methods described herein may be used for the irradiation of multiple patient target regions in a single treatment session or fraction. Methods for the irradiation of multiple patient target regions in a single treatment session may comprise defining a patient region or treatment area (e.g., defined by the treatment planning system, with or without user input) for each patient target region, a localization reference point is selected for each patient treatment area for virtual localization according to the steps described herein, and then emitting therapeutic radiation beams according to the delivery fluence maps calculated by virtual localization for each patient treatment area. A patient treatment area may comprise the region of the patient that is irradiated for a single physical setup and localization. For example, a treatment area may be the region of the patient that is irradiated for a particular patient position on the platform (e.g., location along the platform, patient position such as arm position, etc.) and a set of platform locations in IEC-Y. A physical setup and localization may include one or more of unique laser alignment of the patient and/or the acquisition of a localization image (e.g., a CT or MRI or PET image), patient position (e.g., arms raised, arms lowered, abdominal press, breath hold, etc.), and/or one or more patient platform adjustments so that the patient position matches the position during treatment planning. A patient treatment area may span across a region of the patient that is irradiated for a particular physical setup and localization. Each treatment area may have its own physical setup and localization. A patient treatment area may be, in some variations, represented by a set of patient platform positions in IEC-Y that span across the irradiated region of the patient. For example, the acquired image and/or the treatment planning image may be divided into a first treatment area and a second treatment area. Each treatment area may include one or more patient target regions such that the one or more patient target regions in the acquired image may be compared to one or more corresponding patient target regions in the treatment planning image. Each treatment area may correspond to a portion of a patient within which the one or more patient target regions are located that will be irradiated when a patient is positioned according to a particular setup during a particular portion of a radiation treatment session. A treatment area may map to series of patient platform positions or steps (e.g., beam stations) and/or a range of patient platform motion along its longitudinal axis where the one or more target regions in that treatment area intersect the radiation beam of the therapeutic radiation source. A treatment area may correspond with a particular patient position and/or platform orientation. For example, a first treatment area may be associated with a first patient position and orientation for irradiation of a first patient target region within the first treatment area and a second treatment area may be associated with a second patient position and orientation for irradiation of a second patient target region within the second treatment area. Thus, in some embodiments, the first treatment area may be associated with a first portion of a radiation treatment session (e.g., movement of the patient platform through a first set of beam stations), a first patient target region, and a first position of the patient and the second treatment area may be associated with a second portion of the radiation treatment session (e.g., movement of the patient platform through a second set of beam stations), a second patient target region, and a second position of the patient.

Optionally, the center regions of the defined patient treatment areas may be aligned with each other (e.g., along an "iso-line") so that between the emitting of therapeutic radiation for each patient treatment area, the patient position need not be adjusted (other than the longitudinal IEC-Y motion to each patient platform beam station such that IEC-X and IEC-Z are fixed). This may help to reduce the incidence of a user entering the treatment bunker during a treatment session, which can add substantially to the overall treatment time. For example, a center of a first treatment area and a center of a second treatment area may be collinear along an IEC-Y axis and/or co-planar with the IEC-Y axis. In some variations, the first treatment area and the second treatment area may overlap, while in other variations, the treatment areas may not overlap. A centroid may be along IEC-X in the same plane (e.g., along an "isoline"). The center of a treatment area is not necessarily the center of the target.

The localization reference point for each patient target region (or group of patient target regions) may be different from the center region or point of the treatment area. In some variations, a treatment area defined during treatment planning (e.g., a planned patient treatment area) may be selected based on certain clinical criteria. For example, target regions in different axial planes may be separated into different planned patient treatment areas, and/or a target region that is separated from another target region by more than about 5-10 cm may be separated into different planned patient treatment areas. During treatment planning, a set of shift-invariant firing filters may be calculated for each patient target region and/or group of patient target regions that share a localization reference point using the methods described herein, so that virtual localization of the patient target regions may take place separately during a treatment session, if so desired. The emission of therapeutic radiation beams according to the delivery fluence map of each planned patient target region may be performed sequentially, and may in some variations, include a separate, physical patient setup (e.g., by adjusting the orientation of the patient platform) prior to the delivery of radiation to the patient target region(s) in the next patient treatment area. Alternatively or additionally, the delivery fluence maps for each patient target region may be delivered in parallel, e.g., segmented together and delivered without any physical patient setup between target regions (other than stepping the patient platform through discrete beam station locations along the longitudinal axis, i.e., IEC-Y). For a treatment session where one or more of the patient target regions are to receive BgRT radiation delivery and these BgRT patient target regions have been localized using virtual localization, the virtual shifts are applied to the ROI. A treatment planning method that incorporates virtual localization for one or more BgRT targets may comprise choosing a planned localization reference point for the BgRT patient target region, defining a region of interest (ROI) (e.g., biological-firing zone (BFZ)) around the patient target region, and calculating a shift-invariant firing filter (e.g., radiation-firing matrix (RFM) or radiation firing filters) $p_i$ based on the ROI and a planning guidance image (e.g., a planning PET image, MRI image, etc.) that includes the patient target region. An ROI may be a spatial mask or filter that defines a patient area or region that may include a patient target region and a margin around the patient target region. For example, a ROI may include a tumor region (or any patient target region), and the margin around the tumor region may account for location estimation errors of the tumor region, and/or movement of the tumor region, and/or possible locations of the tumor region during radiation delivery, and/or geometrical changes to the tumor region. During the treatment session, the radiotherapy system may acquire imaging data (e.g., positron annihilation emission path data or LOR data in cases where the patient has been injected with a PET tracer, SPECT data in cases where the patient has been injected with a SPECT tracer, gamma radiation data, MRI data, CT data, and/or X-ray data) that intersects and/or co-localizes with the ROI for that BgRT target region. Imaging data that does not intersect with the ROI, or contains data pertaining to structures that lie outside of the ROI are not included in the calculation of the delivery fluence map. In such fashion, the ROI functions as a spatial mask or filter that may be applied to imaging data acquired during a treatment session.

A radiation delivery method that incorporates virtual localization with BgRT delivery may comprise acquiring an image of a patient in a treatment position that includes the BgRT patient target region and the ROI, selecting a localization reference point within the acquired image, adjusting the ROI by calculating a delta function based on the localization reference point and convolving the delta function with the ROI, acquiring additional imaging data during the session, calculating a fluence for delivery to the patient target region at each firing position of the therapeutic radiation source by convolving the imaging data with the firing filters, and proceeding with emitting the fluence for delivery:

$$(f_i)=(p_i * \text{proj}_i(x \cdot (\text{ROI} * \delta_{delivery})))$$

Where x is the acquired additional imaging data (e.g., partial imaging data, limited-time acquired imaging data, positron annihilation emission path data, MRI data, SPECT data, gamma data, CT data and/or X-ray data), and $p_i$ are the firing filters (a.k.a. the BgRT firing filters or radiation firing matrix), as opposed to filters used by virtual localization. In this case, virtual localization acts to shift the ROI by $\delta_{delivery}$. The additionally acquired imaging data may be spatially filtered (or masked) by the ROI so that only imaging data that co-localizes with the adjusted ROI may be used to calculate the fluence for delivery.

For BGRT, when optionally applying roll correction anytime the filter $p_i$ is rotated, the ROI may rotate by the same degree. One example is to implement a 2-D rotation function that rotates the ROI mask in place for each plane along Z. Order of operations may be important when implanting roll corrections, and in this example, roll correction is applied first and then translated by a virtual offset:

$$\text{ROI}'=\delta(\Delta x, \Delta y) * \text{ROT}(\text{ROI}, \varphi_{roll})$$

$$\Delta x = \Delta x(1-\cos \varphi) + \delta y \sin \varphi$$

$$\Delta y = \Delta y(1-\cos \varphi) + \delta x \sin \varphi$$

The firing filters are now rotated to match the new reference frame:

$$p' = \delta(\varphi_{roll}) \circledast p$$

The fluence at a given firing position $f_i$ is now the projection of the of the imaging data, masked by a rotated and shifted ROI, shifted by a virtual offset $\delta_{delivery}$, projected to a given firing angle i, and convolved with a set of rotated filters $p'_i$:

$$(f_i)=(p'_i * \text{proj}_i(x \cdot (\text{ROI}' * \delta_{delivery})))$$

$$\text{ROI}'=\delta(\Delta x, \Delta y) * \text{rot}(\text{ROI}, \theta_{roll})$$

$$(f_i)=(p_i * \text{proj}_i(x(\text{ROI}' * \delta_{delivery})))$$

Optionally, a delivery fluence map that accounts for both the non-flat therapy beam and the inverse-square beam intensity reduction for a BgRT target region may be calculated as follows:

$$(f_i) = \left(\frac{d'_i}{d_i}\right)^2 \cdot FF \cdot (p_i \star proj_i(x \cdot (ROI \star \delta_{delivery})))$$

Therapeutic radiation may be delivered to BgRT targets and/or SBRT/IMRT targets in a single session, sequentially and/or in parallel, as may be desirable.

Optionally, bounded dose-volume histogram curves (bDVH) that show the minimum and maximum dose values over a patient target region volume, taking into account possible dose variations due to patient target region shifts, may be calculated during treatment planning after the shift-invariant firing filters have been calculated. Outputting a visualization graphic, such as a bDVH or any of the visualization graphics described herein during treatment planning and/or during patient setup and/or target region localization may help a user evaluate whether the treatment plan is appropriate for the patient (e.g., on the day of treatment).

After multi-target virtual localization, each of the patient target regions may have a dose component that is coupled between the different patient treatment areas. This dose coupling may be a consequence of the potential for extra beams of fluence to interact with several patient target regions. Once a set of virtual localizations is known, doses for patient target regions, OARs, and/or treatment areas may be calculated. A set of normalization coefficients can be applied to each patient target region and/or treatment area to ensure certain dosimetric objectives are met, or alternatively, certain OAR doses are constrained. One example of implementing these coefficients for each IMRT/SBRT virtual multi-localization j from a set of N localizations, a coefficient for each localization $\beta_j$ can be solved normalize the joint effect of all virtual localizations (e.g., all virtual localizations in an entire treatment plan, all virtual localizations in each treatment area). One such example of a joint solution is to minimize the mean squared sum of a dosimetric scalar $D_j$ associated with each patient target region and/or treatment area. $D_j^{planned}$ is a dosimetric scalar calculated at planning for the target region j.

For IMRT/SBRT:

$$(f_i) = \left(\frac{d_i'}{d_i}\right)^2 \cdot FF \cdot \beta_j \cdot (p_i \star proj_i(\delta_{delivery}))$$

For BgRT:

$$(f_i) = \left(\frac{d_i'}{d_i}\right)^2 \cdot FF \cdot \beta_j \cdot (p_i \star proj_i(x \cdot (BFZ \star \delta_{delivery})))$$

$$\text{solve } \beta_j \text{ s.t. } \min \sum_{j=1}^{N} (D_j - D_j^{planned})^2$$

The dosimetric scalar $D_j$ could any of the following: the mean dose of the PTV, a percentile dose of the PTV, a maximum of the PTV. Alternatively, this dosimetric scalar $D_j$ could be based on a function of the doses to the OAR that are linked with the target regions. Other convex minimization algorithms may be used instead of mean-squared error such as weighted least squares.

While some of the virtual localization methods described above and herein use a delta function derived from a localization reference point and convolve this delta function with shift-invariant firing filters, it should be understood that virtual localization methods that include other localization functions that encode an orientation of a patient target region based on the pitch, yaw, and roll of the patient platform or couch. For example, the virtual localization methods described herein may include convolving a set of filters with a localization function including a delta function, Gaussian function, and truncated Gaussian function, over a localization reference point that may be selected during a treatment session.

Mosaic Multi-Target Localization

As briefly described above, one of the challenges with treating multiple patient target regions in a single treatment session is that the localization/registration that is appropriate for one patient target region may not be suitable for the other patient target regions. Methods for the localization/registration of multiple patient target regions may comprise localizing/registering each one separately (e.g., using virtual localization methods where the planned fluence map is moved and/or physical localization methods where the patient is moved using the platform). For example, a treatment session may comprise one physical localization/registration for a patient target region and one or more virtual localizations for the other patient target regions. With virtual localization, multiple patient target regions may be irradiated without having to physically move and/or reposition the patient to localize each target region. In the variations where a treatment plan may be calculated and optimized for all of the patient target regions, i.e., a single treatment plan that specifies the 3-D fluence for every patient target region, the "global" treatment plan (e.g., the "global" fluence map) may be partitioned into discrete sub-regions. The target(s) in each sub-region may be independently localized or registered in a multi-target treatment plan, based on a single localization image. Typically, a treatment plan fluence map may comprise high-fluence regions located on (e.g., co-localized with) target regions low-fluence regions nearly everywhere else. These low-fluence regions may be referred to as low-fluence bands or boundary regions. A method for treatment planning may comprising generating a global treatment plan or global fluence map that has high-fluence regions that co-localize with target regions that are surrounded or bounded by low-fluence regions or low-fluence bands, and may further comprise partitioning the global treatment plan or fluence map into sub-regions that are surrounded or bounded by low-fluence regions. Conceptually, the global treatment plan may be "cut" along the center of these low-fluence bands and separated into discrete regions around each target region. These treatment plan fluence map sub-regions or "mosaics" may be independently shifted and oriented around each target using a localization image at the start of a treatment session. While the planned fluence map sub-region shifts may result in fluence overlaps in the low-fluence boundary regions of adjacent sub-regions (i.e., the border regions may receive fluence during the irradiation of the target regions of the two or more adjacent sub-regions), the low fluence levels in these boundary regions may be specified during treatment planning to be low enough such that this fluence overlap is not of clinical concern. During treatment planning, the low-fluence boundary regions may be defined to be wide enough that the amount of overlap that can be accommodated is sufficiently large that all sources of localization/registration error(s) may be addressed. In some variations, tuning structures and/or constraints may be added during treatment planning to attain a desired low-fluence boundary region. After localization of the individual patient target regions in the independent fluence map sub-regions, the delivery fluence map for each sub-region may be segmented into machine instructions for execution by the radiotherapy system. Radiation may be delivered to the multiple localized patient target regions or fluence map sub-regions serially and/or simultaneously. For example, some patient target regions or fluence map sub-regions may be irradiated sequentially while other patient target regions or fluence map sub-regions may be irradiated simultaneously with other patient target regions or fluence map sub-regions. A single localization image that includes all of the patient target regions may be used to localize/register each patient target region, or a plurality of localization images (e.g., one localization image per patient target region or fluence map sub-region). For example, during a treatment session, there may be one physical localization per treatment area (as defined during planning), and one or more virtual localizations for the one or more patient target regions within the treatment area. Mosaic localization methods may be used for SBRT/IMRT delivery and/or BgRT delivery, and may optionally be used in conjunction with other localization methods and patient setup methods (e.g., in combination with moving the patient platform, virtual localization methods, rigid-body multi-localization methods where a "best fit" shift is applied to the patient via the platform based on the localization image).

Hybrid Mosaic Multi-Target Localization

Optionally, during treatment planning for mosaic localization when a global planned fluence map is partitioned into planned fluence map sub-regions, the method may comprise designating whether the patient target region(s) in each fluence map sub-region is to be treated using SBRT/IMRT methods (e.g., designated as a SBRT/IMRT target region) or treated using BgRT methods (e.g., designated as BgRT target region). Shift-invariant firing filters may be calculated based on planned localization references points selected for all target regions, as described herein for virtual localization. Optionally, bDVH curves may be calculated for each patient target region, which may comprise generating a series of simulations of all the potential shifts of the BgRT target regions and/or the SBRT/IMRT target regions. The bDVH curves may be reviewed and approved by a clinician at the time of planning. A method for hybrid mosaic multi-target localization may comprise acquiring a large volume CT (e.g., a single large volume CT) of the multiple SBRT and BgRT target regions, delineating a set of patient platform adjustments (e.g., 6 DOF correction) for each patient target region based on the CT localization image, and selecting a localization reference point for each patient target region. To localize/register a particular patient target region, the patient platform may first be moved according to the delineated set of patient platform adjustment, and the delivery fluence map may be calculated using virtual localization techniques applied to the selected localization reference point for that patient target region. For BgRT delivery, a PET prescan may be acquired in conjunction with the acquisition of the localization image(s). Based on the PET prescan, a predicted dose to BgRT targets may be calculated just before the activation of the therapeutic radiation source for the irradiation of BgRT target region, which may help to ensure that the actual localizations and PET prescan images are within pre-approved dose bounds. The real-time delivery fluence map for BgRT and SBRT/IMRT target regions may be smoothly combined together and segmented into machine instructions on the fly (i.e., minutes or seconds before delivery). In beam station delivery where the patient platform remains stationary at a longitudinal position while the therapeutic radiation source moves about the patient to deliver calculated fluence, the delivery fluence maps for BgRT and SBRT/IMRT target regions at a particular beam station may be added together and segmented into machine instructions together while the platform is stopped at the beam station. In this way, the delivery fluence for multiple BgRT and SBRT/IMRT target regions may be delivered simultaneously.

De-Coupled Multi-Target Localization

Methods for the treatment of multiple patient target regions in a single treatment session may comprise calculating an individual treatment plan (i.e., an individual planned fluence map that specifies the 3-D fluence for an individual patient target region) for each patient target region, instead of calculating a global treatment plan (i.e., a global fluence map that specifies the 3-D fluence for every patient target region). In some variations, a method for treatment planning for de-coupled localization may comprise calculating the individual treatment plans for each target region without regard for the existence of the other target regions, but accounting for the existence and location of OARs and/or other critical structures, combining the individual treatment plans together to form a combined treatment plan, and while still keeping the individual plans as separate entities, constraining the combined plan to not allow high-fluence regions from the individual plans to overlap with other high-fluence regions and to also meet the original objectives of dose coverage, dose limits to OARs, etc. Constraining the combined treatment plan may create a planned global fluence map that has low-fluence regions or bands that surround each patient target region so that some independent motion of the target regions may be accommodated by the treatment plan. In some variations, tuning structures and/or constraints may be added during treatment planning to attain the desired low-fluence boundary regions. The combined treatment plan (i.e., the planned global fluence map) may be reviewed and approved by a clinician prior to treatment.

One example of a treatment planning method for de-coupled multi-target localization may comprise generating treatment plan for the irradiation of a first patient target in a first treatment area and a second patient target region in a second treatment area, partitioning the treatment plan into a first treatment plan for irradiating the first patient target region in the first treatment area with a first prescribed dose while limiting irradiation of an OAR below a first dose quantity and a second treatment plan for irradiating the second patient target region in the second treatment area with a second prescribed dose while limiting irradiation of the OAR below a second dose quantity, combining the first and second treatment plans to generate a combined treatment plan, and iteratively modifying the combined treatment plan to meet desired dose objectives and constraints. Examples of dose objectives and constraints may include preventing hot spots or cold spots in the combined treatment plan. The first treatment plan may include optimized radiation beams that deliver the first prescribed dose to the first patient target region and the second treatment plan may include optimized radiation beams that deliver the second prescribed dose to the second patient target region. The dose quantity or levels to the OAR as a result of the individual (e.g., first and second) treatment plans may be set to a certain proportion of the maximum dose quantity. For example, the first dose quantity to an OAR (e.g., an OAR that is located between or spans across both the first and second treatment areas) from the first treatment plan may be 35% of the maximum dose level, and the second dose quantity to the OAR from the second treatment plan may be 65% of the maximum dose level. The specific contribution values of the first and second treatment plans to the OAR dose may be set dynamically based on the evaluation of objectives in the combined treatment plan based on an iterative calculation within a joint optimization or through a series of separate optimizations at different contribution levels until an acceptable plan is achieved. After the combined treatment plan has been modified to meet desire dose objectives and constraints, it may be partitioned into the first and second treatment plans, but with the optimized beams and/or fluence for delivery. In some examples, the combined treatment plan may include a planned fluence map, and the first treatment plan may include a first fluence sub-map and the second treatment plan may include a second fluence sub-map where the first and second fluence sub-maps combine to form the planned fluence map.

Optionally, in some variations, a user may select one patient target region as higher priority than the other. For example, if a user defines the irradiation of the first patient target region as higher priority than the irradiation of the second patient target region, a treatment planning method may comprise partitioning the treatment plan into a first treatment plan for irradiating the first patient target region in the first treatment area with a first prescribed dose and a second treatment plan for irradiating the second patient target region in the second treatment area with a second prescribed dose while limiting irradiation of the OAR below a selected dose quantity, combining the first and second treatment plans to generate a combined treatment plan, and iteratively modifying the combined treatment plan to meet desired dose objectives and constraints. In this method, the first treatment plan may have fewer dose constraints (e.g., no OAR dose constraints) than the second treatment plan, so that the first treatment plan comprises beams that are optimized for delivering the prescribed dose to the first patient target region, with little or no consideration to the dose to the OAR. The second treatment plan may then consider the dose delivered by the first treatment plan as "prior dose" that constrains its beam optimization for the dose delivery to the second patient target region.

During a treatment session, the individual patient target regions may be individually localized using one or more localization images (e.g., using typical localization methods by adjusting the patient platform or changing radiotherapy machine instructions, and/or using the virtual localization methods described herein). After all of the patient target regions are localized, the delivery fluence maps for each patient may be combined together to confirm whether any "overlap" dose region exceed any constraints. If the desired dose constraints are met, then the radiotherapy system may segment the delivery fluence maps into machine instructions and proceed to deliver therapeutic radiation to the patient target regions. Delaying the segmentation or translation of delivery fluence maps into radiotherapy system instructions so that segmentation occurs as close to delivery as possible allows for the radiotherapy system to update the delivery fluence to reflect the actual location (and/or any changes in location) of the patient target regions, resulting in a more accurate delivery of the overall prescribed dose.

Biologically-Guided Radiotherapy (BgRT) Localization

As briefly described, BgRT is a radiation delivery method that updates the delivery fluence using imaging data acquired during a treatment session, and emits therapeutic radiation within minutes or seconds of acquiring the imaging data. Due to the low-latency nature of BgRT, the imaging data used to update the delivery fluence may be relatively sparse (e.g., "partial image data" that is insufficient for a full image reconstruction, collected over a short or limited time window) and/or noisy (e.g., with a signal-to-noise ratio that does not permit a reliable determination of a patient target region centroid). For example, in BgRT, imaging data used to update or calculate a delivery fluence map may comprise partial PET images comprising one or more lines-of-response (LORs), partial MRI images comprising a sub-sampling in k-space, and/or one or more x-ray projection images. While the examples herein are described in the context of the PET imaging modality, it should be understood that any other imaging modality may be used, alone or in combination with the PET imaging modality. The imaging data may be acquired over a limited-time window that may be, for example, about 3 seconds or less, about 2 seconds or less, about 1 second or less, about 500 ms or less, about 300 ms or less, about 200 ms or less, etc. Because of the low-latency between image acquisition and radiation delivery (e.g., about 10 seconds or less, about 5 seconds or less, about 3 seconds or less, about 1 second or less, about 500 ms or less), radiation may be delivered to a target region before it moves. An ROI (e.g., a biological firing zone or biological target zone) may be defined around each BgRT target region that represents the volume that is used to determine what LORs are used to direct fluence at the target. That is, the ROI may be a spatial filter or mask that may be applied to the LORs; if a detected LOR intersects the ROI, it is used in the BgRT delivery algorithm to update the delivery fluence, otherwise it is ignored. A smaller ROI may be preferred, because it may reduce the chance of including in the ROI PET-avid tissue that is not the target (any PET-avid tissue in the ROI will be treated as if it were the target).

Methods for BgRT-based multi-target localization may comprise designating one of the BgRT target regions as a registration target region, and defining ROIs around the other that are large enough to encompass a range of location shifts of those patient target regions. In some variations, the ROI of the registration target region may be smaller than the ROI of the other BgRT target regions. In some variations, the registration target region may be the BgRT target region that is closest to a critical structure or OAR (e.g., a PET-avid OAR such as the heart). During a treatment session, as long as the ROI of the registration target region is localized/registered, and the other BgRT target regions are within their ROIs (which may be larger or expanded in order to account for anticipated changes in spatial positioning relative to the registration target region), the radiotherapy system may proceed to deliver radiation using BgRT methods (i.e., delivery fluence is calculated by convolving acquired spatially-filtered imaging data with a shift-invariant radiation-firing matrix or firing filters, and then segmented into machine instructions for immediate execution). The impact on dose conformality of the larger ROIs may be calculated and reviewed at the time of treatment planning, and perhaps shaped or designed to help reduce the possibility of including additional PET-avid tissue, while helping to increase the probability that spatial differences between planning and delivery may be accommodated. BgRT-based localization may optionally be used in conjunction with other localization methods and patient setup methods (e.g., in combination with moving the patient platform, virtual localization methods, rigid-body multi-localization methods where a "best fit" shift is applied to the patient via the platform based on the localization image).

Any of the multi-target localization and radiation delivery methods described herein may be used alone or in combination with localization and delivery methods that are typically used for single-patient target irradiation and/or irradiation of multiple target regions over multiple treatment sessions. For example, any of the planning, localization, and delivery methods described herein may be used in combination with physical patient setup (e.g., in serial fashion, one physical patient setup per patient target region or treatment area), rigid-body multi-localization, treatment plan deformation, robust treatment planning (treatment plans that consider positional uncertainties during the optimization process and create plans that do not vary strongly as a function of positional changes), and/or online treatment plan adaptation (generate a new treatment plan based on the localization image). In serial registration and treatment, each patient target region is independently localized and treated, one after the other. Immediate treatment after localization may help reduce the probability of static patient shifts during treatment, however, may require the acquisition of multiple localization images (e.g., multiple kVCT image) for each localization instance. Treatment planning for serial registration and treatment may comprise jointly optimizing the fluence map across the multiple patient target regions and/or may be optimized to be robust to individual shifts of each tumor when localized individually. Rigid-body multi-localization may comprise acquiring a localization image and then calculate a single shift (i.e., perform a "rigid-body" registration) of the localization image with respect to the planning image that minimizes a function of the total registration error(s) across all target regions and/or OARs. Margins around each target region in the original treatment plan may be enlarged to account for these expected registration errors. The targets and OARs in the treatment plan may be shifted and oriented as a rigid body, to find the "best" mapping to the actual positions of the targets and OARs in the localization image. The user may choose to consider all registration errors of equal weight, and minimize the total registration "error volume", or alternately, they may choose to weight some target regions or OARs as more important than others and seek to better align those targets at the expense of a greater registration error or increased tumor margin elsewhere.

For example, mosaic multi-target localization and BgRT-based localization may be combined with one or more of the methods described above. Some of the targets in a multi-target treatment plan may be expected to move more as a rigid body (e.g. target regions that are associated with the same bone), and thus may be grouped together and registered using rigid-body methods, while the other patient target regions may be registered using mosaic multi-target or BgRT-based localization. Robustness algorithms may be used during treatment planning to help ensure that the spatial adjustments made to each treatment plan or fluence map sub-region introduces the least amount of dose variation. Robust planning may also be used in conjunction with BgRT-based virtual localization to optimize the shape and placement of the ROI of each patient target region. It may also be desirable to register a patient target region using mosaic multi-target or BgRT-based localization techniques, and then to apply soft tissue deformation methods to each sub-region or target region. This may help to reduce the amount of tissue deformation that must be accounted for, and thus, help reduce dose variability introduced by soft-tissue methods. Alternatively or additionally, mosaic multi-target localization methods may be used to reduce the computational burden of online treatment plan adaptation. For example, patient target regions may be registered based on the planned fluence map using mosaic multi-target localization methods, and then the fluence map for each patient target region may be adapted individually. In still another example, BgRT treatment planning may be incorporate treatment planning steps from the mosaic multi-target localization method, which may help reduce the size of ROIs for each target region.

In another variation, a treatment plan for multiple patient target regions may comprise multiple treatment areas, where the patient may be physically setup/localized for each treatment area. Each treatment area may have one or more tumors or patient target regions (e.g., ROIs). During a treatment session, a patient may be physically setup/localized for a first treatment area, and the radiation therapy system may virtually localize each of the patient target regions within the first treatment area. For example, the physical localization may provide appropriate positioning for a first patient target region in the first treatment area, and the radiation therapy system then adjusts the fluence for the other patient target regions in the treatment area using the virtual localization methods described herein. The fluence for delivery may be calculated or adjusted according to the localization reference points selected during the treatment session from the localization image. Irradiation of the patient target regions in the first treatment area may be performed serially and/or in parallel. After the first treatment area has been irradiated, the patient may then be physically setup/localized for a second treatment area (e.g., moving the patient platform along IEC-Y), and the radiation therapy system may virtually localize each of the patient target regions within the second treatment area. The patient target regions in the second treatment area may be irradiated as described above for the first treatment area. The first and second treatment areas may overlap in some variations and may not overlap in other variations.

Methods for multi-target treatment planning, localization and radiation delivery may optionally comprise generating one or more visualization graphics that may be output to a display device (e.g., a monitor). Visualization graphics may include dose-volume histograms (DVH) or bounded dose-volume histograms (bDVH) for each of the multiple patient target regions so that the user may be apprised to the dose may be delivered to the patient target region. However, DVH and bDVH curves do not provide information regarding the spatial interactions between the fluence maps of different target regions. For example, as fluence maps are shifted and/or updated during localization, fluence areas that previously did not overlap during treatment planning may overlap during the treatment session. In mosaic localization, the fluence map sub-regions may be individually localized and shifted, and in de-coupled localization, the individual fluence maps of different patient target regions may also be individually localized and shifted. Some areas of overlap may comprise low-fluence areas of two or more individual fluence maps or fluence map sub-regions and so the cumulative fluence in the overlap area may not exceed dose safety thresholds for non-target tissue, however, in some cases, such fluence overlap may exceed dose safety thresholds and/or may co-localize over OARs. Visualization graphics may be generated based on localization data (e.g., the shifted fluence maps or fluence map sub-regions, the localization reference point, localization images, etc.) and output to a display device to help the user to evaluate the dose impact of separate localization of multiple patient target regions, and/or help identify any unwanted dosimetric effects due to these localization fluence map shifts. Visualization graphics may help a user better comprehend inter-target interactions and encode spatial information for evaluation of uncertainties in dose delivery.

Some visualization graphics may be calculated based on bDVH curves and computations, and may refer to the bounds of a bDVH curve: nominal dose ($D_n$), potential minimum dose ($D_{pmin}$), and potential maximum dose ($D_{pmax}$). Visualization graphics may depict representations of the probabilities of certain dose distributions and levels over certain anatomical structures in 2-D slices and/or 3-D renderings. Cines or short animations may also depicts minimum, nominal, and maximum dose levels so that a visual comparison may be made between these levels. Differences or fluctuations from the nominal dose (e.g., delta dose) may provide a visual tool to the user to identify hot spots and cold spots.

Multi-Target Treatment Planning Methods

Treatment planning methods for the treatment of multiple patient target regions in a single treatment session may comprise calculating various fluence maps (e.g., global fluence map for all patient target regions and/or OARs, fluence map sub-regions that include a subset of target regions and/or OARs), firing filters (e.g., shift-invariant firing filters), spatial filters (e.g., for spatial filtering of imaging data, region of interest or ROI, biological firing zone or BFZ, biological target zone), as may be desirable. Treatment planning methods for the treatment of multiple patient target regions in a single treatment session may comprise calculating one or more shift-invariant firing filters for each patient target region for virtual localization, and/or calculating fluence map sub-regions partitioned by low-fluence bands for mosaic multi-target localization, and/or generating separate treatment plans or fluence maps for each patient target region and constraining a cumulative fluence map for de-coupled multi-target localization. BgRT treatment planning methods for the treatment of one or more BgRT patient target regions (alone or in combination with one or more SBRT/IMRT patient target regions) may comprise designating one BgRT patient target region as a registration target region and defining ROIs of the other BgRT patient target regions to accommodate motion of the registration target region and the other target region motion. Treatment planning methods for treating both SBRT/IMRT and BgRT patient target regions (e.g., hybrid mosaic multi-target localization) may further comprise specifying whether a patient target region is a BgRT target region or a SBRT/IMRT target region.

The treatment planning methods described herein may be used separately or in combination to formulate a multi-target treatment plan that is suitable for a particular patient. Some clinicians or clinics may configure their treatment planning systems to calculate treatment plan parameters that can accommodate virtual localization of the multiple patient target regions and mosaic multi-target localization, with serial or parallel radiation delivery to the patient target regions. Alternatively or additionally, treatment planning systems may be configured to calculate treatment plan parameters that can accommodate virtual localization of the multiple patient target regions and de-coupled multi-target localization, with serial or parallel radiation delivery to the patient target regions. For example, some treatment planning systems may be configured to calculate shift-invariant firing filters for all patient target regions, calculate firing filters for any BgRT patient target regions, and/or partition treatment plans or planned fluence maps based on the relative locations of the patient target regions, and/or OARs, and/or low-fluence areas of the planned fluence maps. BgRT patient target regions may be irradiated during a first treatment session and SBRT/IMRT patient target regions may be irradiated during a second treatment session (i.e., on a different day from the first treatment session, where the first and second treatment sessions do not overlap in time, occur at different time intervals in the same day, etc.). Alternatively, BgRT patient target regions and SBRT/IMRT patient target regions may be sequentially irradiated during the same treatment session. For example, BgRT patient target regions may be irradiated during a first shuttle pass and SBRT/IMRT patient target regions may be irradiated during a second shuttle pass.

Figure 1B:
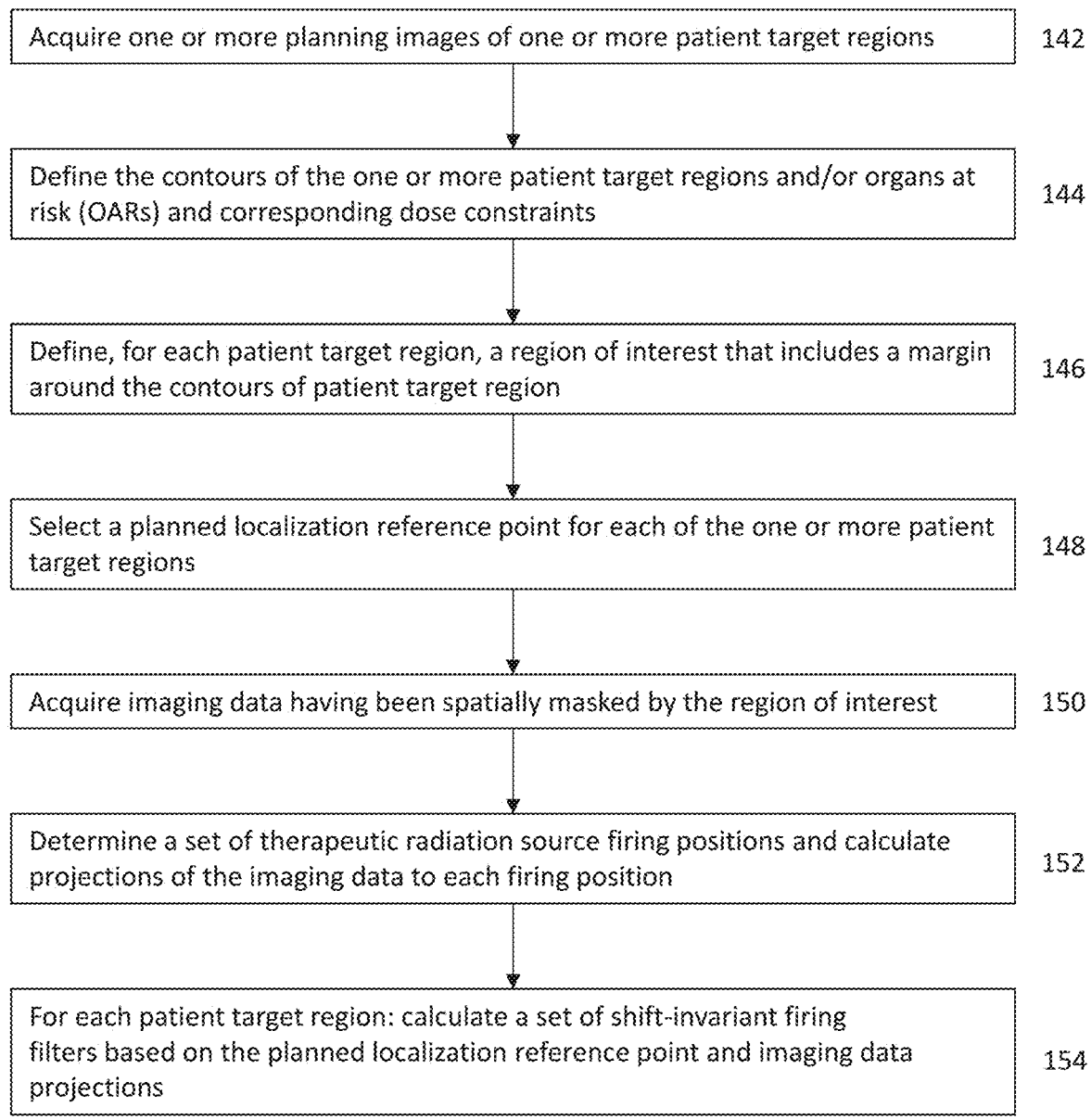
FIG. 1B is a flow chart representation of one variation of a method for treatment planning for virtual localization for BgRT.

FIGS. 1A and 1B are flowchart representations of respective SBRT and BgRT variations of a treatment planning method that use virtual localization for the localization of a single patient target region or multiple patient target regions in a treatment session. FIG. 1A depicts one variation of a treatment planning method that incorporates virtual localization for SBRT/IMRT patient target regions. Method (120) may comprise acquiring (122) one or more treatment planning images of one or more patient target regions, defining (124) the contours of the one or more patient target regions and/or organs at risk (OARs) and corresponding dose constraints, selecting (126) a planned localization reference point for each of the one or more patient target regions and/or treatment areas, calculating (128) corresponding localization functions for each localization reference point, determining (129) a set of therapeutic radiation source firing positions and calculating projections of the localization functions to each firing position, and calculating (130) a set of shift-invariant firing filters for each firing position based on the planned localization reference point for each patient target region and localization function projections. Defining (124) the contours of the one or more patient target regions may comprise defining a group of patient target regions that may be linked or associated (e.g., attached to the same bony structure) such that their position and/or motion are likely to be correlated. Method (120) may comprise selecting (128) a planned localization reference point for the entire group of patient target regions and calculating (130) a set of shift-invariant firing filters based on the planned localization reference point for the group of patient target regions. The calculated set of shift-invariant firing filters and the planned localization reference point for each patient target region, group of patient target regions, and/or treatment area may be transferred (along with other treatment plan parameters) to the radiotherapy system for localization at the time of treatment. In some variations, the calculated shift-invariant firing filters may represent a planned delivery fluence that is based on (e.g., centered around) the planned localization reference point. For example, for a particular patient target region (or group of patient target regions), a localization function may be a delta function that is centered over the planned localization reference point for that patient target region (e.g., tumor centroid). The shift-invariant firing filters for the particular patient target region may represent fluence maps (e.g., planned fluence maps) that are centered around the planned localization reference point.

FIG. 1B depicts one variation of a treatment planning method that incorporates virtual localization for BgRT patient target regions (i.e., patient target regions where the fluence delivered to those target regions are calculated based on acquired imaging and/or biological data, such as PET emission data). Method (140) as depicted in FIB. 1B may comprise acquiring (142) one or more treatment planning images of one or more patient target regions, defining (144) the contours of the one or more patient target regions and/or organs at risk (OARs) and corresponding dose constraints, defining (146) for each patient target region a region of interest that includes a margin around the contours of the patient target region, selecting (148) a planned localization reference point for each of the patient target regions, acquiring (150) imaging data that has been spatially masked by the region of interest, determining (152) a set of therapeutic radiation source firing positions and calculating projections of the acquired imaging data to each firing position, and calculating (154), for each patient target region, a set of shift-invariant firing filters based on the planned localization reference point and imaging data projections. In some variations, the boundary of the planned region of interest may comprise a spatial filter Defining (146) the contours of the one or more patient target regions may comprise defining a group of patient target regions that may be linked or associated (e.g., attached to the same bony structure) such that their position and/or motion are likely to be correlated. Method (140) may comprise selecting (148) a planned localization reference point for the entire group of patient target regions and calculating (154) a set of shift-invariant firing filters based on the planned localization reference point for the group of patient target regions.

Optionally, some treatment planning methods may comprise designating some patient target regions as a SBRT/IMRT target region and other patient target regions as a BgRT target region. Generating a treatment plan for both SBRT/IMRT target regions and BgRT target regions may also comprise acquiring a PET image. For each BgRT patient target region, a method may comprise calculating a shift-invariant firing filters (e.g., radiation-firing matrix (RFM)) based on the ROI, the one or more planning images of the BgRT patient target region, and the prescribed dose to the BgRT patient target region. Optionally, some treatment planning methods may comprise determining a set of therapeutic radiation source firing positions, calculating projections of localization functions such as a delta function, Gaussian function, truncated Gaussian function, etc., to each firing position. Optionally, some treatment planning methods may comprise calculating a cost function from the localization reference point for each patient target region.

A radiation-firing matrix (RFM) or firing filter may be a matrix that designates the conversion from partial images to a fluence map that may include beamlet pattern and/or beamlet intensities to be applied to the patient during a treatment session. A firing filter or RFM may represent the relationship between a fluence map F for radiation delivery to a patient region and an image X of that patient region. That is, a radiation-firing matrix or firing filter P may be any matrix such that F=P·X. A firing filter or RFM may be calculated during a treatment planning session for each patient target region in conjunction with calculating a fluence map that minimizes one or more cost functions, for example, a cost function C(D, F) of a resulting dose distribution D and fluence F, formed based on the radiation dose constraints and objectives, and optional limitations on F. Examples of cost functions may include, but are not limited to, minimum dose to target region, average or maximum dose on OARs, and/or fluence smoothness, total radiation output, total tissue dose, treatment time, etc. In some variations, generating a radiation-firing matrix P may comprise setting up an optimization problem for minimizing the cost function C(D, F), and iterating through different sets of P such that the cost function C(D, F) is minimized while the following conditions are met:

$$F=P \cdot X \text{ and}$$

$$D=A \cdot F=A \cdot P \cdot X;$$

where D is the predicted dose distribution, A is a pre-calculated dose calculation matrix, F is the predicted total delivered radiation fluence, and X is a known full image (e.g., an image acquired during a diagnostic imaging session and/or previous treatment session). The predicted dose distribution D and the predicted radiation fluence F may be calculated using dose constraints, patient target volume, and/or OAR data, and a patient planning CT image. One example of a dose calculation matrix A may be a (k×n) matrix where n may be the number of candidate beamlets $\{b_i\}$ and k may be the number of pre-selected voxels for an ROI. An i-th column of the dose calculation matrix A (which has k elements) represents a dose contribution from a unity-weighted beamlet $b_i$ to each of the k voxels.

Dose calculation matrix A may be calculated column-by-column, for example, by ray-tracing each beamlet's aperture along the path through an ROI or patient volume and calculating the contribution of a unity-weighted beamlet to each of the k voxels. A beamlet aperture may be a MLC aperture defined by a single MLC leaf opening (i.e., of a binary MLC or a 2-D MLC). Examples of dose calculation algorithms that may be used in any of the methods described herein may include Monte-Carlo simulation, collapsed-cone convolution superposition, pencil-beam convolution, and others.

The radiation-firing matrix P (a.k.a. RFM or firing filter) may be a matrix that, when multiplied by the full image X, yields the predicted or desired delivered radiation fluence F that minimizes the cost function. The cost function may be convex, allowing the use of well-known convex optimization algorithms, such as gradient descent, fast proximal gradient method, or interior-point methods. The calculated radiation-firing matrix P may represent a multiplication factor that relates fluence F to the full image X. This relationship may be used during a treatment session to update fluence $f_i$ at a particular time point based on a partial image $x_i$ acquired at that same time point by multiplying the partial image with the radiation-firing matrix P (e.g., $f_i = P \cdot x_i$). Additional details regarding BgRT treatment planning and delivery methods may be found in U.S. patent application Ser. No. 15/993,325, filed May 30, 2018, which is hereby incorporated by reference in its entirety.

Optionally, some methods (120) may comprise determining (132) a set of therapeutic radiation source firing positions and calculating projections of the firing filters to each of the firing positions. For example, a radiotherapy system with a rotatable gantry may have 100 circumferentially distributed firing positions or angle around a bore through which the patient platform may be advanced. Method (120) may comprise calculating projections of each of the firing filters to each of the 100 firing positions. For firing filters convolved with a Gaussian function or truncated Gaussian function, a width (σ) of the Gaussian function may be selected during treatment planning where an average value (μ) is centered over the planned localization reference point. For example, the width (σ) of the Gaussian function or truncated Gaussian function may be based on the width of the MLC leaves.

FIG. 2 depicts a flowchart representation of one variation of a treatment planning method that uses mosaic multi-target localization for the registration of multiple patient target regions in a treatment session. Method (220) may comprise acquiring (222) one or more treatment planning images of one or more patient target regions, defining (224) the contours of the one or more patient target regions and/or OARs and corresponding dose constraints, selecting (228) a planned localization reference point for each of the one or more patient target regions and/or OARs, and calculating (230) a set of shift-invariant firing filters based on the planned localization reference point for each patient target region and/or OARs. Method (220) may comprise generating (234) a treatment plan fluence map based on the firing filters and the one or more planning images and defining (236) perimeters around each patient target region that comprise regions of low fluence values in the treatment plan fluence map. The calculated set of shift-invariant firing filters, the planned localization reference point for each patient target region and/or OAR, and the treatment plan fluence map with the defined perimeters may be transferred (along with other treatment plan parameters) to the radiotherapy system for localization at the time of treatment.

Optionally, some treatment planning methods (220) may comprise designating (226) each of the patient target regions as a SBRT/IMRT target region or a BgRT target region. If a patient target region has been designated as a BgRT target region, the method (220) may comprise calculating an ROI for that patient target region. For each BgRT patient target region, method (220) may also comprise calculating a shift-invariant firing filter (e.g., RFM), as described above.

Optionally, some methods (220) may comprise determining (232) a set of therapeutic radiation source firing positions and calculating projections of the firing filters to each of the firing positions. For example, a radiotherapy system with a rotatable gantry may have 100 circumferentially distributed firing positions or angle around a bore through which the patient platform may be advanced. Method (220) may comprise calculating projections of each of the firing filters to each of the 100 firing positions.

Optionally, some treatment planning methods (220) may comprise calculating (238) bounded dose-volume histogram (bDVH) curves for each patient target region and/or OAR, and displaying (240) the bDVH curves and/or dose calculation data for each patient target region and/or OAR to a display device. bDVH curves may be calculated for a patient target region by calculating the dose per unit volume for each possible location of the patient target region in a motion envelope (or, in the case of a BgRT target, in the ROI), and/or based on biological activity and/or physiological and/or anatomical data acquired before or during the planning session, to generate a family of dose-volume curves. For example, a family of bounded DVH curves may be calculated for each OAR, ROI, and/or patient target region based on the firing filter by performing a rigid shift of the PET image of the patient target region within the ROI, and calculating a corresponding dose to the OAR, ROI, and/or patient target region for that particular shifted target region position. For example, for a patient with a patient target region within an ROI, and one OAR, a family of DVH curves for the patient target region may be calculated for each shifted position of the patient target region within the ROI. The upper threshold boundary of the bDVH curve may comprise the right-most points of the family of dose-volume curves and the lower threshold boundary of the bDVH curve may comprise the left-most points of the family of dose-volume curves. Additional details and variations of methods for calculation bounded DVH curves are provided in U.S. patent application Ser. No. 16/016,272, filed Jun. 22, 2018, which is hereby incorporated by reference in its entirety.

Figure 3B:
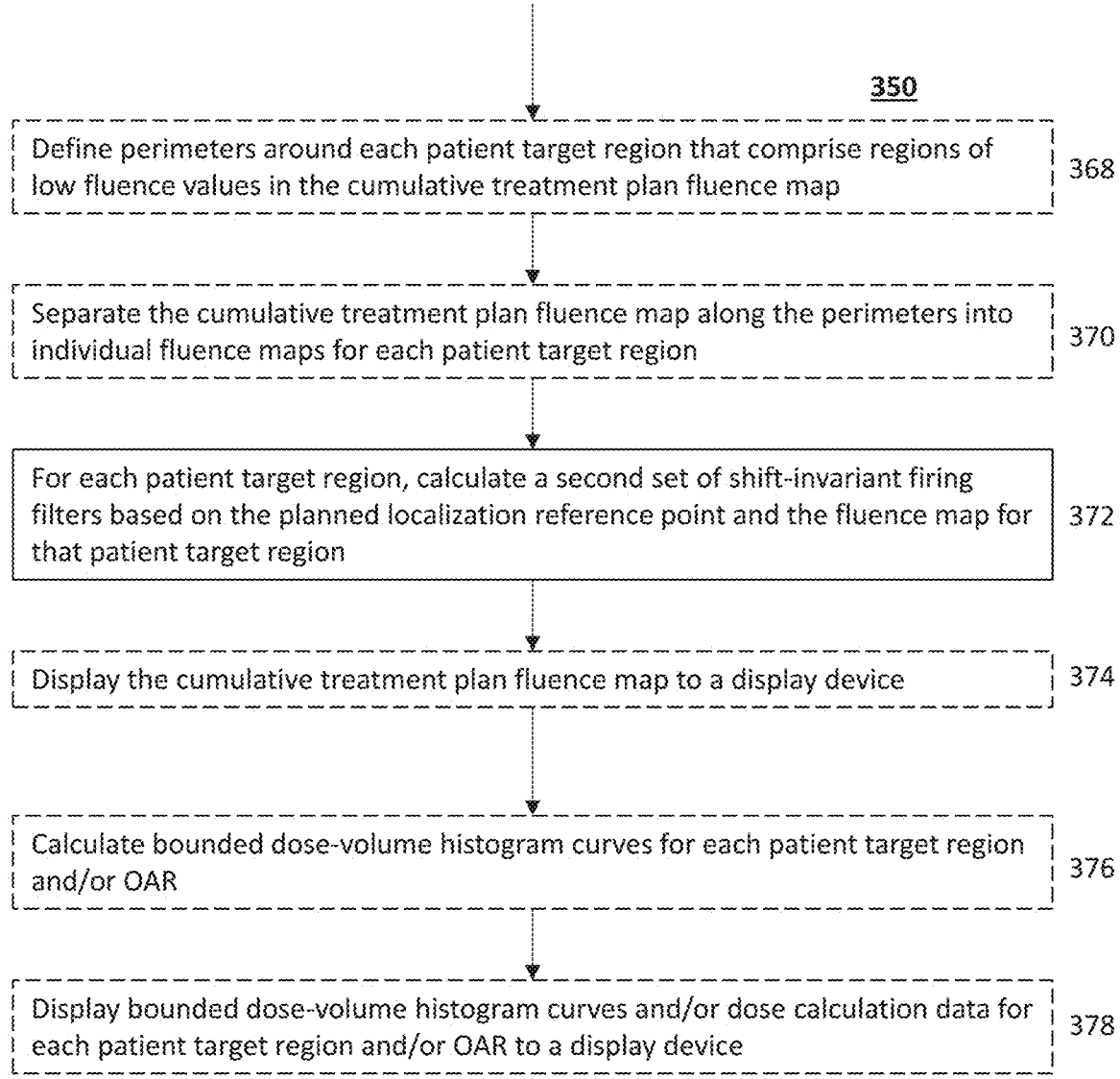

FIGS. 3A and 3B depict a flowchart representation of one variation of a treatment planning method that uses decoupled multi-target localization for the registration of multiple patient target regions in a treatment session. Method (350) may comprise acquiring (352) one or more treatment planning images of one or more patient target regions, defining (354) the contours of the one or more patient target regions and/or OARs and corresponding dose constraints, selecting (358) a planned localization reference point for each of the one or more patient target regions, and calculating (360) a set of shift-invariant firing filters based on the planned localization reference point for each patient target region. Method (350) may comprise generating (362) a fluence map for each patient target region based on the firing filters and the one or more planning images, and combining (364) all of the patient target region fluence maps into a cumulative treatment plan fluence map. Each patient target region may have a separate planned localization reference point when the patient target regions are physically separated from each other (e.g., do not overlap). This allows each patient target region to be independently moved. The corresponding patient target region fluence maps of each patient target region may be added together (since dose delivery is linear) to calculate a total dose. For example, if locations of the first and second planned localization reference points change from a planning session to a treatment session, the new localization reference point locations may be used to recalculate the cumulative treatment plan fluence map. Separate treatment plan fluence maps for multiple patient target regions may allow multiple planned localization reference points to be moved independently of each another, thereby allowing shifting of multiple (e.g., two or more) fluence maps relative to the other to obtain more optimized dose coverage. Additionally or alternatively, respective patient target region fluence maps of each patient target region may be individually constrained.

The method (350) may then comprise iteratively modifying (366) the cumulative treatment plan fluence map based on one or more dose constraints, for example, one or more of (a) high-fluence areas are kept separate from each other, (b) OAR constraints are met, (c) original dose constraints/objectives are fulfilled.

In some variations, each of the constraints on a cumulative treatment plan fluence map may be weighted by a linear factor that defines or approximates their relative importance. In some variations, a fluence map for a target region can be described as the variable x. Summing the combined fluences can be described as $x_{cumulative}$. A dose calculation matrix for the patient can be defined as A. The dose for a particular target region can be defined as Ax. Furthermore, the dose for the entire patient can be defined as $Ax_{cumulative}$. For example, dose constraints may comprise one or more cost functions, and optionally, each cost function may be weighted by an individual scaling factor. Prescribed dose requirements or constraints (C) may comprise one or more cost functions and may include, for example, one or more of a cost function C(x) on radiation fluence (x), and/or a cost function C(Ax) on the dose for a treatment area, and/or a cost function $C(Ax_{cumulative})$ on the summed doses, and/or a cost function $C(x_{cumulative})$ on the summed fluences. These may each optionally be weighted by an individual scaling factor ($w_i$, $w_k$, $w_m$, $w_n$). For example, a cost function on the cumulative fluence map can be used to optimize treatment time in the context of joint delivery. For example, a cost function on dose for each treatment area can be optimized ensuring that a minimum dose is delivered. This ensures that fluences from different a different treatment area does not deliver most of the dose to a given target. This reduces the coupling between treatment areas significantly, and therefore, increases the robustness of the treatment plan to relative shifts between the treatment areas. For example, a cost function on $D_{cumulative}$ can be used to limit the mean combined dose to the heart combined from all treatment areas.

$$C = \Sigma w_i C_i(x) + \Sigma w_k C_k(Ax) + \Sigma w_m C_m(Ax_{cumulative}) + \Sigma w_n C_n(x_{cumulative})$$

Additional details regarding cost functions and other constraints may be found in U.S. Provisional Patent Application No. 62/966,997, filed Jan. 28, 2020, which is hereby incorporated by reference in its entirety.

Additionally or alternatively, one or more tuning constraints (e.g., artificial constraints in addition to tissue constraints, tuning structures) may be applied in addition to a predetermined set of dose constraints to ensure that a dose does not exceed a predetermined threshold in a given zone (e.g., region). In some variations, one or more tuning constraints may enable decoupling of radiation delivery between two or more target regions.

After the cumulative treatment plan fluence map has been modified, the method (350) may comprise defining (368) perimeters around each patient target region that comprise regions of low fluence values in the cumulative treatment plan fluence map (e.g., tuning constraints, cost function), separating (370) the cumulative treatment plan fluence map along the perimeters into individual fluence maps for each patient target region, and calculating (372), for each patient target region, a second set of shift-invariant firing filters based on the planned localization reference point and the fluence map for that patient target region. The second set of shift-invariant firing filters, the planned localization reference point for each patient target region and/or OAR, and the individual treatment plan fluence maps for each patient target region may be transferred (along with other treatment plan parameters) to the radiotherapy system for localization at the time of treatment.

In some variations, such as for SBRT/IMRT delivery, a treatment planning method may comprise calculating the delivery fluence for a patient target region and/or treatment area (e.g., based on the prescribed dose, dose constraints, and/or a dose calculation matrix), where the delivery fluence is linked to (e.g., anchored by) the planned localization reference point. The calculated delivery fluence may then be segmented into machine instructions (either by the treatment planning system and/or the radiation therapy system) for delivery. During a treatment session, the calculated delivery fluence may be updated based on the updated location of the localization reference point (e.g., selected by the user from a localization image acquired during the treatment session). In this variation, firing filters may not need to be calculated by the treatment planning system.

Optionally, some treatment planning methods (350) may comprise designating (356) each of the patient target regions as a SBRT/IMRT target region or a BgRT target region. If a patient target region has been designated as a BgRT target region, the method (350) may comprise calculating an ROI for that patient target region. Each patient target region may have a separate planned localization reference point when the patient target regions are physically separated from each other to allow each patient target region to be independently moved, thereby allowing shifting of fluence maps relative to the other for optimized dose coverage. For each BgRT patient target region, method (350) may also comprise calculating a shift-invariant firing filter, as described above.

Optionally, method (350) may comprise displaying (374) a visualization graphic of the cumulative treatment plan fluence map to a display device. Optionally, some treatment planning methods (350) may comprise calculating (376) bDVH curves for each patient target region and/or OAR, and displaying (378) the bDVH curves and/or dose calculation data for each patient target region and/or OAR to a display device. bDVH curves for a patient target region may be calculated as previously described.

Figure 4:
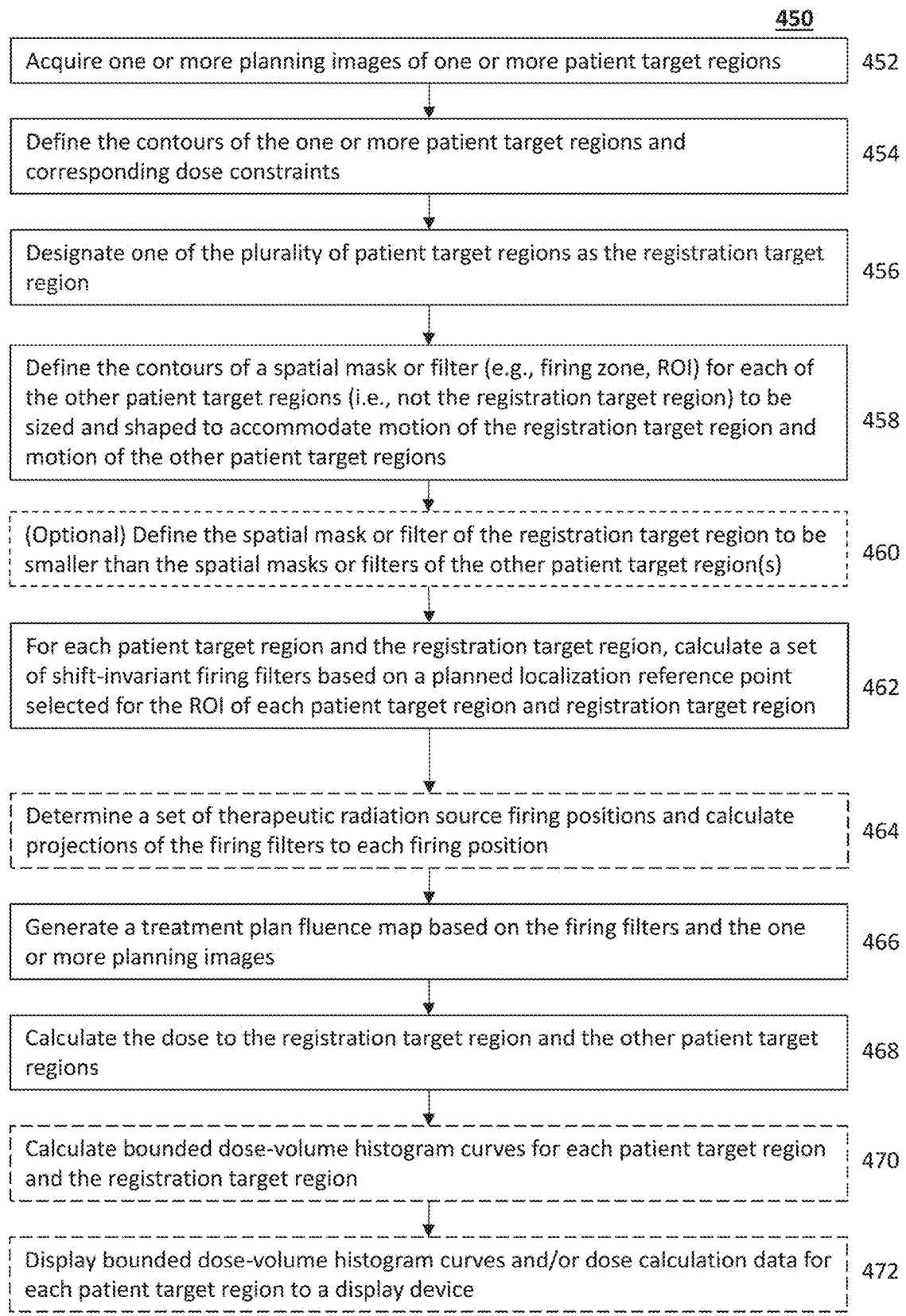
FIG. 4 is a flow chart representation of one variation of a method for treatment planning for BgRT-based localization.

FIG. 4 depicts a flowchart representation of one variation of a treatment planning method that uses BgRT-based multi-target localization for the registration of multiple patient target regions in a treatment session. Method (450) may comprise acquiring (452) one or more treatment planning images of one or more patient target regions, defining (454) the contours of the one or more patient target regions and/or OARs and corresponding dose constraints, designating (456) one of the plurality of patient target regions as the registration target region, and defining (458) the contours of a spatial mask or filter (e.g., ROI, firing zone) for each of the other patient target regions (i.e., not the registration target region) to be sized and shaped to accommodate motion of the registration target region and motion of the other patient target regions. Method (450) may comprise calculating (462) a set of shift-invariant firing filters based on a planned localization reference point selected for the ROI of each patient target region and/or registration target region, generating (466) a treatment plan fluence map based on the firing filters and the one or more planning images, and calculating (468) the dose to the registration target region and the other patient target regions all of the patient target regions. Method (450) may also comprise calculating shift-invariant firing filters such as firing filters for each ROI of each patient target region, which may be calculated as described previously, and the treatment plan fluence map may be generated (466) based on the calculated firing filters along with the one or more planning images. The shift-invariant firing filters for virtual localization of the ROI and/or shift-invariant firing filters for BgRT delivery (e.g., RFMs), the planned localization reference point for each patient target region and/or OAR, and/or any treatment plan fluence maps and/or dose calculations may be transferred (along with other treatment plan parameters) to the radiotherapy system for localization and radiation delivery.

Optionally, some treatment planning methods (450) may comprise defining (460) the contours of a spatial mask or filter (e.g., firing zone, ROI) for the registration target region to be smaller than the spatial masks or filters of the other patient target region(s). For example, the ROI of the registration target region may be smaller than the ROIs of the other patient target regions. In some variations, the patient target region that is selected to be the registration target region may be the patient target region that is closest to a critical structure, such as a highly-radiation sensitive organ, and/or a PET-avid critical structure, and/or a bony structure. In some variations, the patient target region that is selected to be the registration target region may be the target region that is closest to a planning structure (e.g., computed or user-selected), such as an area of potential dose junctioning between two patient target regions. In some variations, the patient target region that is selected to be the registration target region may be the most sensitive to uncertainty, such as a region with a high dose gradient, critical dosimetric objectives or constraints, inconsistent PET activity (e.g., regions of hypoxia or perfusion), or a variable motion trajectory near the edges of the ROI.

Optionally, some methods (450) may comprise determining (464) a set of therapeutic radiation source firing positions and calculating projections of the firing filters to each of the firing positions. For example, a radiotherapy system with a rotatable gantry may have 100 circumferentially distributed firing positions or angle around a bore through which the patient platform may be advanced. Method (450) may comprise calculating projections of each of the firing filters to each of the 100 firing positions. Optionally, method (450) may comprise calculating (470) bDVH curves for each patient target region and/or OAR, and displaying (472) the bDVH curves and/or dose calculation data for each patient target region and/or OAR to a display device. bDVH curves for a patient target region may be calculated as previously described.

Figure 5A:
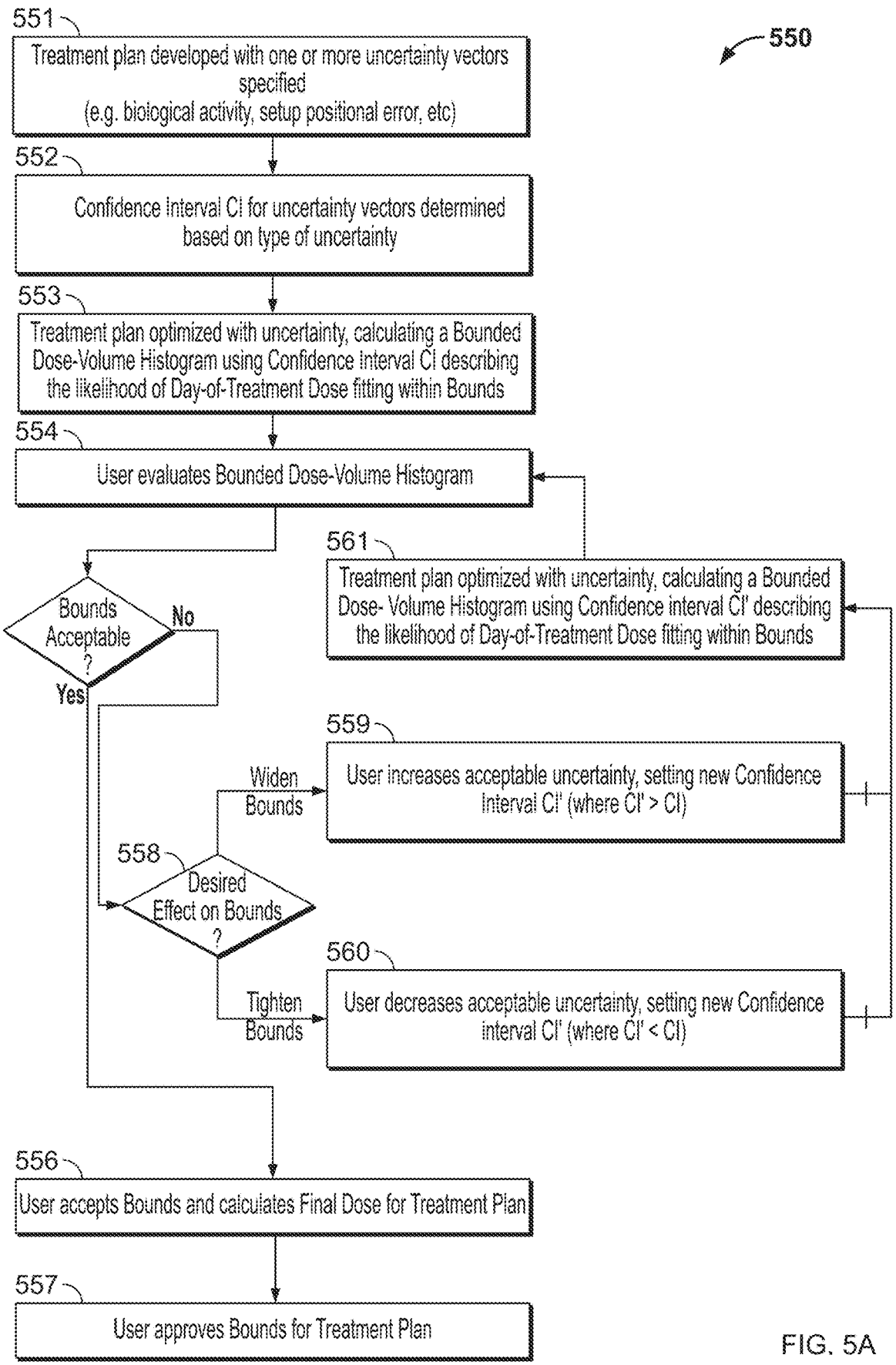
FIG. 5A is a flow chart representation of one variation of a method for treatment planning.
Figure 5B:
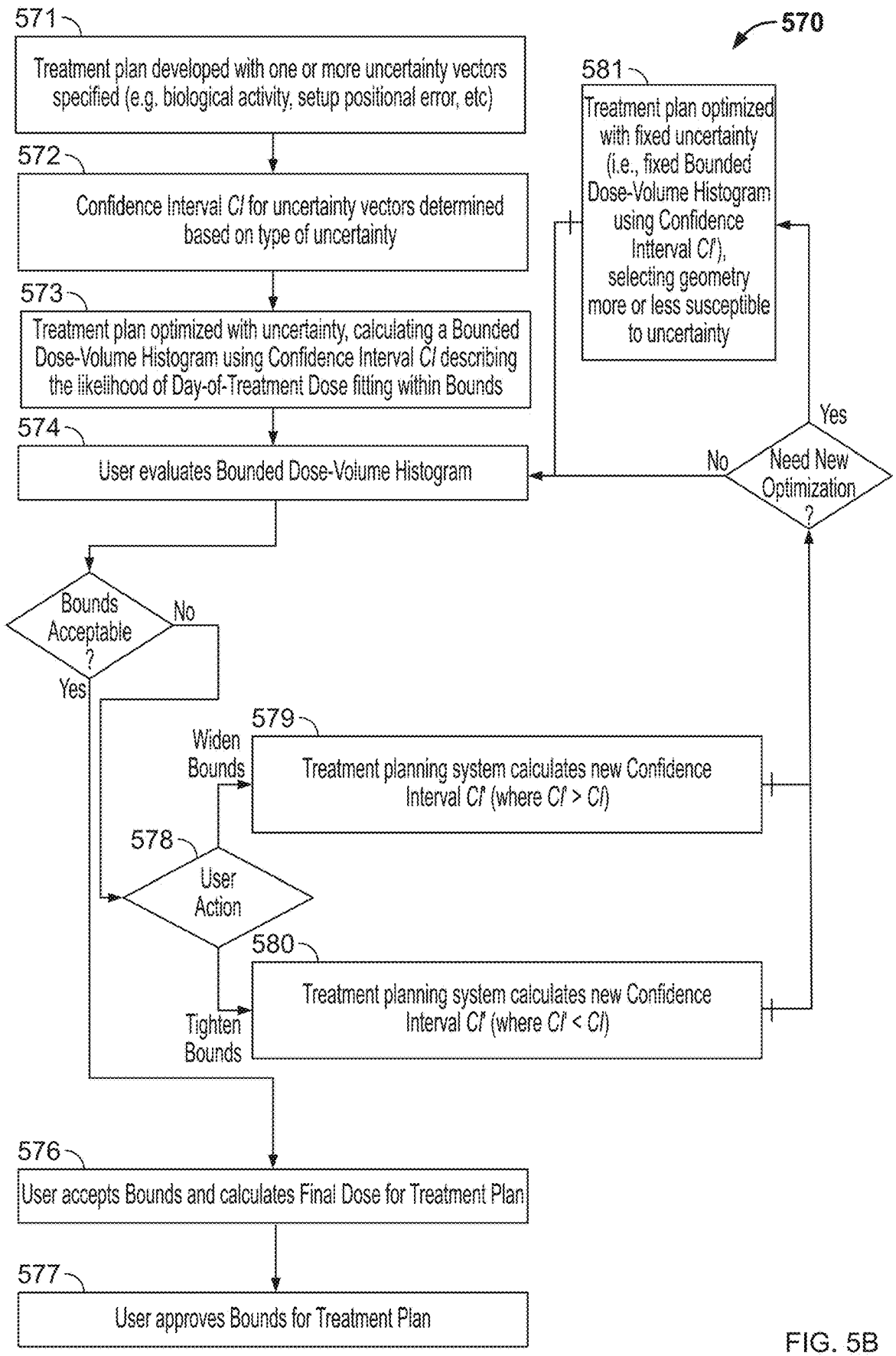
FIG. 5B is a flow chart representation of one variation of a method for treatment planning.
Figure 5C:
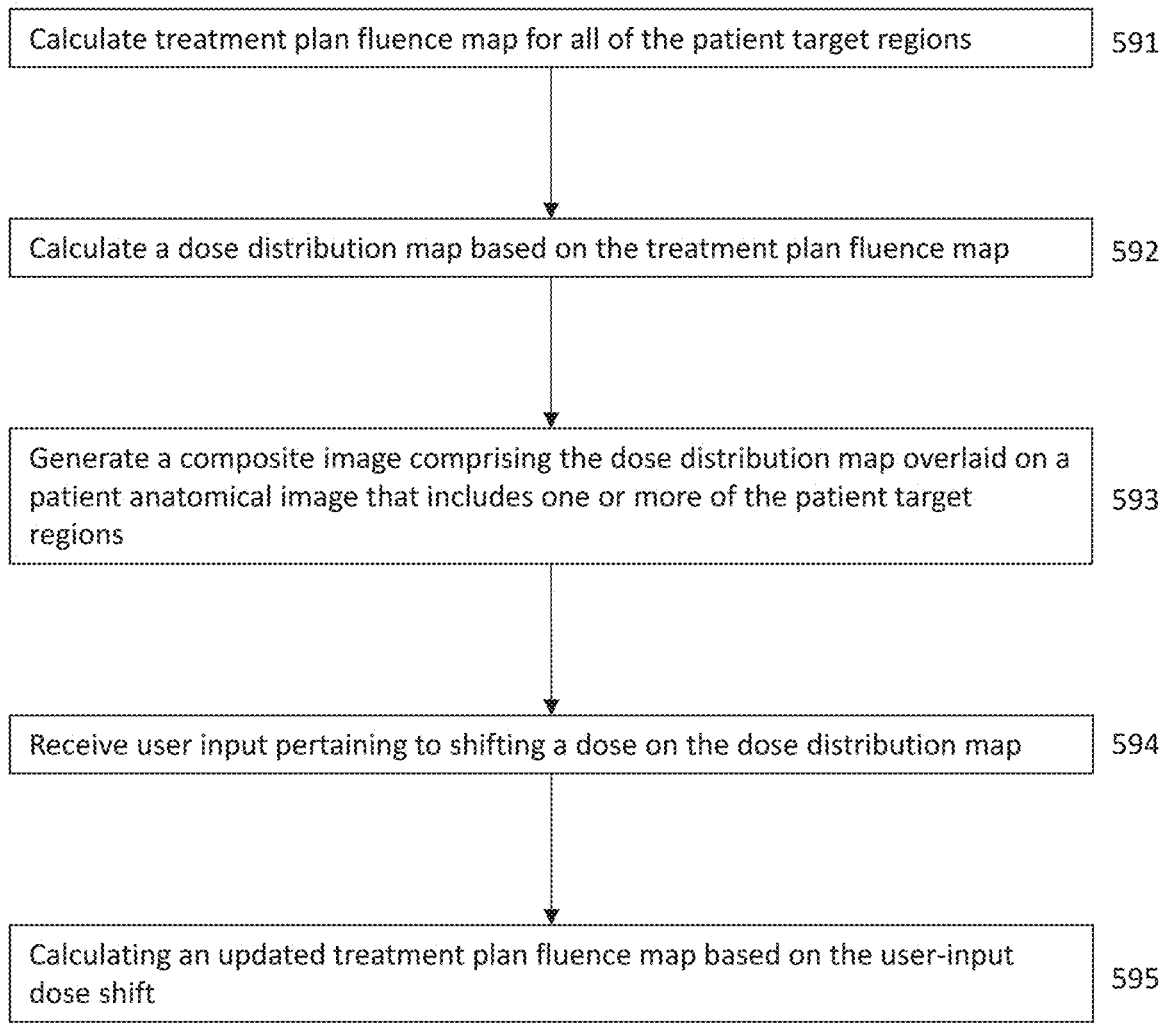
FIG. 5C is a flow chart representation of one variation of a method for treatment planning.

As indicated previously, any of the treatment planning methods for multi-target irradiation may optionally comprise calculating bDVH curves for each patient target region and/or OAR, and displaying DVH and other dose data to a clinician for review and/or approval. In some variations, such dose data may be used to as feedback (i.e., as an additional constraint) to further refine treatment plan fluence maps and/or firing filters that may help improve compliance to dosimetric goals and prescriptions. FIGS. 5A-5C depict flowchart representations of variations of a treatment planning method that modifies the planned fluence map and/or firing filters based on user-selected modifications to the confidence interval of a bDVH for a patient target region and/or shifting a dose distribution.

bDVH Confidence Interval Editing bDVH confidence interval editing may provide a mechanism by which spatial uncertainties may be reduced or eliminated. bDVH calculations may be typically calculated with a 95% confidence interval with the intention that on the day of treatment, the patient will be represented within those bounds. Reducing the width of the bounds in a bDVH is to bring the potential minimum dose $D_{pmin}$ and the potential maximum dose $D_{pmax}$ closer to the nominal dose $D_n$. Methods to reduce the differences from the nominal dose may comprise reducing the confidence interval. For example, an 80% confidence interval may result in a more narrow bDVH curve where $D_{pmax}$ and $D_{pmin}$ may be closer to $D_n$. The trade-off is that instead of expecting, for example, 1 in 20 patients to fail the bDVH safety check at the time of treatment, 1 in 5 patients may fail the bDVH safety check and be rejected for treatment with a non-deterministic treatment method (i.e. BgRT). Similarly, if a target region's bDVH returns as fairly tight upon initial 95% CI calculation, the bDVH may be recalculated with a higher confidence interval (say 99% CI), which would broaden the bDVH, causing $D_{pmin}$ and $D_{pmax}$ to move further away from $D_n$ (i.e., widening/broadening the bDVH curves). Using this functionality, clinicians may be able to reduce or eliminate hot spots and cold spots within the existing bounds.

FIG. 5A depicts a treatment planning method that includes bDVH confidence interval editing. Method (550) may comprise developing (551) a treatment plan with one or more specified uncertainty vectors (e.g., biological activity, setup positional errors, etc.) and selecting (552) a confidence interval (CI) for uncertainty vectors that may be determined based on the type of uncertainty. Method (550) may comprise optimizing (553) the treatment plan fluence map with uncertainty, calculating a bDVH using the CI describing the likelihood of day-of-treatment dose fitting within the bDVH bounds and evaluating (554) the bDVH and determining whether the bounds are acceptable. For example, the bDVH may be output to a display device and viewed by a user. If the bounds are deemed acceptable, method (550) may comprise calculating (556) the final dose for the treatment plan and approving (557) the bounds for the treatment plan. If the bounds are not acceptable, method (550) may comprise determining (558) how to adjust the bounds. In some variations, method (550) may comprise widening the bounds and increasing (559) the acceptable uncertainty and setting a new CI that is greater than the original CI. In some variations, method (550) may comprise tightening the bounds and decreasing (560) the acceptable uncertainty and setting a new CI that is less than the original CI. After the CI has been adjusted, method (550) may comprise optimizing (561) the treatment plan with uncertainty, calculating a new bDVH using the new CI describing the likelihood of day-of-treatment dose fitting within the bDVH bounds, and then evaluating (554) the new bDVH and determining whether the bounds are acceptable. The evaluation and calculation of the bDVH (554-561) may be iterated until a bDVH with acceptable bounds has been calculated.

In some variations, confidence interval editing may comprise determining whether re-optimizing the treatment plan fluence map is needed after the CI have been adjusted. FIG. 5B depicts a treatment planning method that includes a determination as to whether to re-optimize after bDVH confidence interval editing. Method (570) may comprise developing (571) a treatment plan with one or more specified uncertainty vectors (e.g., biological activity, setup positional errors, etc.) and selecting (572) a confidence interval (CI) for uncertainty vectors that may be determined based on the type of uncertainty. Method (570) may comprise optimizing (573) the treatment plan fluence map with uncertainty, calculating a bDVH using the CI describing the likelihood of day-of-treatment dose fitting within the bDVH bounds and evaluating (574) the bDVH and determining whether the bounds are acceptable. For example, the bDVH may be output to a display device and viewed by a user. If the bounds are deemed acceptable, method (570) may comprise calculating (576) the final dose for the treatment plan and approving (577) the bounds for the treatment plan. If the bounds are not acceptable, method (570) may comprise determining (578) how to adjust the bounds. In some variations, method (570) may comprise widening the bounds and increasing (579) the acceptable uncertainty and setting a new CI that is greater than the original CI. In some variations, method (570) may comprise tightening the bounds and decreasing (580) the acceptable uncertainty and setting a new CI that is less than the original CI. After the CI has been adjusted, method (570) may comprise determining whether a new optimization is needed. If so, method (570) may comprise optimizing (581) the treatment plan with uncertainty, calculating a new bDVH using the new CI describing the likelihood of day-of-treatment dose fitting within the bDVH bounds, and then evaluating (574) the new bDVH and determining whether the bounds are acceptable. If it is determined that optimization is not needed, method (570) may proceed from the CI adjustment directly to evaluating (574) the new bDVH. The evaluation and calculation of the bDVH (574-581) may be iterated until a bDVH with acceptable bounds has been calculated. In some variations, a visualization graphic may optionally be included to represent the effect on the bDVH due to changes to the CI.

Some treatment planning methods may comprise displaying treatment plan dose distributions (e.g., calculated from treatment plan fluence map(s)) overlaid on a patient anatomical image that also includes each of the patient target regions to be treated in a treatment session, receiving clinician input pertaining to a dose shift, and re-calculating treatment plan fluence maps and/or firing filters based on the clinician-input dose shift. In some variations, the dose shift may be a rigid shift of the dose by about 0.1 mm to about 1 mm in any direction. These minor dose shifts may help avoid unwanted fluence delivery to the spine and/or to reduce a hot spot caused by two interacting fluence maps between two in-plane target regions. For example, when fluence map sub-regions are separately localized in mosaic multi-target localization, and/or when individual fluence maps of different patient target regions are separately localized in de-coupled multi-target localization, the cumulative delivery fluence map (i.e., the sum of all the delivery fluence map sub-regions and/or the sum of all the individual fluence maps for each patient target region) may have areas with unwanted fluence, such as elevated fluence levels at OARs or healthy tissue regions. These areas of unwanted fluence may not have been present in the planned fluence maps, however, with the fluence map changes (e.g., shifts) enacted during localization, unfavorable fluence map artifacts may emerge in the delivery fluence maps. The radiotherapy system may generate a visualization graphic that reflects these fluence map changes (and/or dose changes) overlaid with an anatomical image of the patient so that the user may decide whether any of the delivery fluence maps may be shifted in order to mitigate any unwanted dose or fluence. Alternatively or additionally, in some variations, the dose shift may be performed after fluence map optimization during treatment planning, which may help facilitate the generation of a treatment plan and/or planned fluence map that meets dosimetric goals. After the dose shift, an additional fluence map optimization step may be optional (i.e., re-optimization may not be necessary). The updated fluence maps and/or firing filters may be transmitted to the radiotherapy system for localization and treatment.

FIG. 5C is a flowchart depiction of one variation of a treatment planning method (590) comprising calculating (591) a treatment plan fluence map (and/or firing filters, such as any described herein) for all of the patient target regions, calculating (592) a dose distribution map based on the treatment plan fluence map, generating (593) a composite image comprising the dose distribution map overlaid on a patient anatomical image that includes one or more of the patient target regions, receiving (594) user (e.g., clinician, dosimetrist) input pertaining to shifting a dose on the dose distribution map, and calculating (595) an updated treatment plan fluence map based on the user-input dose shift. Fluence map optimization after the dose shift may be optional.

Figure 6:
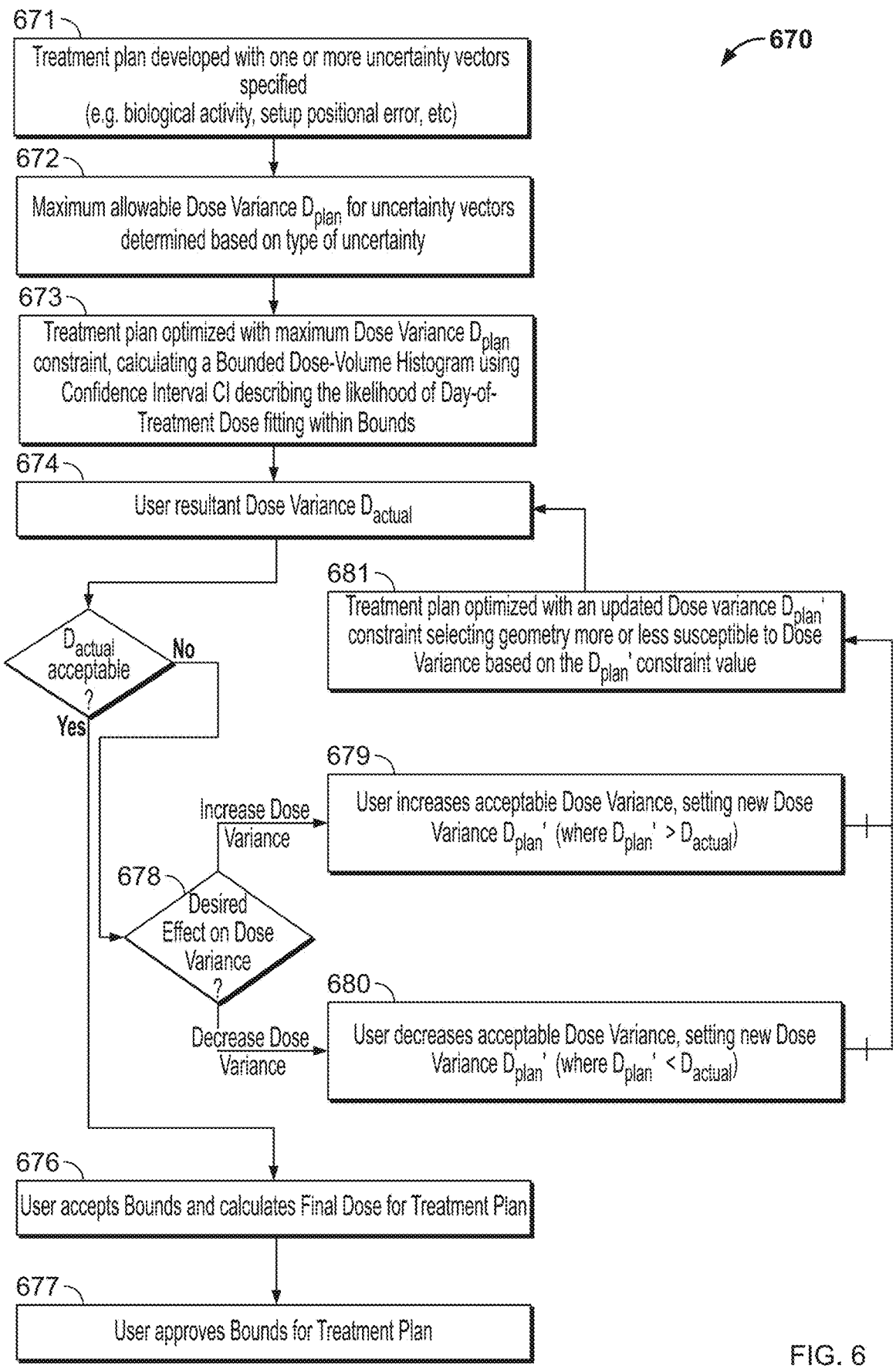
FIG. 6 is a flow chart representation of one variation of a method for treatment planning.

In some treatment planning methods, dose variance (a.k.a. delta dose) may be used as a constraint for optimizing the treatment plan fluence map. A minimum or maximum allowable dose variance may be selected as a constraint. For example, setting a maximum dose variance as treatment plan fluence map optimization constraint may help to reduce the width of the bDVH while maintaining a default confidence interval (e.g., CI=95%). FIG. 6 depicts a treatment planning method that includes setting dose variance as a constraint for generating a treatment plan fluence map. Method (670) may comprise developing (671) a treatment plan with one or more specified uncertainty vectors (e.g., biological activity, setup positional errors, etc.) and selecting (672) a maximum allowable dose variance $D_{plan}$ for uncertainty vectors that may be determined based on the type of uncertainty. Method (670) may comprise optimizing (673) the treatment plan fluence map with maximum allowable dose variance $D_{plan}$, calculating a bDVH using a CI describing the likelihood of day-of-treatment dose fitting within the bDVH bounds, and evaluating (674) the user resultant dose variance $D_{actual}$ and determining whether $D_{actual}$ is acceptable. If $D_{actual}$ is deemed acceptable, method (670) may comprise calculating (676) the final dose for the treatment plan and approving (677) the dose variance for the treatment plan. If $D_{actual}$ is not acceptable, method (670) may comprise determining (678) how to adjust the dose variance. In some variations, method (670) may comprise increasing (559) the acceptable dose variance and setting a new dose variance $D_{plan}'$ that is greater than the original $D_{plan}$. In some variations, method (670) may comprise t decreasing (580) the acceptable dose variance and setting a new dose variance $D_{plan}'$ that is less than the original Dian. After the $D_{plan}$ has been adjusted, method (670) may comprise optimizing (681) the treatment plan with the updated dose variance $D_{plan}'$ constraint, selecting geometry more or less susceptible to dose variance based on the $D_{plan}'$ constraint value, and then evaluating (674) the new $D_{actual}$ and determining whether the dose variance is acceptable. The evaluation and calculation of the dose variance (674-681) may be iterated until an acceptable dose variance has been calculated.

Multi-Target Localization Methods

Methods for virtual localization shift a planned fluence map for a patient target region to reflect the current/real-time location of that patient target region at the time of treatment. During treatment planning, a set of shift-invariant firing filters calculated based on a planned localization reference point and desired dosimetric goals may be calculated, and at a treatment session, the shift-invariant firing filters may be used to calculate a delivery fluence that results in the delivery of the dose to that patient treatment region. A method for virtual localization may comprise selecting a localization reference point that corresponds with the planned localization reference point. For example, if the planned localization reference point is the center of the patient target region, during localization, the localization reference point should also be selected as the center of the patient target region as reflected in the localization image. Then, a localization function (such as a delta function, Gaussian function, truncated Gaussian function, etc.) based on the selected localization reference point may be calculated. For example, the localization function may be a delta function, which may be an impulse function that is centered over the localization reference point, or the localization function may be a Gaussian function with a width (a) selected during treatment planning and where the average value (y) is centered over the localization reference point. The delivery fluence for every firing position of the therapeutic radiation source (which may be predetermined by the treatment plan) may be calculated by convolving a projection of the delta function on that firing position with a projection of the shift-invariant firing filter on that firing position. The delivery fluence for every firing position for that patient target region may then be segmented into radiotherapy system machine instructions for radiation delivery.

Figure 7A:
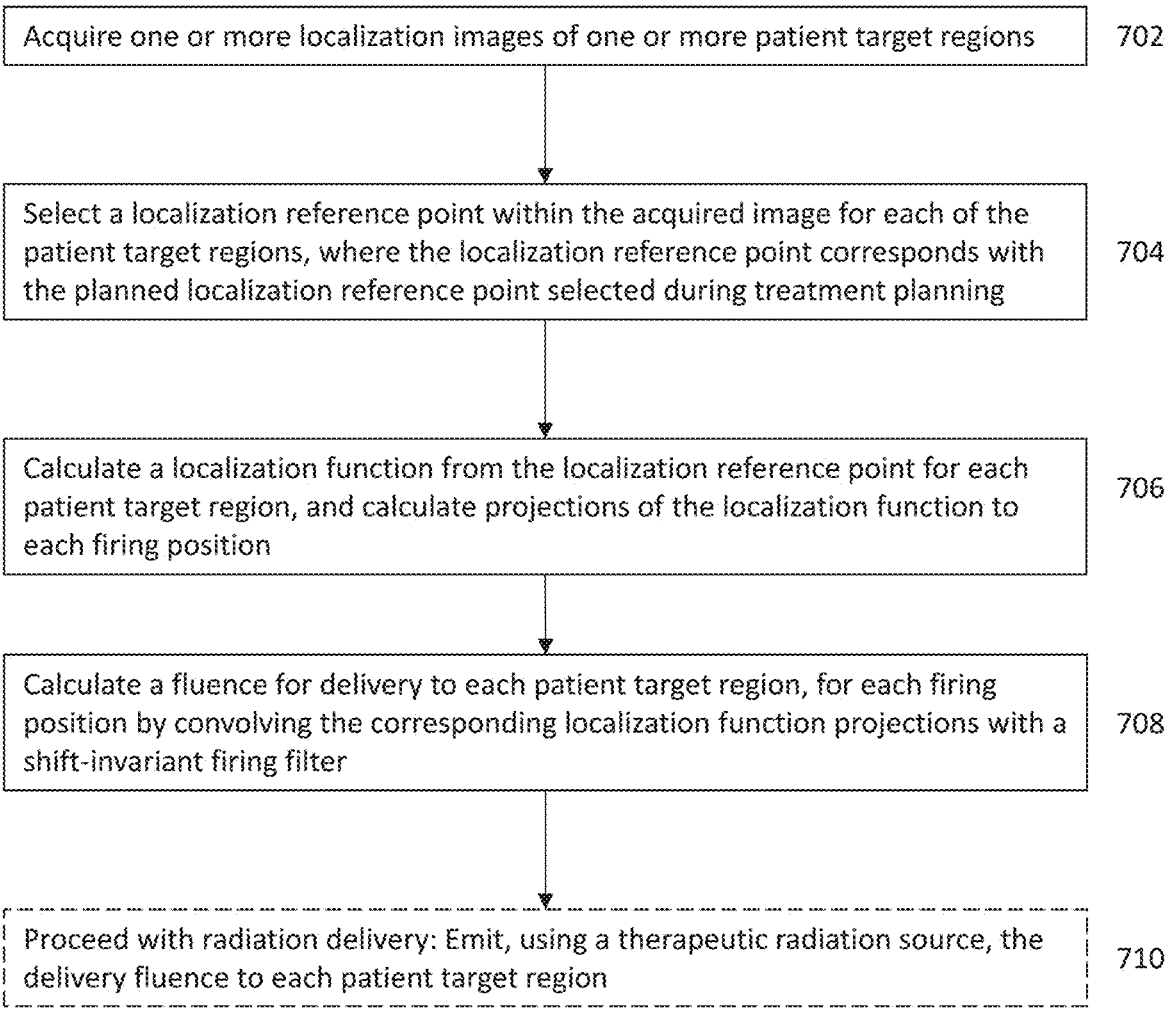
FIG. 7A is a flow chart representation of one variation of a method for virtual localization.

FIG. 7A depicts a flowchart representation of one variation of a method for virtual localization for SBRT/IMRT delivery. This method may be used for the virtual localization of a single patient target region or for multiple patient target regions, and may be used at the beginning of a treatment session or multiple times throughout the treatment session. In some variations, a treatment plan may comprise multiple treatment areas that each have one or more patient target regions. The patient may be physically setup/localized once for treatment area, and each of the patient target regions within a treatment area may be virtually localized. In some variations where groups of patient target regions have been defined during treatment planning, each group may share a single localization reference point and virtually localized together. Method (700) may comprise acquiring (702) one or more localization images of one or more patient target regions, selecting (704) a localization reference point within the acquired image for each of the patient target regions, where the localization reference point corresponds with the planned localization reference point selected during treatment planning, calculating (706) a localization function (e.g., delta, Gaussian, truncated Gaussian, etc.) from the localization reference point for each patient target region and calculating projections of the localization function to each therapeutic radiation source firing position, and calculating (708) a fluence for delivery to each patient target region, for each firing position by convolving the corresponding localization function projections with a shift-invariant firing filter derived based on the planned localization reference point. As described above, in some variations, the fluence for delivery for each firing position of the therapeutic radiation source may be calculated by convolving the projections of the localization function and the firing filters on each firing position. Optionally, method (700) may comprise proceeding (710) with radiation delivery (i.e., emit, using a therapeutic radiation source, the delivery fluence to each patient target region). The shift-invariant firing filters may be calculated during treatment planning based on (e.g., centered around) the planned localization reference point. In some variations, the localization function may be delta function, and the shift-invariant firing filters calculated during treatment planning may represent fluence maps (e.g., planned fluence maps) that are centered around the planned localization reference point. In this example, calculating (708) a fluence for delivery may comprise convolving the calculated delta function (which is centered around the selected localization reference point) with the shift-invariant firing filters, which may result in a delivery fluence map that is a shift of the planned fluence map. In some variations, the radiotherapy system may segment the delivery fluence maps into machine instructions in real-time, i.e., minutes or seconds prior to radiation delivery. The patient target regions to be localized may be included in a single localization image, or may be included in multiple localization images acquired at the beginning of the treatment session and/or throughout the session. For example, a first patient target region may be identified in a first image and a second patient target region may be identified in a second image. These images may be separate images, acquired at separate times or at the same time, or may be sub-regions of a single image. The planned localization reference point may be the treatment isocenter, however, in some variations, the planned localization reference point may be not be the treatment isocenter and may be any point selected by the user. The localization reference point may be designated by coordinates. The localization function used to localize the patient target region may be an impulse function or peak or pixel that is centered around the selected localization reference point, as previously described. Method (700) may be used with any of the treatment planning methods in FIGS. 1-4, e.g., the method of FIGS. 1A, 1B.

Figure 7B:
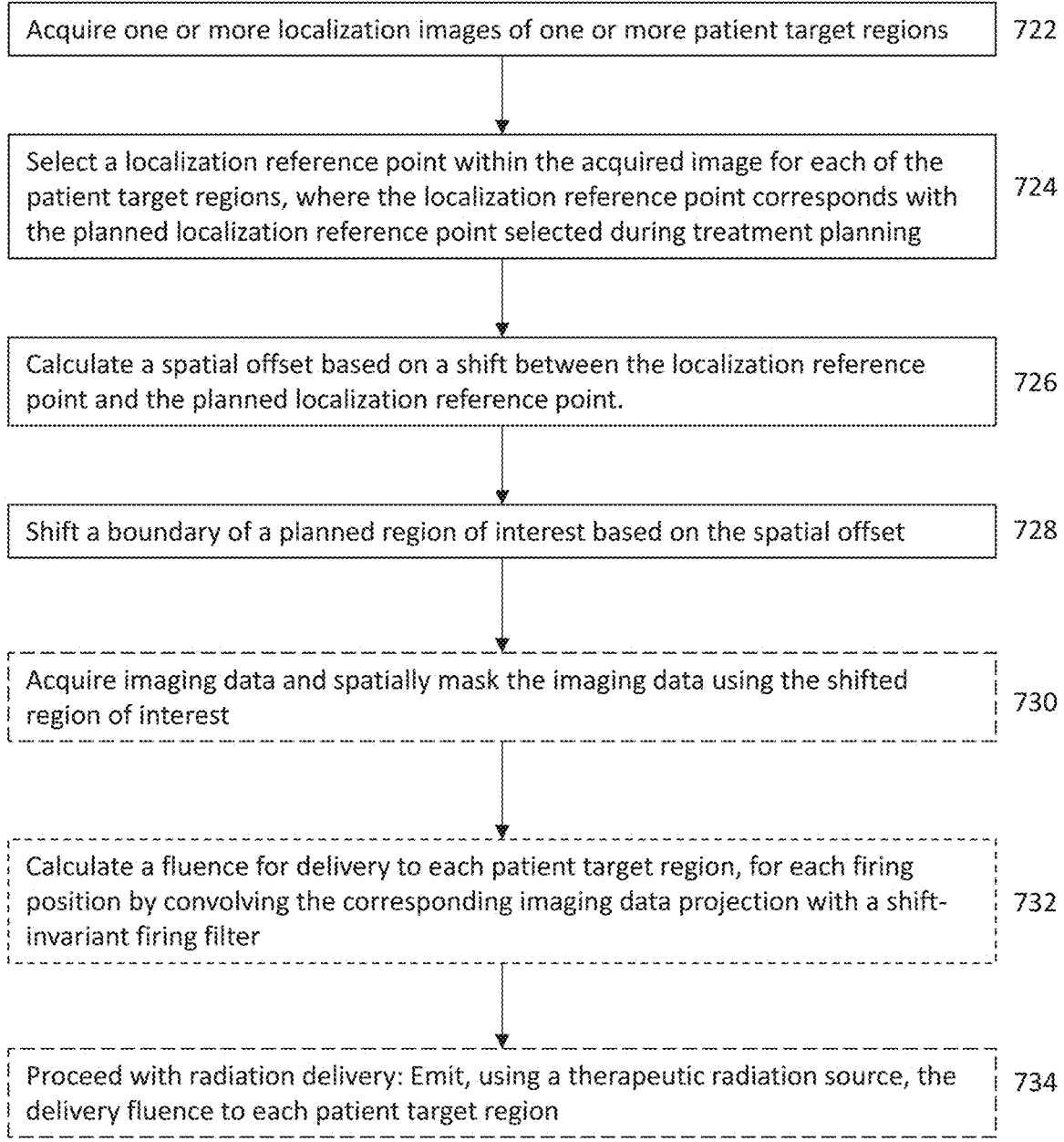
FIG. 7B is a flow chart representation of one variation of a method for virtual localization.

FIG. 7B depicts a flowchart representation of one variation of a method for virtual localization for BgRT delivery to one or more patient target regions. Virtual localization for BgRT patient target regions comprise adjusting the location ROI based on the offset between the planned localization reference point and the localization reference point that is selected during a treatment session. Method (720) may comprise acquiring (722) one or more localization images of one or more patient target regions, selecting (724) a localization reference point within the acquired image for each of the patient target regions, where the localization reference point corresponds with the planned localization reference point selected during treatment planning, calculating (726) a spatial offset based on a shift between the selected localization reference and the planned localization reference point, and shifting (728) a boundary of a planned region of interest (ROI) based on the calculated spatial offset. In some variations, shifting (728) the boundary of the planned region of interest comprises applying a rotation and a shift to the planned region of interest by a roll correction factor (p that represents a rotational translation of the localization reference point relative to the planned localization reference point. The method (720) may further include the steps of acquiring (730) imaging data and spatially masking (e.g., filtering) the imaging data using the shifted region of interest, calculating (732) a fluence for delivery to each patient target region, at each firing position of a therapeutic radiation source by convolving projections of the acquired imaging data with corresponding shift-invariant firing filters, and proceeding (734) with radiation delivery (i.e., emit, using a therapeutic radiation source, the delivery fluence to each patient target region). The acquired imaging data (730) may comprise PET imaging data (e.g., positron annihilation emission paths, LORs), X-ray imaging data, MRI imaging data, ultrasound imaging data, optical imaging data (e.g., from a camera), and the like. Calculating (732) the delivery fluence for a particular firing position may include projecting the acquired, spatially-masked imaging data to that firing position, and convolving the imaging data projection with a firing filter for that firing position and target region. The firing filter may be one of the firing filters that was calculated during treatment planning (e.g., using the method of FIG. 1i). In variations where a roll correction factor has been applied to the planned region of interest, calculating (732) the fluence for delivery may comprise circularly convolving the set of firing filters with the roll correction factor $\varphi$, and in some variations, may comprise shifting the ROI as described above (e.g., as described and depicted in FIG. 34). Method (720) may be used with any of the treatment planning methods in FIGS. 1-4, e.g., the method of FIGS. 1A, 1B.

Figure 8A:
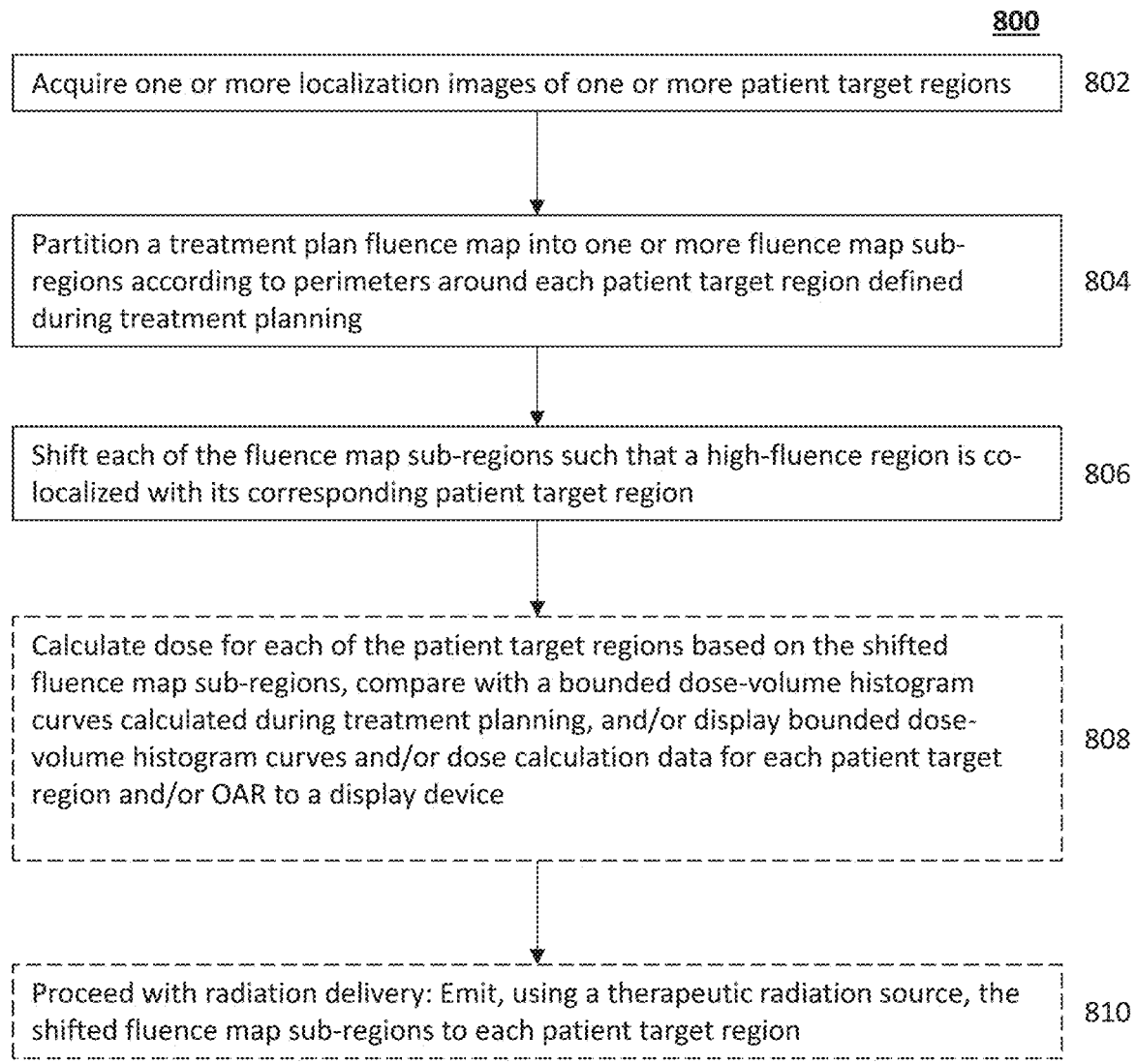
FIG. 8A is a flow chart representation of one variation of a method for mosaic multi-target localization.

FIG. 8A depicts a flowchart representation of one variation of a method for mosaic multi-target localization. This method may be used at the beginning of a treatment session (e.g., to register/localize all of the patient target regions) or multiple times throughout the treatment session (e.g., to register/localize the patient target regions sequentially). Method (800) may comprise acquiring (802) one or more localization images of one or more patient target regions, partitioning (804) a treatment plan fluence map into one or more fluence map sub-regions according to perimeters around each patient target region defined during treatment planning, and shifting (806) each of the fluence map sub-regions such that a high-fluence region is co-localized with its corresponding patient target region. Shifting (806) the fluence map sub-regions may be performed using virtual localization methods described herein (e.g., selecting a localization reference point for each of the patient target regions, calculating a delta function based on the localization reference point, and convolving the delta function with a shift-invariant firing filter). Alternatively or additionally, shifting (806) the fluence map sub-regions may be performed by shifting radiotherapy system machine instructions (e.g., MLC, gantry, linac, jaw, etc.).

Optionally, some variations of the method (800) may comprise calculating (808) dose for each of the patient target regions based on the shifted fluence map sub-regions, comparing the calculated dose with bounded dose-volume histogram curve calculated during treatment planning, and/or displaying bounded dose-volume histogram curves and/or dose calculation data for each patient target region and/or OAR to a display device. Optionally, method (800) may comprise proceeding (810) with radiation delivery (i.e., emit, using a therapeutic radiation source, the delivery fluence to each patient target region). In some variations, the radiotherapy system may segment the delivery fluence maps into machine instructions in real-time, i.e., minutes or seconds prior to radiation delivery. The patient target regions to be localized may be included in a single localization image, or may be included in multiple localization images acquired at the beginning of the treatment session and/or throughout the session, as described above. Method (800) may be used with any of the treatment planning methods in FIGS. 1-4, e.g., the method of FIG. 2.

FIG. 8B depicts a flowchart representation of one variation of a method for mosaic multi-target localization that includes a patient platform shift or adjustment. In some methods, patient setup may comprise adjusting the orientation of the patient platform (e.g., roll, pitch, yaw, x-y-z-translations, and the like) based on the localization images and treatment planning images. This method may be used at the beginning of a treatment session (e.g., to register/localize all of the patient target regions) or multiple times throughout the treatment session (e.g., to register/localize the patient target regions sequentially). Method (820) may comprise acquiring (822) one or more localization images of one or more patient target regions, partitioning (824) a treatment plan fluence map into one or more fluence map sub-regions according to perimeters around each patient target region defined during treatment planning, calculating (826) patient platform position-shift vectors for each fluence map sub-region based on the localization images and the treatment planning images, shifting (828), for each patient platform position, the fluence map sub-regions such that a high-fluence region is co-localized with its corresponding patient target region, and calculating (830) fluence to each patient target region at each patient platform position-shift vector. Shifting (828) the fluence map sub-regions may be performed using virtual localization methods described herein (e.g., selecting a localization reference point for each of the patient target regions, calculating a delta function based on the localization reference point, and convolving the delta function with a shift-invariant firing filter). Alternatively or additionally, shifting (828) the fluence map sub-regions may be performed by shifting radiotherapy system machine instructions (e.g., MLC, gantry, linac, jaw, etc.).

Optionally, some variations of the method (820) may comprise calculating (832) dose for each of the patient target regions based on the shifted fluence map sub-regions, comparing the calculated dose with bounded dose-volume histogram curve calculated during treatment planning, and/or displaying bounded dose-volume histogram curves and/or dose calculation data for each patient target region and/or OAR to a display device. Optionally, method (820) may comprise proceeding (834) with radiation delivery (i.e., emit, using a therapeutic radiation source, the delivery fluence to each patient target region). In some variations, the radiotherapy system may segment the delivery fluence maps into machine instructions in real-time, i.e., minutes or seconds prior to radiation delivery. The patient target regions to be localized may be included in a single localization image, or may be included in multiple localization images acquired at the beginning of the treatment session and/or throughout the session, as described above. Method (820) may be used with any of the treatment planning methods in FIGS. 1-4, e.g., the method of FIG. 2.

Figure 9:
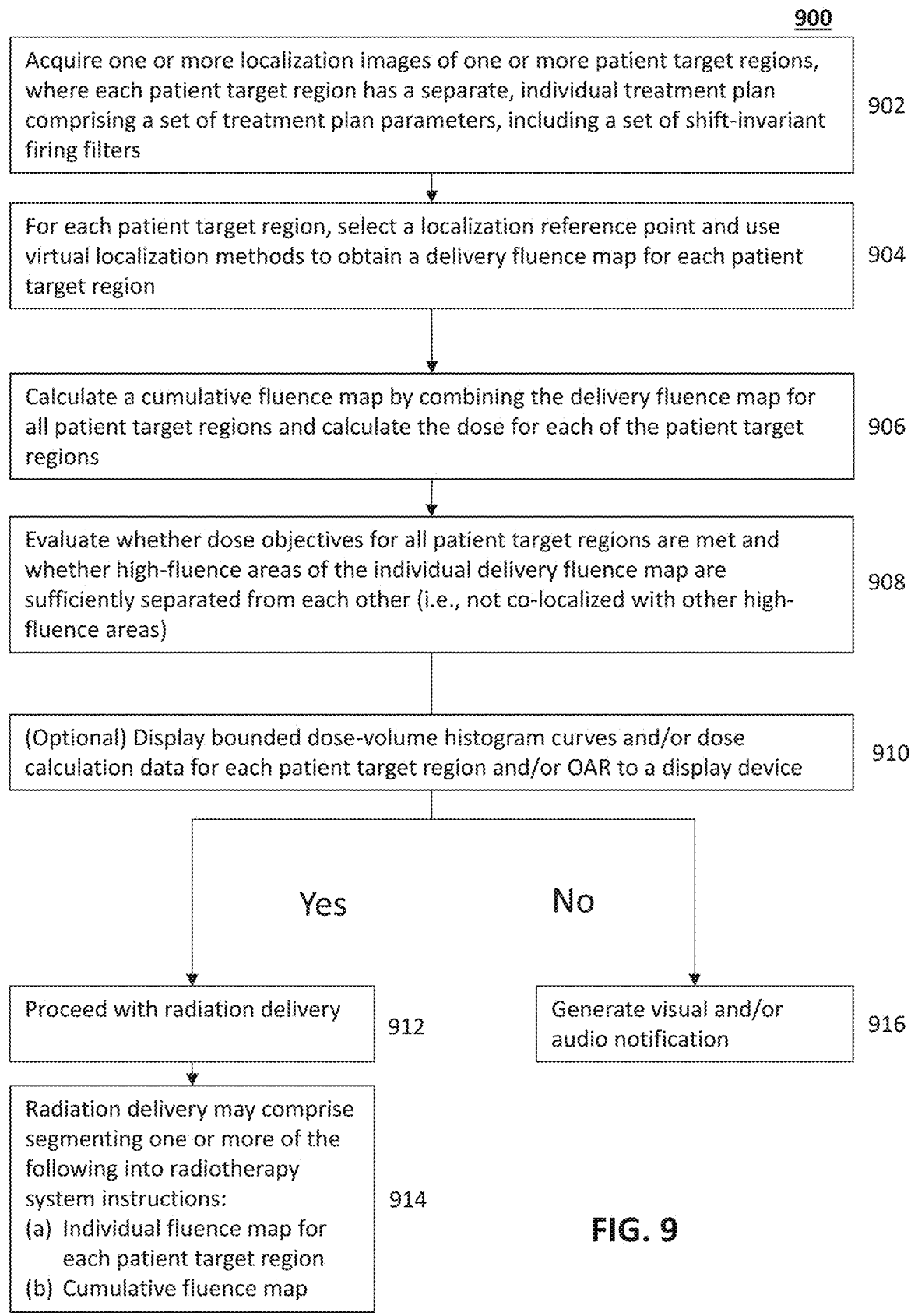
FIG. 9 is a flow chart representation of one variation of a method for de-coupled multi-target localization.

FIG. 9 depicts a flowchart representation of one variation of a method for de-coupled multi-target localization. Method (900) may comprise acquiring (902) one or more localization images of one or more patient target regions, where each patient target region has a separate, individual treatment plan comprising a set of treatment plan parameters, including a set of shift-invariant firing filters, selecting (904), for each patient target region, a localization reference point and using virtual localization methods (e.g., calculating a delta function based on the localization reference point, and convolving the delta function with a shift-invariant firing filter to obtain a delivery fluence map for each patient target region) to calculate a delivery fluence map for each target region, and calculating (906) a cumulative fluence map by combining the delivery fluence map for all patient target regions and calculate the dose for each of the patient target regions. Method (900) may comprise evaluating (908) whether dose objectives for all patient target regions are met and/or whether high-fluence areas of the individual delivery fluence map are sufficiently separated from each other (i.e., not co-localized with other high-fluence areas). If dose objectives for all patient target regions are met and/or high-fluence areas of the individual delivery fluence map are sufficiently separated from each other, method (900) may comprise proceeding (912) with radiation delivery, which may comprise segmenting (914) one or more of the following into radiotherapy system instructions: (a) individual fluence map for each patient target region; and/or (b) cumulative fluence map. If dose objectives for all patient target regions are not met, and/or high-fluence areas of the individual delivery fluence map are not sufficiently separated from each other, method (900) may comprise generating (916) a visual and/or audio notification. The user may optionally be presented with the dose calculation data and/or DVH curves so that they may evaluate the next course of action. In some variations, the radiotherapy system may segment the delivery fluence maps into machine instructions in real-time, i.e., minutes or seconds prior to radiation delivery. The patient target regions to be localized may be included in a single localization image, or may be included in multiple localization images acquired at the beginning of the treatment session and/or throughout the session, as described above. Method (900) may be used with any of the treatment planning methods in FIGS. 1-4, e.g., the method of FIGS. 3A-3B.

Figure 10:
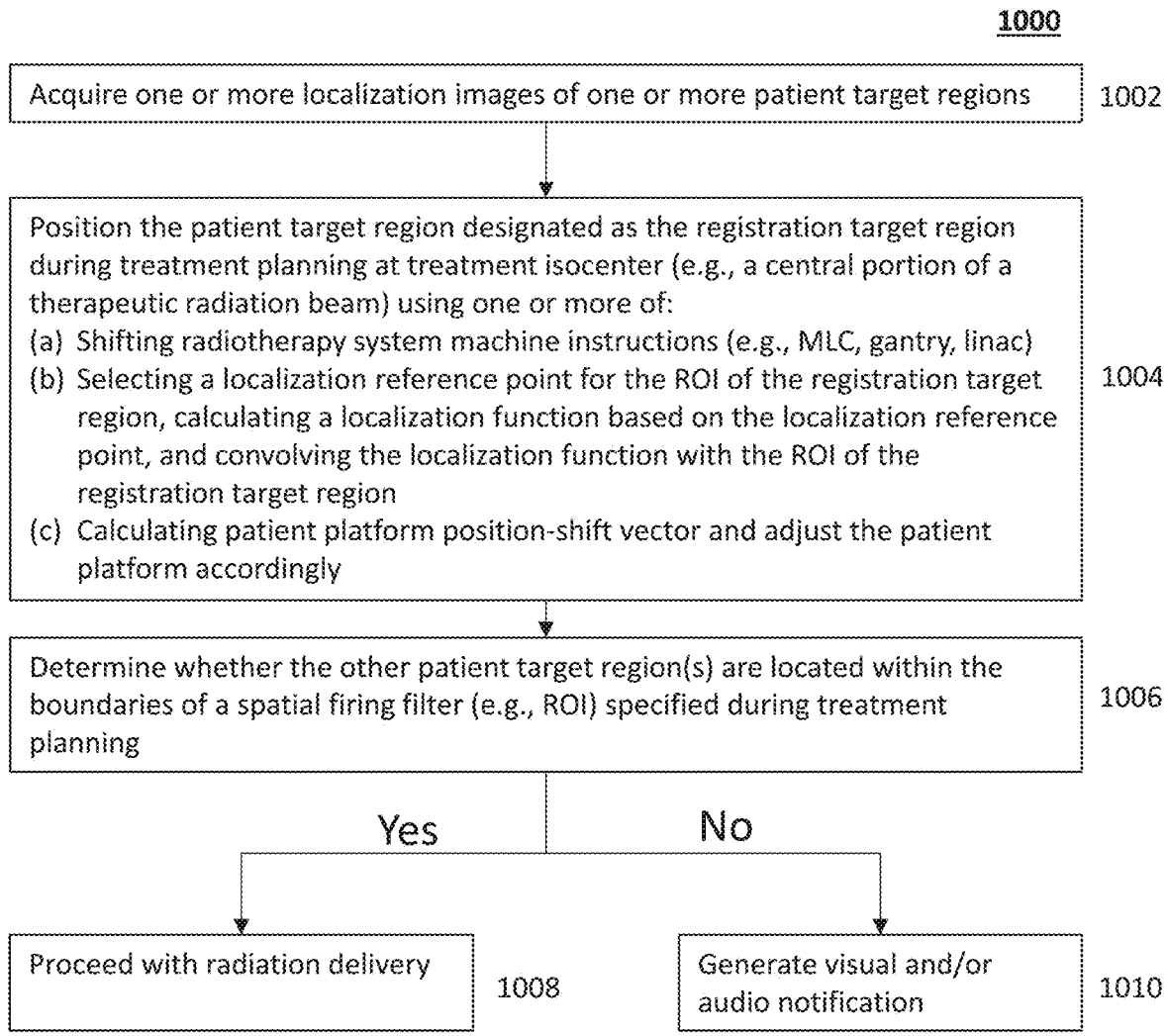
FIG. 10 is a flow chart representation of one variation of a method for BgRT-based localization.

FIG. 10 depicts a flowchart representation of one variation of a method for de-coupled multi-target localization. Method (1000) may comprise acquiring (1002) one or more localization images of one or more patient target regions, positioning (1004) the patient target region designated as the registration target region during treatment planning with treatment isocenter (e.g., a central portion of a therapeutic radiation beam), and determining (1006) whether the other patient target region(s) are located within the boundaries of a spatial firing filter (e.g., firing zone, ROI) specified during treatment planning. If the other patient target region(s) are located within the boundaries of the spatial mask or filter (e.g., located within the ROI), method (1000) may comprise proceeding (1002) with radiation delivery. If the other patient target region(s) are not located within the boundaries of the spatial mask or filter (e.g., not located within the ROI), method (1000) may comprise generating (1010) a visual and/or audio notification. The user may optionally be presented with location data of the patient target regions relative to their associated ROI so that they may evaluate the next course of action. Optionally, the ROI(s) of one or more of these non-registration target regions may be localized using the virtual localization methods described herein. Positioning (1004) the registration target region may use one or more setup and/or localization methods. For example, positioning (1004) the registration target region may comprise one or more of: (a) Shifting radiotherapy system machine instructions (e.g., MLC, gantry, linac), (b) selecting a localization reference point for the ROI of the registration target region, calculating a delta function based on the localization reference point, and convolving the function (e.g., delta, Gaussian, truncated Gaussian) with the ROI, and/or (c) calculating patient platform position-shift vector and adjusting the patient platform accordingly. In some variations, radiation delivery may comprise segmenting one or more of the following into radiotherapy system instructions: (a) individual fluence map for each patient target region; and/or (b) cumulative fluence map. In some variations, the radiotherapy system may segment the delivery fluence maps into machine instructions in real-time, i.e., minutes or seconds prior to radiation delivery. The patient target regions to be localized may be included in a single localization image, or may be included in multiple localization images acquired at the beginning of the treatment session and/or throughout the session, as described above. Method (1000) may be used with any of the treatment planning methods in FIGS. 1-4, e.g., the method of FIG. 4. For example, each of multiple patient target regions may have a separate planned localization reference point and a set of firing filters. During a treatment session, the location of the localization reference point for each of the multiple patient target regions may be updated based on the acquired localization image (e.g., the localization reference point may be user-selected). Separate and/or independent virtual localization of each patient target region based on the updated localization reference point effectively shifts the delivery fluence maps to the real-time location of the multiple patient target regions. In such fashion, the fluence maps for each of the multiple patient target regions may move relative to each other. For example, in a treatment session with two or more patient target regions, a radiation delivery method may comprise performing one or more (e.g., two or more) virtual localizations, shifting the planned fluence maps for each of the two or more patient target regions.

Figure 11A:
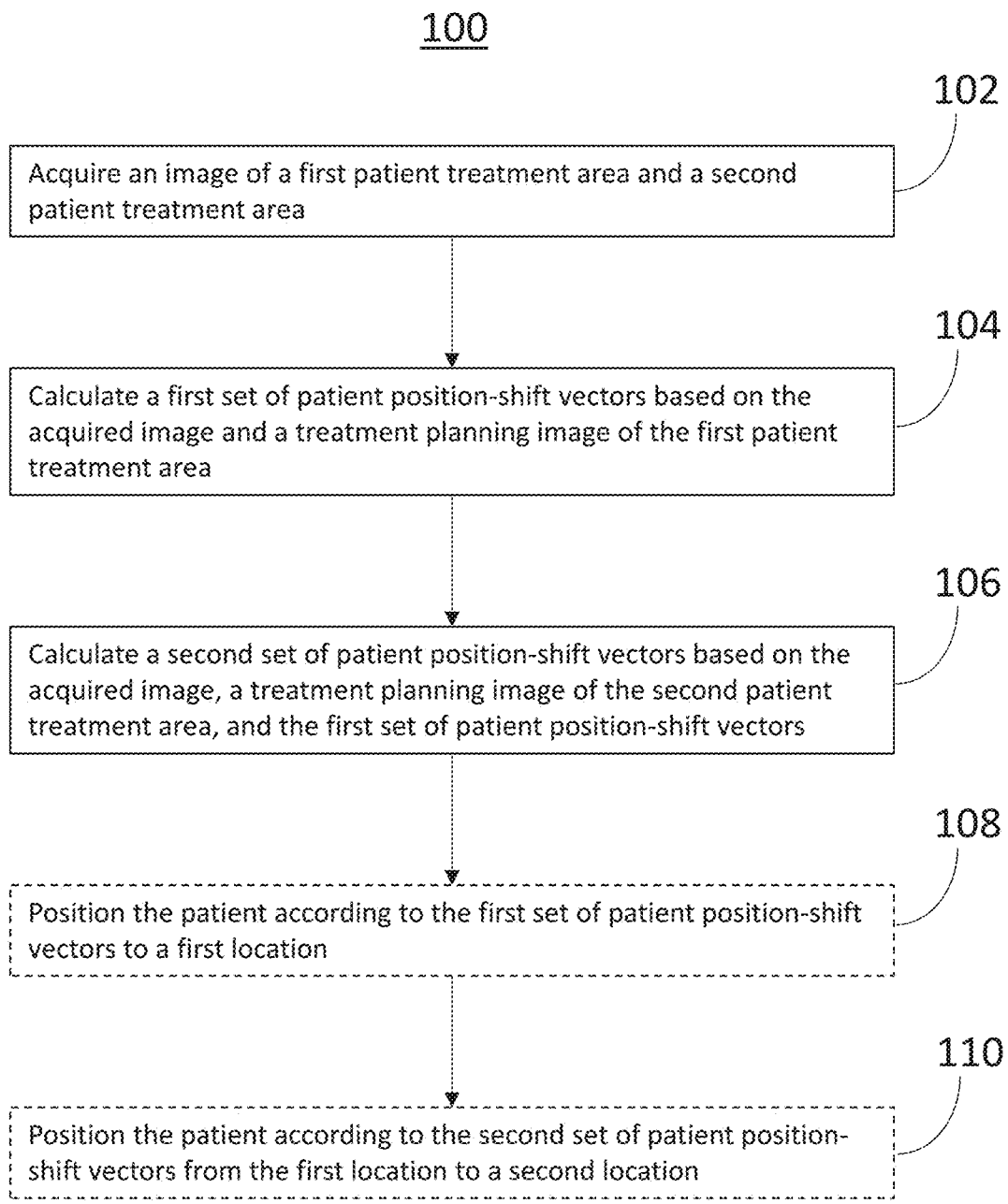
FIG. 11A is a flow chart representation of one variation a method of positioning a patient for radiation therapy.

FIG. 11A is a flow chart illustrating a method (100). The method (100) may be used for positioning a patient for radiation therapy. As shown in FIG. 11A, the method (100) comprises acquiring (102) an image of a first patient treatment area and a second patient treatment area. In some embodiments, the first patient treatment area and the second patient treatment area may comprise one or more tumor regions (e.g., patient target regions). For example, in some embodiments, the first patient treatment area may comprise a first portion of a tumor and the second patient treatment area may comprise a second portion of the tumor. In some embodiments, the first patient treatment area and the second patient treatment area may each comprise one or more discrete tumors located at different regions of the patient's body. The acquired image may be, for example, an image acquired via one or more of PET, CT, MRI, ultrasound, optical imaging modalities, combinations thereof (e.g., surface tracking/map, optical and CT to predict internal positions based on external surface data), and/or any other suitable method. In some embodiments, for example, a CT system may be used to acquire one or more images prior to or at the start of a treatment session. In some embodiments, the CT system may be attached to the same gantry as a radiation source intended for the delivery of radiation therapy during the treatment session. In some embodiments, the CT system may be attached to a separate gantry from the gantry supporting the radiation source. In some embodiments, where radiation is delivered at discrete patient platform locations or positions (i.e., beam stations), the location of the first patient treatment area may correspond to the location of a first beam station of a therapeutic radiation source and the location of the second patient treatment area may correspond to the location of a second beam station. In some variations, the first and second treatment areas may overlap while in other variations, the first and second treatment areas do not overlap.

A first set of patient position-shift vectors may be calculated (104) based on the acquired image and a treatment planning image of the first patient target region (also referred to herein as a "first treatment planning image"). The location of the first treatment area and/or patient target region in the acquired image may be compared with a location of the first treatment area and/or patient target region in the treatment planning image in 2D and/or 3D. For example, in some embodiments, a patient target region may be divided into sub-regions (e.g., sub-volumes) that may be represented by voxels, and the coordinates of each voxel of the acquired image may be compared with the coordinates of a corresponding voxel of the patient target region in the treatment planning image. Each of the vectors of the first set of patient position-shift vectors may represent the distance and directional difference between a coordinate of a voxel of the acquired image and a coordinate of a corresponding voxel of the treatment planning image. In some embodiments, the directional difference may include tilt angles. In some embodiments, the first set of patient position-shift vectors may be calculated by moving the acquired image relative to the treatment planning image to align or register the first patient target region of the treatment planning image with the first patient target region of the acquired image. For example, each voxel of the acquired image may be translated along or about the X, Y, and/or Z axes, maintaining the relative positions of each voxel of the acquired image to one another during movement of the acquired image, until the acquired image and the treatment planning image are approximately aligned with respect to the first patient target region (e.g., aligned within a predetermined acceptable tolerance or margin such that there is an acceptable area or proportion of overlap between the first patient target region in the images). The first set of patient position-shift vectors may then be calculated based on locational and/or positional differences between the acquired image before and after being moved into increased alignment with the treatment planning image. The first set of patient position-shift vectors may reflect the distance and/or direction each voxel of the acquired image is to be translated for acceptable alignment between the first patient target region of the acquired image and the first patient target region of the treatment planning image. Furthermore, the first set of patient position-shift vectors may include or correspond to instructions related to a first position and/or a first orientation of the patient (e.g., a first position and/or a first orientation of a surface on which the patient is disposed) so that the first patient target region of the patient is located in approximately the position that the first patient target region was in when the treatment planning images were acquired. This may facilitate the delivery of therapeutic radiation to the patient target region more closely to the treatment plan. Additionally, the first set of patient position-shift vectors may include information regarding any tilt, pitch, yaw, and/or roll corrections needed to be implemented via positioning of the patient platform and/or via adjusting the roll of a gantry to which the radiation source (e.g., a therapeutic radiation source) is coupled (e.g., for correcting a gantry firing position) such that the location of the first patient target region approximates the location of the first patient target region in the first treatment planning image.

In some embodiments, the acquired image of the first treatment area and/or patient target region and the treatment planning image of the first patient target region may each be a two-dimensional image. The two-dimensional acquired image may be compared to the two-dimensional treatment planning image to calculate the first set of patient position-shift vectors. In some embodiments, a plurality of two-dimensional images of the first treatment area and/or patient target region may be acquired along different orientations or planes (e.g., three or more orientations or planes), and the images may be compared to corresponding treatment planning images of the first patient target region that have been acquired along the same orientations or planes. Changes with respect to the position of the first patient target region along each image plane at each orientation may be used to calculate the first set of patient position-shift vectors. For example, the acquired images may include an acquired axial image, an acquired sagittal image, and an acquired coronal image of the first patient target region of the patient. When the patient is lying on a surface such as a patient platform or treatment couch in a supine position with the patient oriented such that the patient will encounter the therapeutic radiation source head first, the acquired axial image may be taken along an axial plane of the patient (e.g., the plane dividing the body into superior and inferior portions), the acquired sagittal image may be taken along a sagittal plane of the patient (e.g., the plane dividing the patient into right and left portions), and the acquired coronal image may be taken along a coronal plane of the patient (e.g., the plane dividing the patient into ventral and dorsal portions). The axial plane is disposed perpendicularly to the sagittal plane, and the coronal plane is disposed perpendicularly to both the axial plane and the sagittal plane. The treatment planning images may include a treatment planning axial image, a treatment planning sagittal image, and a treatment planning coronal image of the first patient target region of the patient. Thus, the acquired axial image corresponds to the treatment planning axial image, the acquired sagittal image corresponds to the treatment planning sagittal image, and the acquired coronal image corresponds to the treatment planning coronal image.

The amount the patient position and/or orientation should be adjusted along or about each of the X-, Y-, and Z-axes (e.g., via movement of the patient surface and/or rotating the radiation source) for treatment of the first patient target region may be reflected by the first set of patient position-shift vectors based on the differences between the treatment planning images and the respective acquired images taken within each of the axial, sagittal, and coronal planes of the patient. In some embodiments, the X-axis of the patient surface may be parallel to the intersection of the sagittal plane and the coronal plane of the patient and may be disposed in the sagittal plane. The Y-axis of the patient surface may be parallel to the intersection of the axial plane and the coronal plane of the patient and may be disposed in the axial plane. The Z-axis of the patient surface may be parallel to the intersection of the sagittal plane and the axial plane of the patient and may be disposed in the sagittal plane or the axial plane of the patient. To determine the first set of patient position-shift vectors, each of the acquired images of the first patient target region may be compared to a respective treatment planning image of the first patient target region taken within the same plane to determine a distance correction and/or rotation correction of the patient (e.g., via movement of the patient surface and/or rotation of the radiation source) within the same plane. One or more vectors of the first set of patient position-shift vectors may represent a magnitude and direction that the patient surface is to be moved (e.g., shifted and/or rotated) such that the first patient target region approximates the location of the first patient target region in the treatment planning images. One or more vectors of the first set of patient position-shift vectors may also represent a magnitude and direction that the radiation source may be moved (e.g., rotated on a gantry) such that the location of the first patient target region approximates the location of the first patient target region in the treatment planning images. In some embodiments, the first set of patient position-shift vectors may reflect up to six corrections (i.e., the amount of adjustment along or about each of the X-, Y-, and Z-axes of the patient platform). In some embodiments, DICOM Spatial Registration Objects (SROs) may be used to determine each of the six corrections (i.e., the amount of adjustment along or about each of the X-, Y-, and Z-axes of the patient platform) associated with the first set of patient position-shift vectors.

In some embodiments, the first set of patient position-shift vectors may be calculated by moving (e.g., via shifting and/or rotating) each acquired image relative to its respective treatment planning image to align or register the first treatment area and/or patient target region of the treatment planning image with the first patient target region of the acquired image. Each acquired image may be shifted a particular distance and/or rotated a particular amount to improve the registration of the first patient target region of the treatment planning image with the first patient target region of the acquired image. For example, the image acquired along the axial plane at the time of treatment may be compared to a treatment planning image acquired along an axial plane of the patient to determine the amount of correction needed along the lateral axis (i.e., Y-axis) and vertical axis (i.e., Z-axis) of the patient surface (e.g., a platform or couch) within the axial plane and the amount of correction about the gantry roll axis (e.g., about the X-axis) needed. The image acquired along the sagittal plane at the time of treatment may be compared to a treatment planning image acquired along a sagittal plane of the patient to determine the amount of correction needed along the longitudinal axis (i.e., the X-axis) and the vertical axis and the amount of pitch correction (e.g., rotation about the Y-axis) of the patient surface (e.g., a platform or couch) within the sagittal plane. The image acquired along the coronal plane at the time of treatment may be compared to a treatment planning image acquired along a coronal plane of the patient to determine the amount of correction needed along the lateral axis and the longitudinal axis and the amount of yaw correction (i.e., about the Z-axis) of the patient surface (e.g., a platform or couch) within the coronal plane.

The first set of patient position-shift vectors may reflect the amount of correction of the patient surface needed along or about each of the X-, Y-, and Z-axes to improve the alignment between the first patient target region and the location of the first patient target region at the time of the acquisition of the treatment planning images. Thus, in some embodiments, the first set of patient position-shift vectors may include at least one patient position-shift vector reflecting an adjustment along the patient surface's X-axis based on the longitudinal differences determined from the comparison of the acquired sagittal image and the treatment planning sagittal image and/or the comparison of the acquired coronal image and the treatment planning coronal image. The first set of patient position-shift vectors may include at least one patient position-shift vector reflecting an adjustment along the patient surface's Y-axis based on the lateral differences determined from the comparison of the acquired axial image and the treatment planning axial image and/or the comparison of the acquired coronal image and the treatment planning coronal image. The first set of patient position-shift vectors may include at least one patient position-shift vector reflecting an adjustment along the patient surface's Z-axis based on the vertical differences determined from the comparison of the acquired axial image and the treatment planning axial image and/or the comparison of the acquired sagittal image and the treatment planning sagittal image. In some embodiments, the adjustment along the patient surface's Z-axis included in the first set of patient position-shift vectors may be an average of the lateral differences determined from the comparison of the acquired axial image and the treatment planning axial image and the lateral difference determined from the comparison of the acquired sagittal image and the treatment planning sagittal image.

With respect to rotation of the patient surface about the patient surface's axes and/or rotation of the radiation source about the radiation source's axes, the first set of patient position-shift vectors may include a rotational correction of the patient surface about the patient surface's Y-axis based on the comparison of the acquired sagittal image and the treatment planning sagittal image, and/or a rotational correction of the patient surface about the patient surface's Z-axis based on the comparison of the acquired coronal image and the treatment planning coronal image, and/or a rotational correction of the radiation source about the radiation source's X-axis (e.g., the gantry's X-axis which is coextensive with the patient surface's X-axis) based on the comparison of the acquired axial image and the treatment planning axial image. For example, shifting or panning an acquired sagittal or coronal image to match with the treatment planning sagittal or coronal image may translate to a set of patient position-shift vectors that represent shifts in the X-, Y-, and Z-axes. Tilting an acquired sagittal or coronal image to match with the treatment planning sagittal or coronal image may translate to a set of patient position-shift vectors that represent pitch and/or roll positional corrections. Thus, the amount the patient position or orientation should be adjusted along or about each of the X-, Y-, and Z-axes may be reflected by the first set of patient position-shift vectors based on the differences between the treatment planning images and the respective acquired images taken within each of the axial, sagittal, and coronal planes of the patient.

A second set of patient position-shift vectors may be calculated (106) based on the acquired image, a treatment planning image of the second treatment area and/or patient target region (also referred to herein as a "second treatment planning image"), and the first set of patient position-shift vectors. In some embodiments, the second set of position-shift vectors may include distance and/or direction translations. In some embodiments, the direction translations may include tilt angles. In some embodiments, similarly as described above with respect to the first set of patient position-shift vectors, the second set of patient position-shift vectors may be calculated by moving the acquired image relative to the treatment planning image to align or register the second patient target region of the treatment planning image with the second patient target region of the acquired image. For example, each voxel of the acquired image may be translated along or about the X, Y, and/or Z axes, maintaining the relative positions of each voxel of the acquired image to one another during movement of the acquired image, until the acquired image and the treatment planning image have improved alignment with respect to the second patient target region (e.g., overlap between the second patient target region in the images is increased or optimized). The second set of patient position-shift vectors may then be calculated based on locational and/or positional differences between the acquired image before and after being moved into increased alignment with the treatment planning image. The second set of patient position-shift vectors may reflect the distance and/or direction each voxel of the acquired image had to be translated to improve the alignment between the second patient target region of the acquired image and the second patient target region of the treatment planning image. In some embodiments, the second set of position-shift vectors may be calculated based on the first set of patient position-shift vectors such that the distance and/or direction information included in the second set of position-shift vectors is relative to the first set of patient position-shift vectors, rather than to the initial coordinates of the voxels of the acquired image. Thus, the position and/or orientation instructions based on the second set of patient position-shift vectors may include or correspond to instructions reciting modifications to be made to the patient's position and/or orientation relative to the first position and/or the first orientation of the patient based on the first set of patient position-shift vectors such that the patient will be in a second position and/or orientation for irradiation of the second treatment area and/or patient target region.

The patient may be positioned according to the second set of patient position-shift vectors such that the patient is transitioned from the first location to a second location. For example, the therapeutic radiation source may be deactivated such that the first patient target region is not irradiated by the therapeutic radiation source and then the patient may be positioned according to the second set of patient position-shift vectors. Positioning the patient according to the second set of patient position-shift vectors may include moving a radiation therapy patient platform upon which the patient is disposed relative to a therapeutic radiation source and/or adjusting the rotational position of the radiation source according to the second set of patient position-shift vectors. The therapeutic radiation source may then be activated such that the second patient target region is irradiated. In some embodiments, for beam station-based delivery, the patient may be positioned according to the first set of patient position-shift vectors at the first location associated with a first beam station during a period of irradiation and the patient may be positioned according to the second set of patient position-shift vectors during a transition of the patient platform between the first location associated with the first beam station and the second location associated with a second beam station (e.g., a second beam station that is adjacent to the first beam station).

In some embodiments, rather than only defining a first patient target region and a second patient target region, the method may include defining any suitable number of target regions, acquiring images of each of the target regions, and positioning the patient based on position-shift vectors as described above based on the first patient target region and the second patient target region. For example, for beam station-based delivery, the method may include defining a plurality of patient target regions, where each patient target region may span across a plurality of beam stations. In some variations, there may be as many patient target region as there are beam stations. Images may be acquired of each of the patient target regions, and a set of position-shift vectors associated with each defined patient target region may be generated as described above. Each patient target region and associated set of position-shift vectors can be associated with a particular beam station. During the transition of the patient and/or the patient platform to a location associated with each respective beam station, the patient may be positioned based on the set of position-shift vectors associated with that beam station. In some embodiments, the defined target regions (and associated sets of patient position-shift vectors) may be associated with more than one beam station such that a patient may be positioned based on a set of position-shift vectors and not repositioned as the patient platform advances through a series of two or more beam stations. Thus, the number of defined target regions (and associated respective sets of patient position-shift vectors) may be equal or less than the number of beam stations.

Additionally, the second set of patient position-shift vectors may include information regarding any tilt, pitch, yaw, and roll corrections needed to be implemented via movement of the patient platform and/or via adjustment of the roll of a gantry to which the radiation source is coupled (e.g., correcting a gantry firing position) such that the second patient target region has improved alignment with the location of the second patient target region in the second treatment planning image.

In some embodiments, similarly as described above with respect to the first set of patient position-shift vectors, a plurality of two-dimensional images of the second treatment area and/or patient target region may be acquired along different orientations or planes (e.g., three or more orientations or planes), and the images may be compared to corresponding treatment planning images of the second patient target that have been acquired along the same orientations or planes. In some embodiments, the plurality of two-dimensional images of the second patient target region may be the same two-dimensional images acquired of the first patient target region for calculating the first set of patient position-shift vectors. Changes with respect to the position of the second patient target region along each image plane at each orientation may be used to calculate the second set of patient position-shift vectors. For example, the acquired images may include an acquired axial image, an acquired sagittal image, and an acquired coronal image of the second patient target region of the patient. When the patient is lying on a surface such as a patient platform or treatment couch in a supine position with the patient oriented such that the patient will encounter the therapeutic radiation source head first, the acquired axial image may be taken along an axial plane of the patient (e.g., the plane dividing the body into superior and inferior portions), the acquired sagittal image may be taken along a sagittal plane of the patient (e.g., the plane dividing the patient into right and left portions), and the acquired coronal image may be taken along a coronal plane of the patient (e.g., the plane dividing the patient into ventral and dorsal portions). The axial plane is disposed perpendicularly to the sagittal plane, and the coronal plane is disposed perpendicularly to both the axial plane and the sagittal plane. The treatment planning images may include a treatment planning axial image, a treatment planning sagittal image, and a treatment planning coronal image of the second patient target region of the patient. Thus, the acquired axial image corresponds to the treatment planning axial image, the acquired sagittal image corresponds to the treatment planning sagittal image, and the acquired coronal image corresponds to the treatment planning coronal image.

The amount the patient position and/or orientation should be adjusted along or about each of the X-, Y-, and Z-axes (e.g., via movement of the patient surface and/or rotating the radiation source) for treatment of the second patient target region may be reflected by the second set of patient position-shift vectors based on the differences between the treatment planning images of the second patient target region and the respective acquired images of the second patient target region taken within each of the axial, sagittal, and coronal planes of the patient. In some embodiments, the X-axis of the patient surface may be parallel to the intersection of the sagittal plane and the coronal plane of the patient and may be disposed in the sagittal plane. The Y-axis of the patient surface may be parallel to the intersection of the axial plane and the coronal plane of the patient and may be disposed in the axial plane. The Z-axis of the patient surface may be parallel to the intersection of the sagittal plane and the axial plane of the patient and may be disposed in the sagittal plane or the axial plane of the patient. To determine the second set of patient position-shift vectors, each of the acquired images of the second patient target region may be compared to a respective treatment planning image of the second patient target region taken within the same plane to determine a distance correction and/or rotation correction of the patient (e.g., via movement of the patient surface and/or rotation of the radiation source) within the same plane. One or more vectors of the second set of patient position-shift vectors may represent a magnitude and direction that the patient surface is to be moved (e.g., shifted and/or rotated) such that the second patient target region approximates the location of the second patient target region in the treatment planning images. One or more vectors of the second set of patient position-shift vectors may also represent a magnitude and direction that the radiation source may be moved (e.g., rotated on a gantry) such that the location of the second patient target region approximates the location of the second patient target region in the treatment planning images. In some embodiments, the second set of patient position-shift vectors may reflect up to six corrections (i.e., the amount of adjustment along or about each of the X-, Y-, and Z-axes of the patient platform). In some embodiments, DICOM Spatial Registration Objects (SROs) may be used to determine each of the six corrections (i.e., the amount of adjustment along or about each of the X-, Y-, and Z-axes of the patient platform) associated with the second set of patient position-shift vectors.

In some embodiments, the second set of patient position-shift vectors may be calculated by moving (e.g., via shifting and/or rotating) each acquired image relative to its respective treatment planning image to align or register the second patient target region of the treatment planning image with the second patient target region of the acquired image. Each acquired image may be shifted a particular distance and/or rotated a particular amount to improve the registration of the second patient target region of the treatment planning image with the second patient target region of the acquired image. For example, the image acquired along an axial plane at the time of treatment may be compared to a treatment planning image acquired along an axial plane of the patient to determine the amount of correction needed along the lateral axis (i.e., Y-axis) and vertical axis (i.e., Z-axis) of the patient surface (e.g., a platform or couch) within the axial plane and the amount of correction about the gantry roll axis (e.g., about the X-axis) needed. The image acquired along a sagittal plane at the time of treatment may be compared to a treatment planning image acquired along a sagittal plane of the patient to determine the amount of correction needed along the longitudinal axis (i.e., the X-axis) and the vertical axis and the amount of pitch correction (e.g., rotation about the Y-axis) of the patient surface (e.g., a platform or couch) within the sagittal plane. The image acquired along a coronal plane at the time of treatment may be compared to a treatment planning image acquired along a coronal plane of the patient to determine the amount of correction needed along the lateral axis and the longitudinal axis and the amount of yaw correction (i.e., about the Z-axis) of the patient surface (e.g., a platform or couch) within the coronal plane.

The second set of patient position-shift vectors may reflect the amount of correction of the patient surface needed along or about each of the X-, Y-, and Z-axes to improve the alignment between the second patient target region and the location of the second patient target region at the time of the acquisition of the treatment planning images. Thus, in some embodiments, the second set of patient position-shift vectors may include at least one patient position-shift vector reflecting an adjustment along the patient surface's X-axis based on the longitudinal differences determined from the comparison of the acquired sagittal image and the treatment planning sagittal image and/or the comparison of the acquired coronal image and the treatment planning coronal image. The second set of patient position-shift vectors may include at least one patient position-shift vector reflecting an adjustment along the patient surface's Y-axis based on the lateral differences determined from the comparison of the acquired axial image and the treatment planning axial image and/or the comparison of the acquired coronal image and the treatment planning coronal image. The second set of patient position-shift vectors may include at least one patient position-shift vector reflecting an adjustment along the patient surface's Z-axis based on the vertical differences determined from the comparison of the acquired axial image and the treatment planning axial image and/or the comparison of the acquired sagittal image and the treatment planning sagittal image.

With respect to rotation of the patient surface about the patient surface's axes and/or rotation of the radiation source about the radiation source's axes, the second set of patient position-shift vectors may include a rotational correction of the patient surface about the patient surface's Y-axis based on the comparison of the acquired sagittal image and the treatment planning sagittal image, a rotational correction of the patient surface about the patient surface's Z-axis based on the comparison of the acquired coronal image and the treatment planning coronal image, and/or a rotational correction of the radiation source about the radiation source's X-axis (e.g., the gantry's X-axis which is coextensive with the patient surface's X-axis) based on the comparison of the acquired axial image and the treatment planning axial image. For example, shifting or panning an acquired sagittal or coronal image to match with the treatment planning sagittal or coronal image may translate to a set of patient position-shift vectors that represent shifts in the X-, Y-, and Z-axes. Tilting an acquired sagittal or coronal image to match with the treatment planning sagittal or coronal image may translate to a set of patient position-shift vectors that represent pitch and/or roll positional corrections. Thus, the amount the patient position or orientation should be adjusted along or about each of the X-, Y-, and Z-axes may be reflected by the second set of patient position-shift vectors based on the differences between the treatment planning images and the respective acquired images taken within each of the axial, sagittal, and coronal planes of the patient.

In some embodiments, the second set of patient position-shift vectors may reflect an amount of correction of the patient surface needed along or about each of the X-, Y-, and Z-axes relative to the position and/or orientation of the patient surface after being moved according to the first set of patient position-shift vectors to improve the alignment between the second patient target region and the location of the second patient target region at the time of the acquisition of the treatment planning images. Thus, in some embodiments, the amount the patient position or orientation should be adjusted along or about each of the X-, Y-, and Z-axes may be calculated by first determining the differences between the treatment planning images of the second patient target region and the respective acquired images of the second patient target region taken within each of the axial, sagittal, and coronal axes of the patient, and then accounting for the first set of patient position-shift vectors (e.g., subtracting the first set of patient position-shift vectors from the determined differences between the treatment planning images and the acquired images) such that the second set of position-shift vectors are relative to the first set of patient position-shift vectors. Thus, the surface on which the patient is disposed may transition from the position and/or orientation corresponding to the first set of patient position-shift vectors to the position and/or orientation corresponding to the second set of patient position-shift vectors without having to first be returned to the position and/or orientation of the surface at the time the treatment planning images were initially acquired.

In some embodiments, rather than comparing coordinate locations of a particular voxel of an acquired image to a treatment planning image or comparing three two-dimensional acquired images to three respective two-dimensional treatment planning images, the first set of patient position-shift vectors may be calculated by comparing a three-dimensional image acquired of the first patient target region to a three-dimensional treatment planning image of the first patient target region. The second set of patient position-shift vectors may be calculated by comparing the three-dimensional image acquired of the second patient target region (with may be the same image or a different image as the three-dimensional image acquired of the first patient target region) to a three-dimensional treatment planning image of the second patient target region and accounting for the first set of patient position-shift vectors (e.g., subtracting the first set of patient position-shift vectors from an intermediate set of patient position-shift vectors calculated via the comparison of the acquired image of the second patient target region to the treatment planning image of the second patient target region).

In some embodiments, the first and second sets of patient position-shift vectors may be calculated before a therapeutic radiation source is activated. In some embodiments, the first treatment planning image and the second treatment planning image are the same treatment planning image. In some embodiments, the first treatment planning image and the second treatment planning image are different treatment planning images.

In some embodiments, a first location difference and/or a second location difference may be calculated and used to determine if the corresponding tumors or tumor portions of the patient have changed shape, size, or location to the extent that the patient may not be able to be positioned or oriented to effectively or accurately receive radiation using the existing treatment plan. For example, the first location difference may be calculated by comparing a coordinate location of a particular voxel in the first patient target region in the acquired image with a coordinate location of a corresponding voxel of the first patient target region in the treatment planning image. The distance between the location of the particular voxel of the first patient target region in the acquired image and the location of the corresponding voxel of the first patient target region in the treatment planning image may be the first location difference. Similarly, the second location difference may be calculated by comparing a coordinate location of a particular voxel of the second patient target region in the acquired image with a coordinate location of a corresponding voxel in the second target region in the treatment planning image. The distance between the location of the particular voxel of the second patient target region in the acquired image with the location of the corresponding voxel of the second patient target region in the treatment planning image may be the second location difference. In some embodiments, the first location difference may be calculated by comparing a coordinate location within a two-dimensional image of a cross-section of a patient in the first patient target region in the acquired image with a coordinate location within a two-dimensional image of a cross-section of a patient in the first patient target region in the treatment planning image. The second location difference may be calculated by comparing a coordinate location within a two-dimensional image of a cross-section of a patient in the second patient target region in the acquired image with a coordinate location within a two-dimensional image of a cross-section of a patient in the second patient target region in the treatment planning image. The first location difference and the second location difference may be based on the direction and/or distance information included in the first set of patient position-shift vectors and the second set of patient position-shift vectors, respectively, described above. In some embodiments, the second location difference may be calculated based on the direction and/or distance information included in both the first set of patient position-shift vectors and the second set of patient position-shift vectors. In some embodiments, a notification may be generated and/or the radiation treatment session may be automatically paused if the first location difference and/or the second location difference exceed a location difference threshold. For example, the maximum corrective movement of the patient platform for lateral, longitudinal, and vertical corrections is about 3 cm, and the maximum corrective movement for rotation, pitch, and roll corrections are not to exceed 3°. In some embodiments, the maximum corrective movement of the patient platform for lateral, longitudinal, and vertical corrections and the maximum corrective movement for rotation, pitch, and roll corrections may be selected by a clinician or clinic. For example, the maximum corrective movement of the patient platform for lateral, longitudinal, and vertical corrections may be from about 1.5 cm to about 10 cm, and/or the maximum corrective movement for rotation, pitch, and roll corrections may be from about 2° to about 20°. Thus, the location difference threshold would be any location difference that would result in the corrective movement exceeding the maximum corrective movement of the patient platform in any respect.

The patient may be positioned according to the first set of patient position-shift vectors at a first location, at (108). In some embodiments, the patient may be positioned by moving a radiation therapy patient platform upon which the patient is disposed relative to a therapeutic radiation source according to the first set of patient position-shift vectors. For example, the platform may be tilted in any direction prior to irradiation, which may include translation of the platform in the tilted orientation relative to the therapeutic radiation source. In some embodiments, a radiation therapy patient platform upon which the patient is disposed may be moved along or about the radiation therapy patient platform's X-axis, Y-axis, and/or Z-axis (e.g., about a yaw, pitch, and/or roll axis). Furthermore, in some embodiments, the yaw and/or pitch of the radiation therapy patient platform may be adjusted. In some embodiments, a radiation therapy patient platform upon which the patient is disposed may be moved along the radiation therapy patient platform's X-axis, Y-axis, and/or Z-axis and about a yaw and/or pitch axis, while the radiation source may move about a roll axis (via movement of, for example, a gantry). As another example, transitioning the patient from the first location to the second location may include moving and/or bending a portion of the patient on the platform, such as a head, a knee or an elbow. The therapeutic radiation source may then be activated such that the first patient target region is irradiated.

In some embodiments, a roll correction to a patient position (e.g., as defined by the first set of patient position-shift vectors) may be implemented by rotating the radiation source (e.g., via rotating a gantry) in an opposite direction of the calculated roll correction. For example, if the roll correction to the patient position is 3° clockwise, the location of the radiation source may be adjusted to provide radiation from a gantry position (e.g., a gantry firing position) of −3° counter-clockwise relative to each requested radiation source delivery location. Therefore, if the treatment plan includes delivering radiation from the radiation source with a gantry at 0° based on the treatment planning images and the roll correction is 3° based on the differences between the treatment planning images and the acquired images, the radiation source may be adjusted 3° in the counterclockwise direction and deliver radiation (e.g., fire) from 357° rather than 0°.

The patient may then be positioned according to the second set of patient position-shift vectors such that the patient is transitioned from the first location to a second location, at 110. Similarly as described above, positioning the patient according to the second set of patient position-shift vectors may include moving a radiation therapy patient platform upon which the patient is disposed relative to a therapeutic radiation source and/or adjusting the rotational position of the radiation source according to the second set of patient position-shift vectors. The therapeutic radiation source may then be activated such that the second patient target region is irradiated.

In some embodiments, rather than only defining a first patient target region and a second patient target region, the method may include defining any suitable number of target regions, acquiring images of each of the target regions, and positioning the patient based on position-shift vectors as described above based on the first patient target region and the second patient target region.

Figure 11B:
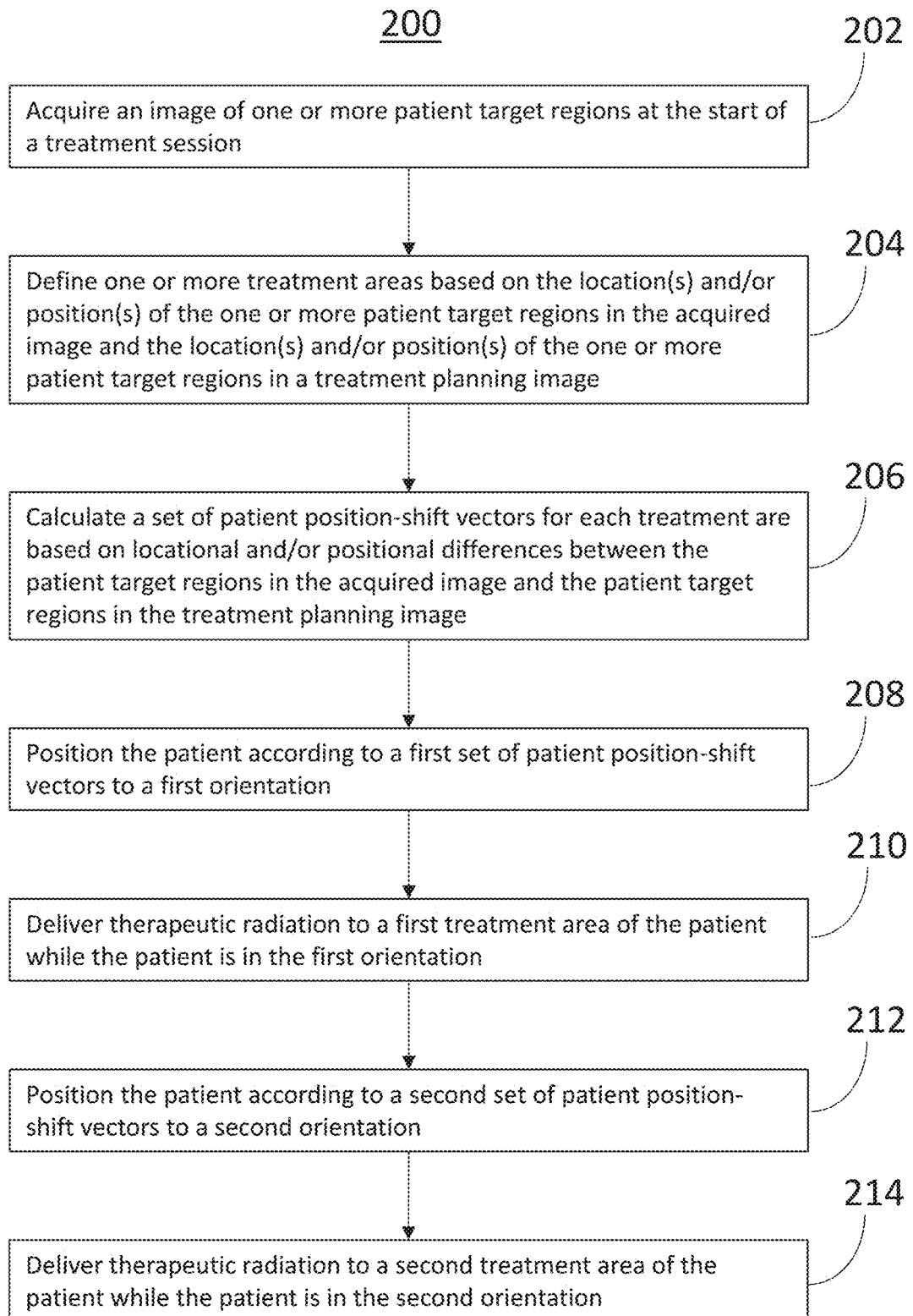
FIG. 11B is a flow chart representation of one variation of a method.

FIG. 11B is a flow chart representation of one variation of a method (200) for patient setup. The method (200) comprises acquiring (202) an image of one or more patient target regions at the start of a radiation treatment session. In some embodiments, for example, a CT system may be used to acquire one or more images prior to or at the start of a treatment session. In some embodiments, the CT system may be attached to the same gantry as a radiation source intended for the delivery of radiation therapy during the treatment session. In some embodiments, the CT system may be attached to a separate gantry from the gantry supporting the radiation source. One or more treatment areas may be defined (204) based on the location(s) and/or position(s) of the one or more patient target regions in the acquired image and the location(s) and/or positions(s) of the one or more patient target regions in a treatment planning image. For example, the acquired image and/or the treatment planning image may be divided into a first treatment area and a second treatment area. Each treatment area may include one or more patient target regions such that the one or more patient target regions in the acquired image may be compared to one or more corresponding patient target regions in the treatment planning image. Each treatment area may correspond to a portion of a patient within which the one or more patient target regions are located that will be irradiated when a patient is positioned according to a particular setup during a particular portion of a radiation treatment session. A treatment area may map to series of patient platform positions or steps (e.g., beam stations) and/or a range of patient platform motion along its longitudinal axis where the one or more target regions in that treatment area intersect the radiation beam of the therapeutic radiation source. A treatment area may correspond with a particular patient position and/or platform orientation. For example, a first treatment area may be associated with a first patient position and orientation for irradiation of a first patient target region within the first treatment area and a second treatment area may be associated with a second patient position and orientation for irradiation of a second patient target region within the second treatment area. Thus, in some embodiments, the first treatment area may be associated with a first portion of a radiation treatment session (e.g., movement of the patient platform through a first set of beam stations), a first patient target region, and a first position of the patient and the second treatment area may be associated with a second portion of the radiation treatment session (e.g., movement of the patient platform through a second set of beam stations), a second patient target region, and a second position of the patient.

A set of patient position-shift vectors may be calculated (206) for each treatment area based on locational and/or positional differences between the patient target regions in the acquired image and the patient target regions in the treatment planning image. The location of the patient target regions in the acquired image may be compared with a location of the patient target regions in the treatment planning image in 2D and/or 3D. In embodiments in which two treatment areas have been defined, a first set of patient position-shift vectors may be calculated for the first treatment area and a second set of patient position-shift vectors may be calculated for the second treatment area. Each set of position-shift vectors may include distance and/or direction translations. In some embodiments, the direction translations may include tilt angles. In some embodiments, the first set of patient position-shift vectors may be calculated by moving the acquired image relative to the treatment planning image to align or register the first patient target region of the treatment planning image with the first patient target region of the acquired image. For example, in some embodiments, the first patient target region may be divided into sub-regions (e.g., sub-volumes) that may be represented by voxels, and the coordinates of each voxel of the first patient target region of the acquired image may be compared with the coordinates of a corresponding voxel of the first patient target region in the treatment planning image. For example, each voxel of the acquired image may be translated along or about the X, Y, and/or Z axes, maintaining the relative positions of each coordinate of each voxel of the acquired image to one another during movement of the acquired image, until the acquired image and the treatment planning image have improved alignment with respect to the first patient target region (e.g., overlap between the first patient target region in the images is increased or optimized). The first set of patient position-shift vectors may then be calculated based on locational and/or positional differences between the acquired image before and after being moved into increased alignment with the treatment planning image. The first set of patient position-shift vectors may reflect the distance and/or direction each voxel of the acquired image had to be translated to improve the alignment between the first patient target region of the acquired image and the first patient target region of the treatment planning image. Furthermore, the first set of patient position-shift vectors may include or correspond to instructions related to a first position and/or a first orientation of the patient (e.g., a first position and/or a first orientation of a surface on which the patient is disposed) so that the first patient target region of the patient is located in approximately the position that the first patient target region was in when the treatment planning images were acquired. This may facilitate the delivery of therapeutic radiation to the patient target region more closely to the treatment plan. Additionally, the first set of patient position-shift vectors may include information regarding any tilt, pitch, yaw, and/or roll corrections needed to be implemented via positioning of the patient platform such that the location of the first patient target region approximates the location of the first patient target region in the first treatment planning image.

In some embodiments, the acquired image of the first patient target region and the treatment planning image of the first patient target region may each be a two-dimensional image. The two-dimensional acquired image may be compared to the two-dimensional treatment planning image to calculate the first set of patient position-shift vectors. In some embodiments, a plurality of two-dimensional images of the first patient target region may be acquired along different orientations or planes (e.g., three or more orientations or planes), and the images may be compared to corresponding treatment planning images of the first patient target region that have been acquired along the same orientations or planes. Changes with respect to the position of the first patient target region along each image plane at each orientation may be used to calculate the first set of patient position-shift vectors. For example, the acquired images may include an acquired axial image, an acquired sagittal image, and an acquired coronal image of the first patient target region of the patient. When the patient is lying on a surface such as a patient platform or treatment couch in a supine position with the patient oriented such that the patient will encounter the therapeutic radiation source head first, the acquired axial image may be taken along an axial plane of the patient (e.g., the plane dividing the body into superior and inferior portions), the acquired sagittal image may be taken along a sagittal plane of the patient (e.g., the plane dividing the patient into right and left portions), and the acquired coronal image may be taken along a coronal plane of the patient (e.g., the plane dividing the patient into ventral and dorsal portions). The axial plane is disposed perpendicularly to the sagittal plane, and the coronal plane is disposed perpendicularly to both the axial plane and the sagittal plane. The treatment planning images may include a treatment planning axial image, a treatment planning sagittal image, and a treatment planning coronal image of the first patient target region of the patient. Thus, the acquired axial image corresponds to the treatment planning axial image, the acquired sagittal image corresponds to the treatment planning sagittal image, and the acquired coronal image corresponds to the treatment planning coronal image.

The amount the patient position and/or orientation should be adjusted along or about each of the X-, Y-, and Z-axes (e.g., via movement of the patient surface and/or rotating the radiation source) for treatment of the first patient target region may be reflected by the first set of patient position-shift vectors based on the differences between the treatment planning images and the respective acquired images taken within each of the axial, sagittal, and coronal planes of the patient. In some embodiments, the X-axis of the patient surface may be parallel to the intersection of the sagittal plane and the coronal plane of the patient and may be disposed in the sagittal plane. The Y-axis of the patient surface may be parallel to the intersection of the axial plane and the coronal plane of the patient and may be disposed in the axial plane. The Z-axis of the patient surface may be parallel to the intersection of the sagittal plane and the axial plane of the patient and may be disposed in the sagittal plane or the axial plane of the patient. To determine the first set of patient position-shift vectors, each of the acquired images of the first patient target region may be compared to a respective treatment planning image of the first patient target region taken within the same plane to determine a distance correction and/or rotation correction of the patient (e.g., via movement of the patient surface and/or rotation of the radiation source) within the same plane. One or more vectors of the first set of patient position-shift vectors may represent a magnitude and direction that the patient surface is to be moved (e.g., shifted and/or rotated) such that the first patient target region approximates the location of the first patient target region in the treatment planning images. One or more vectors of the first set of patient position-shift vectors may also represent a magnitude and direction that the radiation source may be moved (e.g., rotated on a gantry) such that the location of the first patient target region approximates the location of the first patient target region in the treatment planning images. In some embodiments, the first set of patient position-shift vectors may reflect up to six corrections (i.e., the amount of adjustment along or about each of the X-, Y-, and Z-axes of the patient platform). In some embodiments, DICOM Spatial Registration Objects (SROs) may be used to determine each of the six corrections (i.e., the amount of adjustment along or about each of the X-, Y-, and Z-axes of the patient platform) associated with the first set of patient position-shift vectors.

In some embodiments, the first set of patient position-shift vectors may be calculated by moving (e.g., via shifting and/or rotating) each acquired image relative to its respective treatment planning image to align or register the first patient target region of the treatment planning image with the first patient target region of the acquired image. Each acquired image may be shifted a particular distance and/or rotated a particular amount to improve the registration of the first patient target region of the treatment planning image with the first patient target region of the acquired image. For example, the image acquired along an axial plane at the time of treatment may be compared to a treatment planning image acquired along an axial plane of the patient to determine the amount of correction needed along the lateral axis (i.e., Y-axis) and vertical axis (i.e., Z-axis) of the patient surface (e.g., a platform or couch) within the axial plane and the amount of correction about the gantry roll axis (e.g., about the X-axis) needed. The image acquired along a sagittal plane at the time of treatment may be compared to a treatment planning image acquired along a sagittal plane of the patient to determine the amount of correction needed along the longitudinal axis (i.e., the X-axis) and the vertical axis and the amount of pitch correction (e.g., rotation about the Y-axis) of the patient surface (e.g., a platform or couch) within the sagittal plane. The image acquired along a coronal plane at the time of treatment may be compared to a treatment planning image acquired along a coronal plane of the patient to determine the amount of correction needed along the lateral axis and the longitudinal axis and the amount of yaw correction (i.e., about the Z-axis) of the patient surface (e.g., a platform or couch) within the coronal plane.

The first set of patient position-shift vectors may reflect the amount of correction of the patient surface needed along or about each of the X-, Y-, and Z-axes to improve the alignment between the first patient target region and the location of the first patient target region at the time of the acquisition of the treatment planning images. Thus, in some embodiments, the first set of patient position-shift vectors may include at least one patient position-shift vector reflecting an adjustment along the patient surface's X-axis based on the longitudinal differences determined from the comparison of the acquired sagittal image and the treatment planning sagittal image and/or the comparison of the acquired coronal image and the treatment planning coronal image. The first set of patient position-shift vectors may include at least one patient position-shift vector reflecting an adjustment along the patient surface's Y-axis based on the lateral differences determined from the comparison of the acquired axial image and the treatment planning axial image and/or the comparison of the acquired coronal image and the treatment planning coronal image. The first set of patient position-shift vectors may include at least one patient position-shift vector reflecting an adjustment along the patient surface's Z-axis based on the vertical differences determined from the comparison of the acquired axial image and the treatment planning axial image and/or the comparison of the acquired sagittal image and the treatment planning sagittal image.

With respect to rotation of the patient surface about the patient surface's axes and/or rotation of the radiation source about the radiation source's axes, the first set of patient position-shift vectors may include a rotational correction of the patient surface about the patient surface's Y-axis based on the comparison of the acquired sagittal image and the treatment planning sagittal image, a rotational correction of the patient surface about the patient surface's Z-axis based on the comparison of the acquired coronal image and the treatment planning coronal image, and/or a rotational correction of the radiation source about the radiation source's X-axis (e.g., the gantry's X-axis which is coextensive with the patient surface's X-axis) based on the comparison of the acquired axial image and the treatment planning axial image. For example, shifting or panning an acquired sagittal or coronal image to match with the treatment planning sagittal or coronal image may translate to a set of patient position-shift vectors that represent shifts in the X-, Y-, and Z-axes. Tilting an acquired sagittal or coronal image to match with the treatment planning sagittal or coronal image may translate to a set of patient position-shift vectors that represent pitch and/or roll positional corrections. Thus, the amount the patient position or orientation should be adjusted along or about each of the X-, Y-, and Z-axes may be reflected by the first set of patient position-shift vectors based on the differences between the treatment planning images and the respective acquired images taken within each of the axial, sagittal, and coronal planes of the patient.

In some embodiments, similarly as described above with respect to the first set of patient position-shift vectors, the second set of patient position-shift vectors may be calculated by moving the acquired image relative to the treatment planning image to align the second patient target region of the treatment planning image with the second patient target region of the acquired image. For example, in some embodiments, the second patient target region may be divided into sub-regions (e.g., sub-volumes) that may be represented by voxels, and the coordinates of each voxel of the second patient target region of the acquired image may be compared with the coordinates of a corresponding voxel of the second patient target region in the treatment planning image. For example, each voxel of the acquired image may be translated along or about the X, Y, and/or Z axes, maintaining the relative positions of each voxel of the acquired image to one another during movement of the acquired image, until the acquired image and the treatment planning image have improved alignment with respect to the second patient target region (e.g., overlap between the second patient target region in the images is increased or optimized). The second set of patient position-shift vectors may then be calculated based on locational and/or positional differences between the acquired image before and after being moved into increased alignment with the treatment planning image. The second set of patient position-shift vectors may reflect the distance and/or direction each voxel of the acquired image had to be translated to improve the alignment between the second patient target region of the acquired image and the second patient target region of the treatment planning image. In some embodiments, the second set of position-shift vectors may be calculated based on the first set of patient position-shift vectors such that the distance and/or direction information included in the second set of position-shift vectors is relative to the first set of patient position-shift vectors, rather than to the initial coordinates of the voxels of the acquired image. Thus, the position and/or orientation instructions based on the second set of patient position-shift vectors may include or correspond to instructions reciting modifications to be made to the patient's position and/or orientation relative to the first position and/or the first orientation of the patient based on the first set of patient position-shift vectors such that the patient will be in a second position and/or orientation for irradiation of the second patient target region. Additionally, the second set of patient position-shift vectors may include information regarding any tilt, pitch, yaw, and roll corrections needed to be implemented via movement of the patient platform and/or via adjustment of the roll of a gantry to which the radiation source is coupled (e.g., correcting a gantry firing position) such that the second patient target region has improved alignment with the location of the first patient target region in the first treatment planning image.

In some embodiments, similarly as described above with respect to the first set of patient position-shift vectors, a plurality of two-dimensional images of the second patient target region may be acquired along different orientations or planes (e.g., three or more orientations or planes), and the images may be compared to corresponding treatment planning images of the second patient target that have been acquired along the same orientations or planes. In some embodiments, the plurality of two-dimensional images of the second patient target region may be the same two-dimensional images acquired of the first patient target region for calculating the first set of patient position-shift vectors. Changes with respect to the position of the second patient target region along each image plane at each orientation may be used to calculate the second set of patient position-shift vectors. For example, the acquired images may include an acquired axial image, an acquired sagittal image, and an acquired coronal image of the second patient target region of the patient. When the patient is lying on a surface such as a patient platform or treatment couch in a supine position with the patient oriented such that the patient will encounter the therapeutic radiation source head first, the acquired axial image may be taken along an axial plane of the patient (e.g., the plane dividing the body into superior and inferior portions), the acquired sagittal image may be taken along a sagittal plane of the patient (e.g., the plane dividing the patient into right and left portions), and the acquired coronal image may be taken along a coronal plane of the patient (e.g., the plane dividing the patient into ventral and dorsal portions). The axial plane is disposed perpendicularly to the sagittal plane, and the coronal plane is disposed perpendicularly to both the axial plane and the sagittal plane. The treatment planning images may include a treatment planning axial image, a treatment planning sagittal image, and a treatment planning coronal image of the second patient target region of the patient. Thus, the acquired axial image corresponds to the treatment planning axial image, the acquired sagittal image corresponds to the treatment planning sagittal image, and the acquired coronal image corresponds to the treatment planning coronal image.

The amount the patient position and/or orientation should be adjusted along or about each of the X-, Y-, and Z-axes (e.g., via movement of the patient surface and/or rotating the radiation source) for treatment of the second patient target region may be reflected by the second set of patient position-shift vectors based on the differences between the treatment planning images of the second patient target region and the respective acquired images of the second patient target region taken within each of the axial, sagittal, and coronal planes of the patient. In some embodiments, the X-axis of the patient surface may be parallel to the intersection of the sagittal plane and the coronal plane of the patient and may be disposed in the sagittal plane. The Y-axis of the patient surface may be parallel to the intersection of the axial plane and the coronal plane of the patient and may be disposed in the axial plane. The Z-axis of the patient surface may be parallel to the intersection of the sagittal plane and the axial plane of the patient and may be disposed in the sagittal plane or the axial plane of the patient. To determine the second set of patient position-shift vectors, each of the acquired images of the second patient target region may be compared to a respective treatment planning image of the second patient target region taken within the same plane to determine a distance correction and/or rotation correction of the patient (e.g., via movement of the patient surface and/or rotation of the radiation source) within the same plane. One or more vectors of the second set of patient position-shift vectors may represent a magnitude and direction that the patient surface is to be moved (e.g., shifted and/or rotated) such that the second patient target region approximates the location of the second patient target region in the treatment planning images. One or more vectors of the second set of patient position-shift vectors may also represent a magnitude and direction that the radiation source may be moved (e.g., rotated on a gantry) such that the location of the second patient target region approximates the location of the second patient target region in the treatment planning images. In some embodiments, the second set of patient position-shift vectors may reflect up to six corrections (i.e., the amount of adjustment along or about each of the X-, Y-, and Z-axes of the patient platform). In some embodiments, DICOM Spatial Registration Objects (SROs) may be used to determine each of the six corrections (i.e., the amount of adjustment along or about each of the X-, Y-, and Z-axes of the patient platform) associated with the second set of patient position-shift vectors.

In some embodiments, the second set of patient position-shift vectors may be calculated by moving (e.g., via shifting and/or rotating) each acquired image relative to its respective treatment planning image to align or register the second patient target region of the treatment planning image with the second patient target region of the acquired image. Each acquired image may be shifted a particular distance and/or rotated a particular amount to improve the registration of the second patient target region of the treatment planning image with the second patient target region of the acquired image. For example, the image acquired along an axial plane at the time of treatment may be compared to a treatment planning image acquired along an axial plane of the patient to determine the amount of correction needed along the lateral axis (i.e., Y-axis) and vertical axis (i.e., Z-axis) of the patient surface (e.g., a platform or couch) within the axial plane and the amount of correction about the gantry roll axis (e.g., about the X-axis) needed. The image acquired along a sagittal plane at the time of treatment may be compared to a treatment planning image acquired along a sagittal plane of the patient to determine the amount of correction needed along the longitudinal axis (i.e., the X-axis) and the vertical axis and the amount of pitch correction (e.g., rotation about the Y-axis) of the patient surface (e.g., a platform or couch) within the sagittal plane. The image acquired along a coronal plane at the time of treatment may be compared to a treatment planning image acquired along a coronal plane of the patient to determine the amount of correction needed along the lateral axis and the longitudinal axis and the amount of yaw correction (i.e., about the Z-axis) of the patient surface (e.g., a platform or couch) within the coronal plane.

The second set of patient position-shift vectors may reflect the amount of correction of the patient surface needed along or about each of the X-, Y-, and Z-axes to improve the alignment between the second patient target region and the location of the second patient target region at the time of the acquisition of the treatment planning images. Thus, in some embodiments, the second set of patient position-shift vectors may include at least one patient position-shift vector reflecting an adjustment along the patient surface's X-axis based on the longitudinal differences determined from the comparison of the acquired sagittal image and the treatment planning sagittal image and/or the comparison of the acquired coronal image and the treatment planning coronal image. The second set of patient position-shift vectors may include at least one patient position-shift vector reflecting an adjustment along the patient surface's Y-axis based on the lateral differences determined from the comparison of the acquired axial image and the treatment planning axial image and/or the comparison of the acquired coronal image and the treatment planning coronal image. The second set of patient position-shift vectors may include at least one patient position-shift vector reflecting an adjustment along the patient surface's Z-axis based on the vertical differences determined from the comparison of the acquired axial image and the treatment planning axial image and/or the comparison of the acquired sagittal image and the treatment planning sagittal image.

With respect to rotation of the patient surface about the patient surface's axes and/or rotation of the radiation source about the radiation source's axes, the second set of patient position-shift vectors may include a rotational correction of the patient surface about the patient surface's Y-axis based on the comparison of the acquired sagittal image and the treatment planning sagittal image, a rotational correction of the patient surface about the patient surface's Z-axis based on the comparison of the acquired coronal image and the treatment planning coronal image, and/or a rotational correction of the radiation source about the radiation source's X-axis (e.g., the gantry's X-axis which is coextensive with the patient surface's X-axis) based on the comparison of the acquired axial image and the treatment planning axial image. For example, shifting or panning an acquired sagittal or coronal image to match with the treatment planning sagittal or coronal image may translate to a set of patient position-shift vectors that represent shifts in the X-, Y-, and Z-axes. Tilting an acquired sagittal or coronal image to match with the treatment planning sagittal or coronal image may translate to a set of patient position-shift vectors that represent pitch and/or roll positional corrections. Thus, the amount the patient position or orientation should be adjusted along or about each of the X-, Y-, and Z-axes may be reflected by the second set of patient position-shift vectors based on the differences between the treatment planning images and the respective acquired images taken within each of the axial, sagittal, and coronal planes of the patient.

In some embodiments, the second set of patient position-shift vectors may reflect an amount of correction of the patient surface needed along or about each of the X-, Y-, and Z-axes relative to the position and/or orientation of the patient surface after being moved according to the first set of patient position-shift vectors to improve the alignment between the second patient target region and the location of the second patient target region at the time of the acquisition of the treatment planning images. Thus, in some embodiments, the amount the patient position or orientation should be adjusted along or about each of the X-, Y-, and Z-axes may be calculated by first determining the differences between the treatment planning images of the second patient target region and the respective acquired images of the second patient target region taken within each of the axial, sagittal, and coronal axes of the patient, and then accounting for the first set of patient position-shift vectors (e.g., subtracting the first set of patient position-shift vectors from the determined differences between the treatment planning images and the acquired images) such that the second set of position-shift vectors are relative to the first set of patient position-shift vectors. Thus, the surface on which the patient is disposed may transition from the position and/or orientation corresponding to the first set of patient position-shift vectors to the position and/or orientation corresponding to the second set of patient position-shift vectors without having to first be returned to the position and/or orientation of the surface at the time the treatment planning images were initially acquired.

In some embodiments, rather than comparing coordinate locations of a particular voxel of an acquired image to a treatment planning image or comparing three two-dimensional acquired images to three respective two-dimensional treatment planning images, the first set of patient position-shift vectors may be calculated by comparing a three-dimensional image acquired of the first patient target region to a three-dimensional treatment planning image of the first patient target region. The second set of patient position-shift vectors may be calculated by comparing the three-dimensional image acquired of the second patient target region (with may be the same image or a different image as the three-dimensional image acquired of the first patient target region) to a three-dimensional treatment planning image of the second patient target region and accounting for the first set of patient position-shift vectors (e.g., subtracting the first set of patient position-shift vectors from an intermediate set of patient position-shift vectors calculated via the comparison of the acquired image of the second patient target region to the treatment planning image of the second patient target region).

The patient may be positioned (208) according to a first set of patient position-shift vectors to a first orientation. The positioning may include, for example, arranging the patient in a particular pose on a patient platform and/or orienting or tilting the patient platform in any suitable direction according to the first set of patient position-shift vectors. Therapeutic radiation may be delivered (210) to a first target region of the patient while the patient is in the first orientation, as further described below. In some embodiments, rather than the first orientation of the patient being associated with a first set of patient platform movements, the first orientation may be associated with only one patient platform step or position (e.g., a beam station).

The patient may be positioned (212) according to the second set of patient position-shift vectors to a second orientation. The positioning may include, for example, arranging the patient in a particular pose on a patient platform and/or orienting or tilting the patient platform in any suitable direction according to the second set of patient position-shift vectors. Therapeutic radiation may then be delivered (214) to the second target region of the patient while the patient is in the second orientation. In some embodiments, rather than the second orientation of the patient being associated with a second set of patient platform movements, the second orientation may be associated with only one patient platform step or position (e.g., beam station adjacent to a beam station associated with the first orientation).

In some embodiments, the patient may be moved continuously relative to a source of therapeutic radiation while therapeutic radiation is delivered to the patient. For example, the patient may be positioned in the first orientation via rotating and/or tilting the patient platform and/or rotating a gantry on which the source of therapeutic radiation is disposed. The patient platform may then be continuously moved relative to (e.g., through) a radiation beam path or beam plane of a therapeutic radiation source such that radiation is delivered to the first target region of the patient. After delivery of the radiation to the first target region of the patient, the patient may be positioned in the second orientation via rotating and/or tilting the patient platform and/or rotating the gantry on which the source of therapeutic radiation is disposed. The patient platform may then be continuously moved relative to (e.g., through) the radiation beam path or beam plane of the therapeutic radiation source such that radiation is delivered to the second target region of the patient.

In some embodiments, the patient may be moved through a series of discrete, predefined positions relative to the therapeutic radiation source and the radiation may be delivered when the patient is stationary relative to the therapeutic radiation source. For example, the patient may be moved to the first orientation and positioned relative to the therapeutic radiation source such that the patient is immobilized and stationary relative to the therapeutic radiation source. Radiation beams may then be applied to the first patient target region of the patient for a particular length of time and/or during a first series of stepped movements of the patient platform relative to the therapeutic radiation source. In variations where the therapeutic radiation source is mounted on a rotatable gantry that rotates around the patient, radiation may be applied over one or more rotations or cycles around the patient. For example, in a circular, continuously rotating gantry, radiation may be applied over several rotations of the therapeutic radiation source around the patient. After a patient target region has been irradiated according to the treatment plan, the beam of radiation may be turned off and the patient platform may be moved to the next predefined position, and radiation may be applied to the patient as described above (and repeated as desired). Thus, after radiation beams have been applied to the first target region according to the treatment plan, the platform and/or the patient may be adjusted so that the patient is transitioned to the second orientation and position. When in the second orientation and position, the patient may be immobilized and stationary relative to the therapeutic radiation source. Radiation beams may then be applied to the second target region of the patient for a particular length of time, during a second series of stepped movements of the patient platform relative to the therapeutic radiation source, and/or for application of radiation to the second target region over on or more rotations or cycles of a rotatable gantry (similarly as described above). After the second patient target region has been irradiated according to the treatment plan, the beam of radiation may be turned off. If there are additional patient target regions to be irradiated, the patient and/or the patient platform may be adjusted to the next predefined position. Additional details and variations of a radiation therapy system comprising methods of radiation delivery is described in U.S. Provisional Appl. No. 62/562,212, filed Sep. 22, 2017, which is herein incorporated by reference in its entirety.

In some embodiments, the user may specify criterion limiting the automatic application of setup correction to avoid clinically inaccurate position corrections and/or unfeasible position corrections. For example, the user may set a threshold time duration from the time of image acquisition to irradiation. The threshold time duration may be based on the time period during which the acquired image is still likely to be accurate. If the time threshold elapses, the user may be alerted and the radiation treatment session halted. Similarly, the user may limit automatic application of setup correction based on elapsed treatment time. Thus, if the calculated position of the target or targets are only likely to be consistent for a certain time duration, the user may set a limit on the treatment time duration before the radiation treatment session must be discontinued and/or fresh/updated images of the target region or target regions acquired. Another criterion that may be included is the distance between target regions or targeted tumors may be limited such that if the distance between the target regions or target tumors exceeds a distance threshold, the user may be notified prior to the initiation of the radiation treatment session. The distance may be based on the distance at which accuracy of the position of one or both of the target regions is likely inaccurate. In some embodiments, the distance threshold may be based on clinical protocol. For example, the distance threshold may be about 30 cm. Additionally, the amount of monitor units (MU) delivered may be used to determine if the system is likely to provide clinically inaccurate position corrections. For example, a notification may be provided to the user prior to the initiation of the radiation treatment session based on the total MU planned to be delivered.

Furthermore, in some embodiments, if a set of patient shift vectors is generated and the corresponding patient position is not feasible, a notification to the user may be generated and/or adjustments may be made. For example, if the set of patient shift vectors suggests a tilt angle that is too steep of an incline to be able to be safely implemented, the user may be notified and/or adjustments made. Additionally, if the set of patient shift vectors suggests a positioning of the patient and/or platform that would result in a collision with another portion of the patient therapy system, the user may be notified and/or adjustments made. In some embodiments, the system may be configured to notify the user and/or make adjustments based on pre-determined thresholds and/or boundary conditions, such as pre-determine platform incline thresholds or boundaries representing the locations of other system components. In some embodiments, alternative positioning instructions may be generated representing, for example, alternative tilt angles. In some embodiments, notifications representing the effect of the alternative positioning instructions may be generated (e.g., representing that a particular number of degrees different in the tilt angle changes alignment with a patient target region by a particular amount) for the user's consideration.

Figure 12A:
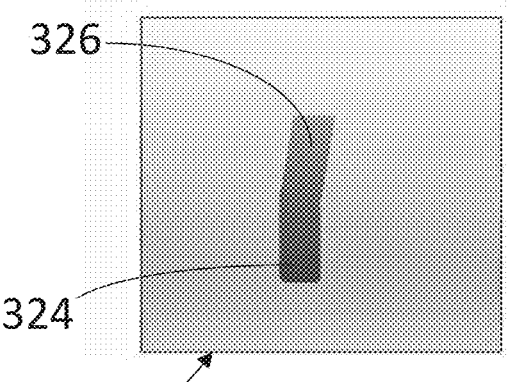
FIGS. 12A-12F illustrate one variation of a procedure by which the position of a patient may be adjusted.
Figure 12B:
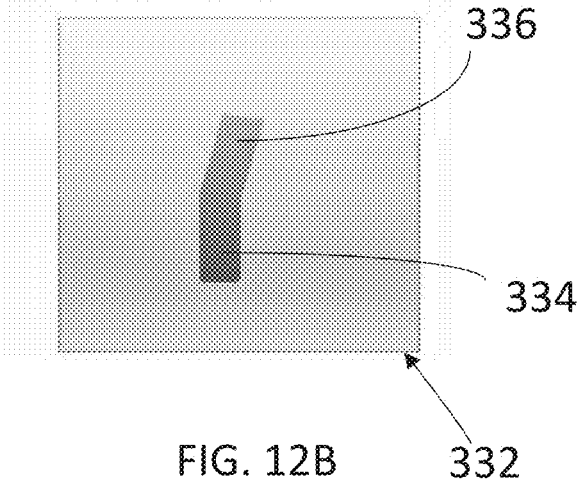

FIGS. 12A-12F illustrate a procedure by which the position of a patient may be adjusted. For example, FIG. 12A represents a treatment planning image (322) acquired in advance of a radiation treatment session. The treatment planning image (322) may be used to prepare a treatment plan for irradiating a tumor of the patient during a radiation treatment session. As shown, the treatment planning image (322) may include a first patient target region (324) and a second patient target region (326), representing a first portion and a second portion of a tumor, respectively. FIG. 12B represents an acquired image (332) acquired via imaging prior to or at the start of a radiation treatment session. The acquired image (332) may include a first patient target region (334) and a second patient target region (336), representing the first portion and the second portion of the tumor, respectively. The treatment planning image (322) and the acquired image (332) may be acquired via any suitable imaging method, such as, for example, via PET or CT scans. The treatment planning image (322) and the acquired image (332) may be two-dimensional images.

Figure 12C:
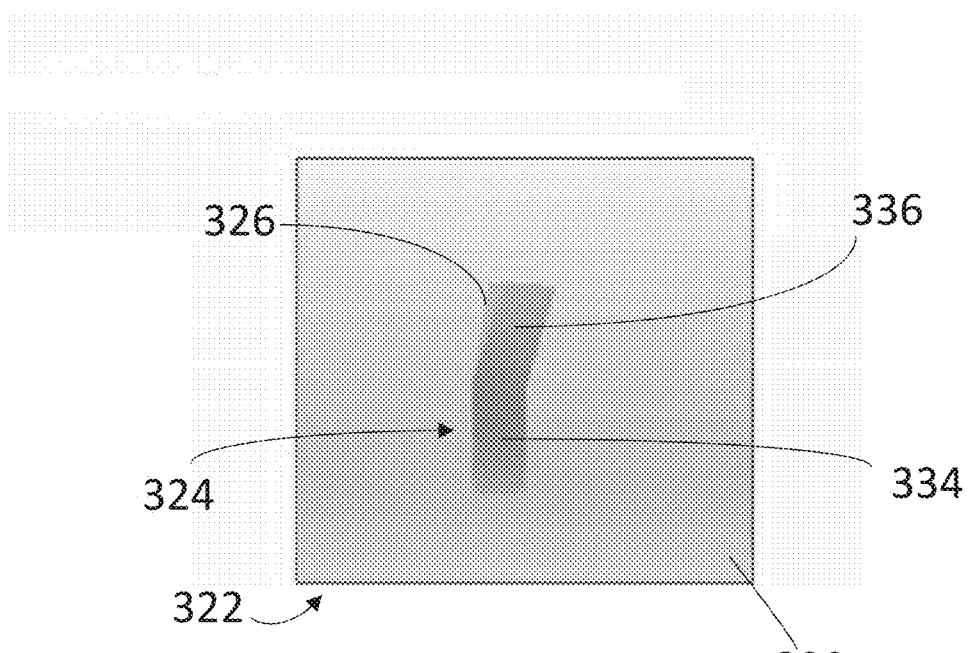

FIG. 12C is a representation of the acquired image (332) overlapped with the treatment planning image (322) such that the shape, size, and location of the first patient target region (324) and the second patient target region (326) of the treatment planning image (322) may be compared to the shape, size, and location of the first patient target region (334) and the second patient target region (336) of the acquired image (332). As shown in FIG. 12C, the first patient target region (324) and the second patient target region (326) of the treatment planning image (322) and the first patient target region (334) and the second patient target region (336) of the acquired image (332) are not aligned or perfectly coincident. In particular, the first patient target region (324) of the treatment planning image (322) and the first patient target region (334) of the acquired image (332) are co-located and appear to align, but the second patient target region (326) of the treatment planning image (322) and the second patient target region (336) of the acquired image (332) are not co-located. As may be seen in FIG. 12C, the second patient target region (336) of the acquired image (332) is disposed at an angle relative to the second patient target region (326) of the treatment planning image (322). The accuracy of the treatment plan may be improved by positioning and orienting the patient such that the second patient target region of the patient is co-located or more closely co-located with the location of the second patient target region (326) of the treatment planning image (322) for the delivery of radiation to the second patient target region.

Figure 12D:
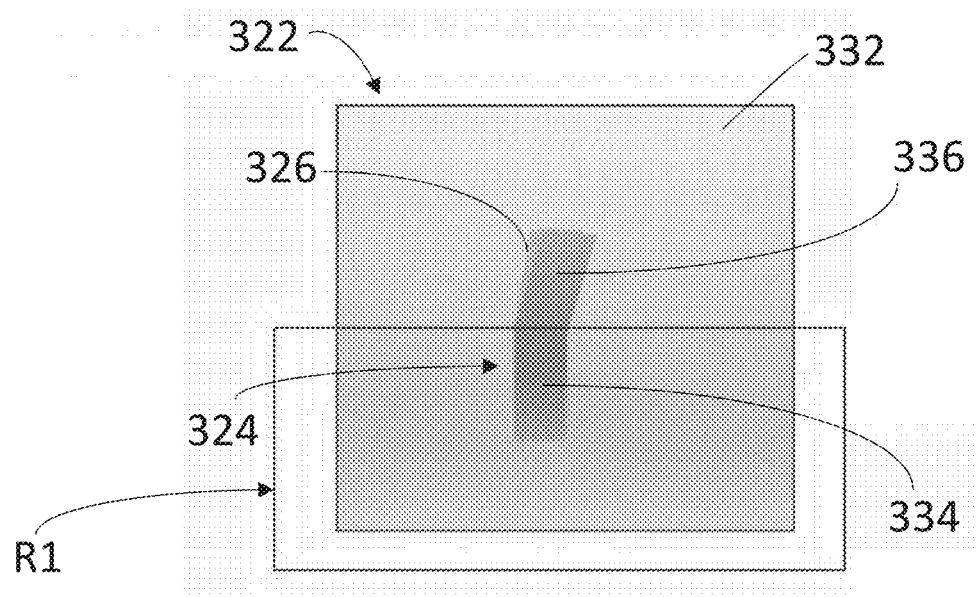

One or more treatment areas may be defined based on the location and position of each portion of the acquired image (332) and the location and position of each portion of the treatment planning image (322). As shown in FIG. 12D, the user may specify a first treatment area R1 (e.g., via a graphic user interface associated with a radiation therapy system). Since the first patient target region (324) of the treatment planning image (322) and the first patient target region (324) of the acquired image (332) are shown to be co-located and coextensive in the initial comparison shown in FIG. 12C, no locational and/or positional differences exist between the treatment planning image (322) and the acquired image (332) within the first treatment area R1. Thus, no position-shifting is necessary prior to delivery of therapeutic radiation to the patient within the first treatment area R1. In some embodiments, a first set of patient position-shift vectors may be calculated for the first treatment area R1 reflecting that no translation along or about the X, Y, and Z axes (e.g., about a yaw, pitch, and/or roll axis) is necessary during patient set up prior to initiation of the delivery of therapeutic radiation to the first patient target region. For example, in some embodiments, the first patient target region may be divided into sub-regions (e.g., sub-volumes) that may be represented by voxels, and the coordinates of each voxel of the first patient target region (334) of the acquired image (332) may be compared with the coordinates of a corresponding voxel of the first patient target region (324) in the treatment planning image (322). If the first set of patient position-shift vectors reflects new coordinate locations for each voxel of the acquired image (332) corresponding to the differences between the acquired image (332) and the treatment planning image (322) by including a position-change vector for each voxel of the acquired image (332), the position-shift vectors corresponding to the first treatment area R1 may be reflected as zeros. In some embodiments, rather than dividing the first patient target region into sub-regions for comparison of the locations of the sub-regions in the acquired image (332) to the treatment planning image (322), the first set of patient position-shift vectors may reflect distance and/or direction the acquired image (332) may be moved (e.g., translated and/or rotated) relative to the treatment planning image (322) in the same plane to improve the alignment (e.g., overlap) between the first patient target region (324) and the second patient target region (326). If no movement of the acquired image (332) relative to the treatment planning image (322) would improve the alignment between the first patient target region (324) and the second patient target region (326), the first set of position-change vectors corresponding to the first treatment area R1 may be reflected as zeros.

Figure 12E:
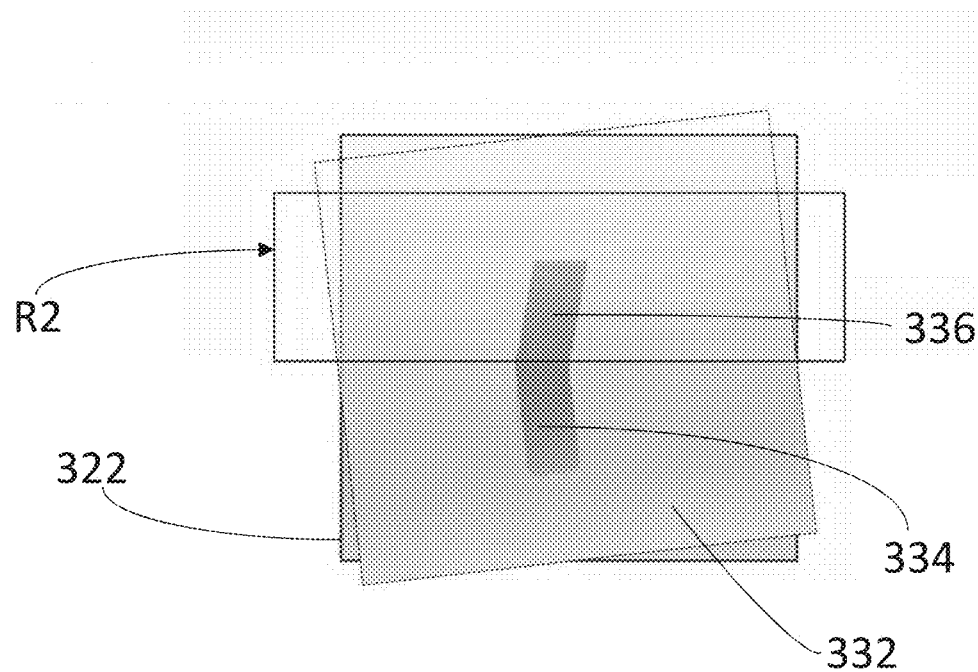

As shown in FIG. 12E, the user may specify a second treatment area R2. The acquired image (332) may be moved relative to the treatment planning image (322) to align the treatment planning image (322) with the acquired image (332) within in the second treatment area R2. In some embodiments, the second patient target region may be divided into sub-regions (e.g., sub-volumes) that may be represented by voxels, and the coordinates of each voxel of the second patient target region (336) of the acquired image (332) may be compared with the coordinates of a corresponding voxel of the second patient target region (326) in the treatment planning image (322). For example, each voxel of the acquired image (332) may be translated along or about the X, Y, and/or Z axes until the second patient target region (326) of the treatment planning image (322) and the second patient target region (336) of the acquired image (332) are aligned and/or co-located. For example, as shown in FIG. 12E, the acquired image (332) may be rotated counterclockwise relative to the treatment planning image (322) until the treatment planning image (322) and the acquired image (332) are aligned and/or the overlap between the second patient target region (336) and the second patient target region (326) is increased within the second treatment area R2. A second set of patient position-shift vectors may be calculated corresponding to the second treatment area R2 based on locational and/or positional differences between the treatment planning image (322) and the acquired image (332) in the second treatment area R2 prior to the movement of the acquired image (332) to improve the overlap with the treatment planning image (322). In some embodiments, the second set of patient position-shift vectors may reflect the distance and/or direction each voxel of the acquired image (332) is translated to improve the alignment between the second patient target region (336) and the second patient target region (326). In some embodiments, the second set of patient position-shift vectors may reflect the distance and/or direction the acquired image (332) may be translated and/or rotated relative to the treatment planning image (322) in the same plane to improve the alignment (e.g., overlap) between the second patient target region (336) and the second patient target region (326). Furthermore, the second set of patient position-shift vectors may include and/or correspond to instructions as to how a patient should be positioned and oriented for the delivery of therapeutic radiation (e.g., via the positioning and/or orienting of a platform upon which the patient is disposed) such that the second target region of the patient may be irradiated more accurately than if the patient is arranged in the position they were in during the acquisition of treatment planning images (e.g., if the platform on which the patient is disposed is in the same position and/or orientation as during the acquisition of the treatment planning images).

Figure 12F:
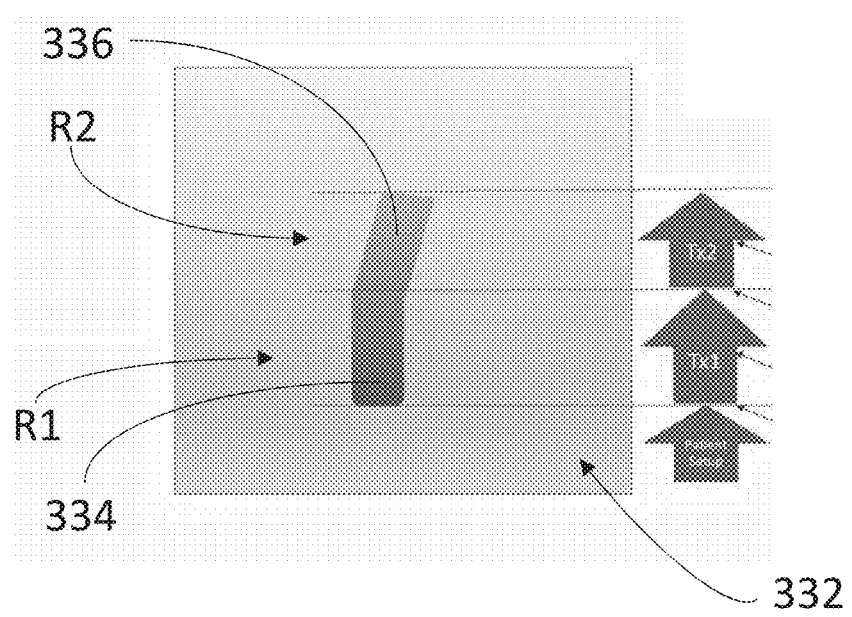

As represented in FIG. 12F, the patient may then be positioned relative to a therapeutic radiation source of a radiation therapy system such that radiation may be applied effectively to the target regions of the patient. For example, the patient may be positioned in a first orientation according to the first set of patient position-shift vectors during patient setup. In this case, the first set of patient position-shift vectors represent no locational or positional differences from the first patient target region (324) in the treatment planning image (322) to the first patient target region (334) in the acquired image (332). Thus, the patient may be positioned according to the treatment plan as represented in the treatment planning image (322). Next, therapeutic radiation may be delivered to the first patient target region while the patient is in the first orientation (e.g., while translating the patient through the radiation therapy system relative to the therapeutic radiation source), as represented by arrow Tx1.

After delivering therapeutic radiation to the first patient target region while the patient is in the first orientation, the patient may be positioned in a second orientation according to the second set of patient position-shift vectors. Next, therapeutic radiation may be delivered to the second patient target region while the patient is in the second orientation (e.g., while translating the patient through the radiation therapy system relative to the therapeutic radiation source), as represented by arrow Tx2.

Figure 13D:
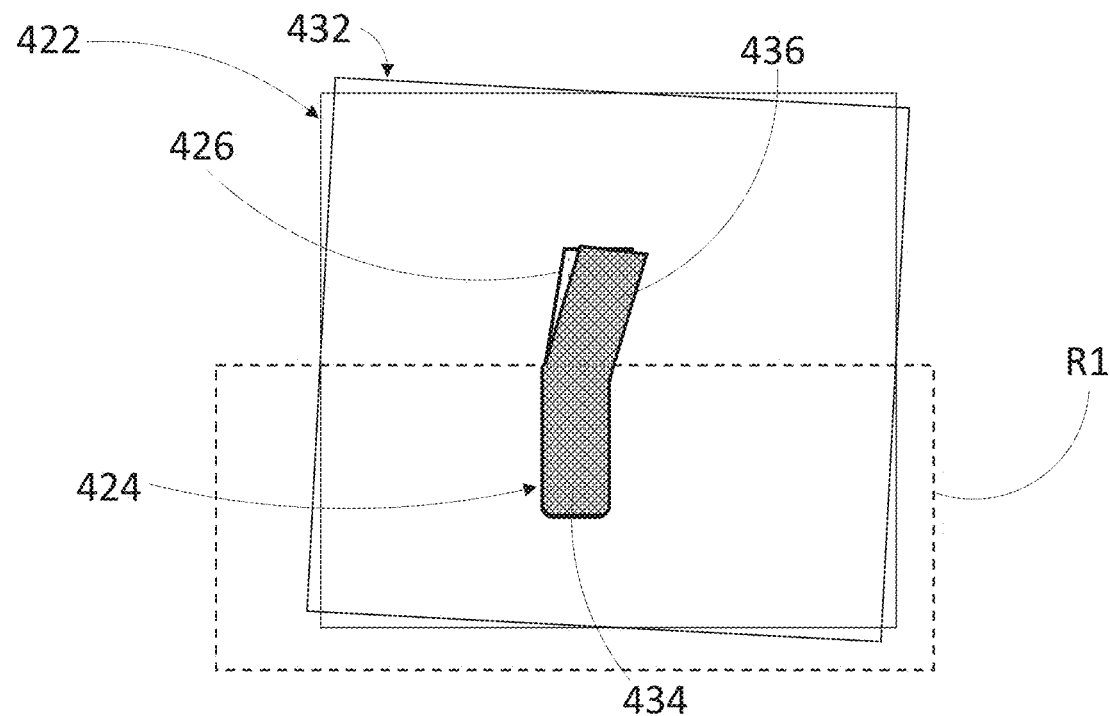

FIGS. 13A-13F illustrate a procedure by which the position of a patient may be adjusted. For example, FIG. 13A represents a treatment planning image (422) acquired in advance of a radiation treatment session. The treatment planning image (422) may be used to generate a treatment plan for irradiating a tumor of the patient during a radiation treatment session. As shown, the treatment planning image (422) may include a first patient target region (424) and a second patient target region (426), representing a first portion and a second portion of a tumor, respectively. FIG. 13B represents an acquired image (432) acquired via imaging prior to or at the start of a radiation treatment session. The acquired image (432) may include a first patient target region (434) and a second patient target region (436), representing the first portion and the second portion of the tumor, respectively. The treatment planning image (422) and the acquired image (432) may be acquired via any suitable imaging method, such as, for example, via PET or CT scans. The treatment planning image (422) and the acquired image (432) may be two-dimensional images.

FIG. 13C is a representation of the acquired image (432) overlapped with the treatment planning image (422) such that the shape, size, and location of the first patient target region (424) and the second patient target region (426) of the treatment planning image (422) may be compared to the shape, size, and location of the first patient target region (434) and the second patient target region (424) of the acquired image (432). As shown in FIG. 13C, the first patient target region (424) and the second patient target region (426) of the treatment planning image (422) are not aligned or perfectly coincident with the first patient target region (434) and the second patient target region (436), respectively, of the acquired image (432). As may be seen in FIG. 13C, the first patient target region (434) and the second patient target region (436) of the acquired image (432) are each disposed at an angle relative to the first patient target region (424) and the second patient target region (426), respectively, of the treatment planning image (422). Thus, the accuracy of the treatment plan may be improved by positioning and/or orienting the patient such that the first patient target region is co-located or more closely co-located with the location of the first patient target region (424) of the treatment planning image (422) for the delivery of radiation to the first patient target region, and to reposition and/or reorient the patient such that the second patient target region of the patient is co-located or more closely co-located with the location of the second patient target region (426) of the treatment planning image (422) for the delivery of radiation to the second patient target region.

One or more treatment areas may be defined based on the location and position of each portion of the acquired image (432) and the location and position of each portion of the treatment planning image (422). As shown in FIG. 13D, the user may specify a first treatment area R1 (e.g., via a graphic user interface associated with a radiation therapy system). The acquired image (432) may be moved relative to the treatment planning image (422) to align the treatment planning image (422) with the acquired image (432) within in the first treatment area R1. In some embodiments, the first patient target region may be divided into sub-regions (e.g., sub-volumes) that may be represented by voxels, and the coordinates of each voxel of the first patient target region (434) of the acquired image (432) may be compared with the coordinates of a corresponding voxel of the first patient target region (424) in the treatment planning image (422). For example, each voxel of the acquired image (432) may be translated along or about the X, Y, and/or Z axes until the acquired image (432) and the treatment planning image (422) are aligned and/or co-located. For example, as shown in FIG. 13D, the acquired image (432) may be rotated clockwise relative to the treatment planning image (422) until the treatment planning image (422) and the acquired image (432) are aligned and/or the overlap between the first patient target region (424) and the first patient target region (426) is increased within the first treatment area R1. A first set of patient position-shift vectors may be calculated corresponding to the first treatment area R1 based on locational and/or positional differences between the treatment planning image (422) and the acquired image (432) in the first treatment area R1 prior to the movement of the acquired image (432) to improve the overlap with the treatment planning image (422). The first set of patient position-shift vectors may reflect the distance and/or direction each voxel of the acquired image (432) is translated to improve the alignment between the first patient target region (434) of the acquired image (432) and the first patient target region (424) of the treatment planning image (422). In some embodiments, rather than dividing the first patient target region into sub-regions for comparison of the locations of the sub-regions in the acquired image (432) to the treatment planning image (422), the first set of patient position-shift vectors may reflect the distance and/or direction the acquired image (432) may be moved (e.g., translated and/or rotated) relative to the treatment planning image (422) in the same plane to improve the alignment (e.g., overlap) between the first patient target region (424) and the first patient target region (426). Furthermore, the first set of patient position-shift vectors may include and/or correspond to instructions as to a first position and/or orientation of the patient for the delivery of therapeutic radiation (e.g., via the positioning and/or orienting of a platform upon which the patient is disposed) such that the first patient target region of the patient may be irradiated more accurately than if the patient is arranged in the position they were in during the acquisition of treatment planning images (e.g., if the platform on which the patient is disposed is in the same position and/or orientation as during the acquisition of the treatment planning images).

Figure 13E:
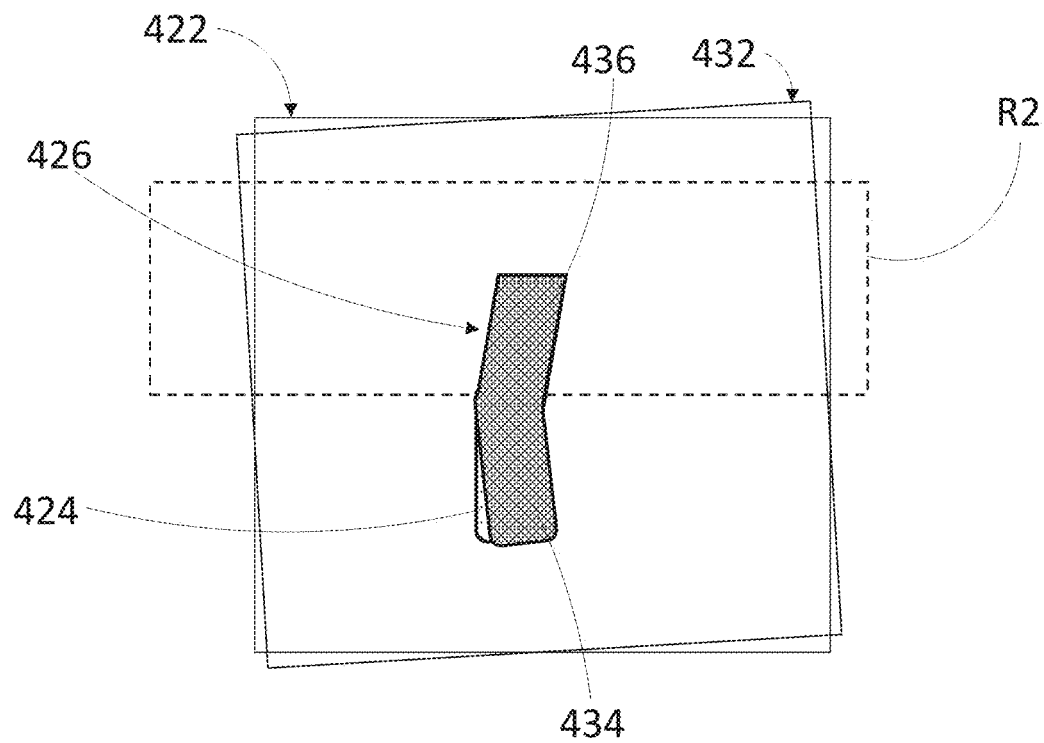

As shown in FIG. 13E, the user may specify a second treatment area R2. Similarly as described above with reference to FIG. 13D, the acquired image (432) may be moved relative to the treatment planning image (422) to align and/or co-located the treatment planning image (422) with the acquired image (432) within in the second treatment area R2. In some embodiments, the second patient target region may be divided into sub-regions (e.g., sub-volumes) that may be represented by voxels, and the coordinates of each voxel of the second patient target region (436) of the acquired image (432) may be compared with the coordinates of a corresponding voxel of the second patient target region (426) in the treatment planning image (422). As shown in FIG. 13E, the acquired image (432) may be rotated counterclockwise relative to the treatment planning image (422) until the treatment planning image (422) and the acquired image (432) are aligned and/or the overlap between the second patient target region (426) and the second patient target region (436) is increased within the second treatment area R2. A second set of patient position-shift vectors may be calculated corresponding to the second treatment area R2 based on locational and/or positional differences between the treatment planning image (422), the acquired image (432) in the second treatment area R2, and the first set of patient position-shift vectors. For example, the second set of patient position-shift vectors may be calculated based on the differences between the treatment planning image (422) and the acquired image (432) prior to the movement of the acquired image (432) to improve the overlap with the treatment planning image (422). In some embodiments, the second set of patient position-shift vectors may reflect the distance and/or direction each voxel of the acquired image (432) is translated to improve the alignment between the second patient target region (436) of the acquired image (432) and the second patient target region (426) of the treatment planning image (422). In some embodiments, the second set of patient position-shift vectors may reflect the distance and/or direction the acquired image (432) may be translated and/or rotated relative to the treatment planning image (422) in the same plane to improve the alignment (e.g., overlap) between the second patient target region (436) and the second patient target region (426). The second set of patient position-shift vectors may be calculated based on the first set of patient position-shift vectors in that, after determining a preliminary set of position shift vectors reflecting the differences between the treatment planning image (422) and the acquired image (432), the second set of patient position-shift vectors may be calculated based on the first position and/or orientation of the patient during irradiation of the first patient target region of the patient. Furthermore, the second set of patient position-shift vectors may include instructions for repositioning and/or reorienting the patient (e.g., via the positioning and/or orienting of a platform upon which the patient is disposed) for the delivery of therapeutic radiation based on the first position/orientation of the patient.

Figure 13F:
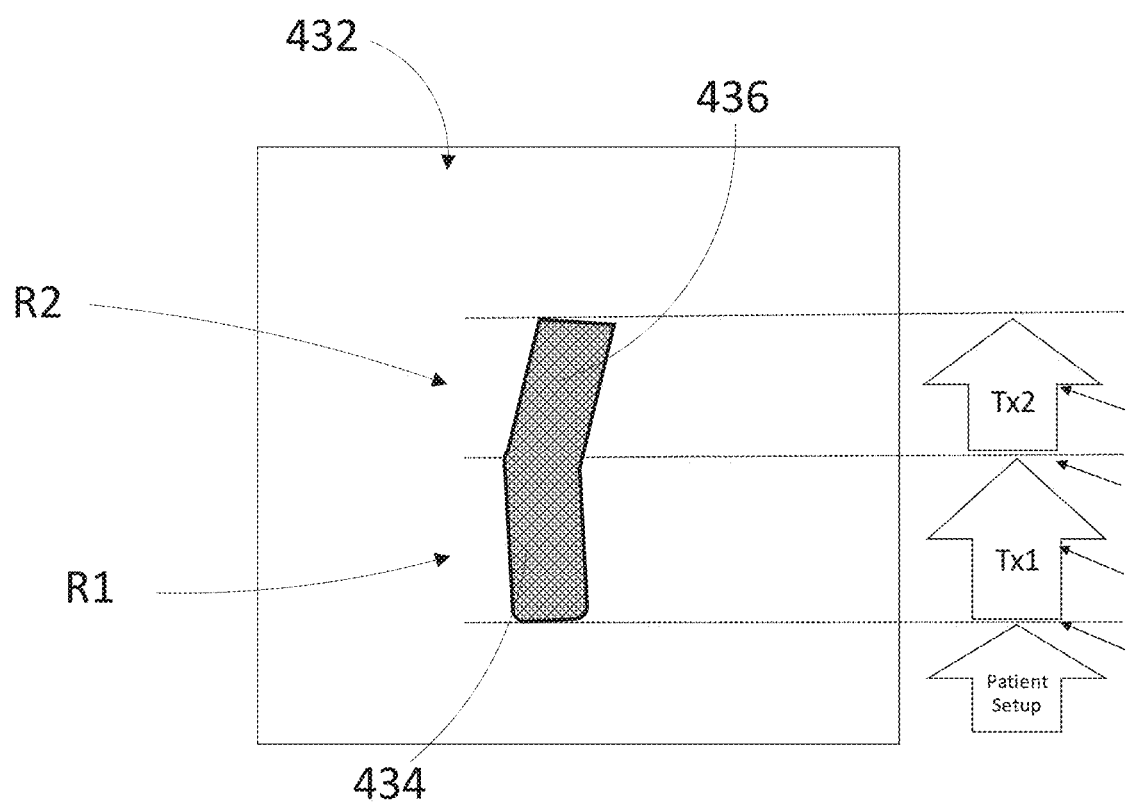

As represented in FIG. 13F, the patient may then be positioned relative to a therapeutic radiation source of a radiation therapy system such that radiation may be applied effectively to the target regions of the patient. For example, the patient may be positioned in a first orientation on the patient platform according to the first set of patient position-shift vectors during patient setup. Therapeutic radiation may then be delivered to the first patient target region while the patient is in the first orientation and moved through a range of patient platform positions into the radiation beam of the therapeutic radiation source, as represented by arrow Tx1. For example, a first range or set of patient platform movements may correspond to the irradiation of the first patient target region and a second range or set of patient platform movements may correspond to the irradiation of the second patient target region. Thus, the platform may move through the first range set of patient platform movements (e.g., a first set of patient platform steps or positions) relative to the therapeutic radiation source in the first orientation and with the patient arranged in the first position on the patient platform while the therapeutic radiation is delivered. In some embodiments, rather than the first orientation of the patient being associated with a first set of patient platform movements, the first orientation may be associated with a first set of one or more patient platform steps or positions (e.g., one or more beam stations). For example, the first orientation may be associated with a single first beam station. In some embodiments, the patient platform may move continuously (e.g., along the Y-axis of the patient surface) relative to (e.g., through) a radiation beam path or beam plane of the therapeutic radiation source during delivery of therapeutic radiation to the first patient region while the patient is in the first orientation. Alternatively or additionally, the patient platform may be stepped through a plurality of beam stations and stopped at a beam station during delivery of therapeutic radiation.

After delivering therapeutic radiation to the first patient target region while the patient is in the first orientation, the delivery of therapeutic radiation may be ceased and the patient may be positioned in a second orientation according to the second set of patient position-shift vectors. For example, the patient platform may cease progressing through the system and the user may be notified to adjust the setup position. Next, therapeutic radiation may be delivered to the second patient target region while the patient is in the second orientation and moved through a range of patient platform positions into the radiation beam of the therapeutic radiation source, as represented by arrow Tx2. For example, the platform may move through a second range or set of patient platform movements (e.g., a second range or set of patient platform steps or positions, or beam stations) relative to the therapeutic radiation source in the second orientation and with the patient arranged in the second position orientation on the patient platform while the therapeutic radiation is delivered. In some embodiments, rather than the second orientation of the patient being associated with a second set of patient platform movements, the second orientation may be associated with a second set of one or more patient platform steps or positions (e.g., one or more beam stations, a beam station adjacent to the beam station associated with the first orientation). For example, the second orientation may be associated with a single second beam station. In some embodiments, the patient platform may move continuously (e.g., along the Y-axis of the patient surface) relative to (e.g., through) a radiation beam path or beam plane of the therapeutic radiation source during delivery of therapeutic radiation to the second patient region while the patient is in the second orientation. Alternatively or additionally, the patient platform may be stepped through a plurality of beam stations and stopped at a beam station during delivery of therapeutic radiation.

Figure 14A:
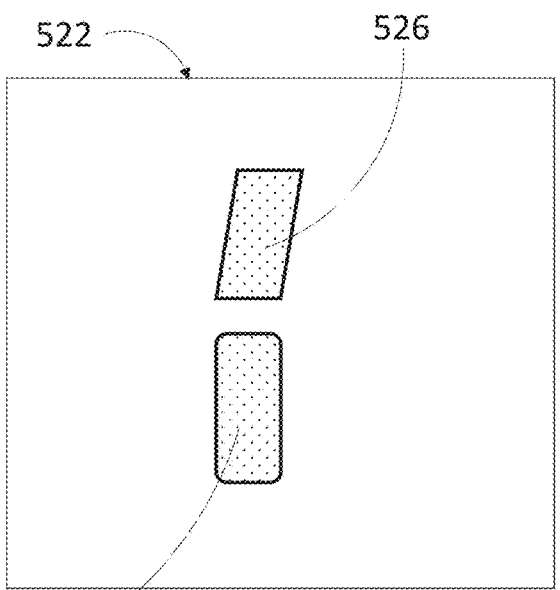
FIGS. 14A-14F illustrate one variation of a procedure by which the position of a patient may be adjusted to irradiate two discrete patient target regions.
Figure 14B:
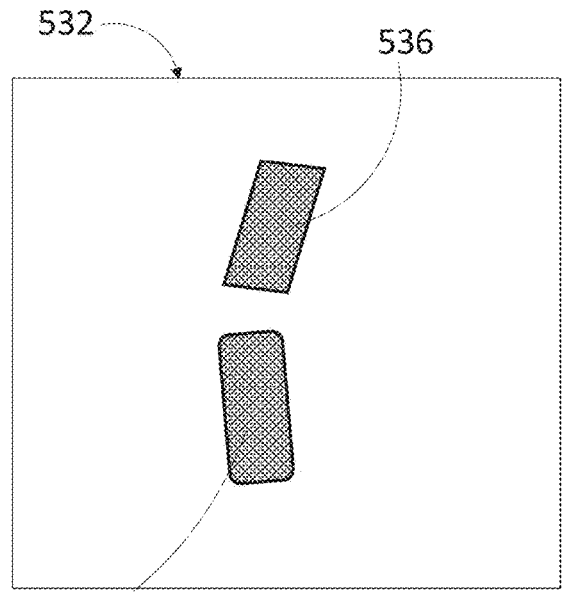

FIGS. 14A-14F illustrate a procedure by which the position of a patient may be adjusted. For example, FIG. 14A represents a treatment planning image (522) acquired in advance of a radiation treatment session. The treatment planning image (522) may be used to prepare a treatment plan for irradiating two or more tumors of the patient, e.g., tumors located at different body regions of a patient, during a radiation treatment session. For example, the tumors may be located in a patient's head and chest or in a patient's neck and lungs. As shown, the treatment planning image (522) may include a first patient target region (524) and a second patient target region (526), representing a first tumor and a second tumor, respectively. FIG. 14B represents an acquired image (532) acquired via imaging prior to or at the start of a radiation treatment session. The acquired image (532) may include a first patient target region (534) and a second patient target region (536), representing the first tumor and the second tumor, respectively. As may be seen in the representative treatment planning image (522) and the acquired image (532) of FIGS. 14A and 14B, respectively, the first tumor and the second tumor have different shapes, with the first tumor having rounded edges and the second tumor having sharp edges. The treatment planning image (522) and the acquired image (532) may be acquired via any suitable imaging method, such as, for example, via PET or CT scans. The treatment planning image (522) and the acquired image (532) may be two-dimensional images.

Figure 14C:
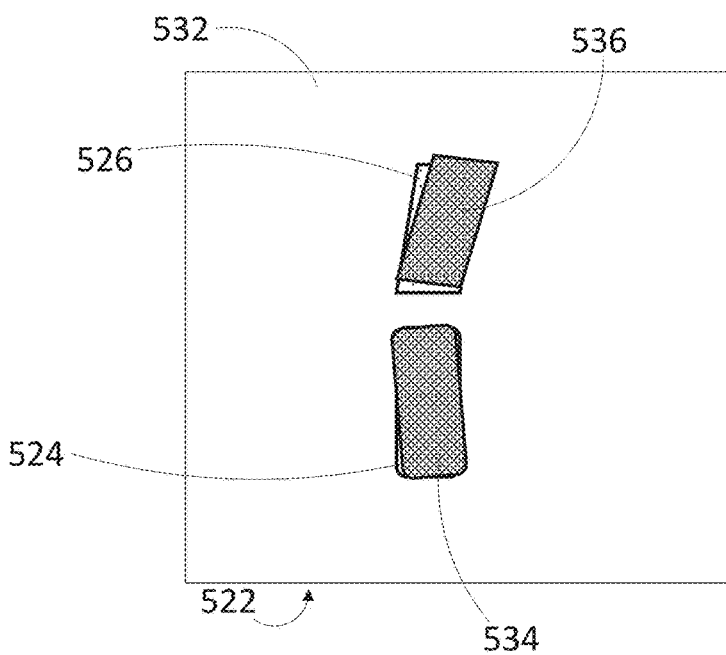

FIG. 14C is a representation of the acquired image (532) overlapped with the treatment planning image (522) such that the shape, size, and location of the first patient target region (524) and the second patient target region (526) of the treatment planning image (522) may be compared to the shape, size, and location of the first patient target region (534) and the second patient target region (536) of the acquired image (532). As shown in FIG. 14C, the first patient target region (524) and the second patient target region (526) of the treatment planning image (522) are not aligned or perfectly coincident with the first patient target region (534) and the second patient target region (536), respectively, of the acquired image (532). As may be seen in FIG. 14C, the first patient target region (534) and the second patient target region (536) of the acquired image (532) are each disposed at an angle relative to the first patient target region (524) and the second patient target region (526), respectively, of the treatment planning image (522). Thus, the accuracy of the treatment plan may be improved by positioning and/or orienting the patient such that the first patient target region is co-located or more closely co-located with the location of the first patient target region (524) of the treatment planning image (522) for the delivery of radiation to the first patient target region, and to reposition and/or reorient the patient such that the second patient target region of the patient is co-located or more closely co-located with the location of the second patient target region (526) of the treatment planning image (522) for the delivery of radiation to the second patient target region.

Figure 14D:
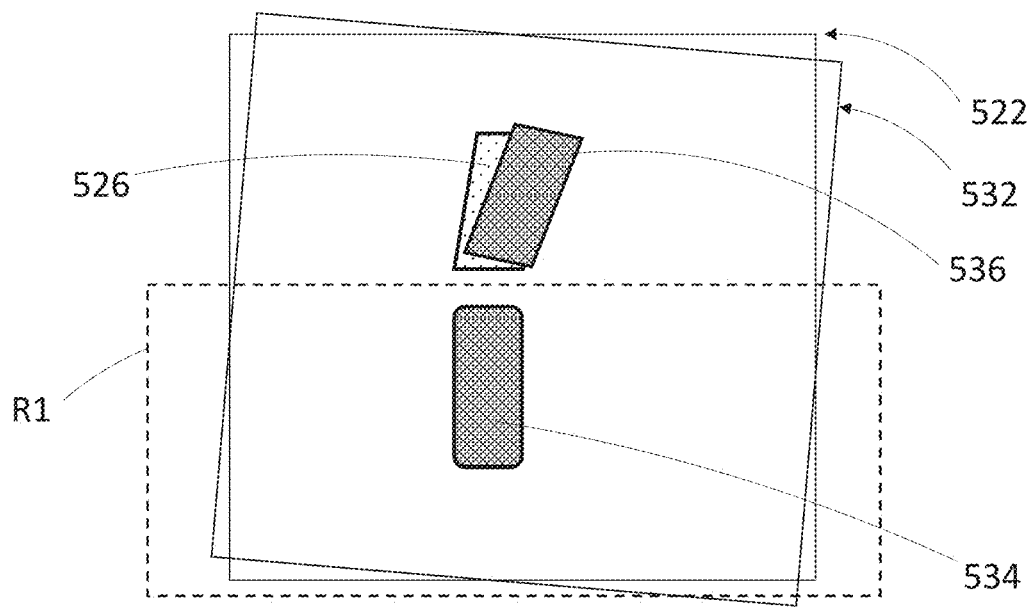

One or more treatment areas may be defined based on the location and position of each portion of the acquired image (532) and the location and position of each portion of the treatment planning image (522). As shown in FIG. 14D, the user may specify a first treatment area R1 (e.g., via a graphic user interface associated with a radiation therapy system). The acquired image (532) may be moved relative to the treatment planning image (522) to align the treatment planning image (522) with the acquired image (532) within in the first treatment area R1. In some embodiments, the first patient target region may be divided into sub-regions (e.g., sub-volumes) that may be represented by voxels, and the coordinates of each voxel of the first patient target region (534) of the acquired image (532) may be compared with the coordinates of a corresponding voxel of the first patient target region (524) in the treatment planning image (522). For example, each voxel of the acquired image (532) may be translated along or about the X, Y, and/or Z axes until the acquired image (532) and the treatment planning image (522) are aligned and/or co-located. For example, as shown in FIG. 14D, the acquired image (532) may be rotated clockwise relative to the treatment planning image (522) until the treatment planning image (522) and the acquired image (532) are aligned and/or the overlap between the first patient target region (524) and the first patient target region (534) is increased within the first treatment area R1. A first set of patient position-shift vectors may be calculated corresponding to the first treatment area R1 based on locational and/or positional differences between the treatment planning image (522) and the acquired image (532) in the first treatment area R1 prior to the movement of the acquired image (532) to improve the overlap with the treatment planning image (522). The first set of patient position-shift vectors may reflect the distance and/or direction each voxel of the acquired image (532) is translated to improve the alignment between the first patient target region (534) of the acquired image (532) and the first patient target region (524) of the treatment planning image (522). In some embodiments, rather than dividing the first patient target region into sub-regions for comparison of the locations of the sub-regions in the acquired image (532) to the treatment planning image (522), the first set of patient position-shift vectors may reflect the distance and/or direction the acquired image (532) may be moved (e.g., translated and/or rotated) relative to the treatment planning image (522) in the same plane to improve the alignment (e.g., overlap) between the first patient target region (524) and the first patient target region (526). Furthermore, the first set of patient position-shift vectors may include and/or correspond to instructions as to a first position and/or orientation of the patient for the delivery of therapeutic radiation (e.g., via the positioning and/or orienting of a platform upon which the patient is disposed) such that the first patient target region of the patient may be irradiated more accurately than if the patient is arranged in the position they were in during the acquisition of treatment planning images (e.g., if the platform on which the patient is disposed is in the same position and/or orientation as during the acquisition of the treatment planning images).

Figure 14E:
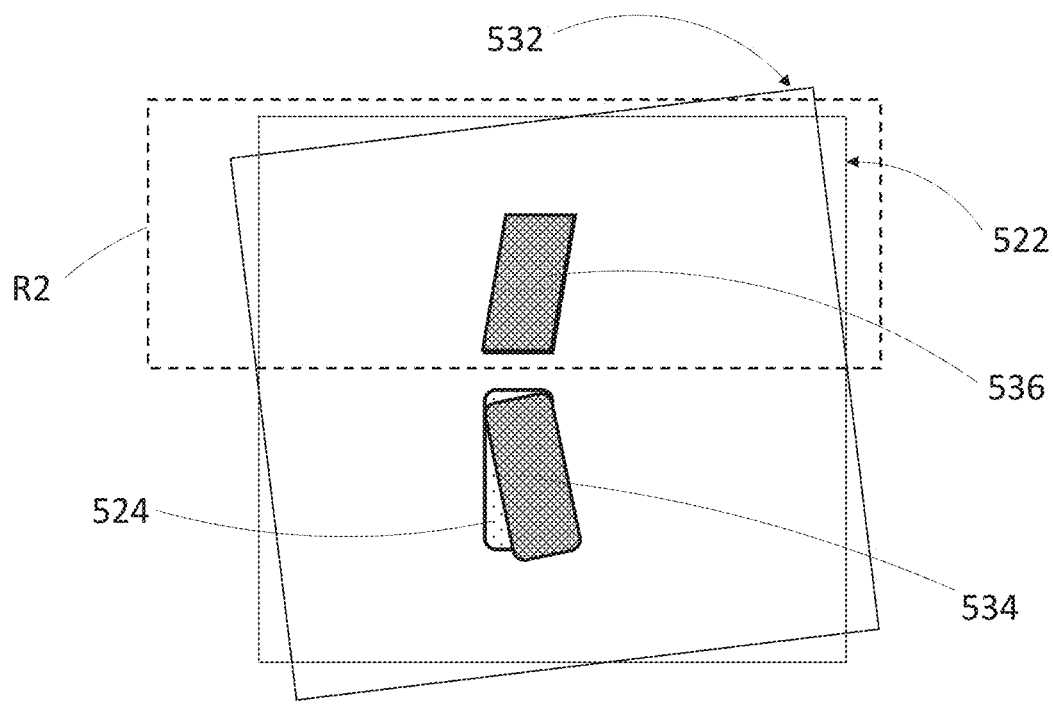

As shown in FIG. 14E, the user may specify a second treatment area R2. Similarly as described above with reference to FIG. 14D, the acquired image (532) may be moved relative to the treatment planning image (522) to align and/or co-located the treatment planning image (522) with the acquired image (532) within in the second treatment area R2. In some embodiments, the second patient target region may be divided into sub-regions (e.g., sub-volumes) that may be represented by voxels, and the coordinates of each voxel of the second patient target region (536) of the acquired image (532) may be compared with the coordinates of a corresponding voxel of the second patient target region (526) in the treatment planning image (522). As shown in FIG. 14E, the acquired image (532) may be rotated counterclockwise relative to the treatment planning image (522) until the treatment planning image (522) and the acquired image (532) are aligned and/or the overlap between the second patient target region (526) and the second patient target region (536) is increased within the second treatment area R2. A second set of patient position-shift vectors may be calculated corresponding to the second treatment area R2 based on locational and/or positional differences between the treatment planning image (522), the acquired image (532) in the second treatment area R2, and the first set of patient position-shift vectors. For example, the second set of patient position-shift vectors may be calculated based on the differences between the treatment planning image (522) and the acquired image (532) prior to the movement of the acquired image (532) to improve the overlap with the treatment planning image (522). In some embodiments, the second set of patient position-shift vectors may reflect the distance and/or direction each voxel of the acquired image (532) is translated to improve the alignment between the second patient target region (536) of the acquired image (532) and the second patient target region (526) of the treatment planning image (522). In some embodiments, the second set of patient position-shift vectors may reflect the distance and/or direction the acquired image (532) may be translated and/or rotated relative to the treatment planning image (522) in the same plane to improve the alignment (e.g., overlap) between the second patient target region (536) and the second patient target region 526. The second set of patient position-shift vectors may be calculated based on the first set of patient position-shift vectors in that, after determining a preliminary set of position shift vectors reflecting the differences between the treatment planning image (522) and the acquired image (532), the second set of patient position-shift vectors may be calculated based on the first position and/or orientation of the patient during irradiation of the first patient target region of the patient. Furthermore, the second set of patient position-shift vectors may include instructions for repositioning and/or reorienting the patient (e.g., via the positioning and/or orienting of a platform upon which the patient is disposed) for the delivery of therapeutic radiation based on the first position/orientation of the patient.

Figure 14F:
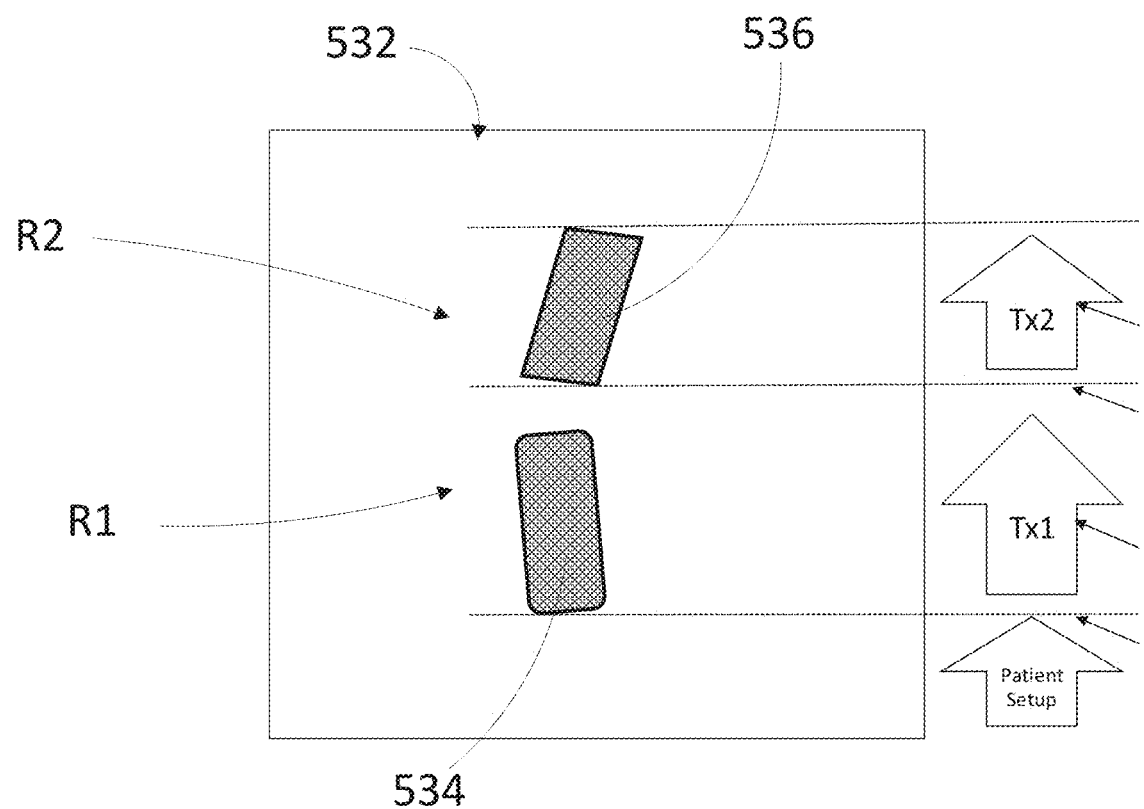

As represented in FIG. 14F, the patient may then be positioned relative to a therapeutic radiation source of a radiation therapy system such that radiation may be applied effectively to the target regions of the patient. For example, the patient may be positioned in a first orientation according to the first set of patient position-shift vectors during patient setup. Therapeutic radiation may then be delivered to the first patient target region while the patient is in the first orientation (e.g., while translating the patient through the radiation therapy system relative to the therapeutic radiation source), as represented by arrow Tx1. For example, a first set of patient platform movements may correspond to the irradiation of the first patient target region and a second set of patient platform movements may correspond to the irradiation of the second patient target region. Thus, the platform may move through the first set of patient platform movements (e.g., a first set of patient platform steps or positions) relative to the therapeutic radiation source in the first orientation and with the patient arranged in the first position on the patient platform while the therapeutic radiation is delivered.

After delivering therapeutic radiation to the first patient target region while the patient is in the first orientation, the patient may be positioned in a second orientation according to the second set of patient position-shift vectors. For example, the patient platform may cease progressing through the system and the user may be notified to adjust the setup position. Next, therapeutic radiation may be delivered to the second patient target region while the patient is in the second orientation (e.g., while translating the patient through the radiation therapy system relative to the therapeutic radiation source), as represented by arrow Tx2, to irradiate the second tumor. For example, the platform may move through a second set of patient platform movements (e.g., a second set of patient platform steps or positions) relative to the therapeutic radiation source in the second orientation and with the patient arranged in the second position orientation on the patient platform while the therapeutic radiation is delivered.

Visualization Graphics

Figure 15A:
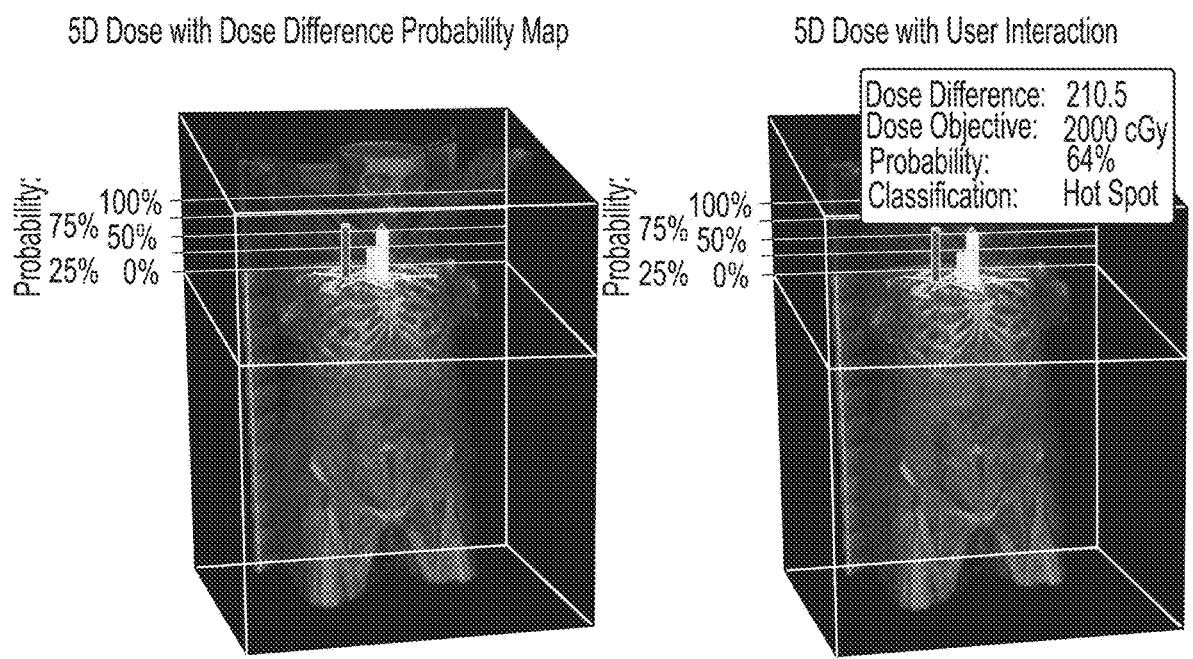
FIG. 15A depicts one variation of visualization graphics that represent dose distribution(s) and/or probabilities.

FIG. 15A depicts one variation of a visualization graphic that represents an overlay of dose values on patient anatomy and the probability values of that those dose values. This may assist a user in identify and/or evaluating hot spots and cold spots within a patient's treatment plan, which may be useful for the evaluation of treatment plans for multiple patient target regions. For each slice within a patient's treatment plan (e.g., for a 3-D rendering, DCM-X, -Y, and -Z), two parametric dose maps of the dose intensities may be generated. In one variation, a method for calculating these dose maps comprise taking the variations of dose calculated for a target region's bDVH and assigning the maximum value at each voxel across the variations to one 3-D dose image and the minimum value at each voxel to another 3-D dose image. Alternatively, a method for calculating these dose maps may comprise calculating the statistically likely value of minimum and maximum dose based on other functions. In one variation, a user may specify tolerance levels for an upper and lower relative limit of dose for a given volumetric region within the patient (e.g. $D_{max}$ and $D_{min}$ tolerance values, in percentage of nominal dose). The parametric dose maps would then be calculated by multiplying the nominal dose value at each voxel within the specified volumetric region by the user-defined tolerance values (e.g., resulting in $D_{pmax}$ and $D_{pmin}$ dose maps, for the $D_{max}$ and $D_{min}$ tolerance values, respectively). Regardless of the chosen method, this results in two 3-D dose distributions that may represent the Maximum Intensity Projection and Minimum Intensity Projection, respectively. Each of these intensities, when visualized, may have a color LUT applied to visually distinguish between high and low values. When combined into a single, binned image with the nominal Dose image, a 4-D Dose image may be visualized in a number of ways. For example, a user may select which bin (e.g., min, max, or nominal) they wish to visualize while using a standard 3-D image viewer. Alternatively or additionally, these bins may be represented as a cinegraph by playing the existing bins as a movie, iterating through them, i.e., a short animation that cycles through each bin on a frame-by-frame basis. Alternatively or additionally, a visualization graphic may comprise depicting these bins with an interpolation function (e.g., interpolation between $D_{pmin}-D_n$, and $D_n-D_{pmax}$), allowing the user to interpolate between the different bins (typically using a slider, but also being able to specify percentages between two bins using a textual input). Alternatively or additionally, the interpolation function may also be rendered as a cinegraph by playing the interpolated bins as a movie on some arbitrary number of steps between bins.

A visualization graphic may optionally incorporate dose probabilities by applying a matrix of probabilities at each voxel of a 4-D dose image and visualizing these as vectors extending out from a plane, such as a plane that represents the nominal probability. One example of such visualization graphics is depicted in FIG. 15B. A user may select a 2-D slice that may be visualized with a colorized dose image. Each voxel of the image may be passed through a probability distribution function to determine the likelihood of that value occurring across the variations calculated for the bDVH. This probability value may be represented in the 3-D image's Z-axis, as depicted in the rightmost image of FIG. 15B. This example shows a single-directional 3-D extrusion on top of a single slice of a CT image. The extrusion level of each pixel in the current 3-D dose image's slice is the probability of variance at that voxel. From this visualization, a user may be able to see that the hottest regions in the patient's dose distribution are also the regions where there is the most variability. Similarly, one of the cold spots has an elevated level of variability. The top, middle, and bottom rows of FIG. 15B depict the nominal, minimum and maximum 3-D dose maps. The left column depicts a view of a selected slice, the middle and right columns depict the location of the selected slide relative to other patient anatomical structures.

Figure 15C:
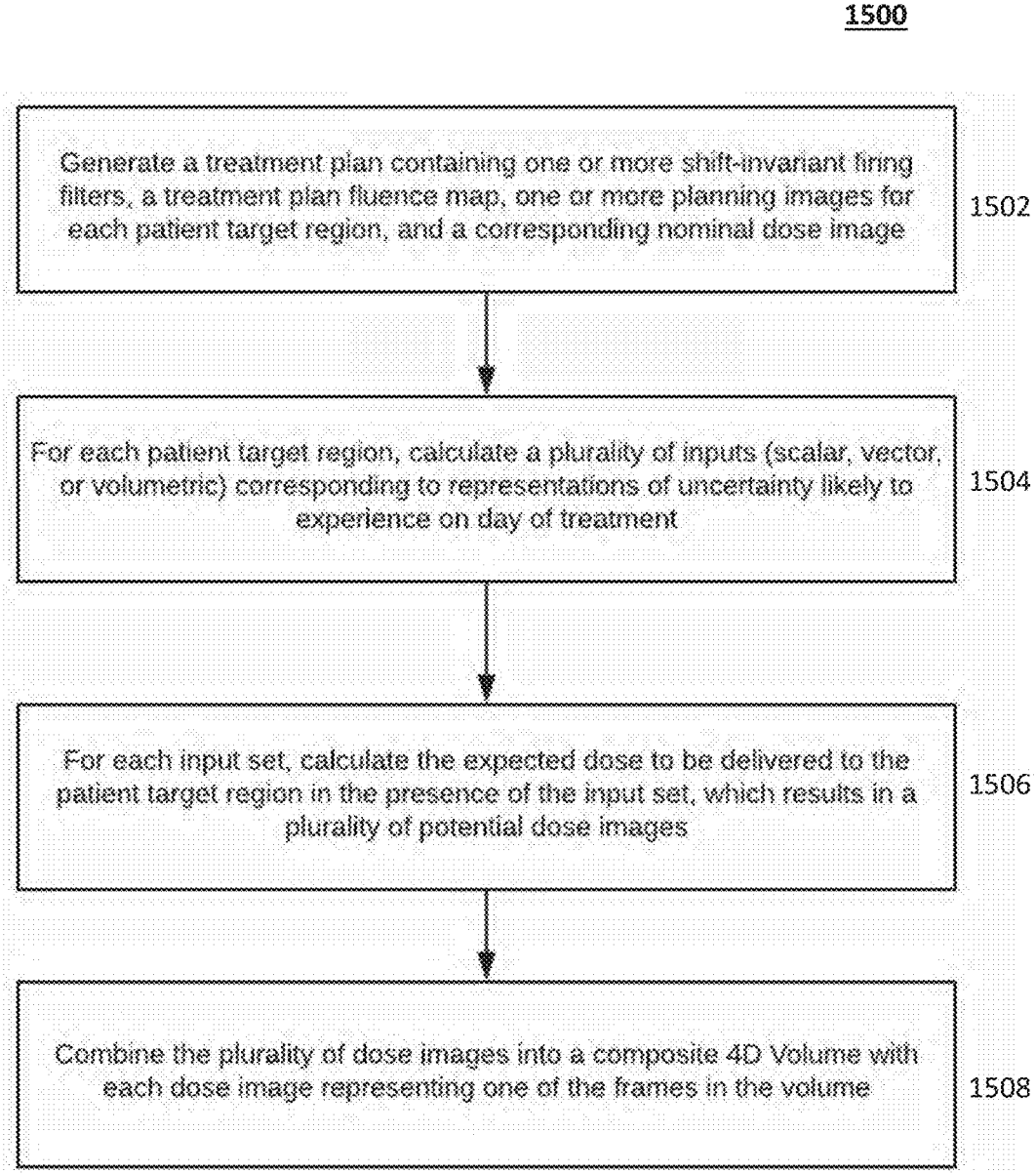
FIG. 15C is a flow chart representation of one variation a method of generating a visualization graphic.
Figure 15D:
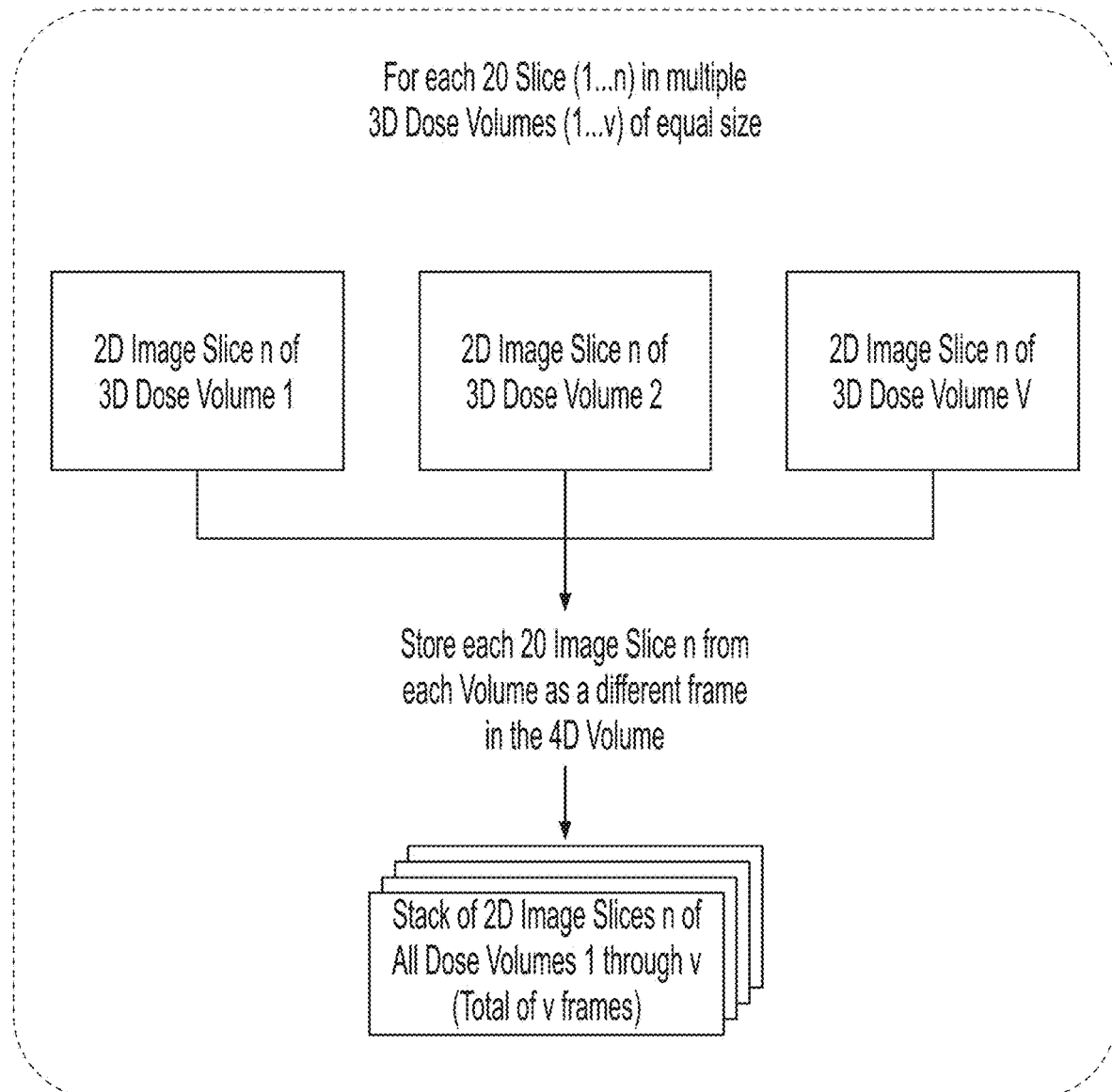
FIG. 15D is a block diagram of one variation a method of generating a visualization graphic.
Figure 15E:
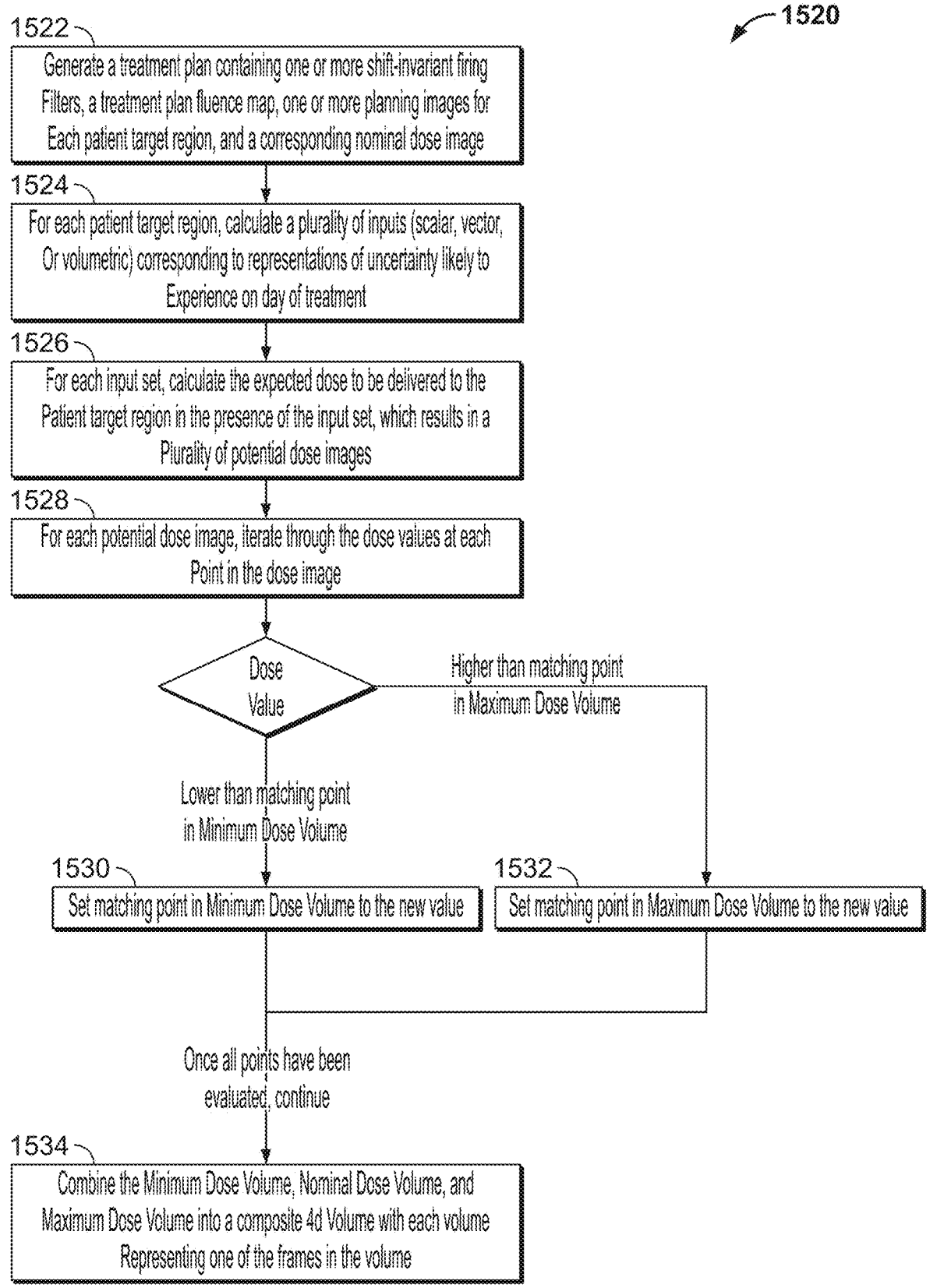
FIG. 15E is a flow chart representation of one variation a method of generating a visualization graphic.

FIGS. 15C-15E depict methods that may be used to generate a visualization graphic, such as the one shown in FIGS. 15A-15B. Method (1500) may comprise generating (1502) a treatment plan containing one or more shift-invariant firing filters, a treatment plan fluence map, one or more planning images for each patient target region, and a corresponding nominal dose image, calculating (1504), for each patient target region, a plurality of inputs (scalar, vector, or volumetric) corresponding to representations of uncertainty likely to be experienced on the day of treatment, calculating (1506), for each input set, the expected dose to be delivered to the patient target region in the presence of the input set, which may result in a plurality of potential dose images, and combining (1508) the plurality of dose images into a composite 4-D volume with each dose image representing one of the frames in the volume.

FIG. 15D is block diagram representing the combination of image slices to form a stack of 2-D image slices to generate a 4-D visualization graphic. The resultant 4-D visualization graphic represents a plurality of dose image volumes, with the fourth dimension in the volume being uncertainty (as opposed to time, as is considered in 4D imaging).

FIG. 15E depicts another variation of a method for generating a visualization graphic, such as the visualization graphics of FIGS. 15A-15B. Method (1520) may comprise generating (1522) a treatment plan containing one or more shift-invariant firing filters, a treatment plan fluence map, one or more planning images for each patient target region, and a corresponding nominal dose image, calculating (1524), for each patient target region, a plurality of inputs (scalar, vector, or volumetric) corresponding to representations of uncertainty on the likely to be experienced on the day of treatment, calculating (1526), for each input set, the expected dose to be delivered to the patient target region in the presence of the input set, which may result in a plurality of potential dose images, and for each potential dose image, iterating (1528) through the dose values at each point in the dose image. If the dose value is lower than the matching point in the minimum dose volume, method (1520) may comprise setting (1530) the matching point in the minimum dose volume to the new value. If the dose value is higher than the matching point in the maximum dose volume, method (1520) may comprise setting (1532) the matching point in the minimum dose volume to the new value. Once all of the points have been evaluated, method (1520) may comprise combining (1534) the minimum dose volume, nominal dose volume, and maximum dose volume into a computer 4D volume with each volume representing one of the frames in the volume.

Figure 16A:
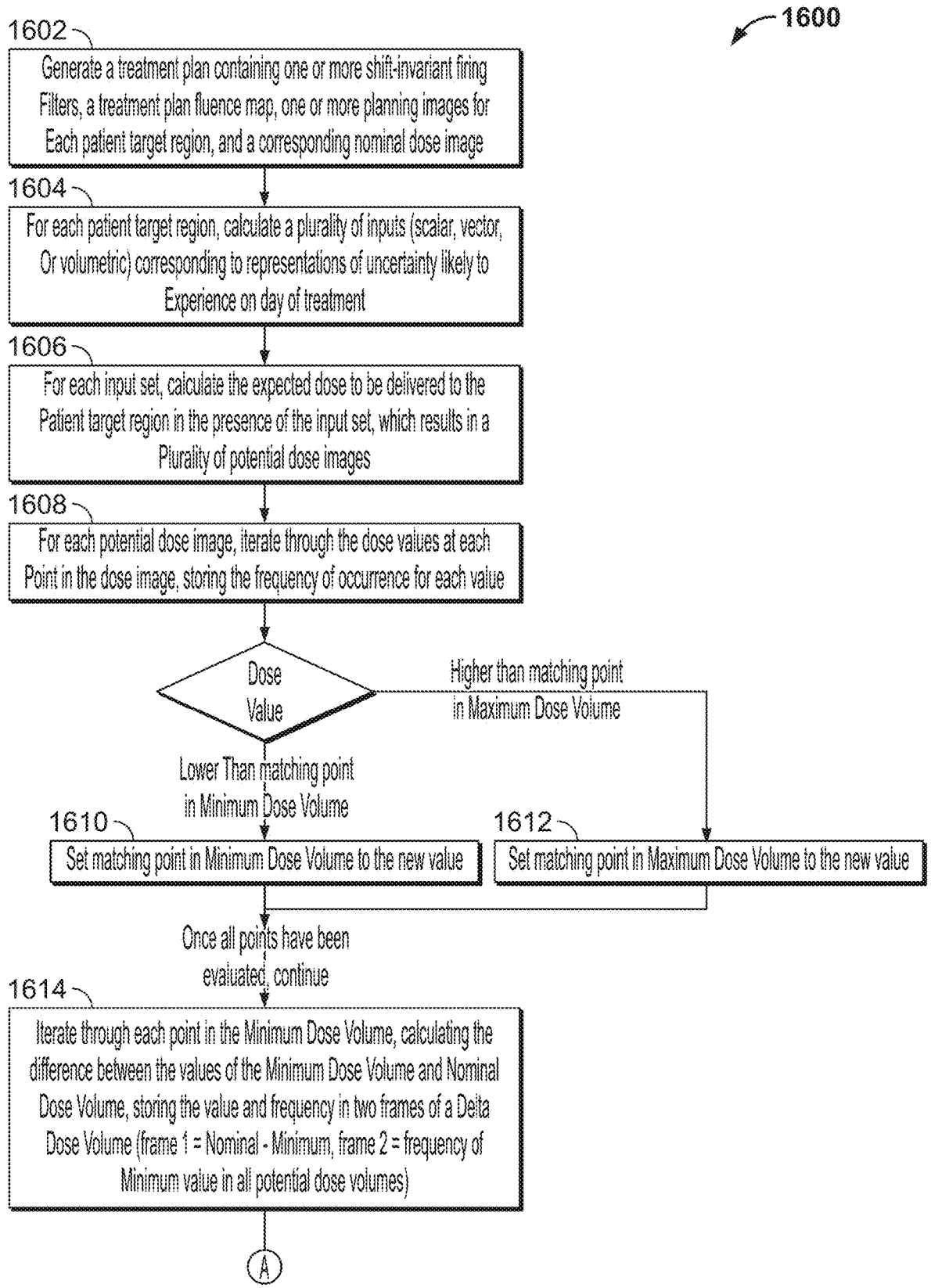
FIG. 16A is a flow chart representation of one variation a method of generating a visualization graphic.
Figure 16A:
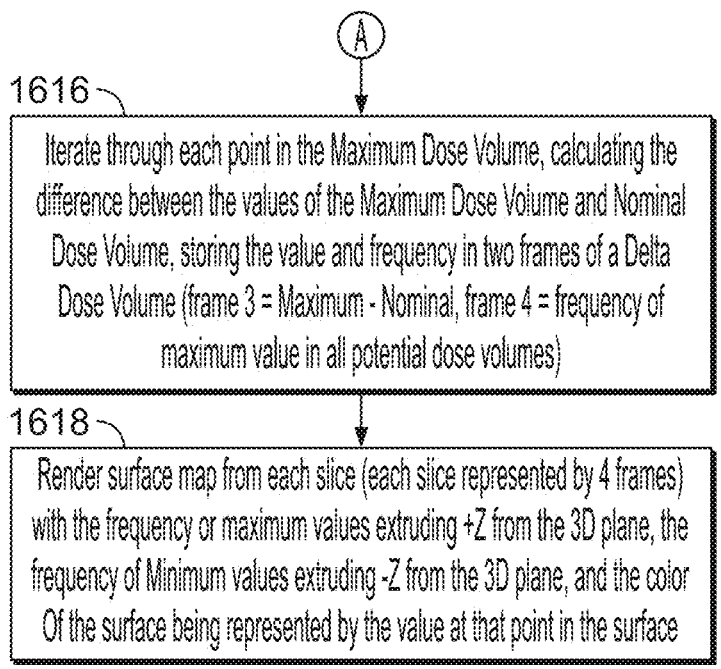
Figure 16B:
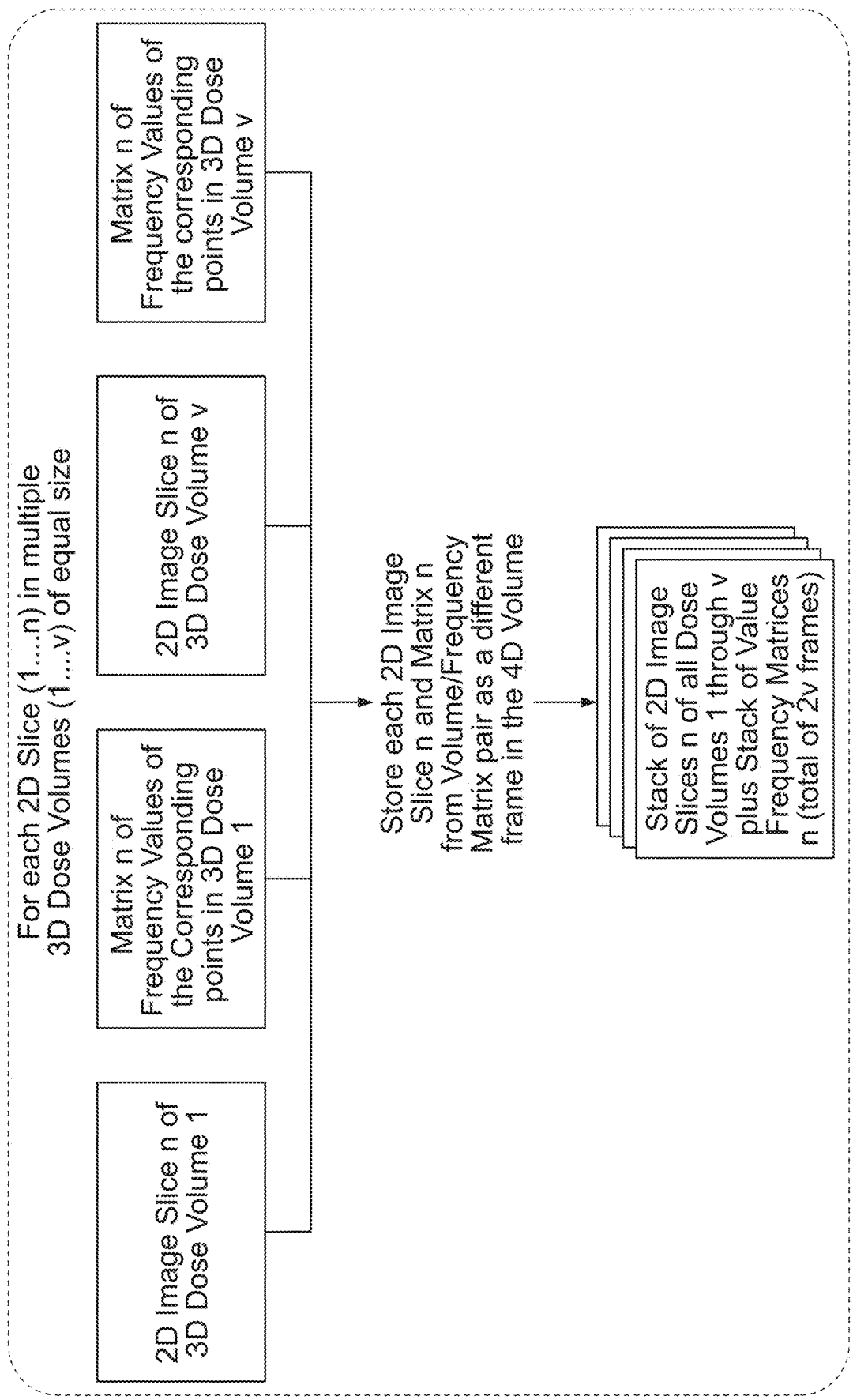
FIG. 16B is a block diagram of one variation a method of generating a visualization graphic.
Figure 17A:
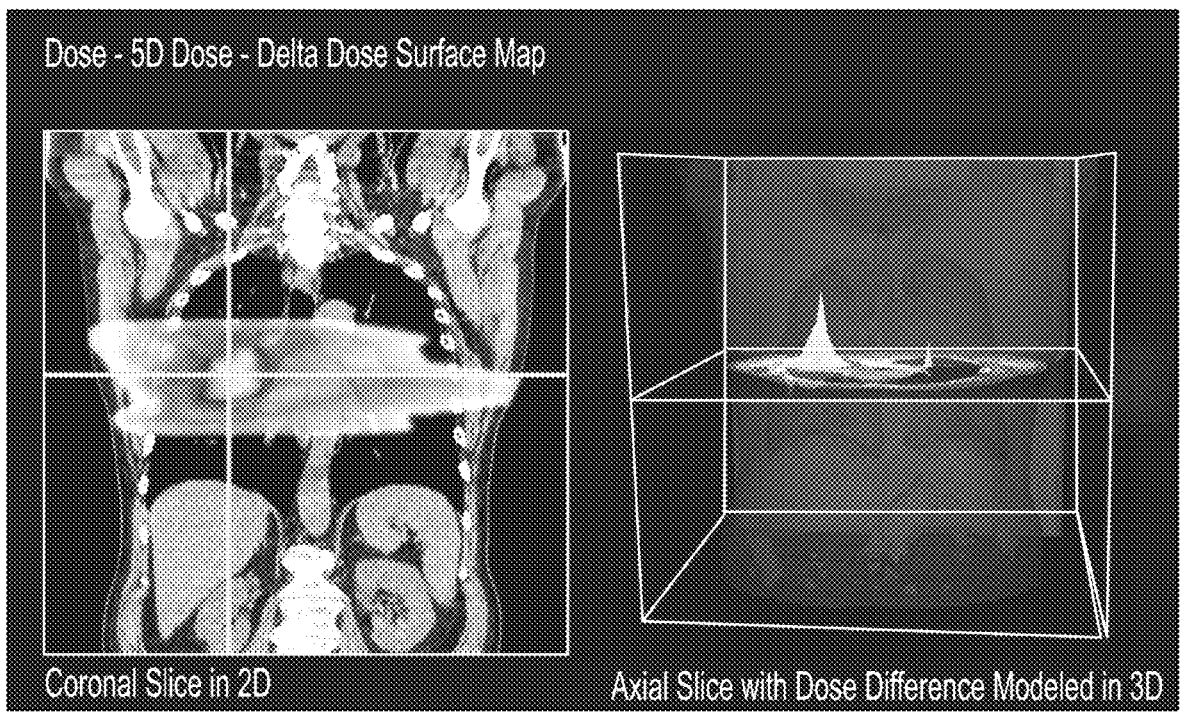
FIG. 17A depicts one variation of visualization graphics that represent delta dose distribution(s).
Figure 17B:
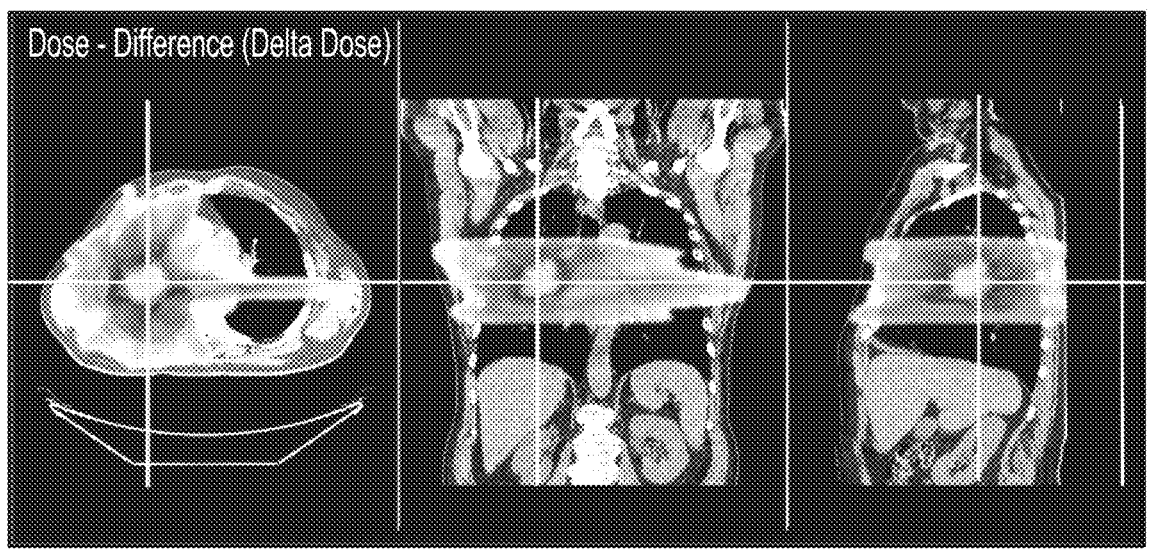
FIG. 17B depicts one variation of visualization graphics that represent delta dose distribution(s).
Figure 17C:
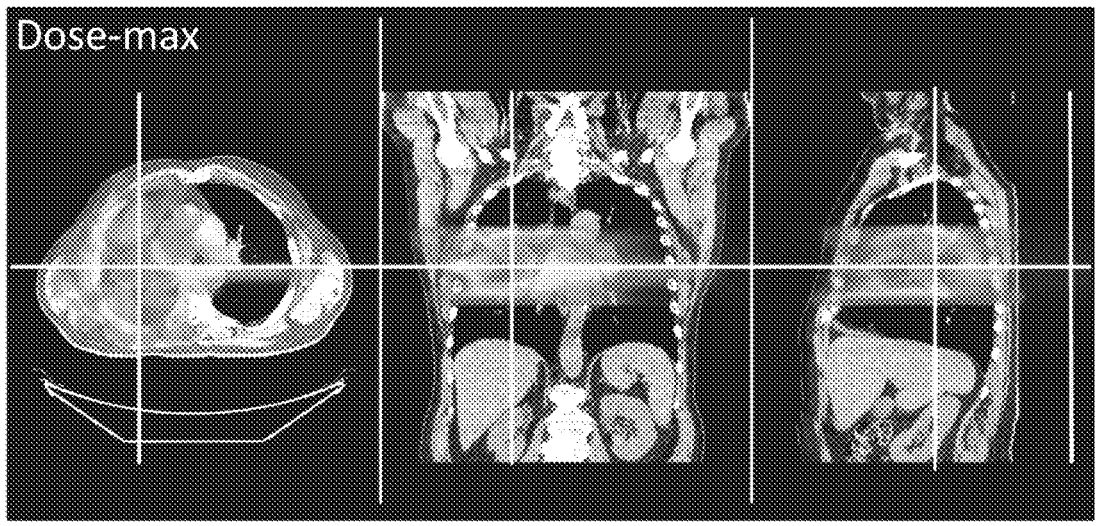
FIG. 17C depicts one variation of visualization graphics that represent delta dose distribution(s) for a maximum dose level.
Figure 17D:
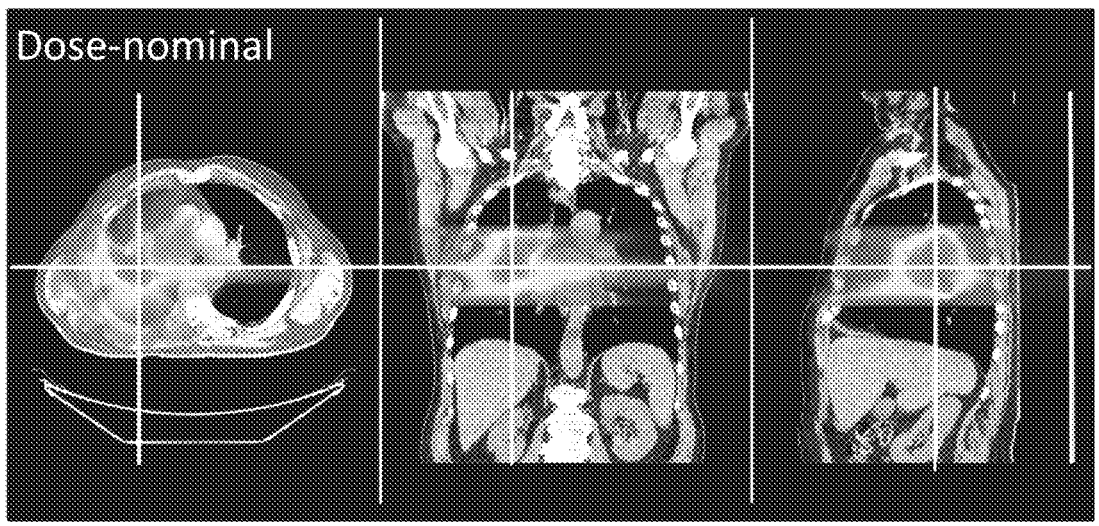
FIG. 17D depicts one variation of visualization graphics that represent delta dose distribution(s) for a nominal dose level.
Figure 17E:
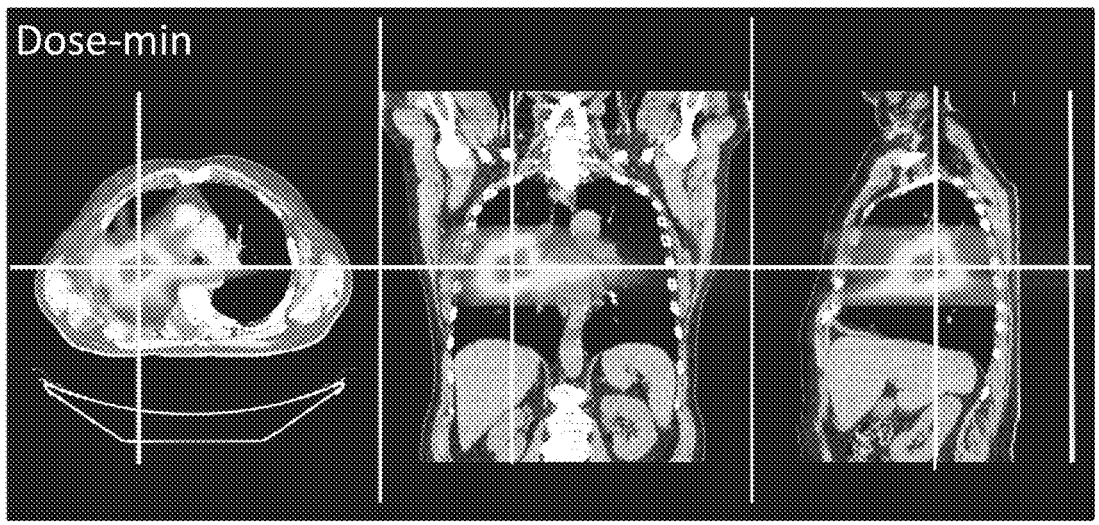
FIG. 17E depicts one variation of visualization graphics that represent delta dose distribution(s) for a minimum dose level.
Figure 17F:
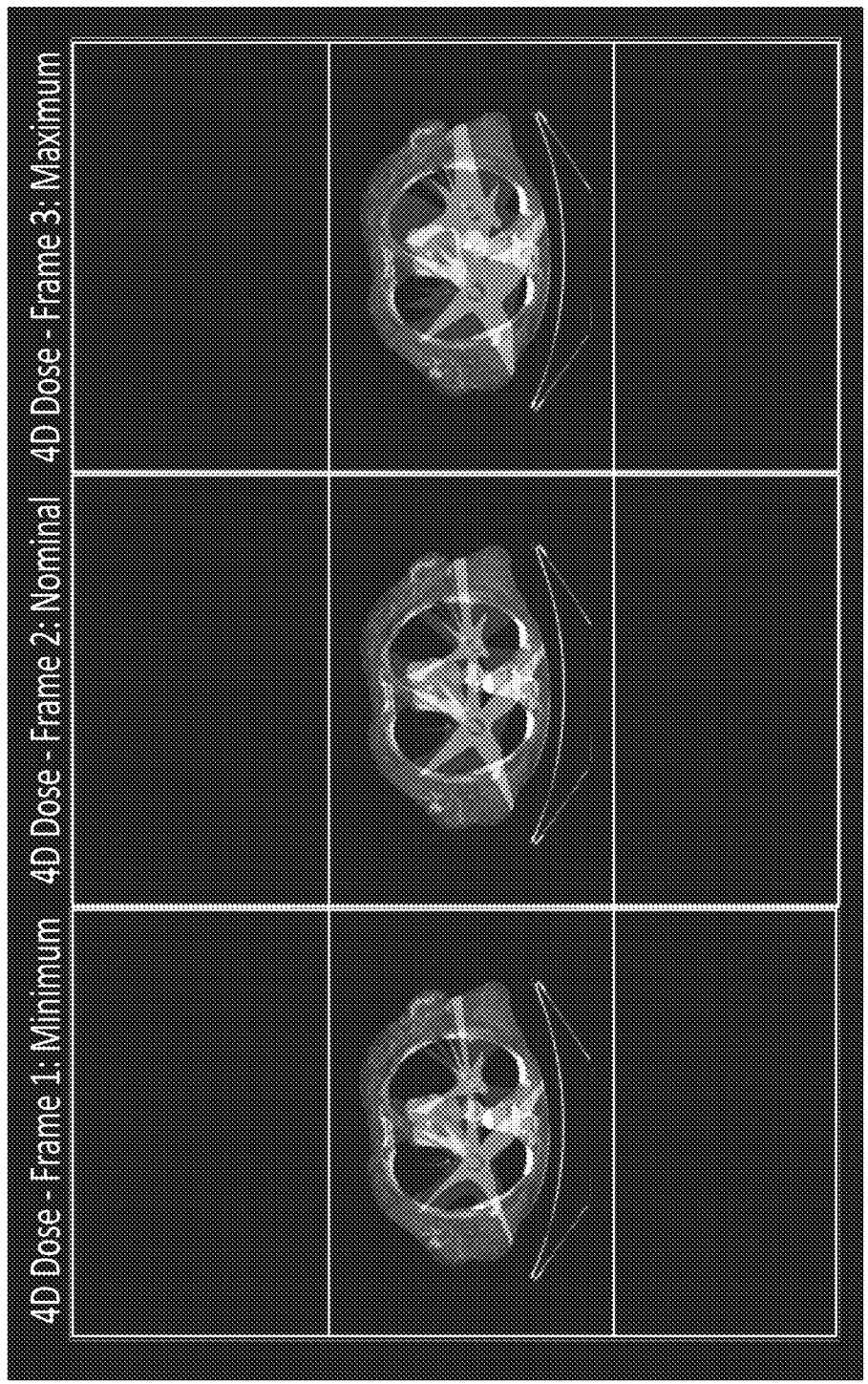
FIG. 17F depicts one variation of visualization graphics (nominal, minimum, maximum dose levels).

FIGS. 16A-16B depict variations of methods that may be used to generate the visualization graphics of FIGS. 17A-17F. FIG. 17A depicts a coronal 2-D slice (left) and an axial slice (right) of a delta dose from a nominal plane. FIG. 17B depicts a 2-D slice (left), coronal 2-D slide (middle), and an profile view of a 2-D slide (right) of a delta dose visualization graphic. FIGS. 17C-17D depict maximum dose, nominal dose, and minimum dose 2-D slices, respectively, with the same views as FIG. 17B. FIG. 17F depicts minimum dose, nominal dose, and maximum dose 2-D slices, respectively. A method for generating the delta dose visualization graphics of FIGS. 17A-17B, may comprise taking the 3-D dose images of $D_n$, $D_{pmin}$, and $D_{pmax}$, and creating 3-D delta dose projections as follows: (a) Minimum Delta Dose Projection ($D_{ddmin}$): $D_n$ minus $D_{pmin}$ at each voxel; (b) Maximum Delta Dose Projection ($D_{ddmax}$): $D_{pmax}$ minus $D_n$ at each voxel, and then combining $D_{ddmin}$, $D_n$, and $D_{ddmax}$ projections and overlaying them over 4-D dose images/cines. Optionally, a third delta dose projection may be created called Total Delta Dose Projection, which may represent the width of the bounds in the bDVH (i.e. $D_{pmax}$ minus $D_{pmin}$ at each voxel). Some visualization graphics may represent the probability of variability as the factor determining mesh extrusion, the factor for extrusion would be the delta dose (i.e. difference from nominal). This may help a user to compare the $D_{pmin}$ and $D_{pmax}$ dose images with the $D_n$ dose image quickly to identify hot and cold spots. Hot spots would appear extruding towards the top of the 3-D visualization while cold spots would appear extruding down towards the bottom of the 3-D visualization, while no extrusion would represent values where the nominal and $D_{pmin}$ or $D_{pmax}$ match. This may be used to visualize different perturbations of bDVH curves (in addition to the $D_{pmin}$ or $D_{pmax}$).

Turning now to FIG. 16A, method (1600) may comprise generating (1600) a treatment plan containing one or more shift-invariant firing filters, a treatment plan fluence map, one or more planning images for each patient target region, and a corresponding nominal dose image, calculating (1604), for each patient target region, a plurality of inputs (scalar, vector, or volumetric) corresponding to representations of uncertainty on the likely to be experienced on the day of treatment, calculating (1606), for each input set, the expected dose to be delivered to the patient target region in the presence of the input set, which may result in a plurality of potential dose images, and for each potential dose image, iterating (1608) through the dose values at each point in the dose image. If the dose value is lower than the matching point in the minimum dose volume, method (1600) may comprise setting (1610) the matching point in the minimum dose volume to the new value. If the dose value is higher than the matching point in the maximum dose volume, method (1600) may comprise setting (1612) the matching point in the minimum dose volume to the new value. Once all of the points have been evaluated, method (1600) may comprise iterating (1614) through each point in the minimum dose volume, calculating the difference between the values of the minimum dose volume and nominal dose volume, storing the value and frequency in two frames of a delta dose volume (frame 1=nominal-minimum, frame 2=frequency of minimum value in all potential dose volumes). Method (1600) may then comprise iterating (1616) through each point in the maximum dose volume, calculating the difference between the values of the maximum dose volume and nominal dose volume, storing the value and frequency in two frames of a delta dose volume (frame 3=maximum−nominal, frame 4=frequency of maximum value in all potential dose volumes). Method (1600) may then comprise rendering (1618) a surface map for each slice (each slice represented by 4 frames) with the frequency of maximum values extruding from +Z from the 3-D plane, the frequency of minimum values extruding −Z from the 3-D plane, and the color of the surface being represented by the value at that point in the surface.

FIG. 16B is block diagram representing the combination of image slides to form a stack of 2-D image slides to generate a 3-D visualization graphic that includes delta dose information.

Localization Graphical User Interface

Figure 37A:
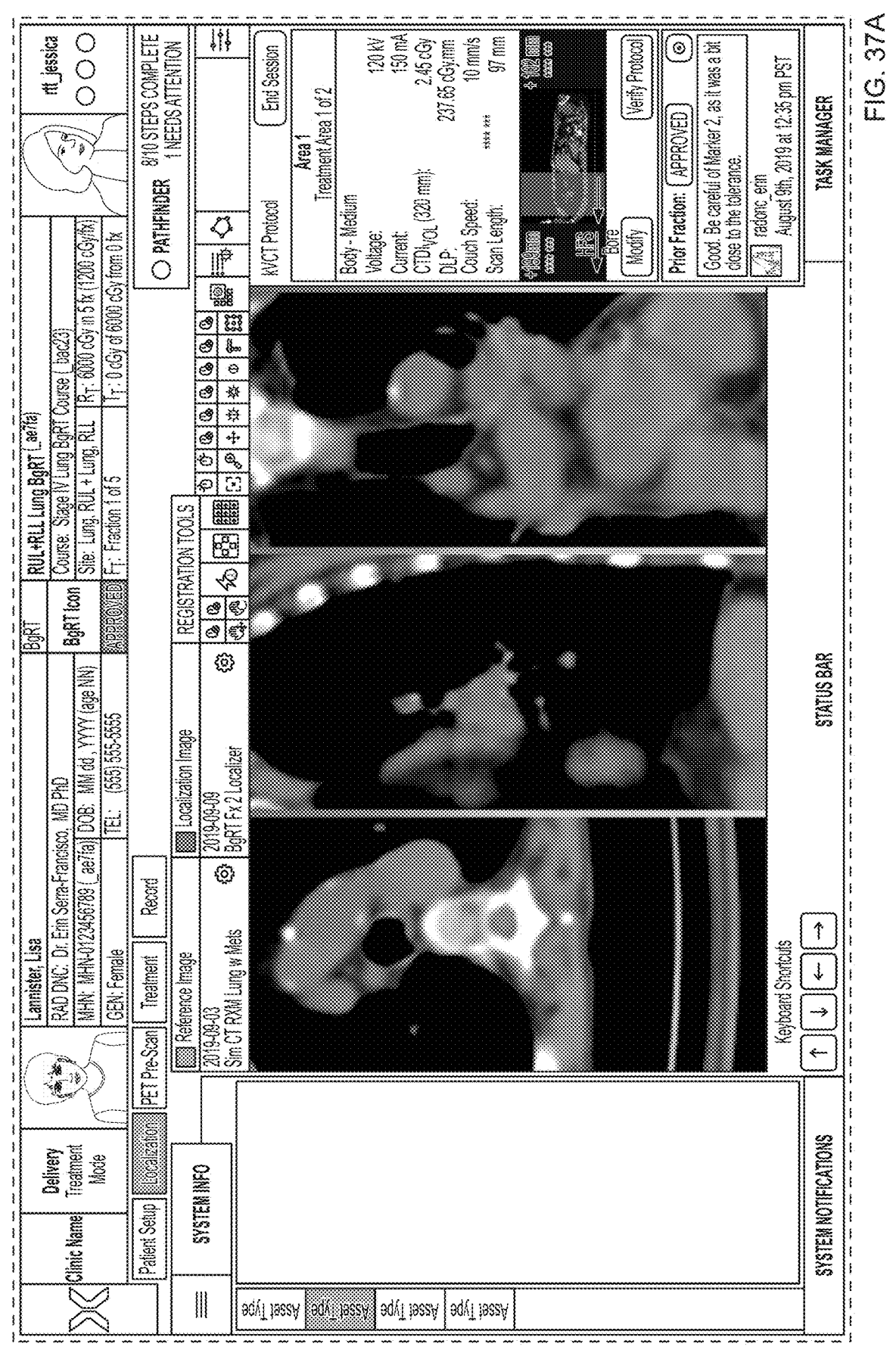
Figure 37B:
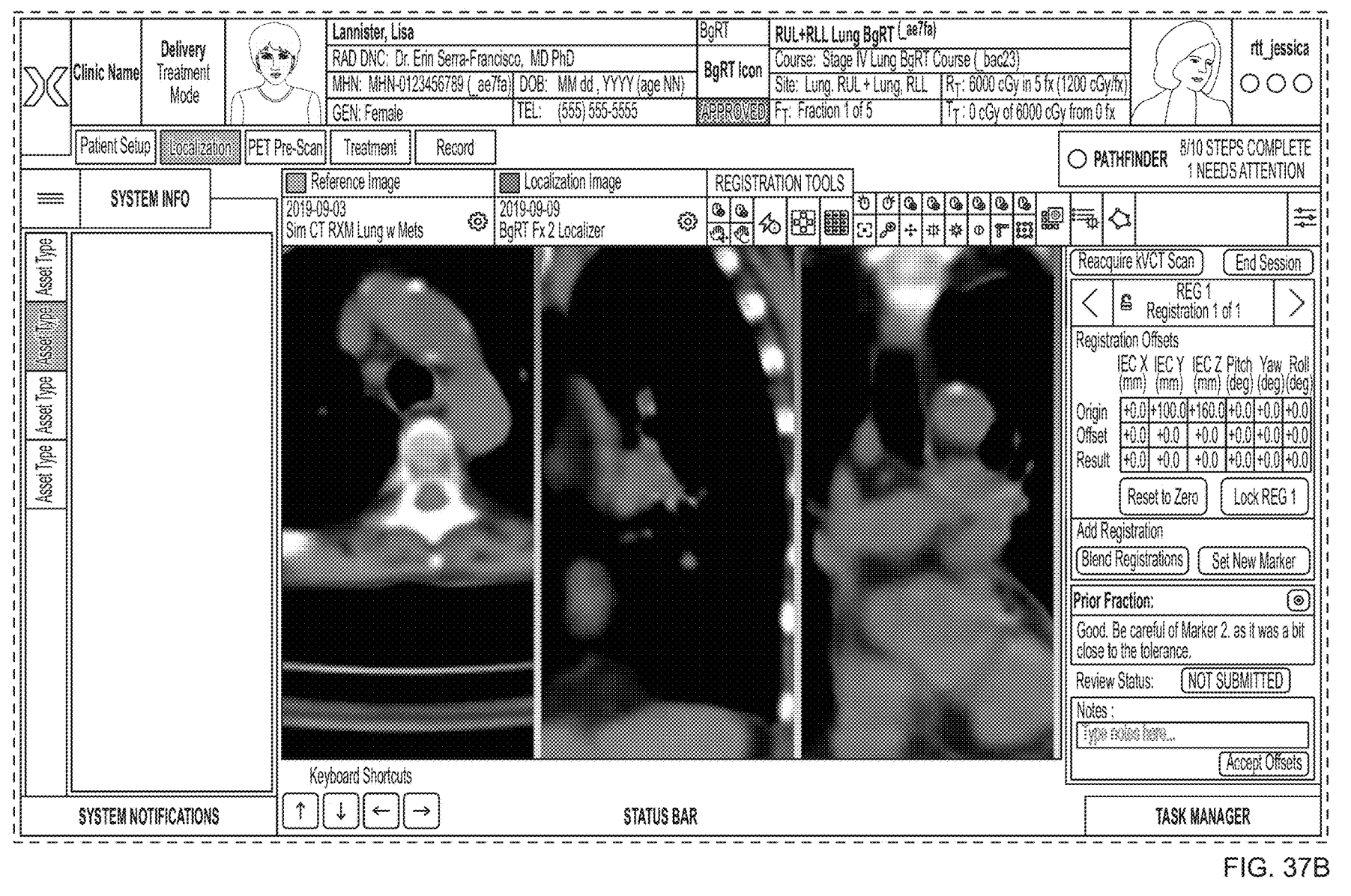
Figure 37C:
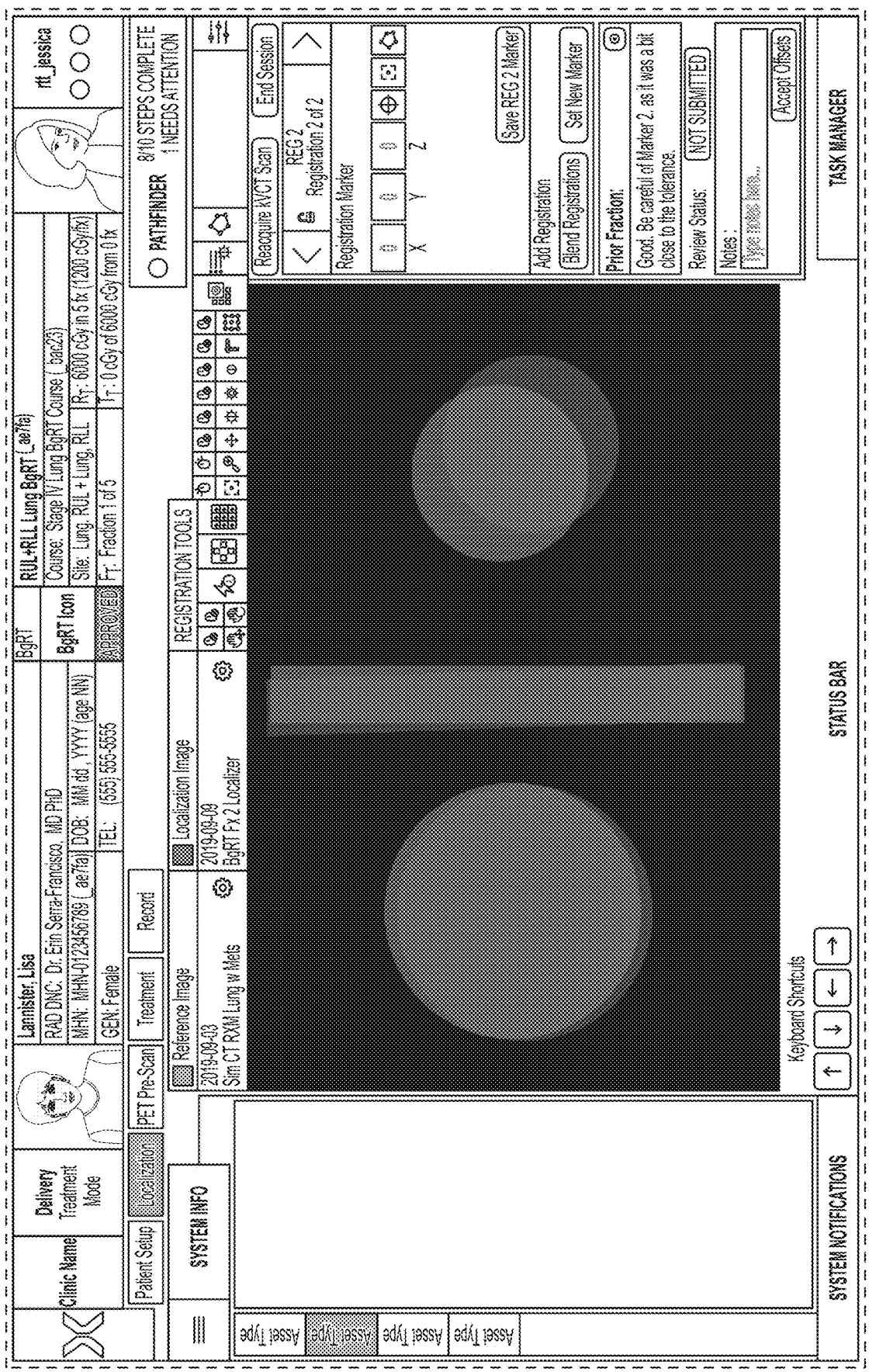
FIGS. 37A-37N depict graphical user interfaces for a multi-target blended localization.
Figure 37D:
Figure 37E:
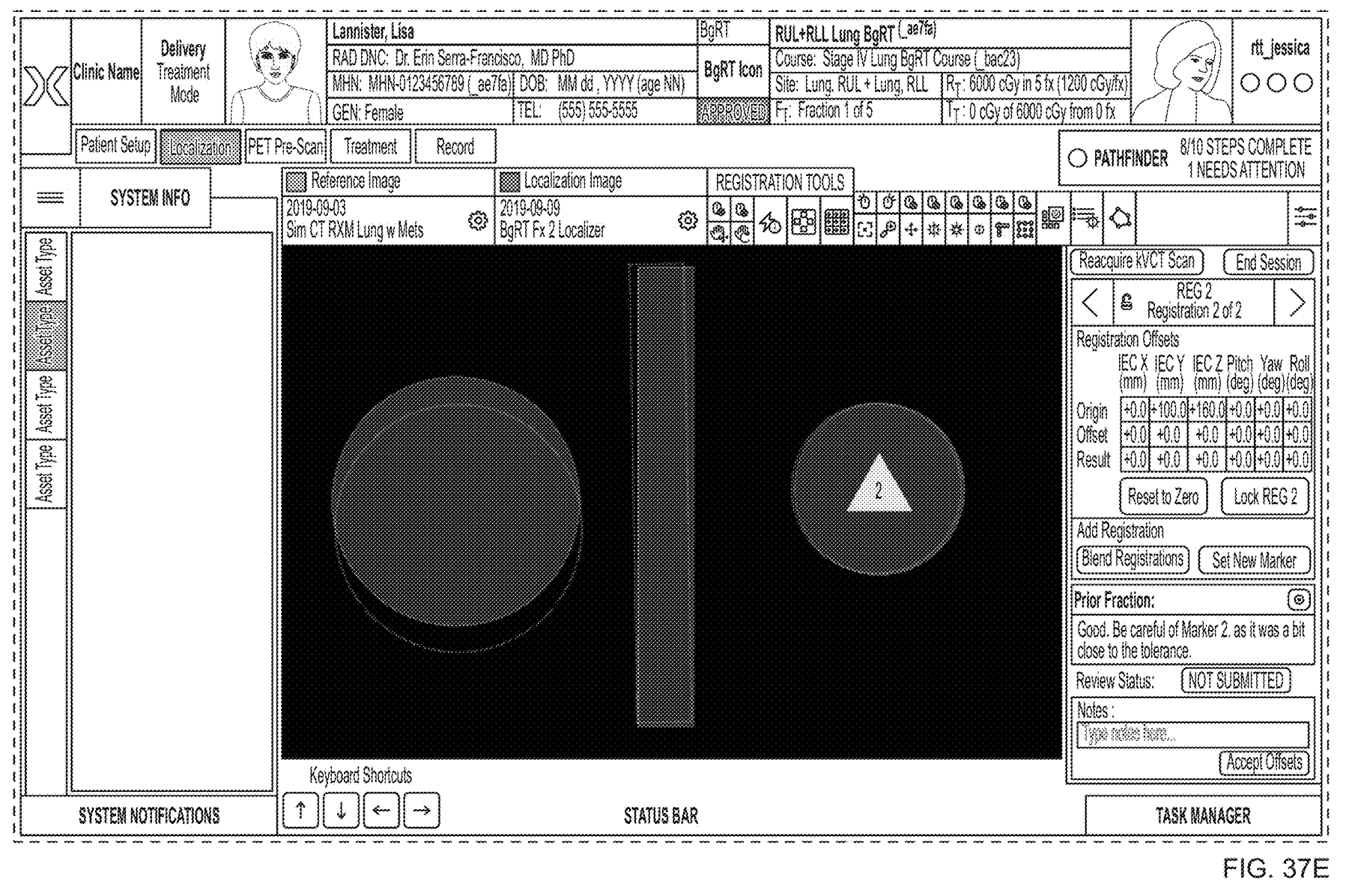
Figure 37F:
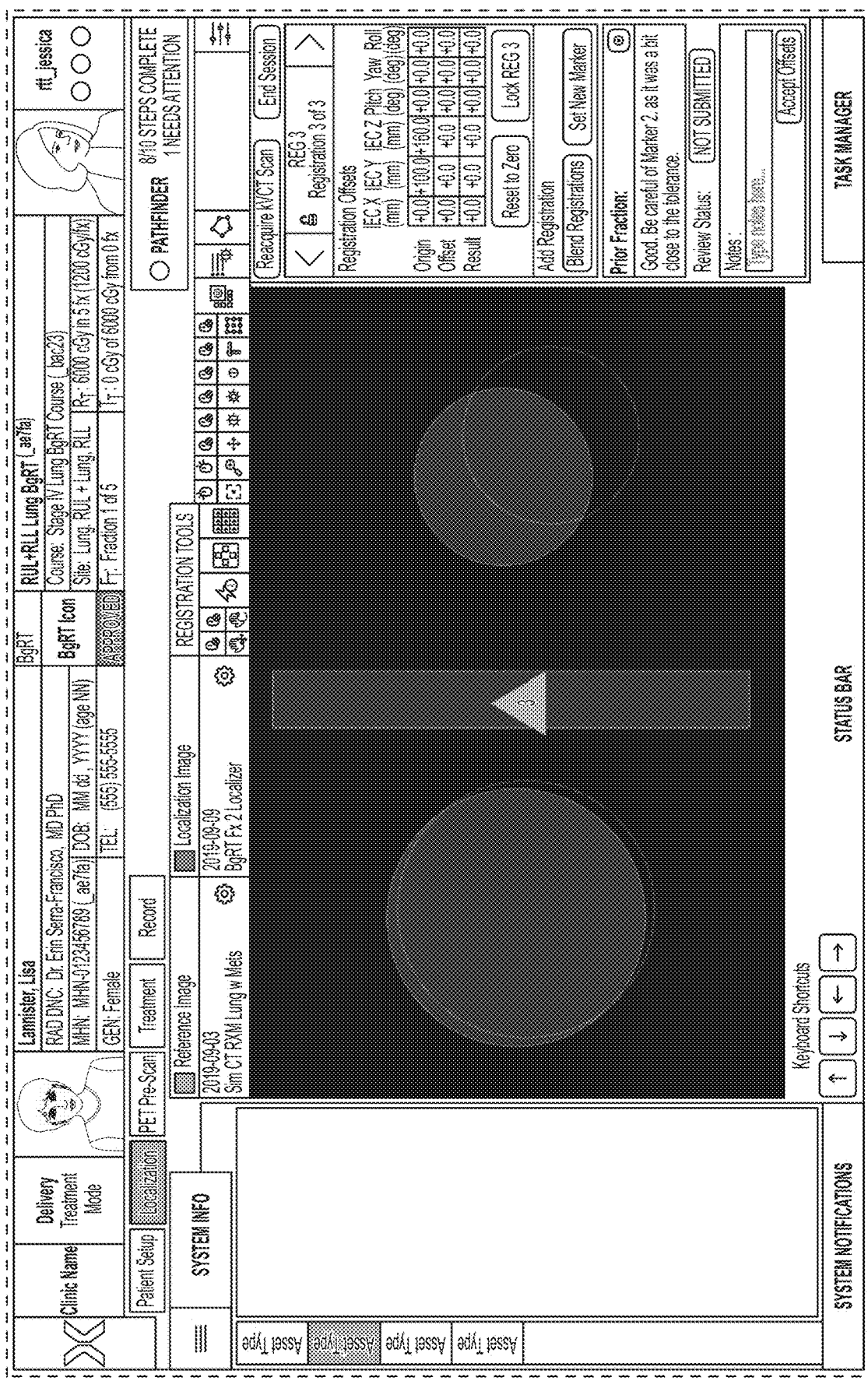
Figure 37G:
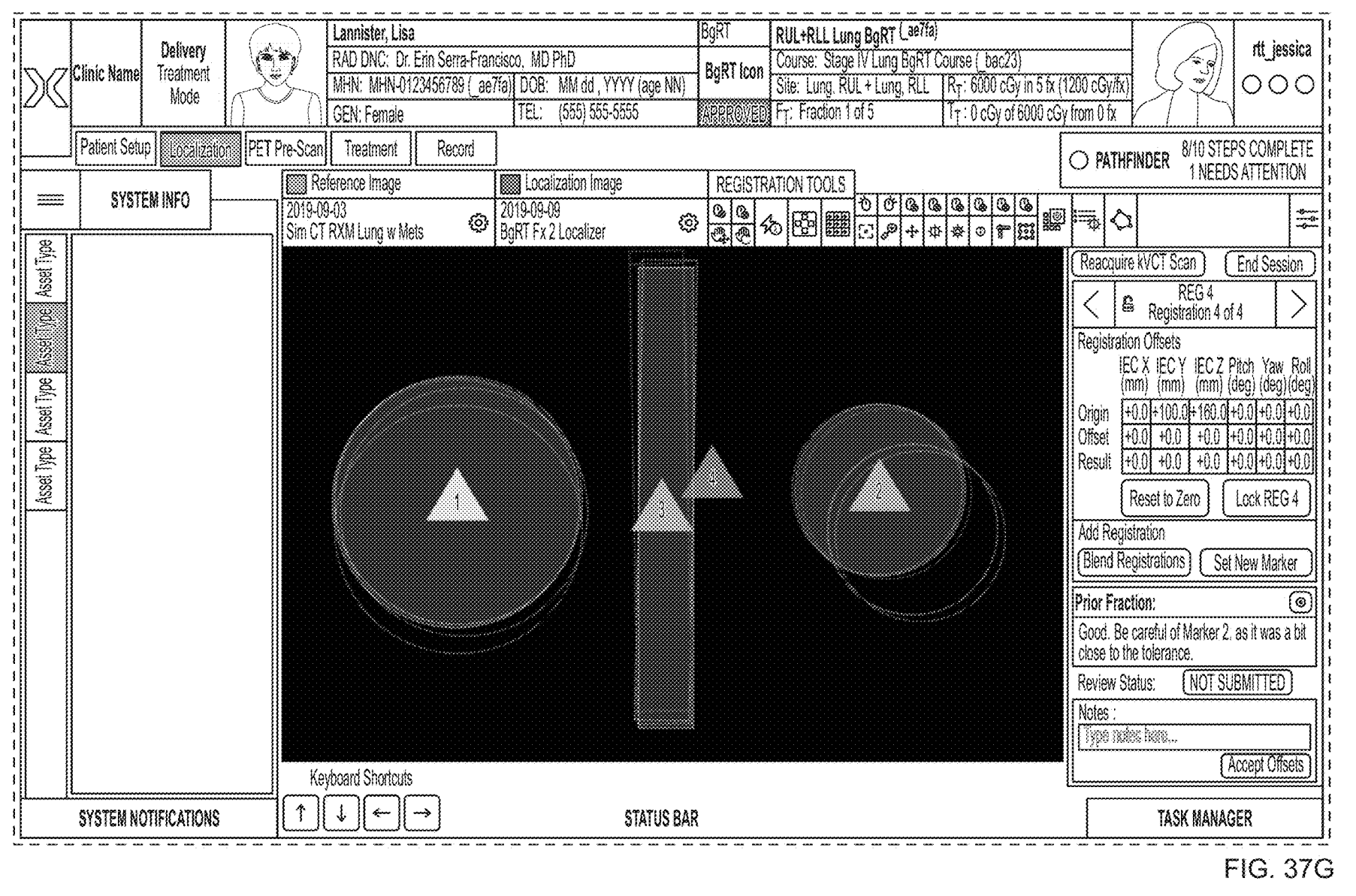
Figure 37H:
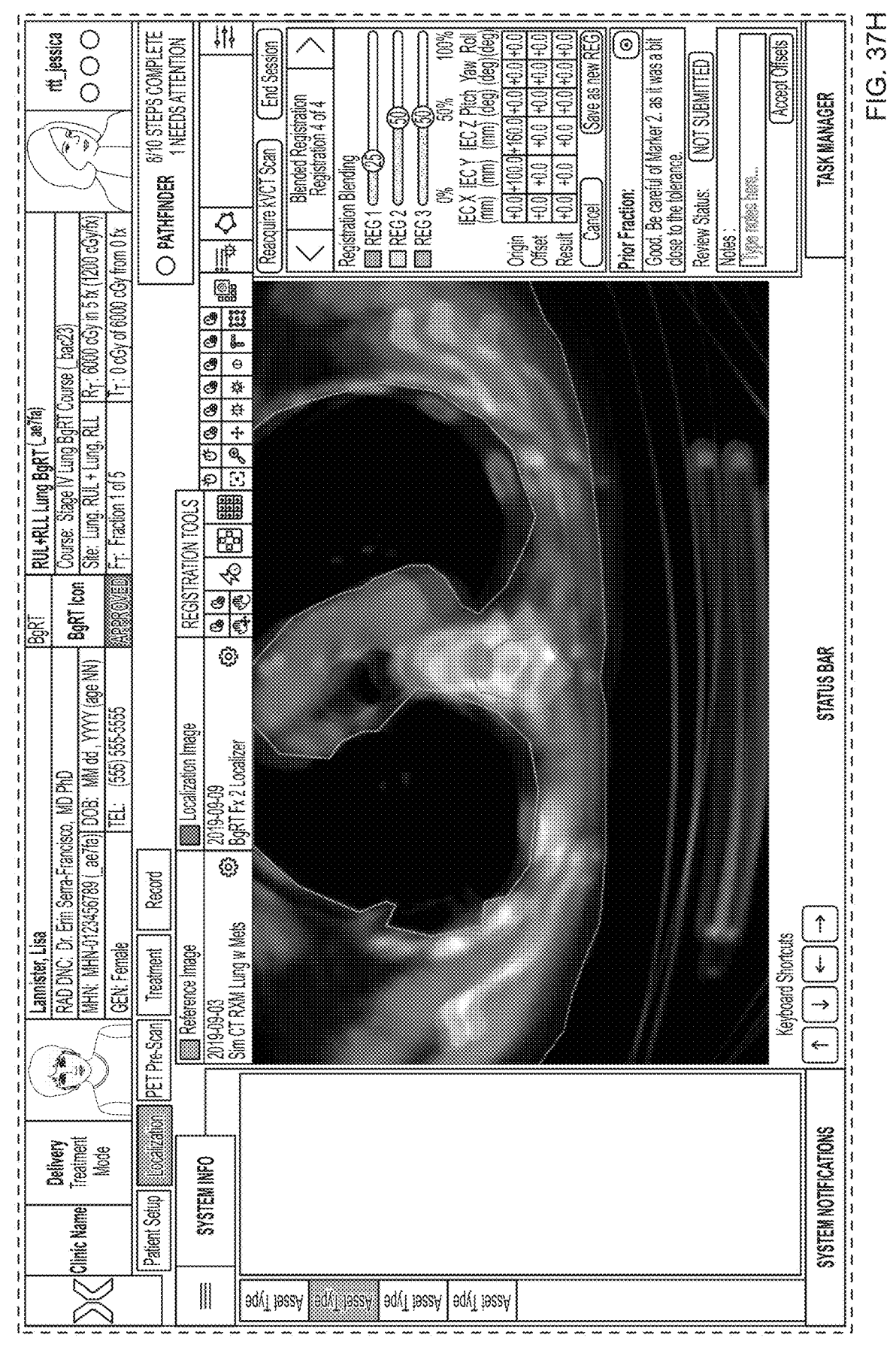

FIGS. 37A-37N depict graphical user interfaces for multi-target localization. In some variations, the user interfaces depicted in FIGS. 37A-37N for virtual localization may comprise a switch (e.g., toggle) between blended and individual localizations of a patient target region and/or OAR. FIG. 37A depicts reference images (e.g., planning images) of patient target regions and/or OARs. The left and right panels are images of two patient target regions and the middle panel is an image of an OAR. FIG. 37B depicts a delivery workspace localization user interface after a localization image scan(s) of the two patient target regions and the OAR has been taken. In some variations, the anatomical structures of the target regions and/or OARs in the reference images and the localization images may be approximated by geometric shapes. The user (e.g., clinician and/or technician) may specify a registration centroid for each of the target regions and/or OARs, which may be, for example, the volume centroid. Alternatively or additionally, the volume centroid of a target region and/or OAR may be calculated by the radiotherapy system. The graphical user interface for localization may comprise a schematic approximation or geometric representation of the patient target regions and/or OARs in the reference image(s) and localization image(s). This may facilitate visual inspection of the relative alignment between the reference and localization images, and/or reduce the computational complexity of calculating the shifts and/or deviations of the target regions and/or OARs in the reference and localization images. The schematic representations may bear some resemblance to the actual anatomical structure of the target region and/or OAR, or may be arbitrarily selected. FIG. 37C depicts an example of a delivery workspace localization before registration, where the first target region is represented by a large circle in the left panel, the second target region is represented by a small circle in the right panel, and the OAR is represented by a vertical bar or rectangle in the middle panel. The differences (e.g., misalignment) in position of the geometric shapes may be used to adjust the patient's position and localize the patient target region. FIGS. 37D-37F depicts a delivery workspace localization user interface during localization and registration. As the user and/or radiotherapy system evaluates various positional shifts (either virtual shifts and/or actual physical shifts), the graphical user interface may update the alignment of various patient structures. For example, when a patient structure is aligned, a visual indicator (e.g., a triangle) may be presented over the aligned patient structure, which may have different colors for each patient structure. The user and/or radiotherapy system may then evaluate the alignment of the other patient structures to determine whether such alignment is acceptable. FIG. 37D depicts the relative positions of the two patient target regions and OAR when the first target region is shifted such that its position in the localization image matches its position in the reference image. FIG. 37E depicts the relative positions of the two patient target regions and OAR when the second target region is shifted such that its position in the localization image matches its position in the reference image. FIG. 37F depicts the relative positions of the two patient target regions and OAR when the OAR is shifted such that its position in the localization image matches its position in the reference image.

Figure 37I:
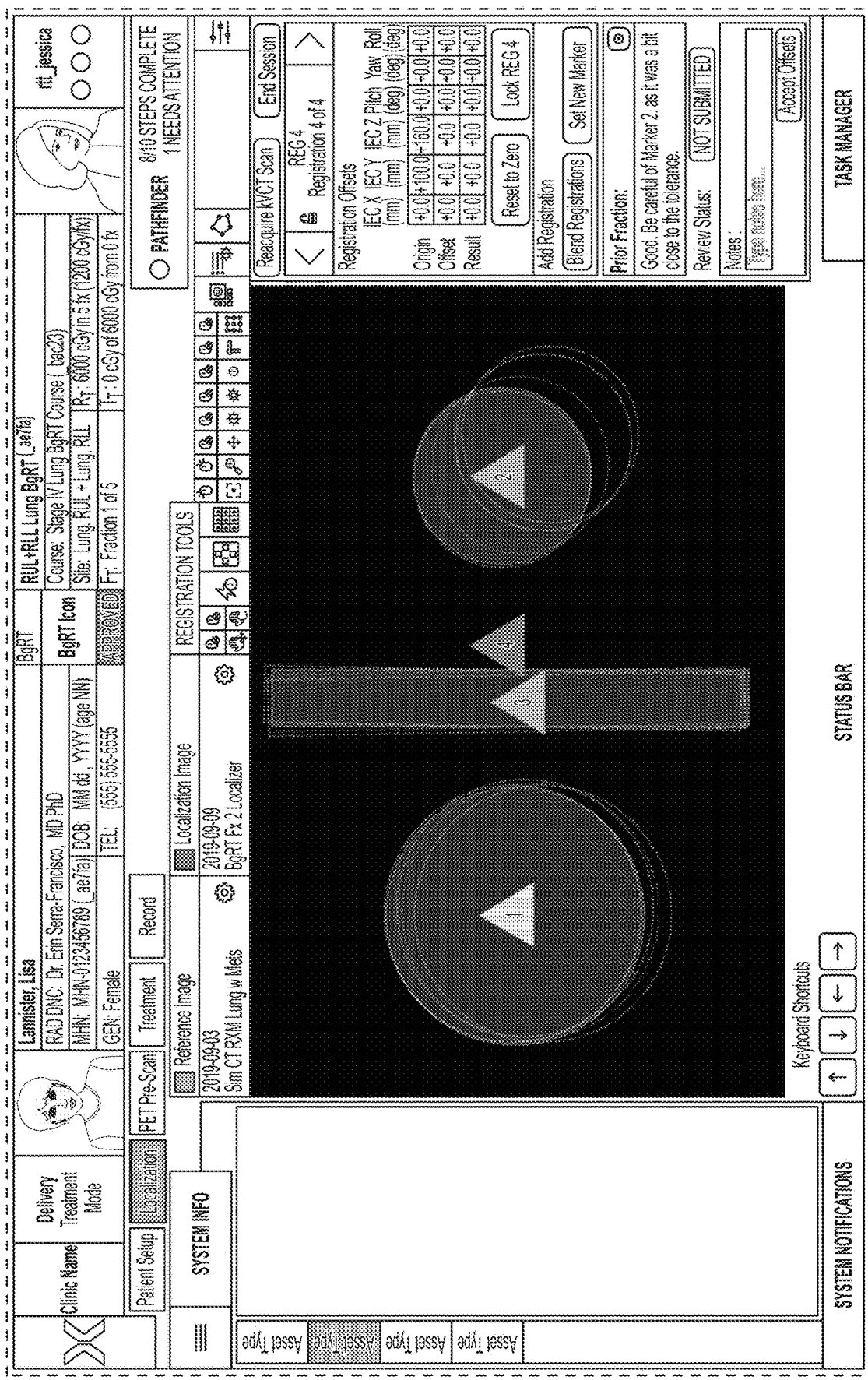
Figure 37J:
Figure 37K:
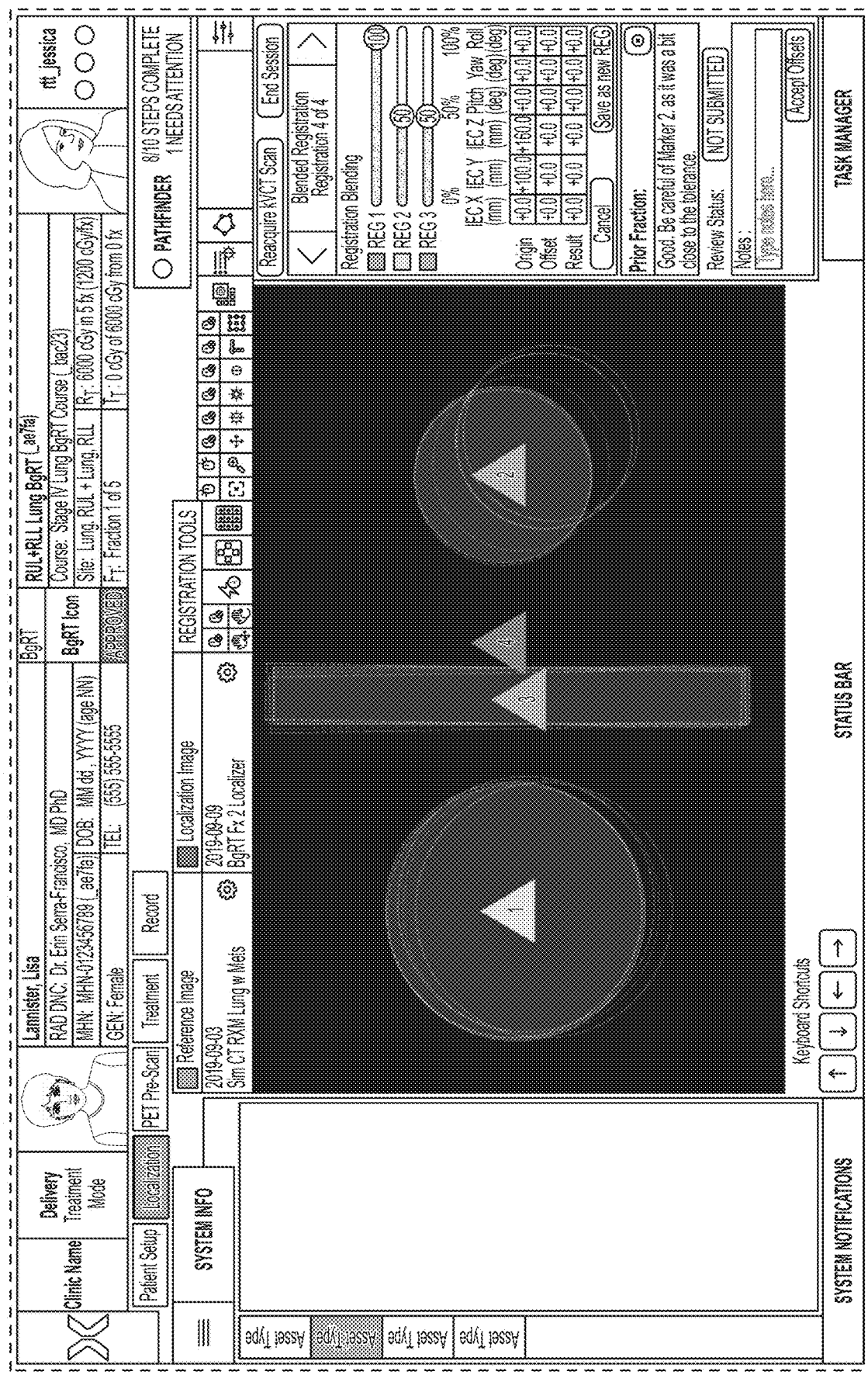
Figure 37L:
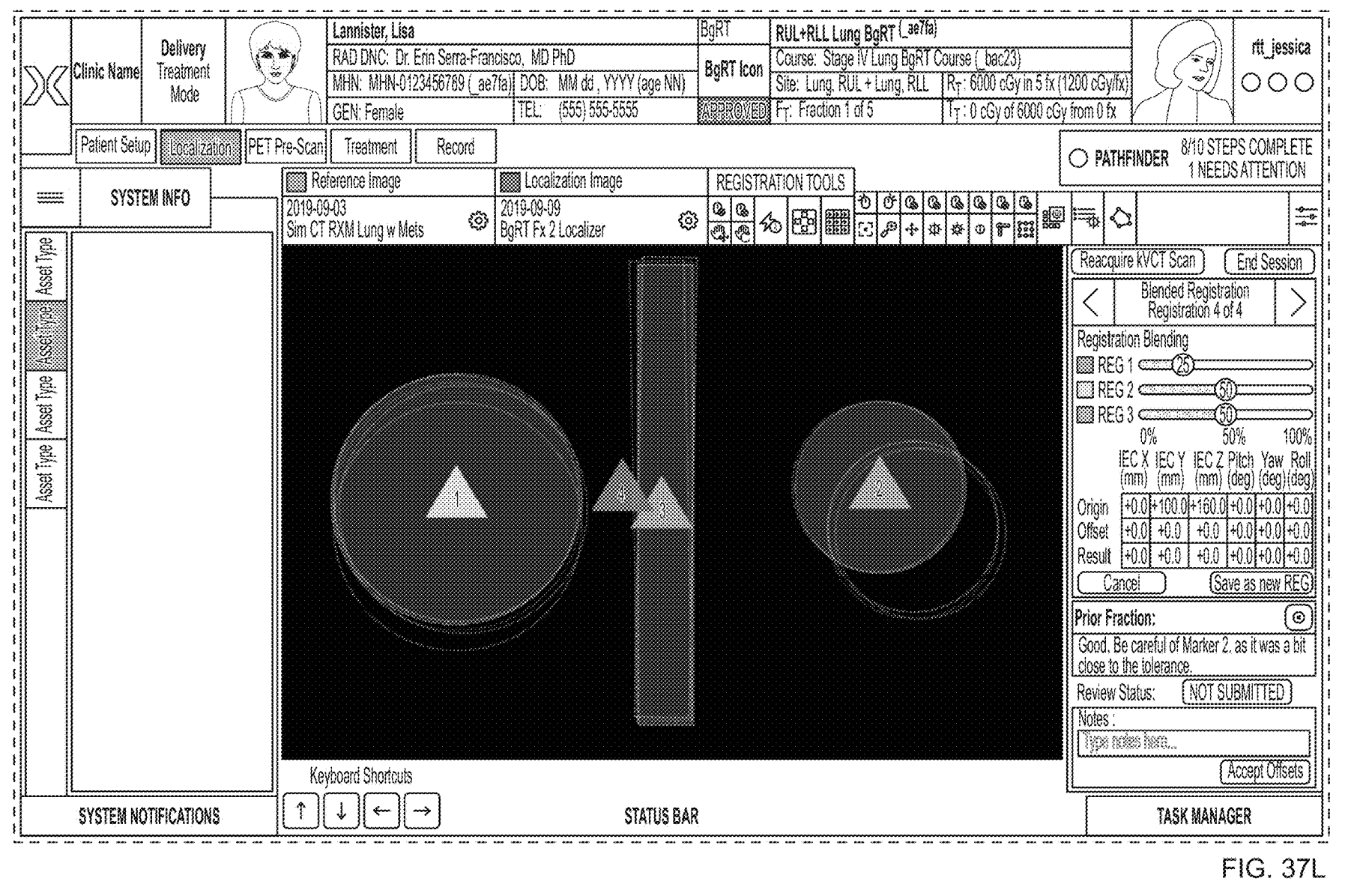
Figure 37M:
Figure 37N:
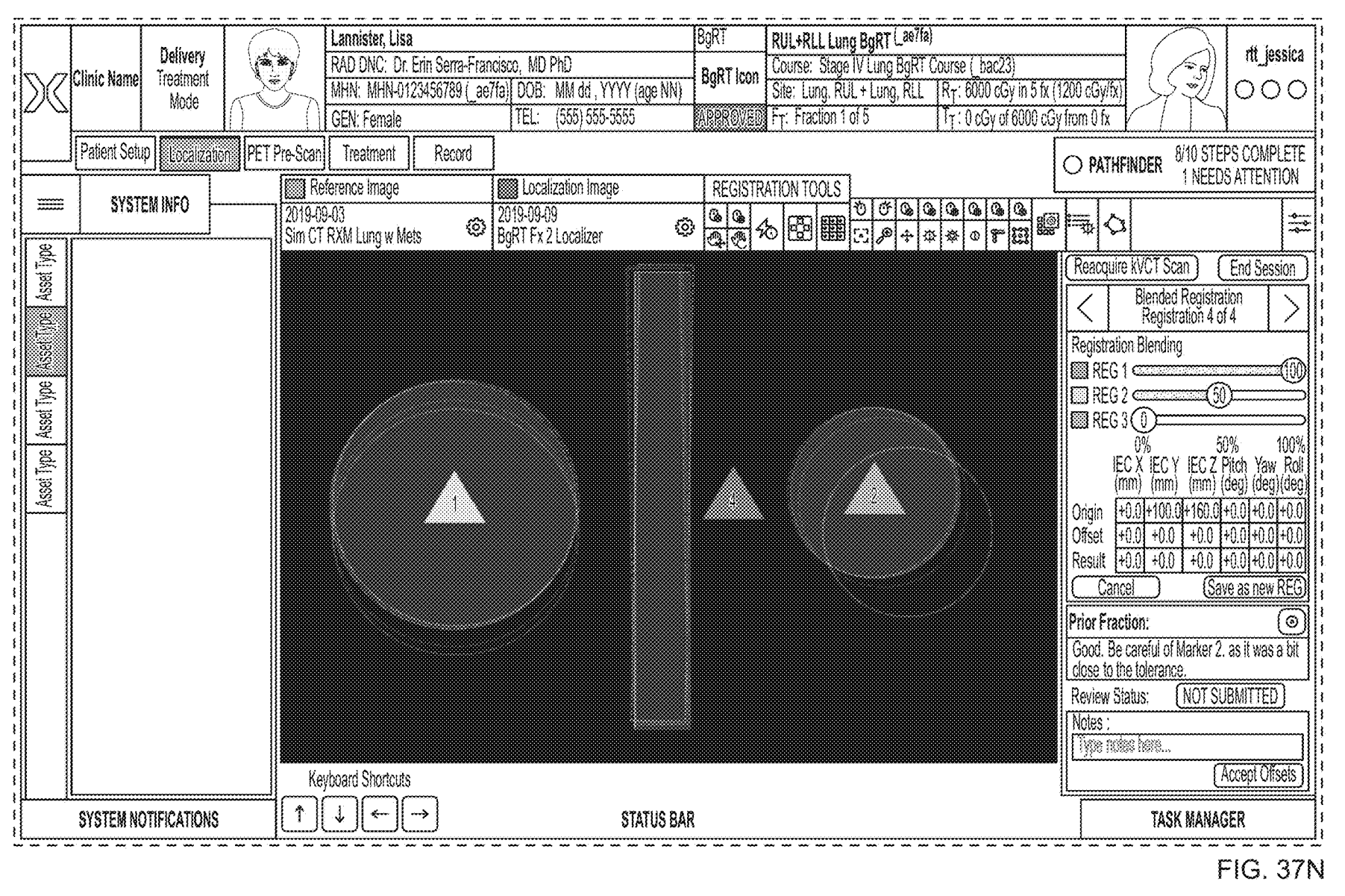

The individual shifts and/or alignments for each of the target regions and/or OARs in FIGS. 37D-37F may be performed sequentially, for example, by presenting a visual representation of each patient structure alignment for user inspection and/or approval before calculating the alignment for another patient structure. Alternatively or additionally, the shifts and/or alignments may be automatically calculated by an auto-calculation method (e.g., that may be activated by selecting a button), and may be depicted in the graphical user interface individually or in combination. For example, a graphical user interface may comprise overlaying the separate alignment configurations for each of the patient structures on a single graphical representation. FIG. 37G depicts a graphical user interface that includes representations of the relative positions of the two patient target regions and OAR for each of the alignments/registrations depicted in FIGS. 37D-37F, each represented by its own visual indicator depicted over the aligned patient structure (e.g., the triangle 1, triangle 2, and triangle 3 centered over the first target region, second target region, and OAR, respectively). The visual indicator(s) may have a distinctive color or shape for each patient structure. The graphical user interface in FIG. 37G may optionally include a visual indicator (e.g., triangle 4) that represents a blended alignment/registration, where the radiotherapy system may calculate the alignment that meets specified criteria. For example, the blended registration may prioritize alignment with the OAR over alignment with either of the target regions. Some variations of a graphical user interface may include a slider bar that allows a user to adjust the relative alignment priorities and the graphical representation may update in real-time to reflect adjusted positional alignment between the different patient structures. In some variations, the blended registration may be used as the physical localization, and the patient target regions may be virtually localized using any of the methods described herein. In some variations, a graphical user interface may include a toggle that allows the user to switch between the anatomical views and the schematic views of various alignments. This may allow the user to future adjust the relative weights (e.g., alignment priorities) between the patient structures. For example, FIG. 37H depicts anatomical images of a blended registration that may have been calculated based on the schematic representation of FIG. 37G. In this view, a user may determine whether the alignment with surrounding anatomical structures is acceptable. The blended registration may be adjusted using slider bars provided in the graphical user interface. FIG. 37I depicts a graphical user interface that overlays the registrations of the individual patient structures with a proposed blended registration. The outlines of each patient structure and their shifts relative to each other in the different registrations may help a user determine whether further adjustments are desired. The graphical user interface may include one slider bar for each patient structure so that the relative registrations may be adjusted. For example, FIG. 37J depicts a localization graphical user interface where the slider bars for the first and second patient target regions have been adjusted such that the alignment weight for the first patient target region (the left target region) is 25 and the weight for the second patient target region (the right target region) is 50. Triangle 4 in the center represents the physical location of the localization reference point based on the alignment weights specified by the slider bars. FIG. 37K depicts a localization graphical user interface where the slider bars for the first and second patient target regions and the OAR have been adjusted such that the alignment weight for the first patient target region (the left target region) is 50, the weight for the second patient target region (the right target region) is 100, and the weight for the OAR (the center structure) is 50. FIG. 37L depicts a localization graphical user interface that depicts the relative alignments of each of these patient structures when the alignment weight for the first patient target region (the left target region) is 50, the weight for the second patient target region (the right target region) is 25, and the weight for the OAR (the center structure) is 50. FIG. 37M depicts a localization graphical user interface that depicts the relative alignments of each of these patient structures when the alignment weight for the first patient target region (the left target region) is 50, the weight for the second patient target region (the right target region) is 50, and the weight for the OAR (center structure) is zero. FIG. 37N depicts a localization graphical user interface that depicts the relative alignments of each of these patient structures when the alignment weight for the first patient target region (the left target region) is 50, the weight for the second patient target region (the right target region) is 100, and the weight for the OAR (center structure) is zero. FIG. 37N depicts a delivery workspace localization user interface for registration blending having a ratio of 100 to 50. After reviewing various alignments, the user may select the desired alignment for the patient setup. In some variations, the blended registration may be used to calculate the positional coordinates and/or vectors for physical localization, where the patient may be moved on the platform, and the platform position and/or orientation may also be adjusted. The patient target regions may then be virtually localized using the methods described herein, and optionally, the physical localization and virtual localizations may be depicted in the same plot in the localization graphical user interface. In such fashion, additional localization scans may be reduced or avoided, which may help expedite the treatment session.

Treatment Planning Graphical User Interface

Some variations of a treatment planning graphical user interface may comprise graphical representations of multiple treatment areas in a single view. Depicting multiple treatment areas in a single view may facilitate geometric definition, dosimetric definition, and dosimetric evaluation of a treatment plan that contains multiple treatment areas. The treatment planning graphical user interface may include control features for a user to visualize each treatment area independently or in summation during each of the steps of geometric definition, dosimetric definition, and dosimetric evaluation. As described previously, a treatment area is the region of patient that is irradiated for a uniquely physical localization. Treatment areas may overlap or may not overlap with each other. This planning graphical user interface may allow the user (e.g., clinician, dosimetrist, technician, etc.) to view the effects of changes in one treatment area on other treatment areas and/or OARs. For example, a planning graphical user interface may comprise depicting treatment area boundaries and corresponding dosimetric data overlaid onto anatomical images. Adjusting the dose distribution, for example, for a patient target region in one treatment area may affect the dose distribution to another patient target region in another treatment area. FIG. 38A-38E depict treatment planning graphical user interfaces for multi-target treatment area definitions which may be used to generate independent isocenters per target (e.g., a planned localization reference point for each patient target region) within a single treatment area, thereby enabling virtual localization. The graphical user interface may comprise a first graphical representation (i.e., graphical element(s)) of one or more treatment areas that each contain one or more patient target regions, and a second graphical representation of dosimetric characteristics for each treatment area. For example, the first graphical representation may comprise a band that represents each treatment area. A third graphical representation may comprise one of more of the patient target regions. In some variations, the first graphical representation may be overlaid onto the third graphical representation so that a user may identify the patient target regions that are within the boundaries of a treatment area by visual inspection. In some variations, the planning graphical user interface may further comprise a fourth graphical representation that comprises a view of multiple organs-at-risk (OARs) across the multiple treatment areas, and visual indicia that represents each OAR's relative spatial relationship to one or more treatment areas. In some variations, the treatment planning graphical user interface may further comprise a graphical representation that comprises a view of all patient target regions across the multiple treatment areas and visual indicia that represents relative spatial relationships between one or more of the patient target regions. The planning graphical user interface may also comprise a graphical representation that has a view of multiple OARs across the multiple treatment areas, and visual indicia that represents each OAR's relative spatial relationship to one or more treatment areas. Optionally, one or more of the first, second, and/or third graphical representations (e.g., graphical element(s), any of the graphical representation described herein) may be overlaid onto a 2-D or 3-D rendering of the patient's anatomy (e.g., CT images, PET images, MRI images, ultrasound images, etc.). In some variations, the dosimetric characteristics of all the multiple treatment areas may be visualized simultaneously on a treatment planning graphical user interface. In some variations, the dosimetric characteristics of each treatment area may be visualized individually. In some variations, dosimetric characteristics of each treatment area may comprise one or more of dosimetric objectives, dose-volume histograms, dose statistics, and objective performance.

Figure 38A:
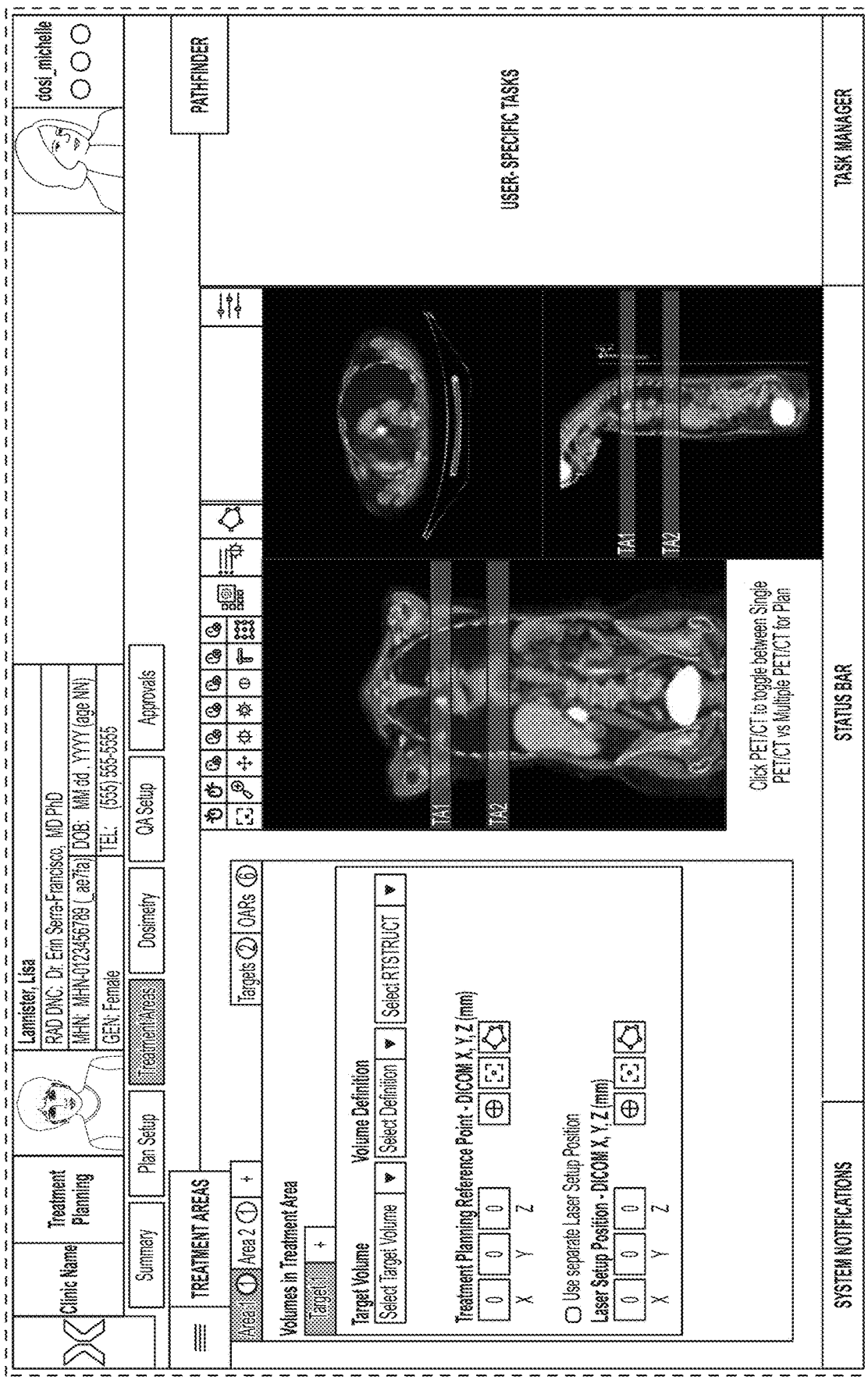
Figure 38B:
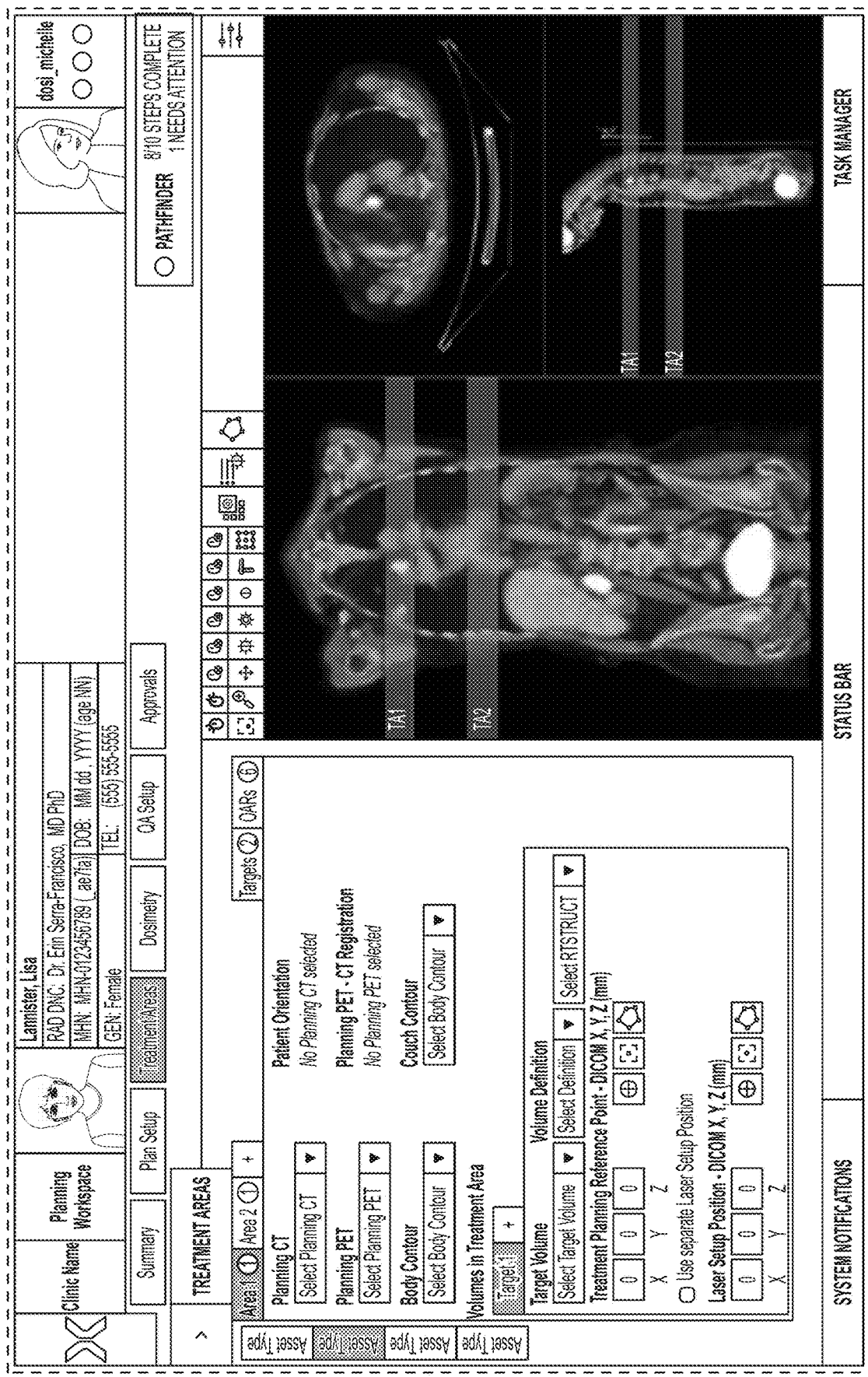
Figure 38C:
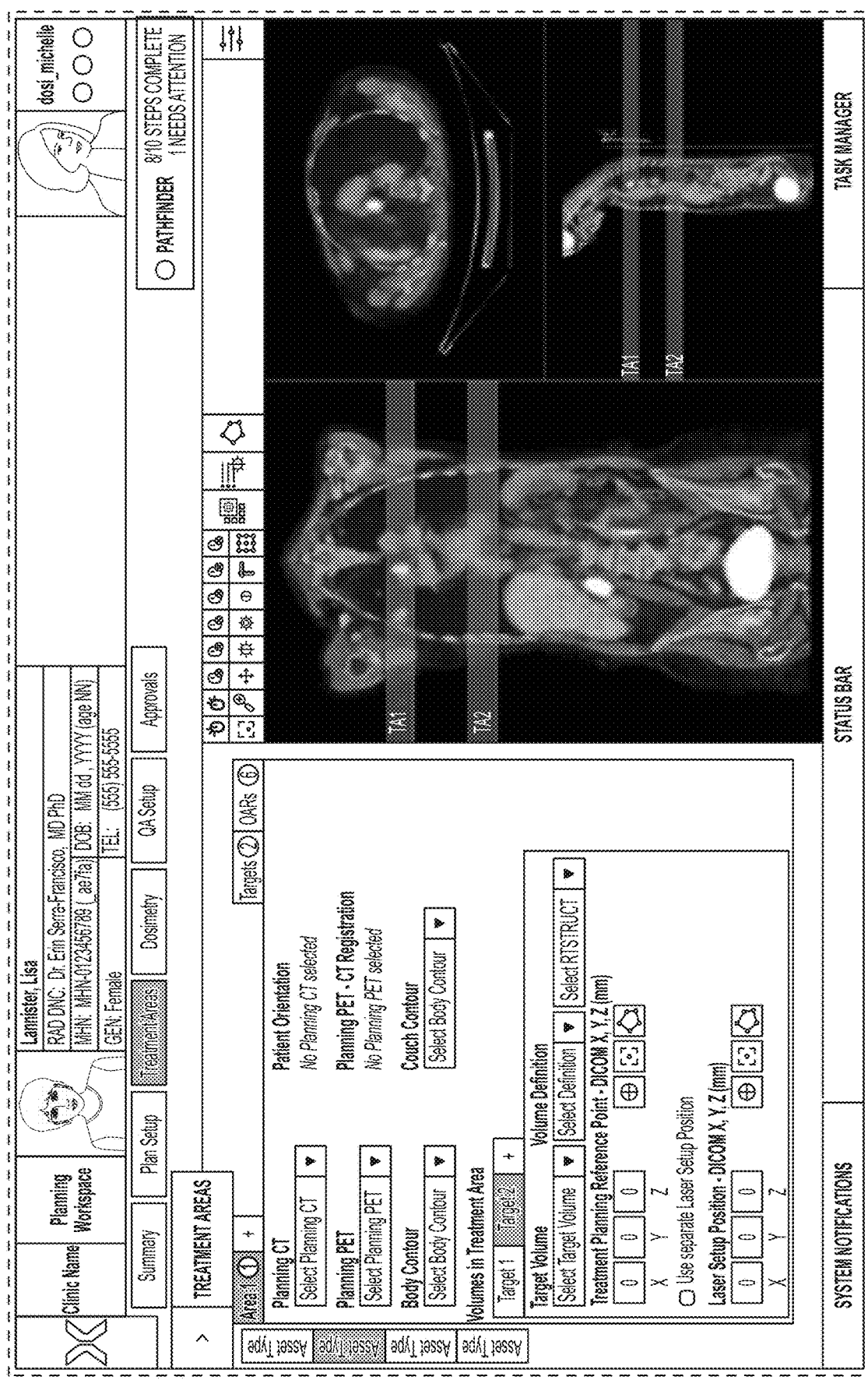
Figure 38D:
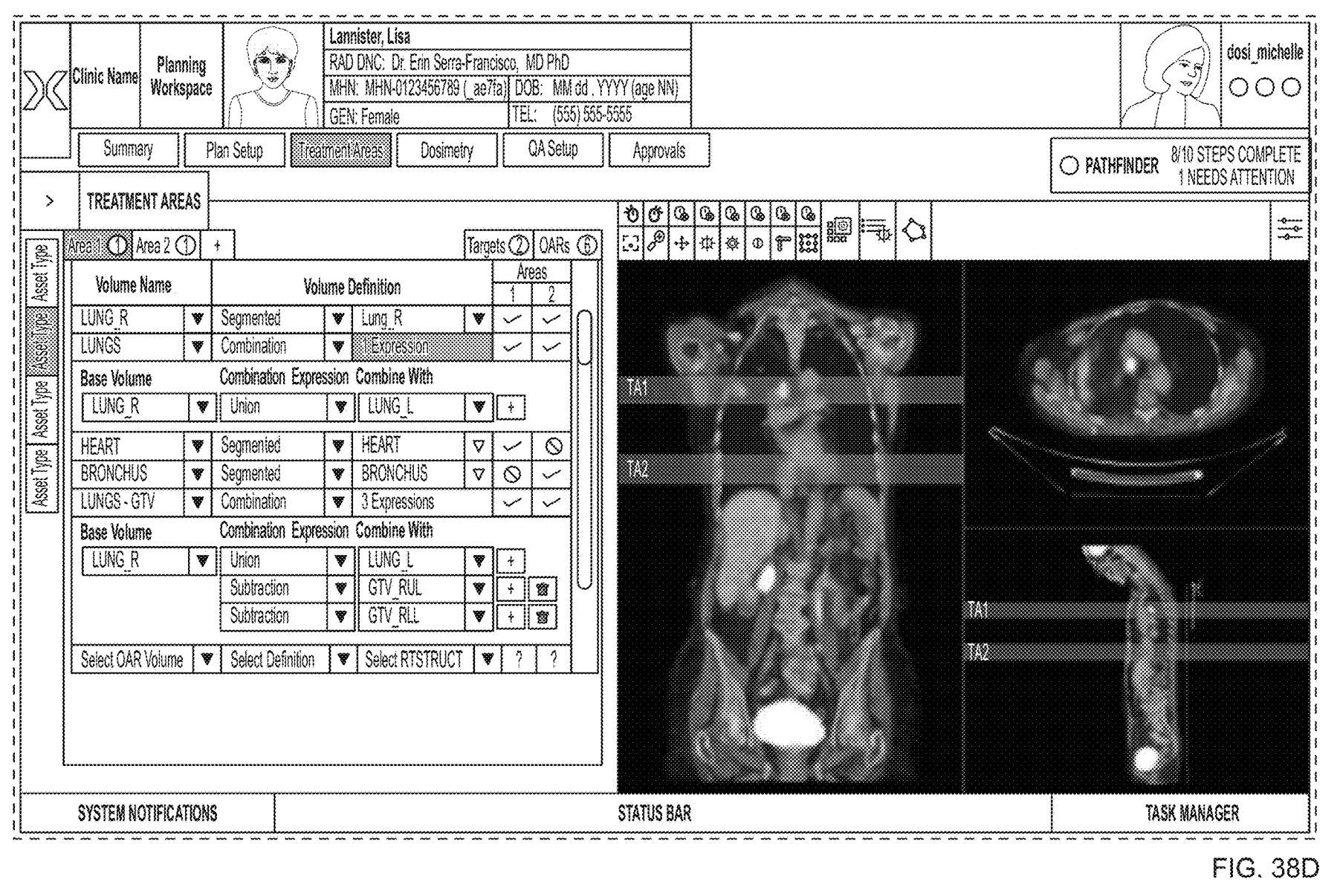
Figure 38E:
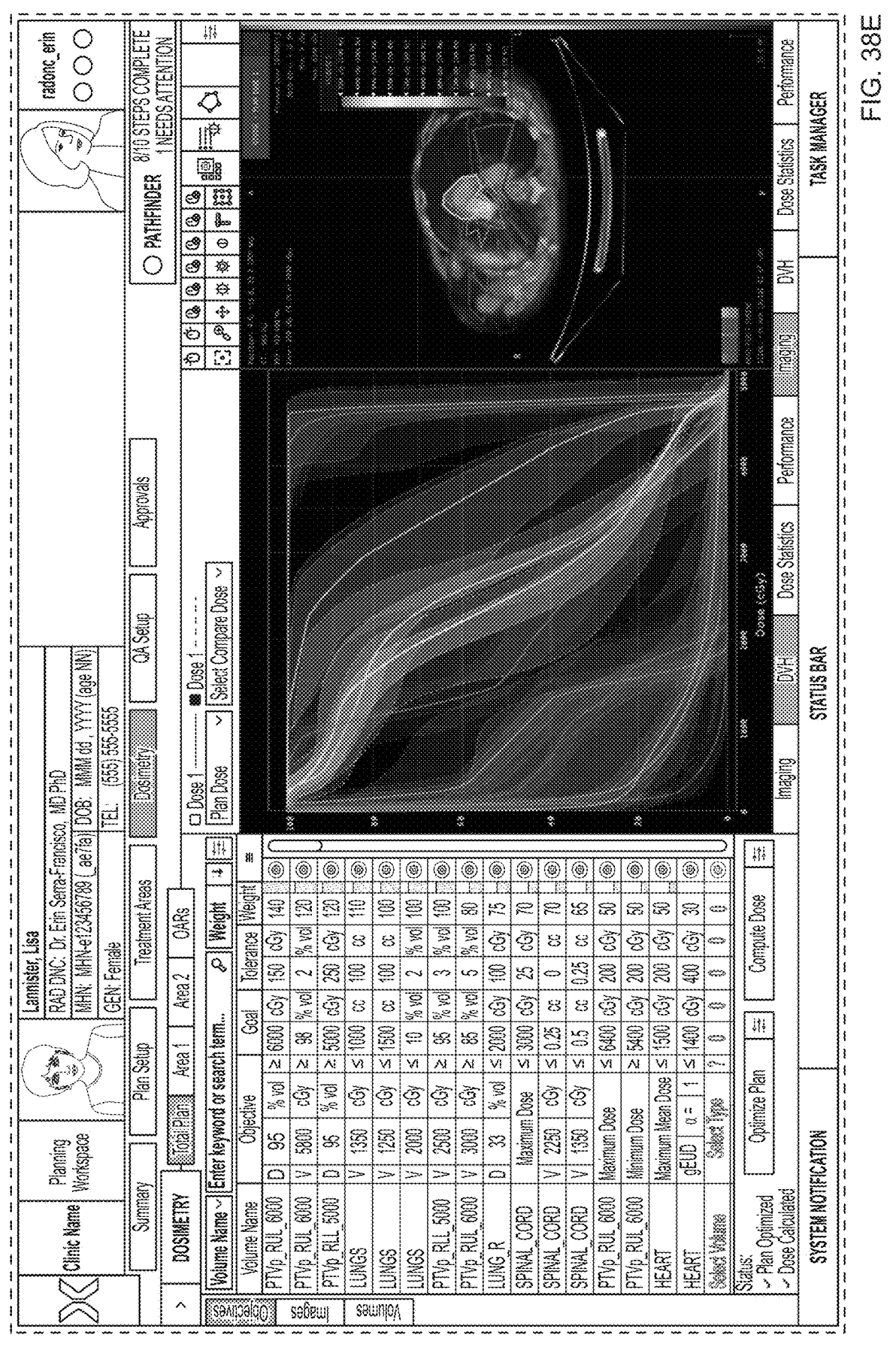

FIG. 38A depicts a treatment planning graphical user interface that depicts a treatment plan that has two treatment areas overlaid on an anatomical CT-PET scan. In this example, the two separate treatment areas are represented by two translucent horizontal bands overlaid onto the anatomical image that are displayed simultaneously to the user. The treatment planning graphical user interface may have a button that allows the user to toggle between a view of both treatment areas and a view of one treatment area at a time. FIG. 38B depicts an example of a treatment planning graphical user interface that has a graphical representation of multiple (e.g., two) treatment areas overlaid onto a single CT-PET image and a menu that presents different viewing options, such as viewing the CT-PET image for all treatment areas or a subset of the treatment areas, and allows the user to select the planning/reference images that may be used to comprise the CT-PET image for each treatment area. The treatment planning graphical user interface may include viewing tabs that facilitate the selection of the treatment areas and/or patient structures that the user wishes to view. For example, FIG. 38C depicts a first view-selection tab that allows the user to select a treatment area for viewing (e.g., Area 1), and a second view-selection tab that that allows the user to select the patient target regions and/or OARs within the selected treatment area for viewing (e.g., either Target 1 or Target 2 in Area 1). A treatment planning graphical user interface may also include viewing tabs that facilitate the selection of OARs for viewing, and may optionally include data fields that indicate the OAR participation and/or co-localization with each treatment area. FIG. 38D depicts one variation of a treatment planning graphical user interface that includes a viewing-tab that allows for the selection of viewing OARs, and within the OAR viewing-tab, the interface includes one or more fields that indicate whether an OAR spans one or more treatment areas. For example, the interface may include a table that lists each OAR and indicia as to whether each OAR co-localizes (e.g., overlaps) with Area 1 or Area 2 (or both). A treatment planning graphical user interface may also comprise views of the dosimetric characteristics of multiple treatment areas, patient target regions, and/or OARs. The dosimetric characteristics of one or more of the above may be visualized simultaneously or individually. Dosimetric characteristics may comprise one or more dosimetric objectives, dose-volume histograms, dose statistics, and objective performance. FIG. 38E depicts a treatment planning graphical user interface that comprises a first panel that lists the volumes that the user is interested in viewing and a second panel that depicts a graphical representation of the dose-volume histograms (DVH) for the volumes listed in the first panel. The first panel may comprise tabs or buttons that allow a user to select the type of dosimetric information, as well as the treatment areas, patient target regions, and/or OARs, that are to be depicted in the second panel. In the viewing mode depicted in FIG. 38E, the DVH curves/profiles for the "Total Plan" (e.g., all patient target regions and OARs across all treatment areas) are depicted in the second panel. In other viewing modes, a user may select to view the DVH curves/profiles for Area 1 only, Area 2 only, OARs only, and any combination thereof. The DVH curves may be bounded DVH curves that represent a range of dose (e.g., upper bounds and lower bounds) delivered to that volume based on variabilities in position, motion, and/or other parameters. In some variations, the bounded DVH curves may represent an acceptable dose variance tolerance as set by the clinician and/or clinic. Optionally, a graphical user interface may comprise a third panel that depicts an anatomical image (e.g., CT-PET, MRI-PET, etc.) of the patient, with visual indicia (e.g., outlines or shading) of the treatment areas, patient target regions, and/or OARs. Dose characteristics may be overlaid or superimposed over their corresponding anatomical regions.

Multi-Target Radiation Delivery Methods

After at least one of a plurality of patient target regions has been localized using one or more of the methods described above, radiation delivery may be delivered to the patient target regions that have been localized. Therapeutic radiation may be delivered to the patient target regions sequentially or simultaneously. In one variation, radiation delivery to a plurality of patient target regions in a single treatment session may comprise localizing a first patient target region based on a first localization image, delivering therapeutic radiation to the first patient target region, and then localizing a second patient target region, delivering therapeutic radiation to the second patient target region, and so on, until all of the patient target regions have been irradiated with the prescribed dose. The serial localizations may be done using the same localization images, or each successive localization may be based on newly acquired or updated localization images. Alternatively or additionally, some radiation delivery methods may comprise localizing all patient target regions all at once (e.g., using the same set of localization images acquired at the beginning of the treatment session), and then irradiating all of the patient target regions as the patient is moved through the therapeutic radiation beam plane and/or as the therapeutic radiation source moves about the patient. In variations where virtual localization is used to localize the patient target regions, the delivery fluence maps for each of the patient target regions may be segmented into radiotherapy system machine instructions after virtual localization, and the radiotherapy system may then step through the segmented machine instructions and deliver radiation accordingly. In variations where at least some of the patient target regions are BgRT target regions, the delivery fluence maps (e.g., calculated during virtual localization) for those target regions may not be segmented into radiotherapy machine instructions until the delivery fluence maps have been further updated with imaging data acquired during the treatment session. For example, about a minute or less or a second or less (e.g., about 500 ms or less) from when radiation is emitted to a patient target region at the next firing position, imaging data acquired in a limited-time window may be used to calculate the delivery fluence for the upcoming firing position (e.g., by convolving a projection of the firing filter at that firing position with the partial imaging data). Moments before the therapeutic radiation arrives at the next firing position (e.g., less than about 1 second before, less than about 0.5 second before, less than about 0.25 second before, etc.), the radiotherapy system may segment the delivery fluence for that firing position into radiotherapy system instructions and the delivery fluence may be emitted according to those instructions. In some variations, the patient platform may be configured to move the patient such that all of the patient target regions pass through the therapeutic radiation beam plane more than once per treatment session. Each of such patient "sweep" through the beam plane may be called a shuttle pass. For example, moving the patient from the first location to a second location may define a first shuttle pass, and moving the patient from the second location to the first location may define a second shuttle pass. The patient platform may be moved continuously as radiation is delivered or may be stepped to a series of couch locations along the longitudinal axis (along IEC-Y) such that radiation is delivered only when the couch is stopped at these pre-determined locations (or beam stations). A treatment area may be defined by a set of beam stations or pre-determined patient platform locations in IEC-Y. In some variations, one or more patient target regions are irradiated during a first shuttle pass while one or more other patient target regions are irradiated during a second shuttle pass. In some variations, the BgRT patient target regions may be irradiated during a first shuttle pass and SBRT/IMRT target regions may be irradiated during a second shuttle pass. Alternatively or additionally, all of the patient target regions may be irradiated during the same shuttle pass. Optionally, after each complete BgRT pass, a set of normalization coefficients for all target regions can be calculated based on the previous BgRT pass. Additional details on methods for calculating and applying normalization coefficients and shuttle-mode radiation delivery are provided in U.S. patent application Ser. No. 16/138,631, filed Sep. 21, 2018, which is hereby incorporated by reference in its entirety.

In some variations, multi-target radiation delivery for a patient may comprise segmenting (e.g., dividing, partitioning, etc.) the patient regions to be treated into a plurality of treatment areas that each have one or more patient target regions, performing physical localization for a treatment area (e.g., couch shifts and/or patient position adjustment), and then performing virtual localization for one or more of the patient target regions in the treatment area. In some variations, a patient treatment plan may comprise a set of treatment areas that represent patient regions to which radiation is to be delivered for a single patient immobilization. For example, a treatment area (TA) may comprise a patient region that is to be irradiated with a set of beams delivered with a single kVCT localization and optional laser setup. In some variations, a treatment area (TA) may correspond to a respective PET prescan and evaluation, and fraction counter. For example, each treatment area (TA) may comprise a respective laser setup and physical localization and/or a virtual localization. A fluence map may be represented by a set of irradiation sinograms across one or more beam stations. In some variations, the fluence map may be configured to be delivered within a single treatment session without interruption. FIGS. 35A-35C are diagrams that depict three different patient treatment plan variations. FIG. 35A is an example of a treatment plan with three treatment areas (regions enclosed by solid lines) across two patient setups (regions enclosed by grey dotted lines) with three target region groups (enclosed by dark dotted lines) that each have a corresponding fluence map. During a treatment session, this would result in a total of three localization CTs to be acquired with up to three physical localizations and three virtual localizations. In this example, the treatment plan has three target region groups (TRG1, TRG2, and TRG3), where TRG1 comprises two fluence maps for two patient target regions, and both TRG2 and TRG3 each comprise one planned fluence map for one patient target region. FIG. 35B is an example of a treatment plan with a single patient setup (enclosed by grey dotted lines) and single treatment area (enclosed by solid lines) with four target region groups (enclosed by dark dotted lines) that each have a corresponding fluence map. During a treatment session, this would result in a single localization CT to be acquired with up to one physical localization and four virtual localizations. FIG. 35C is an example of a treatment plan with four treatment areas (enclosed by solid lines) each with their own localization CT, physical localization, and/or virtual localization. Each of the target region groups in FIGS. 35B and 36C have one planned fluence map for each (since each group of target regions has just one target region).

FIG. 36A and FIG. 36B are diagrams that depict examples of treatment plans comprising two different target region group configurations for a patient. While FIGS. 35A-35C depict examples of treatment plans with different treatment areas, FIGS. 36A and 36B depict examples of treatment plans with different target region groups are depicted in FIGS. 36A and 36B. In this example, there are four patient target regions (represented by the circles) that are to be irradiated by the treatment plan. During treatment planning, the user may define treatment area and target region group configurations where each treatment area and target region group may encompass different patient target regions. Each target region group (enclosed by dark dotted lines) may comprise one or more fluence maps that are associated with each of the four patient target regions. As described previously, each treatment area may comprise its own kVCT-based localization, optional laser setup, and/or optional patient position. Each target region group may comprise its own virtual localization. The fluence maps for each of the patient target regions within a target region group may be delivered sequentially or in parallel as the treatment area is irradiated. In some variations, virtual localization may be performed for one or more target region groups. For example, virtual localization of the treatment plan may reduce or eliminate a patient platform shift (e.g., couch shift) and provide the same or similar safety profile as conventional couch shift except that the virtual localization replaces the couch shift. A localization reference point may be set for each treatment area and/or target region group and may increase a safety margin for a patient target region and/or organ at risk (OAR). In some variations, a treatment area may be defined by the treatment plan, which may be approved by a clinician such that a treatment area does not change at the time of treatment delivery. Additionally or alternatively, one of the target region groups may be selected for a couch shift while the remaining target region groups may undergo virtual localization.

The treatment plan depicted in FIG. 35A may comprise three treatment areas, where the first treatment area includes the first patient target region group (TRG1 with corresponding fluence map), the second treatment area includes the second patient target region group (with corresponding fluence map), and the third treatment area includes the third patient target region group (with corresponding fluence map). During a treatment session, a patient may be physically setup/localized for the first treatment area to deliver radiation to the first two patient target regions. Then, the patient may be physically setup/localized (for a second time) for the second treatment area to deliver radiation to the third patient target region. Finally, the patient may be physically setup/localized (for a third time) for the third treatment area to deliver radiation to the fourth patient target region. Optionally, the patient may be virtually setup/localized for at least one of the three treatment areas and/or target region groups, such that the patient is not physically setup/localization for a second or third time.

The treatment plan depicted in FIG. 35B may comprise a single treatment area containing four target region groups. During a treatment session, a patient may be physically setup/localized just once for the defined treatment area. Then, the patient may be virtually localized for each of the four target region groups to deliver radiation to all four patient target regions.

The treatment plan depicted in FIG. 35C may comprise four treatment areas, where each target region group is contained within a separate treatment area. During a treatment session, a patient may be physically setup/localized once for each treatment area and/or virtually localized once for each target region group to deliver radiation to the respective patient target region contained within.

The treatment plan depicted in FIG. 36A may comprise two treatment areas, one that includes the first three patient target regions (with corresponding fluence maps) and a second that includes the fourth patient target region. During a treatment session, a patient may be physically setup/localized once for each of the two defined treatment areas and/or virtually localized once for each of the two defined target region groups.

The treatment plan depicted in FIG. 36B may comprise two treatment areas, where the first treatment area includes the first and second patient target region groups (with corresponding fluence maps for the first three patient target regions) and the second treatment area includes the third patient target region group (with corresponding fluence map for the fourth patient target region). During a treatment session, a patient may be physically setup/localized for the first treatment area and virtually localized for one or both the first and second patient target region groups to deliver radiation to the patient target regions contained within. Then, the patient may be physically setup/localized (for a second time) for the second treatment area to deliver radiation to the fourth patient target region. Optionally, the patient may be virtually setup/localized for one of the two treatment areas and/or target region groups, such that the patient is not physically setup/localization for a second time.

Figure 18A:
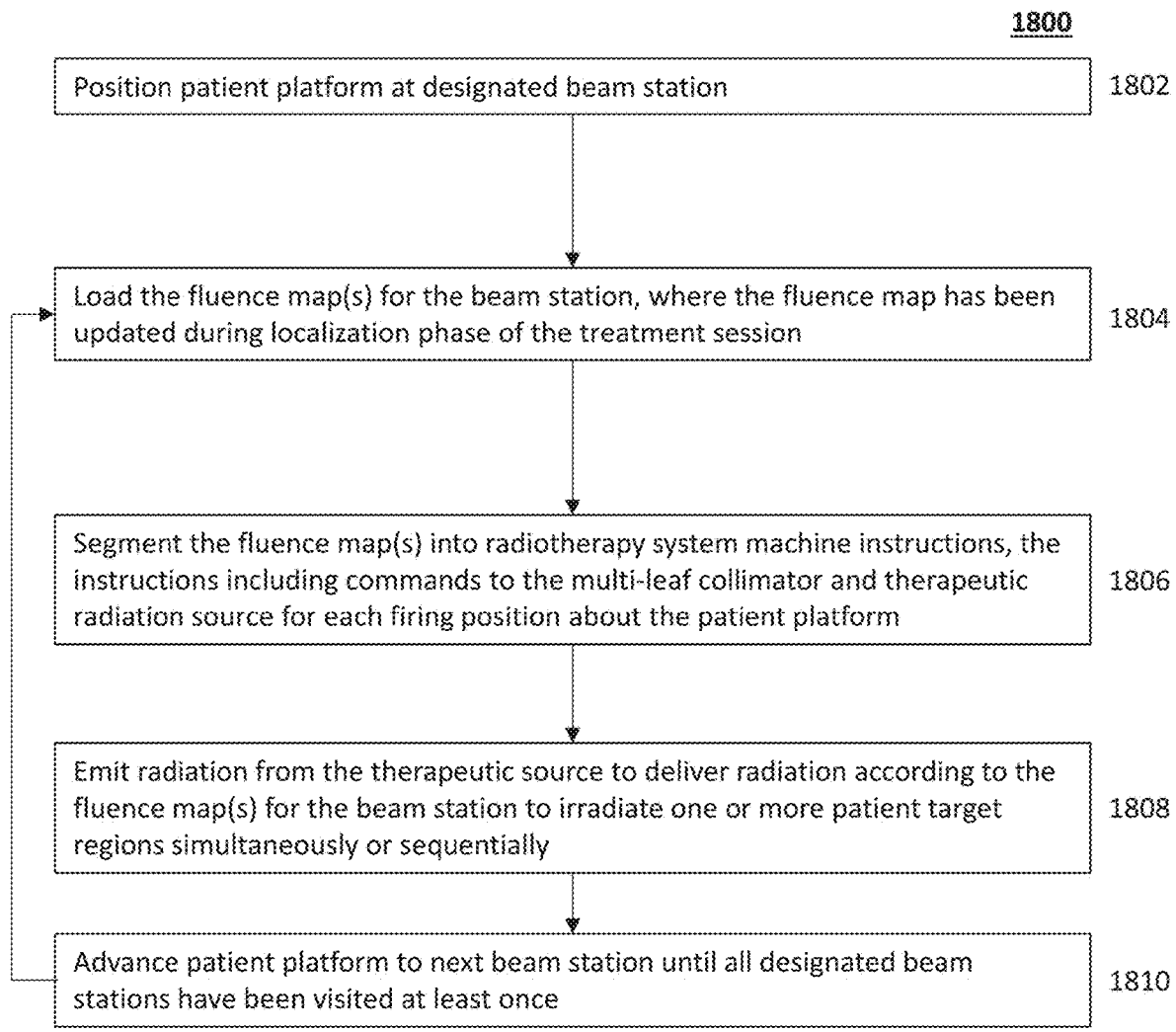
FIG. 18A is a flow chart representation of one variation of a method for multi-target radiation delivery.

FIG. 18A depicts a flowchart representation of a method for treating multiple patient target regions (e.g., SBRT/IMRT patient target regions) in a treatment session, where the fluence maps are segmented into radiotherapy machine instructions during the treatment session. Method (1800) may comprise positioning (1802) a patient platform at a designated beam station, loading (1804) the fluence map(s) for the beam station, where the fluence map has been updated during localization phase of the treatment session, segmenting (1806) the fluence map(s) into radiotherapy system machine instructions, the instructions including commands to the multi-leaf collimator and therapeutic radiation source for each firing position about the patient platform, emitting (1808) radiation from the therapeutic source to deliver radiation according to the fluence map(s) for the beam station to irradiate one or more patient target regions simultaneously or sequentially, and advancing (1810) the patient platform to next beam station until all designated beam stations have been visited at least once. Localization may be performed using physical localization, virtual localization, and/or any other methods that shift the planned fluence map to reflect the actual location of the corresponding patient target region. The fluence map(s) that may be loaded (1804) may include one or more of: (a) a cumulative delivery fluence map for multiple patient target regions, and/or (b) individual fluence maps for multiple patient target regions. For example, the fluence map(s) that are delivered may have been updated using the virtual localization methods described herein. Method (1800) may comprise repeating (1804)-(1810) until all beam stations have been visited one or more times (e.g., one or more shuttle passes).

Figure 18B:
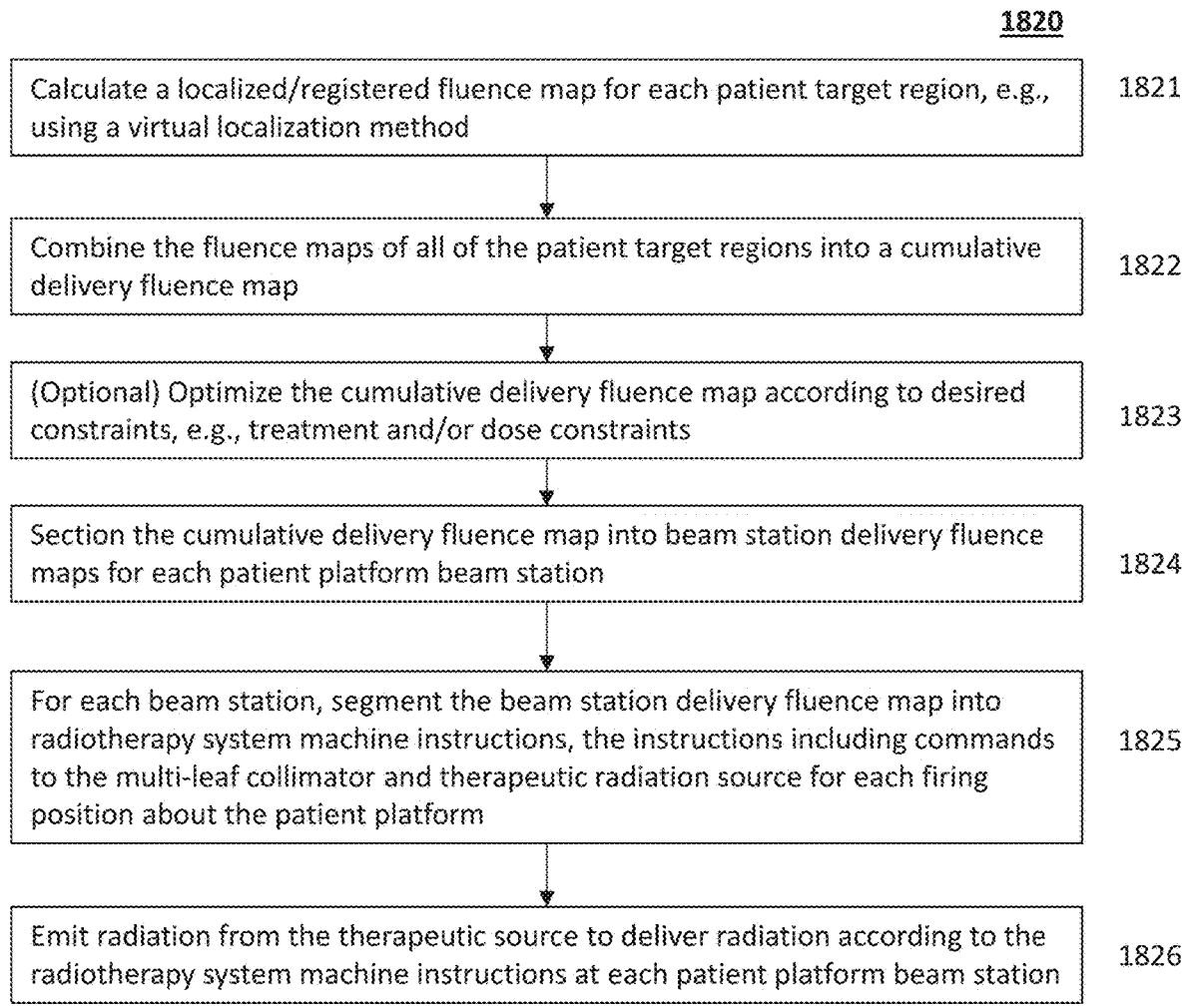
FIG. 18B is a flow chart representation of one variation of a method for multi-target radiation delivery.

FIG. 18B depicts a flowchart representation of a method for treating multiple patient target regions (e.g., SBRT/IMRT patient target regions) in a treatment session, where the fluence maps are segmented into radiotherapy machine instructions during the treatment session and multiple patient target regions may be irradiated concurrently. Method (1820) may comprise calculating (1821) a localized/registered fluence map for each patient target region, e.g., using a virtual localization method, combining (1822) the fluence maps of all of the patient target regions into a cumulative delivery fluence map, sectioning (1824) the cumulative delivery fluence map into beam station delivery fluence maps for each patient platform beam station, segmenting (1825), for each beam station, the beam station delivery fluence map into radiotherapy system machine instructions, the instructions including commands to the multi-leaf collimator and therapeutic radiation source for each firing position about the patient platform, and emitting (1826) radiation from the therapeutic source to deliver radiation according to the radiotherapy system machine instructions at each patient platform beam station. Optionally, the method (1820) may comprise optimizing (1823) the cumulative delivery fluence map according to desired constraints, e.g., treatment and/or dose constraints before sectioning (1823) the cumulative delivery fluence map into beam station delivery fluence maps. Optionally, the cumulative delivery fluence map may be optimized by calculating a set of scalar normalization coefficients that solve minimize mean-square error dosimetric objective.

Figure 18C:
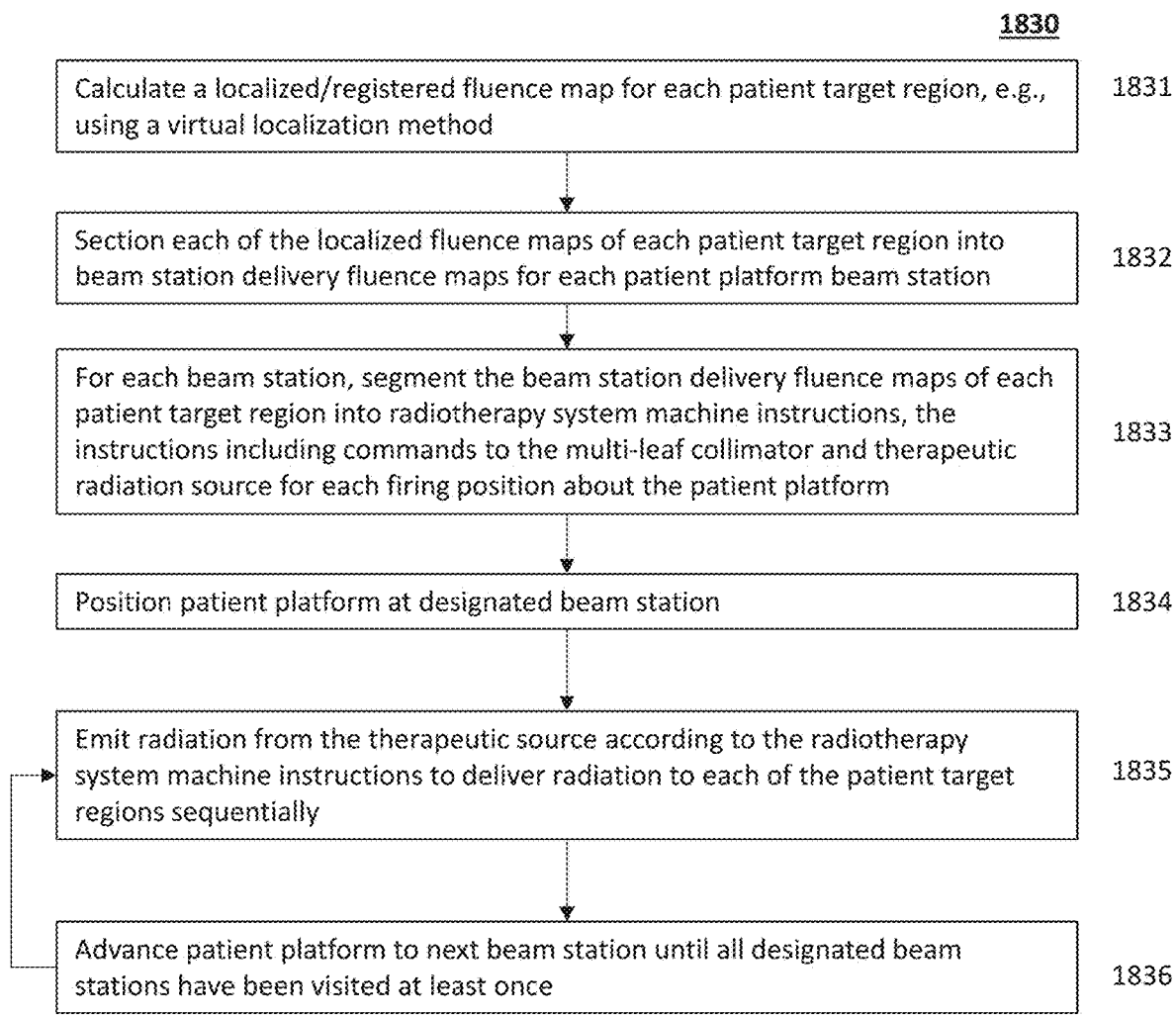
FIG. 18C is a flow chart representation of one variation of a method for multi-target radiation delivery.

FIG. 18C depicts a flowchart representation of a method for treating multiple patient target regions (e.g., SBRT/IMRT patient target regions) in a treatment session, where the fluence maps are segmented into radiotherapy machine instructions during the treatment session and multiple patient target regions may be irradiated sequentially. Method (1830) may comprise calculating (1831) a localized/registered fluence map for each patient target region, e.g., using a virtual localization method and/or a physical setup/localization method, sectioning (1832) each of the localized fluence maps of each patient target region into beam station delivery fluence maps for each patient platform beam station, segmenting (1833), for each beam station, the beam station delivery fluence maps of each patient target region into radiotherapy system machine instructions, the instructions including commands to the multi-leaf collimator and therapeutic radiation source for each firing position about the patient platform, positioning (1834) the patient platform at designated beam station, and emitting (1835) radiation from the therapeutic source according to the radiotherapy system machine instructions to deliver radiation to each of the patient target regions sequentially. Method (1830) may comprise advancing (1836) the patient platform to next beam station until all designated beam stations have been visited at least once.

Figure 18D:
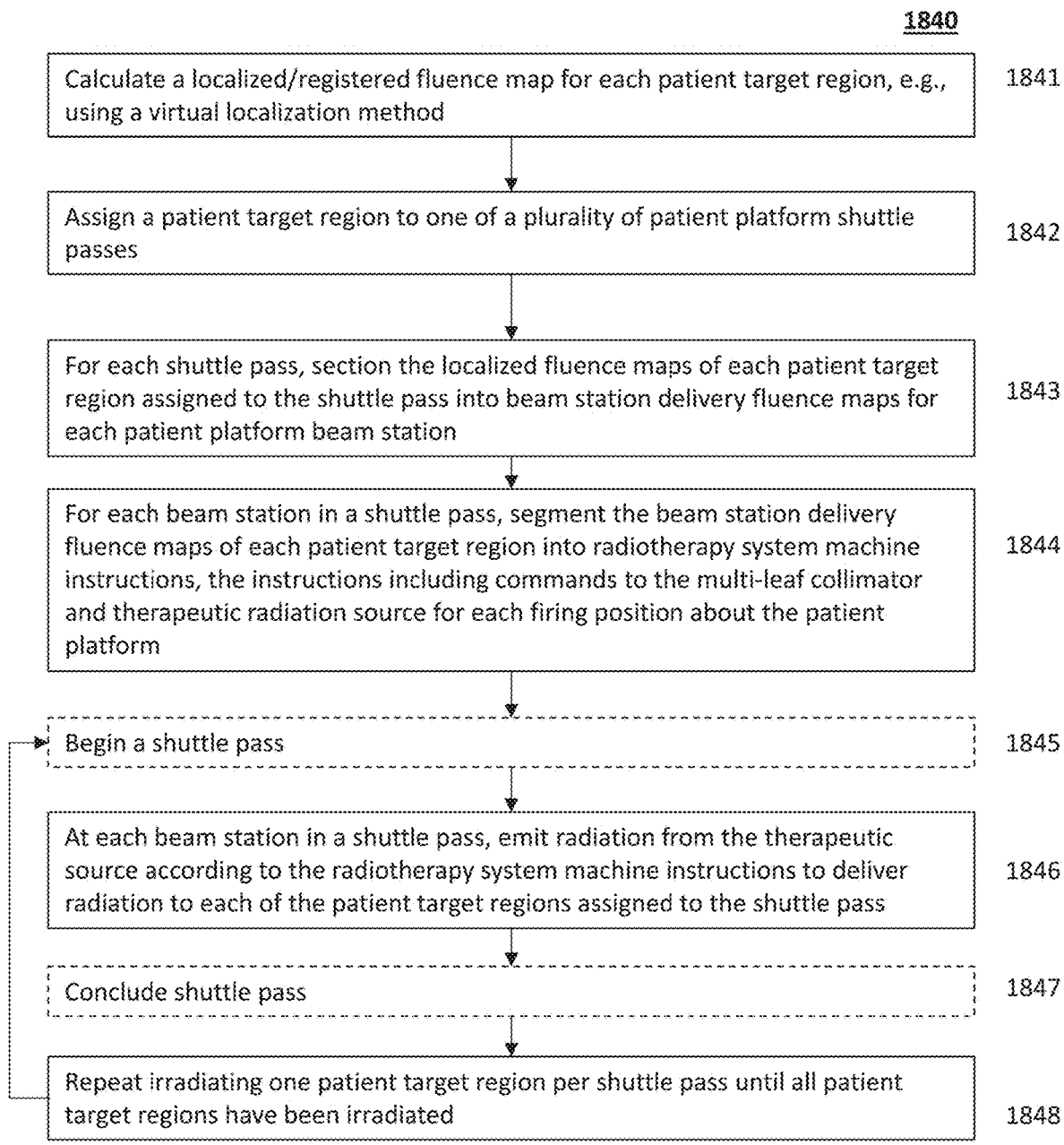
FIG. 18D is a flow chart representation of one variation of a method for multi-target radiation delivery.

FIG. 18D depicts a flowchart representation of a method for treating multiple patient target regions (e.g., SBRT/IMRT patient target regions) in a treatment session, where the fluence maps are segmented into radiotherapy machine instructions during the treatment session and multiple patient target regions may be irradiated sequentially over multiple shuttle passes. Method (1840) may comprise calculating (1841) a localized/registered fluence map for each patient target region, e.g., using a virtual localization method and/or a physical setup/localization method, and assigning (1842) a patient target region to one of a plurality of patient platform shuttle passes. Method (1840) may then comprise sectioning (1843), for each shuttle pass, the localized fluence maps of each patient target region assigned to the shuttle pass into beam station delivery fluence maps for each patient platform beam station, and segmenting (1844), for each beam station in a shuttle pass, the beam station delivery fluence maps of each patient target region into radiotherapy system machine instructions, the instructions including commands to the multi-leaf collimator and therapeutic radiation source for each firing position about the patient platform. The method (1840) may then comprise beginning (1845) a shuttle pass, emitting (1846), at each beam station in the shuttle pass, radiation from the therapeutic source according to the radiotherapy system machine instructions to deliver radiation to each of the patient target regions assigned to the shuttle pass, concluding (1847) the shuttle pass, and repeating (1848) irradiating one patient target region per shuttle pass until all patient target regions have been irradiated.

Figure 19:
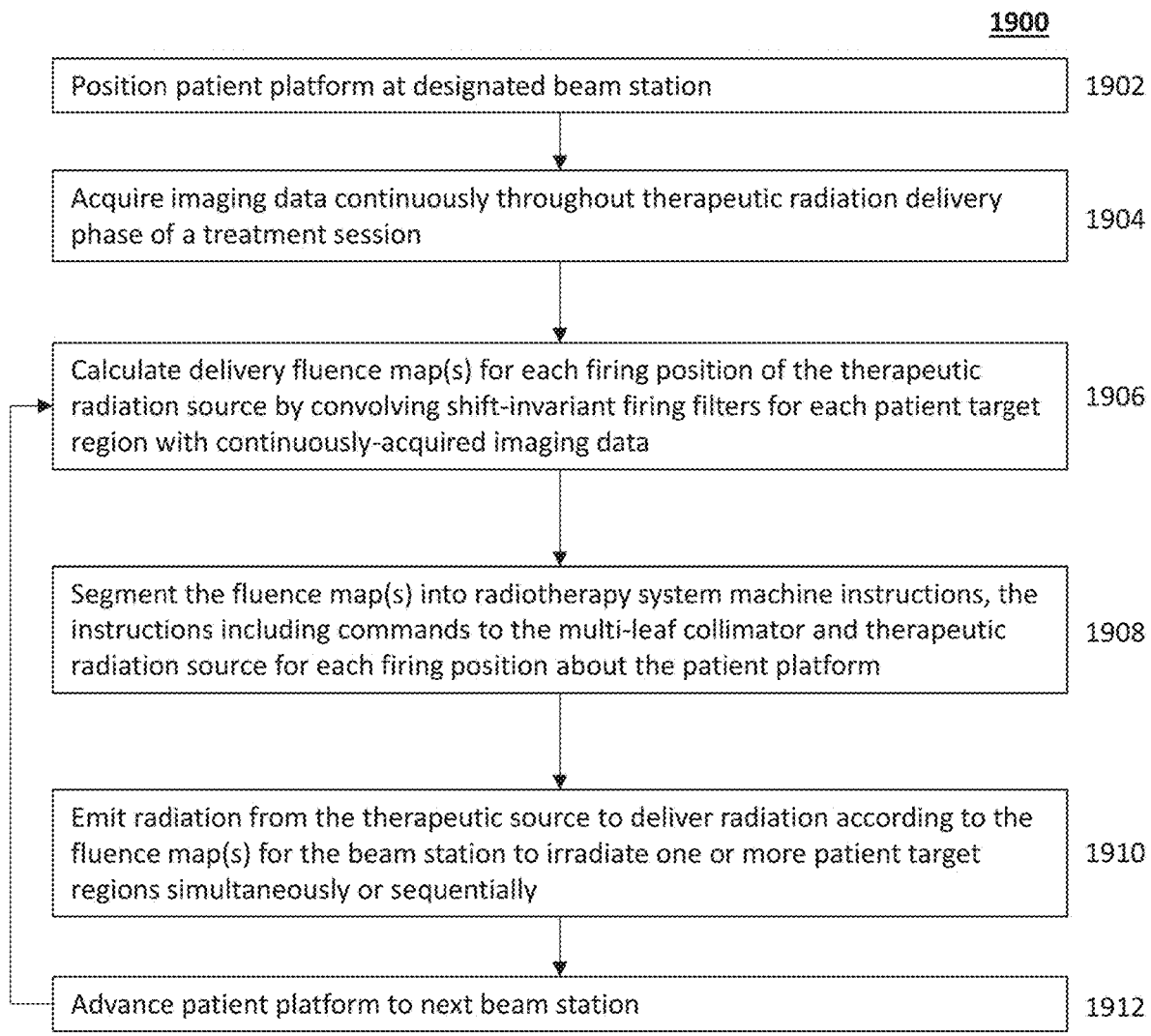
FIG. 19 is a flow chart representation of one variation of a method for multi-target BgRT-based radiation delivery.

FIG. 19 depicts a flowchart representation of a method for treating multiple BgRT patient target regions in a treatment session. BgRT patient target regions may be registered using virtual localization methods, as described previously. In some variations of BgRT radiotherapy, the patient is injected with a PET tracer that accumulates at tumor regions that may be designated at patient target regions. The radiotherapy system may comprise arrays of PET detectors to detect positron annihilation emission path data (LORs) and a therapeutic radiation source such as a linac configured to deliver radiation based on the detected LOR data. Method (1900) may comprise positioning (1902) a patient platform at designated beam station, acquiring (1904) imaging data continuously throughout therapeutic radiation delivery phase of a treatment session, calculating (1906) delivery fluence map(s) for each firing position of the therapeutic radiation source by convolving shift-invariant firing filters for each patient target region with continuously-acquired imaging data, segmenting (1908) the fluence map(s) into radiotherapy system machine instructions, the instructions including commands to the multi-leaf collimator and therapeutic radiation source for each firing position about the patient platform, emitting (1910) radiation from the therapeutic source to deliver radiation according to the fluence map(s) for the beam station to irradiate one or more patient target regions simultaneously or sequentially, and advancing (1912) the patient platform to the next beam station. As described previously in BgRT delivery, imaging data may be acquired over a limited-time window (e.g., about 1 second or less, about 500 ms or less, about 250 ms or less), and the acquired imaging data may be used to calculate the fluence to be delivered at a future firing position and segmented into radiotherapy system instructions moments before the therapeutic radiation source is located at that firing position. In some systems with a linear accelerator mounted on a fast-rotating gantry (e.g., about 40 RPM, about 50 RPM, about 60 RPM, about 70 RPM), the latency between imaging data acquisition and therapeutic radiation emission may be about 2 seconds or less, about 1 second or less, about 500 ms or less, etc.). Such frequent calculation and/or updating of the delivery fluence and real-time segmentation may allow the prescribed radiation dose to be more precisely delivered to the intended patient target region. The calculation (1906) of the delivery fluence may use one or more of the methods described above, including, but not limited to, fluence maps derived from virtual localization, convolving shift-invariant firing filters or radiation-firing matrices (RFM) with partial image data (e.g., LOR data that has been spatially filtered by the ROI and backprojected onto a firing position), convolution with virtual flattening filters, distance compensation scaling factors, etc. Optionally, the cumulative delivery fluence map may be optimized by calculating a set of scalar normalization coefficients that solve minimize mean-square error dosimetric objective for each target region.

Figure 20:
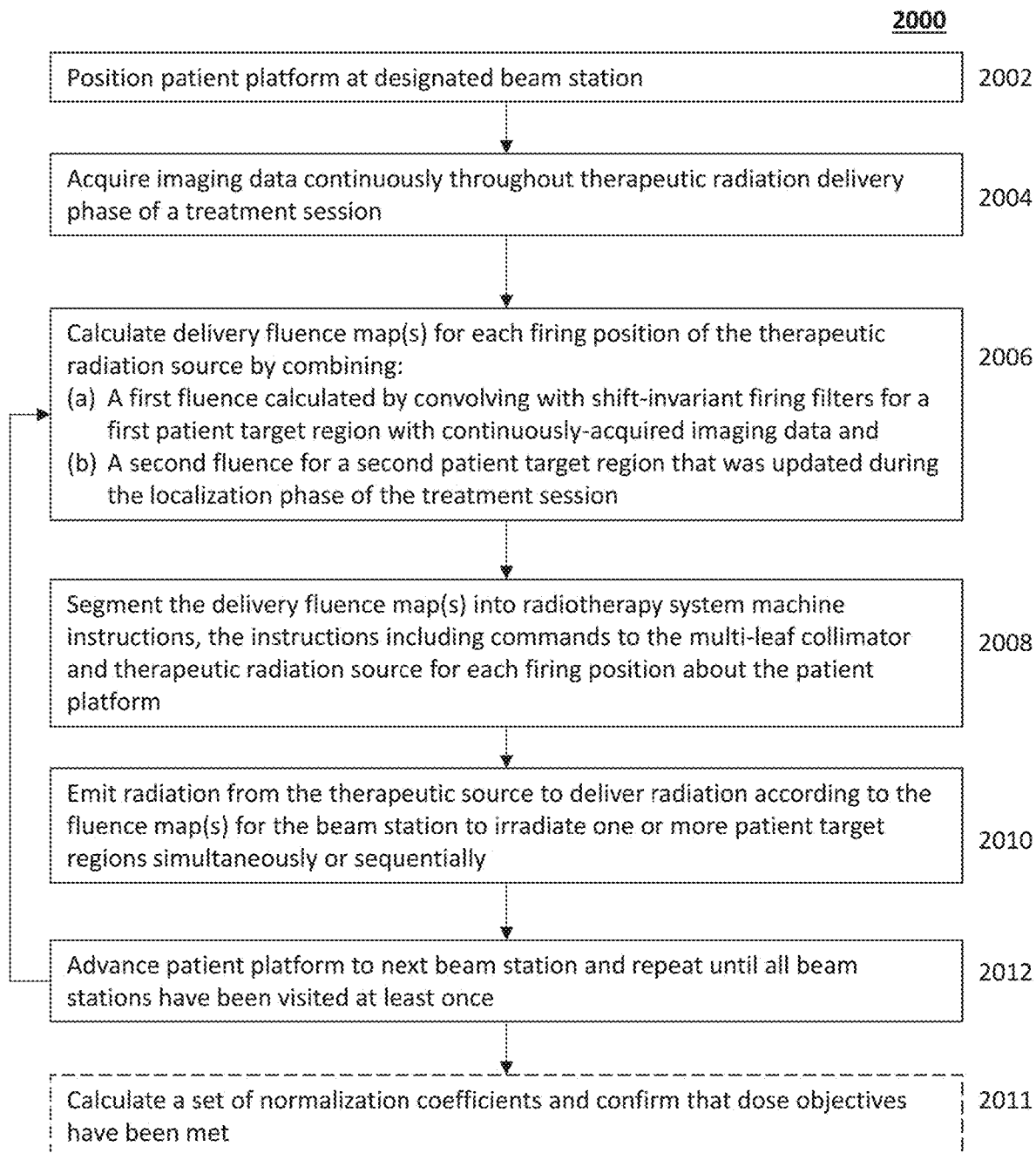
FIG. 20 is a flow chart representation of one variation of a method for multi-target radiation delivery.

FIG. 20 depicts a flowchart representation of a method for treating multiple patient target regions in a treatment session, where some patient target regions may be BgRT targets and others may be SBRT/IMRT targets. The patient target regions may be registered using virtual localization methods, as described previously. In some variations of BgRT radiotherapy, the patient is injected with a PET tracer that accumulates at tumor regions that may be designated at patient target regions. The radiotherapy system may comprise arrays of PET detectors to detect positron annihilation emission path data (LORs) and a therapeutic radiation source such as a linac configured to deliver radiation based on the detected LOR data. Method (2000) may comprise positioning (2002) a patient platform at designated beam station, acquiring (2004) imaging data continuously throughout therapeutic radiation delivery phase of a treatment session, calculating (2006) delivery fluence map(s) for each firing position of the therapeutic radiation source by combining a first fluence calculated by convolving with shift-invariant firing filters for a first patient target region with continuously-acquired imaging data and a second fluence for a second patient target region that was updated during the localization phase of the treatment session, segmenting (2008) the delivery fluence map(s) into radiotherapy system machine instructions, the instructions including commands to the multi-leaf collimator and therapeutic radiation source for each firing position about the patient platform, emitting (2010) radiation from the therapeutic source to deliver radiation according to the fluence map(s) for the beam station to irradiate one or more patient target regions simultaneously or sequentially, and advancing (2012) the patient platform to the next beam station and repeat until all beam stations have been visited at least once. Optionally, after all beam stations have been visited at least once, method (2000) may comprise calculating a set of normalization coefficients to determine whether dose objectives have been met. As described previously in BgRT delivery, imaging data may be acquired over a limited-time window (e.g., about 1 second or less, about 500 ms or less, about 250 ms or less), and the acquired imaging data may be used to calculate the fluence to be delivered at a future firing position and segmented into radiotherapy system instructions moments before the therapeutic radiation source is located at that firing position. In some systems with a linear accelerator mounted on a fast-rotating gantry (e.g., about 50 RPM or more, about 60 RPM, about 70 RPM), the latency between imaging data acquisition and therapeutic radiation emission may be about 2 seconds or less, about 1 second or less, about 500 ms or less, etc.). Such frequent calculation and/or updating of the delivery fluence and real-time segmentation may allow the prescribed radiation dose to be more precisely delivered to the intended patient target region. The calculation (1906) of the delivery fluence may use one or more of the methods described above, including, but not limited to, fluence maps derived from virtual localization, convolving shift-invariant firing filters or radiation-firing matrices (RFM) with partial image data (e.g., LOR data that has been spatially filtered by the ROI and backprojected onto a firing position), convolution with virtual flattening filters, distance compensation scaling factors, etc. Optionally, calculating the delivery fluence map(s) (2006) may comprise optimizing a cumulative delivery fluence map (i.e., that sums all of the radiation fluence that has been delivered thus far in the treatment session) by calculating a set of scalar normalization coefficients that solve minimize mean-square error dosimetric objective for each target region.

Systems

As described above, a radiotherapy system, such as any of the radiotherapy systems described herein, may be used to provide image-guided radiation therapy (IGRT) including any of the methods described above. The radiotherapy system may comprise an imaging system comprising any suitable imaging modality, for example, PET, CT, MRI, ultrasound, etc. In some variations, a radiotherapy system may comprise a motion system to which the imaging system may be mounted. Optionally, a therapeutic radiation source and one or more beam-shaping components of the radiotherapy system may be mounted on the same gantry. In some variations, the imaging system may be mounted on a circular gantry configured to rotate around a patient area at a speed of about 30 RPM or more (e.g., about 60 RPM, about 65 RPM, about 70 RPM). Alternatively or additionally, the imaging system may be capable of acquiring tomographic imaging data without any rotation, for example, MRI imaging systems.

A radiotherapy system that may be used to provide IGRT as described above may comprise a therapeutic radiation source that is configured to deliver therapeutic radiation beams in real-time. That is, the therapeutic radiation source may be mounted on a motion system that rapidly moves the radiation source to each firing position around a patient area and the beam-shaping components are configured to change beam-shaping configurations in the time interval between firing positions so that a radiation beam may be applied to a target region before it moves substantially. The greater the latency between image acquisition and radiation delivery, the greater the likelihood that the target region would have moved by the time radiation is delivered. Accordingly, the motion system (e.g., gantry, chassis, arms, etc.) and the beam-shaping components (e.g., jaws, collimators, etc.) may be configured to move (e.g., motion system to move the radiation source to a new firing position) and change configuration (e.g., collimators or jaws to move/change the positioning of the radiopaque elements) in about 10 ms or less. For example, a radiotherapy system may comprise an imaging system (PET, CT, MRI, for example), a rotatable gantry, a linac mounted on the rotatable gantry, and a dynamic multi-leaf collimator mounted on the gantry and disposed in the beam path of the linac. The dynamic multi-leaf collimator may be, for example, a binary multi-leaf collimator, where each leaf is either in an open or closed configuration when located at a firing location, and may be in transit between the open and closed configurations while moving between firing positions. One example of a radiotherapy system may have a gantry that rotates at about 30 RPM or more (e.g., about 40 RPM, about 50 RPM, about 60 RPM, about 70 RPM), a dynamic multi-leaf binary collimator may change configuration in 10 ms, and a synchronous therapeutic radiation source may fire several pulses within 10 ms. A synchronous therapeutic radiation source pulses radiation while the leaves of the binary multi-leaf collimator are stationary for a brief period between moving between configurations. The instructions for moving the binary multi-leaf collimator may be generated with a latency as low as 10 ms after the acquisition of the image. Another example of a radiotherapy system may have a gantry that rotates at 5 rpm, a dynamic 2D multi-leaf collimator that is continuously changing configuration, where each leaf may be at any intermediate position between its fully closed and fully open positions when located at a firing position, and asynchronous therapeutic radiation source either pulsing at a rate of about 100 Hz or more or continuously emitting. In some variations, the leaves of the 2D dynamic multi-leaf collimator may be able to move at a velocity that may track twice the velocity of the tumor. The velocity may be based on a geometric calculation using the location of the therapeutic radiation source relative to both the 2D multi-leaf collimator and the target. The latency between the desired 2D multi-leaf collimator leaf position and the corresponding target position may be as low as 10 ms from the acquisition of the image.

The methods and systems described herein may include any suitable patient platform, such as a movable table or couch as described above. For example, the patient platform may comprise any of the patient platforms described in U.S. patent application Ser. No. 15/814,276, filed Nov. 15, 2017, which is hereby incorporated by reference in its entirety.

Rapid Gantry System

One variation of a motion system may comprise a rotatable gantry. For example the rotatable gantry may be a continuously rotating gantry, configured to rotate 360 degrees around a patient area. FIG. 5A depicts an example of such a gantry, which may be configured to rotate at a rate of about 30 RPM or more (e.g., about 40 RPM, about 50 RPM, about 60 RPM, about 70 RPM).

In some variations, a radiotherapy system may rotate a therapeutic radiation source and collimator around an axis, and may optionally stop at various firing angles. A controller for the radiotherapy system may track the speed of the gantry as it rotates about the patient area. The gantry may rotate relatively slowly with a low or fixed angular velocity, or may rotate relatively quickly with a higher angular velocity such that it completes one revolution on the order of the frame rate of the imaging system.

Additional details and variations of a radiotherapy system comprising a high-speed gantry is described in U.S. patent application Ser. No. 15/814,222, filed Nov. 15, 2017, which is hereby incorporated by reference in its entirety.

Dynamic MLC

A radiotherapy system may comprise a beam-shaping component such as an MLC that is configured to change the configuration of the leaves within a selected time interval. For example, the selected time interval may be the time it takes for the motion system to move the linac from a first firing position to a second firing position. The position of the leaf as a function of time may be determined at least in part by the temporal bandwidth and/or configuration transition speed of each MLC leaf. Some radiotherapy systems may comprise a high-speed binary MLC that may comprise leaf-actuation mechanisms that move each of the leaves to a new MLC configuration or pattern on every firing position or gantry angle. This architecture may facilitate generalized target tracking, even of multiple simultaneous targets. Further details of a dynamic binary multi-leaf collimator that may be used in a radiotherapy system are provided in U.S. patent application Ser. No. 15/179,823, filed Jun. 10, 2016, which is hereby incorporated by reference in its entirety.

Figure 21A:
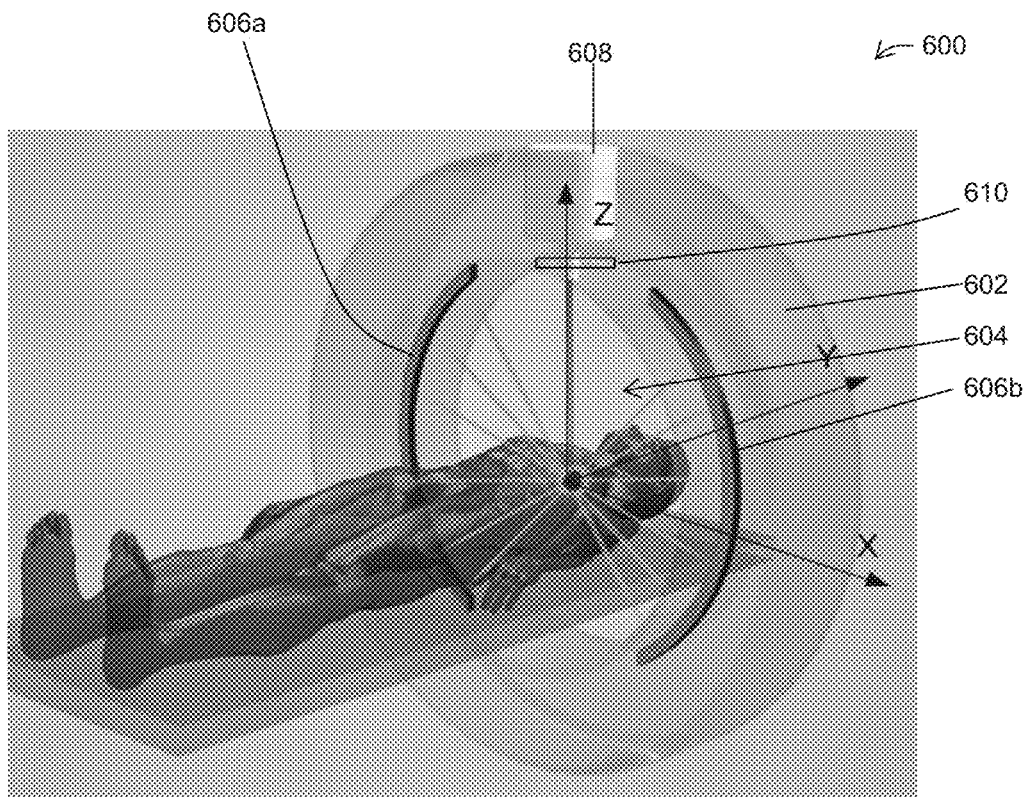
FIG. 21A depicts one variation of a radiation therapy system that may be used with any of the methods described herein.

FIG. 21A depicts one variation of a radiotherapy system that may be used for image-guided radiation therapy implementing any of the methods described herein. The radiotherapy system (600) may comprise a gantry (602) rotatable about a patient area (604), one or more PET detectors (606) mounted on the gantry, a therapeutic radiation source (608) mounted on the gantry, and a dynamic multi-leaf collimator (610) disposed in the beam path of the therapeutic radiation source. In some variations, the radiotherapy system may comprise a first array of PET detectors (606a) and a second array of PET detectors (606b) disposed across from the first array, a linear accelerator (608) or linac, and a dynamic binary multi-leaf collimator (610). The system may further comprise a controller that is in communication with the gantry, PET detectors, linac, and MLC, where the controller has one or more memories that may store treatment plans, radiation-firing matrices, fluence maps, system instructions/commands, and a processor configured to execute the calculations and methods described herein. A patient disposed within the patient area may have been injected with a PET tracer that emits positrons, and the PET tracer may accumulate at particular regions of the patient (e.g., irradiation-target regions such as tumor regions). The annihilation of a positron with a nearby electron may result in the emission of two photons traveling in opposite directions to define a line. One or more acquired partial images or detected partial image data may comprise one or more positron annihilation emission paths (i.e., lines of response or LORs, emission paths). In some variations, the PET detectors may be time-of-flight PET detectors, which may help to identify the location of the positron annihilation event. Optionally, radiotherapy system (600) may comprise a CT imaging system mounted on the same gantry as the therapeutic radiation source or mounted on a separate gantry. Additional details and examples of PET-based radiotherapy systems are described in U.S. patent application Ser. No. 15/814,222, filed Nov. 15, 2017 which is hereby incorporated by reference in its entirety.

Figure 21B:
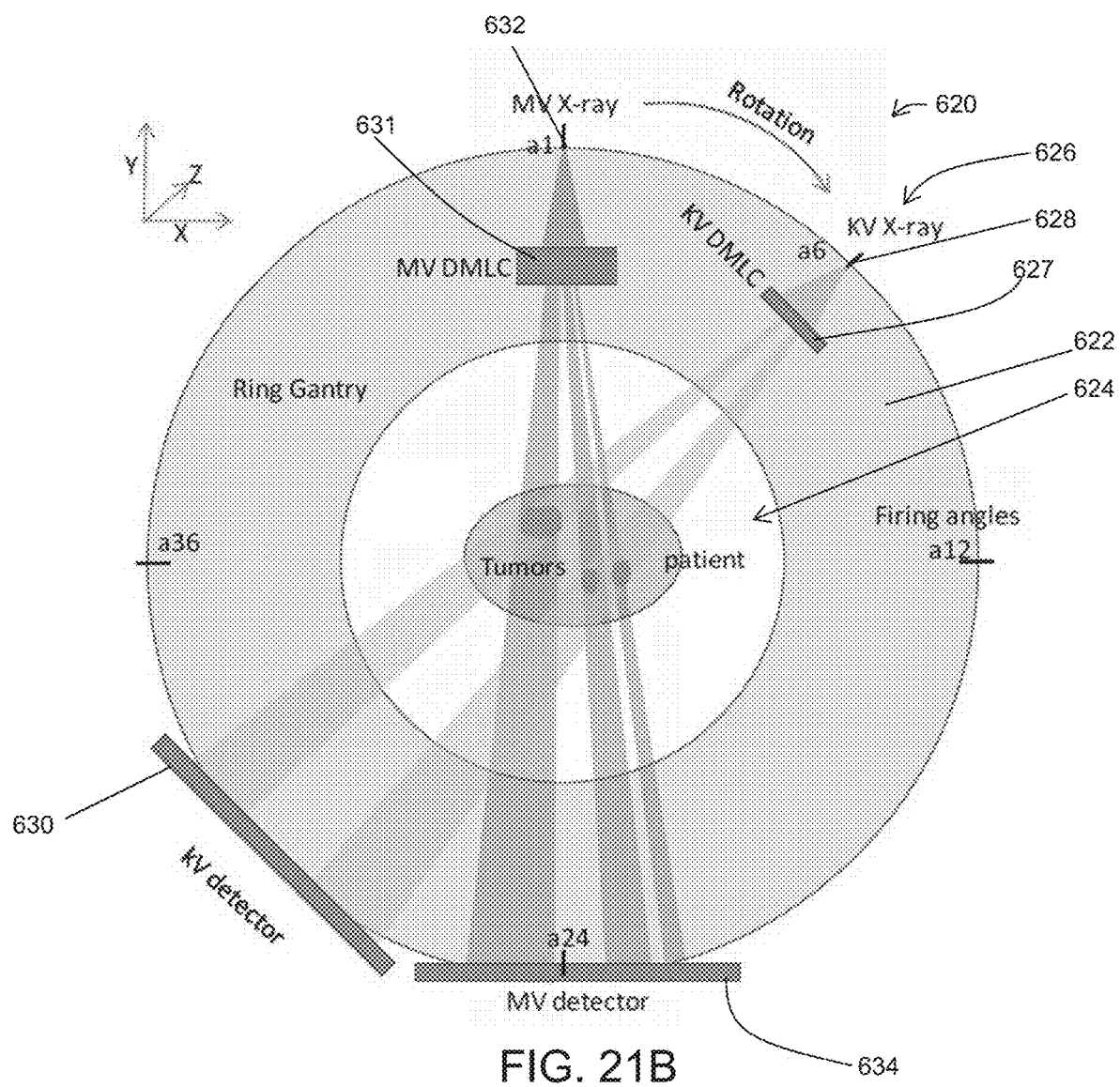
FIG. 21B depicts a cross-sectional view of another variation of a radiation therapy system that may be used with any of the methods described herein.

FIG. 21B depicts another one variation of a radiotherapy system that may be used for image-guided radiation therapy implementing any of the methods described herein. The radiotherapy system (620) may comprise a gantry (622) rotatable about a patient area (624), a kV imaging system (626) having a kV X-ray source (628) and a kV detector (630) mounted on the gantry, and a therapeutic radiation source (632) (e.g., MV X-ray source) and a MV detector (634) mounted on the gantry (622). The kV detector (630) may be located across the kV X-ray source (628) and the MV detector (634) may be located across the MV X-ray source (632). Optionally, the kV imaging system may comprise a dynamic MLC (627) over the kV X-ray source (628). The system may comprise a dynamic MLC (631) disposed over the MV X-ray source (632). Partial images or imaging data may comprise image data acquired by the kV detector after each kV X-ray source pulse. Examples of partial kV X-ray images may include X-ray projection image data, such as 2D projection data. Additional details and examples of PET-based radiotherapy systems are described in PCT/US18/25252, filed Mar. 29, 2018, which is hereby incorporated by reference in its entirety.

Figure 21C:
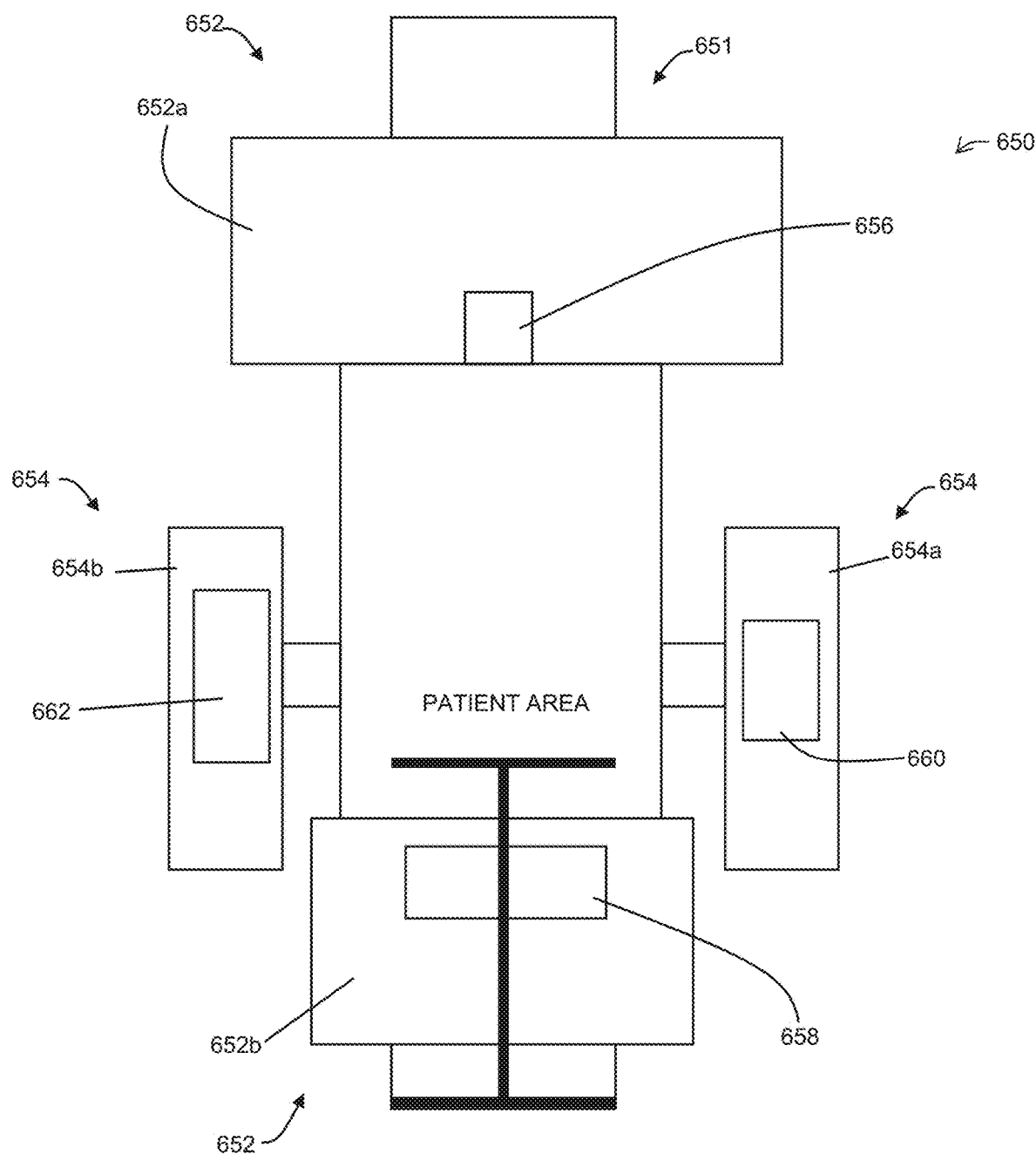
FIG. 21C depicts a schematic representation of another variation of a radiation therapy system that may be used with any of the methods described herein.

FIG. 21C depicts another one variation of a radiotherapy system (650) that may be used for image-guided radiation therapy implementing any of the methods described herein. Radiotherapy system (650) may comprise a gantry (651) comprising a first pair of arms (652) rotatable about a patient area and a second pair of arms (654) rotatable about the patient area, an imaging system comprising a kV radiation source (656) mounted on a first arm (652*a*) of the first pair of arms (652) and a kV detector (658) mounted on a second arm (652*b*) of the first pair of arms (652), and a therapeutic radiation system comprising an MV radiation source (660) mounted on a first arm (654*a*) of the second pair of arms (654) and an MV detector (662) mounted on a second arm (654*b*) of the second pair of arms (654). The first and second arms of the first pair of arms (652) may be located opposite each other (e.g., on opposite sides of the patient area, across from each other, and/or about 180 degrees from each other), such that the kV radiation source (656) and the kV detector (658) are located opposite each other (e.g., the kV detector is located in the beam path of the kV radiation source). The first and second arms of the second pair of arms (654) may be located opposite each other (e.g., on opposite sides of the patient area, across from each other, and/or about 180 degrees from each other), such that the MV radiation source (660) and the MV detector (662) are located opposite each other (e.g., the MV detector is located in the beam path of the MV radiation source). Partial images or imaging data may comprise image data acquired by the kV detector after each kV X-ray source pulse. Examples of partial kV X-ray images may include X-ray projection image data, such as 2D projection data. Additional details and examples of PET-based radiotherapy systems are described in PCT/US18/25252, filed Mar. 29, 2018, which is hereby incorporated by reference in its entirety.

Controller

A system (e.g., a treatment planning system, radiotherapy system) that may be configured to provide patient positioning and/or orientation instructions based on updated patient images may comprise a controller in communication with the imaging system of the radiotherapy system and/or the therapeutic radiation source and/or the multi-leaf collimator and/or gantry. The controller may comprise one or more processors and one or more machine-readable memories in communication with the one or more processors. The controller may be connected to a radiotherapy system and/or other systems by wired or wireless communication channels. In some variations, the controller of a treatment planning system may be located in the same or different room as the patient. For example, the controller may be coupled to a patient platform or disposed on a trolley or medical cart adjacent to the patient and/or operator.

The controller may be implemented consistent with numerous general purpose or special purpose computing systems or configurations. Various exemplary computing systems, environments, and/or configurations that may be suitable for use with the systems and devices disclosed herein may include, but are not limited to software or other components within or embodied on personal computing devices, network appliances, servers or server computing devices such as routing/connectivity components, portable (e.g., hand-held) or laptop devices, multiprocessor systems, microprocessor-based systems, and distributed computing networks.

Examples of portable computing devices include smart-phones, personal digital assistants (PDAs), cell phones, tablet PCs, phablets (personal computing devices that are larger than a smartphone, but smaller than a tablet), wearable computers taking the form of smartwatches, portable music devices, and the like.

Processor

In some embodiments, a processor may be any suitable processing device configured to run and/or execute a set of instructions or code and may include one or more data processors, image processors, graphics processing units, physics processing units, digital signal processors, and/or central processing units. The processor may be, for example, a general purpose processor, Field Programmable Gate Array (FPGA), an Application Specific Integrated Circuit (ASIC), or the like. The processor may be configured to run and/or execute application processes and/or other modules, processes and/or functions associated with the system and/or a network associated therewith. The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, or the like.

Memory

In some embodiments, memory may include a database and may be, for example, a random access memory (RAM), a memory buffer, a hard drive, an erasable programmable read-only memory (EPROM), an electrically erasable read-only memory (EEPROM), a read-only memory (ROM), Flash memory, etc. The memory may store instructions to cause the processor to execute modules, processes and/or functions associated with the system, such as one or more treatment plans, full or high SNR images, partial or low SNR images, the calculation of fluence maps based on treatment plan and/or clinical goals, segmentation of fluence maps into radiotherapy system instructions (e.g., that may direct the operation of the gantry, the patient table, therapeutic radiation source, multi-leaf collimator, and/or any other components of a radiotherapy system and/or diagnostic or treatment planning system), and image and/or data processing associated with treatment planning and/or delivery.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs); Compact Disc-Read Only Memories (CD-ROMs), and holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other embodiments described herein relate to a computer program product, which may include, for example, the instructions and/or computer code disclosed herein.

A user interface may serve as a communication interface between an operator or clinician and the treatment planning system. The user interface may comprise an input device and output device (e.g., touch screen and display) and be configured to receive input data and output data from one or more of the support arm, external magnet, sensor, delivery device, input device, output device, network, database, and server. Sensor data from one or more sensors may be received by user interface and output visually, audibly, and/or through haptic feedback by one or more output devices. As another example, operator control of an input device (e.g., joystick, keyboard, touch screen) may be received by user and then processed by processor and memory for user interface to output a control signal to one or more support arms, external magnets, intracavity devices, and delivery devices. In some variations, an output device may comprise a display device including at least one of a light emitting diode (LED), liquid crystal display (LCD), electroluminescent display (ELD), plasma display panel (PDP), thin film transistor (TFT), organic light emitting diodes (OLED), electronic paper/e-ink display, laser display, and/or holographic display.

Communication

In some embodiments, a treatment planning system and/or radiotherapy system may be in communication with other computing devices via, for example, one or more networks, each of which may be any type of network (e.g., wired network, wireless network). A wireless network may refer to any type of digital network that is not connected by cables of any kind. Examples of wireless communication in a wireless network include, but are not limited to cellular, radio, satellite, and microwave communication. However, a wireless network may connect to a wired network in order to interface with the Internet, other carrier voice and data networks, business networks, and personal networks. A wired network is typically carried over copper twisted pair, coaxial cable and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, and virtual private networks (VPN). Hereinafter, network refers to any combination of wireless, wired, public and private data networks that are typically interconnected through the Internet, to provide a unified networking and information access system.

Cellular communication may encompass technologies such as GSM, PCS, CDMA or GPRS, W-CDMA, EDGE or CDMA2000, LTE, WiMAX, and 5G networking standards. Some wireless network deployments combine networks from multiple cellular networks or use a mix of cellular, Wi-Fi, and satellite communication. In some embodiments, the systems, apparatuses, and methods described herein may include a radiofrequency receiver, transmitter, and/or optical (e.g., infrared) receiver and transmitter to communicate with one or more devices and/or networks.

Examples

Figure 23A:
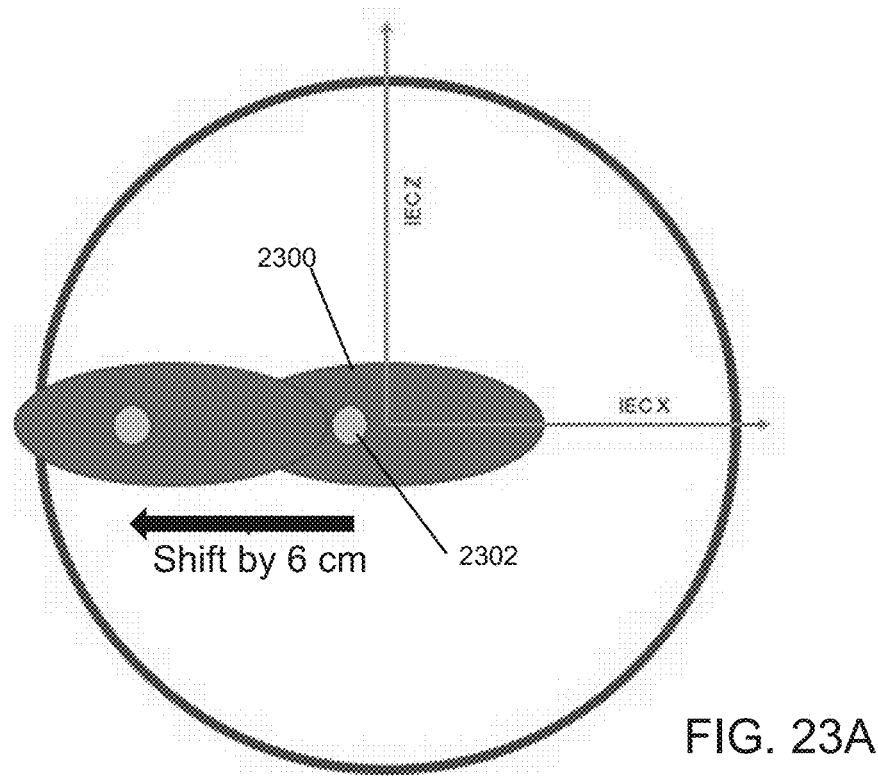
FIG. 23A is a schematic diagram that depicts a shifted localization image of a patient.
Figure 23B:
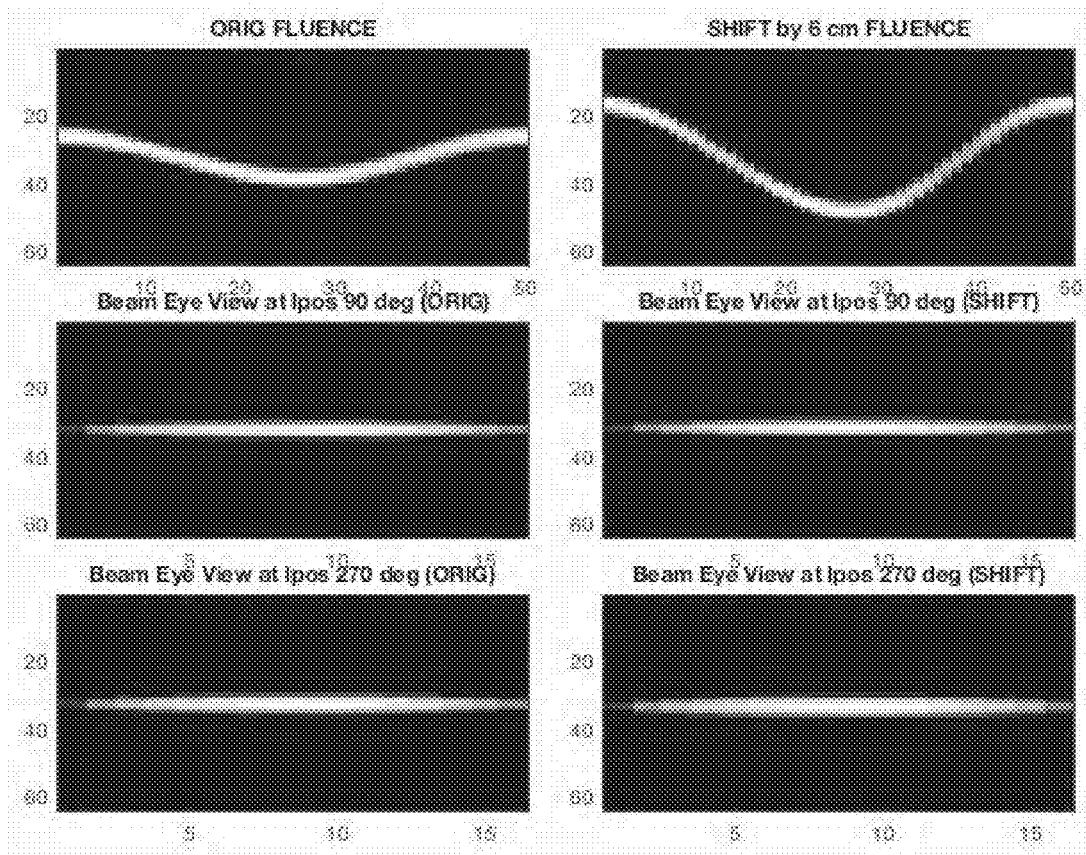
FIG. 23B depicts sinograms that have rows and columns that correspond to the number of MLC leaves and the number of firing positions.

FIGS. 23A-23D depict simulation results that demonstrate the principle of virtual localization and demonstrate that shifting the fluence causes a corresponding shift in dose. The simulation is implemented using a BgRT workflow where an image is forward-projected and filtered to create the fluence. For the purposes of these simulations, the radiotherapy system comprises a patient platform or couch, a rotatable (e.g., circular) gantry that may move about the couch (e.g., from 0 degrees to 360 degrees or more), and a therapeutic radiation source (e.g., linac) mounted on the gantry that can fire radiation to a patient on the couch from various gantry angles (firing positions or firing angles). A multi-leaf collimator (MLC) may be located in the radiation beam path of the therapeutic radiation source. FIG. 23A is a schematic diagram that depicts a localization image of a patient (2300) and target region (2302) that has shifted to the left by 6 cm (e.g., −6 cm along IEC-X) as compared to the planning image. For the results depicted in FIGS. 23B-23D, the planning CT image was shifted by 6 cm along IEC-X. Because of the shift, there is a change in magnification as the target moves away (or closer to) the therapeutic radiation source. FIG. 23B depicts sinograms that have rows and columns that correspond to the number of MLC leaves and the number of firing positions, where the top row shows the projection of a localization function, the middle row shows the beam's eye view of the patient target region from a linac located at the 90 degree firing angle/position, and the bottom row shows the beam's eye view of the patient target region from a linac located at the 270 degree firing angle/position. The sinograms on the left column are calculated based on the planning image and the sinograms on the right column are calculated based on a 6 cm fluence shift to reflect a 6 cm shift in the patient target region at the time of treatment.

Figure 23C:
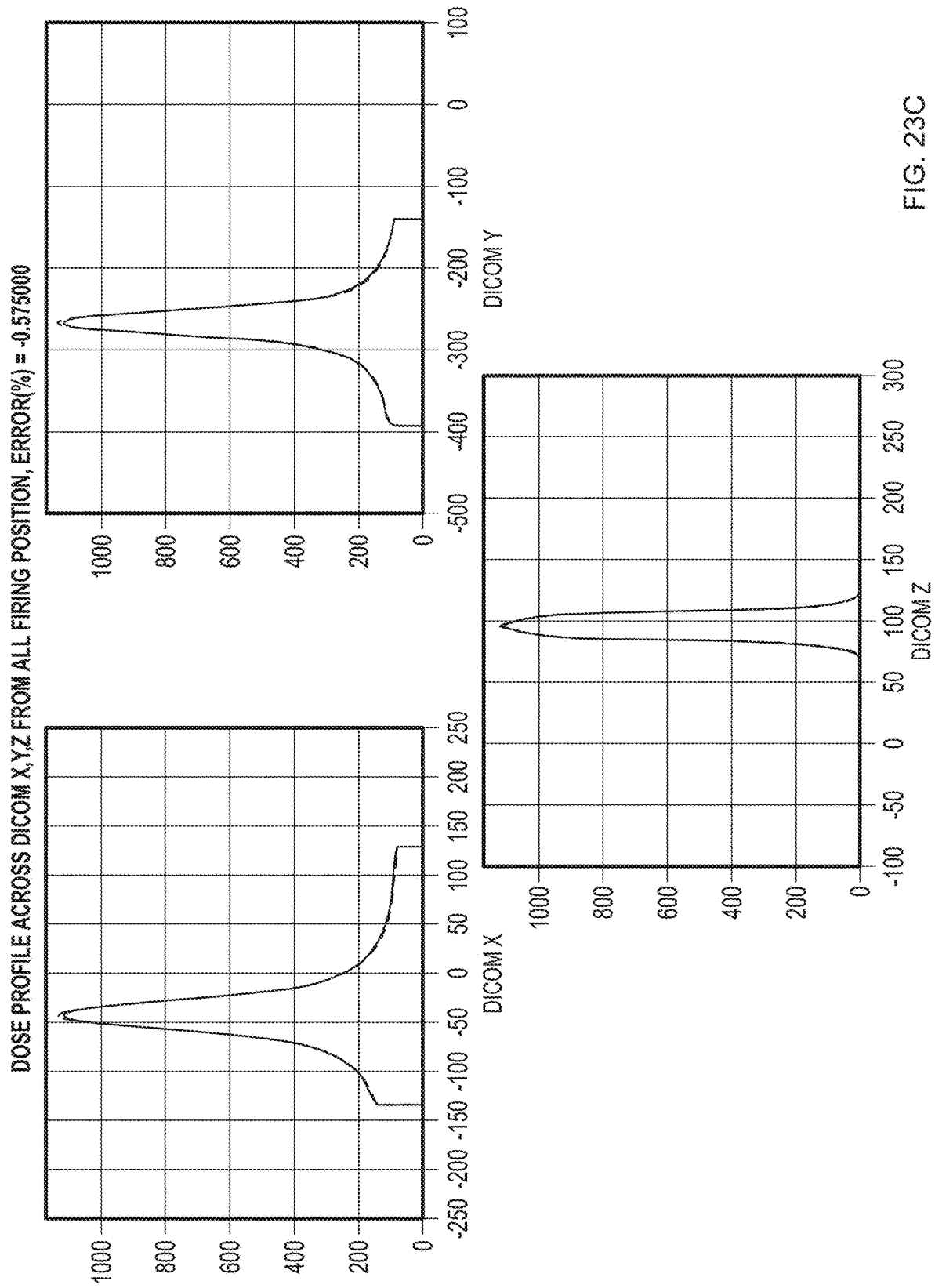
FIG. 23C depicts a dose profile (along the X-, Y-, and Z-axes, from left to right) before and after a fluence shift.

FIG. 23C shows the dose (along the X-, Y-, and Z-axes) before and after the 6 cm fluence shift. The dose profiles before and after 6 cm fluence shift (applied using the virtual localization methods described herein) is shown as well. As seen in FIG. 23C, the planned fluence and the shifted fluence nearly coincide. With accurate fluence map segmentation into machine instructions, it may be possible to closely maintain dose equivalence between the delivered dose and the planned dose.

Figure 23D:
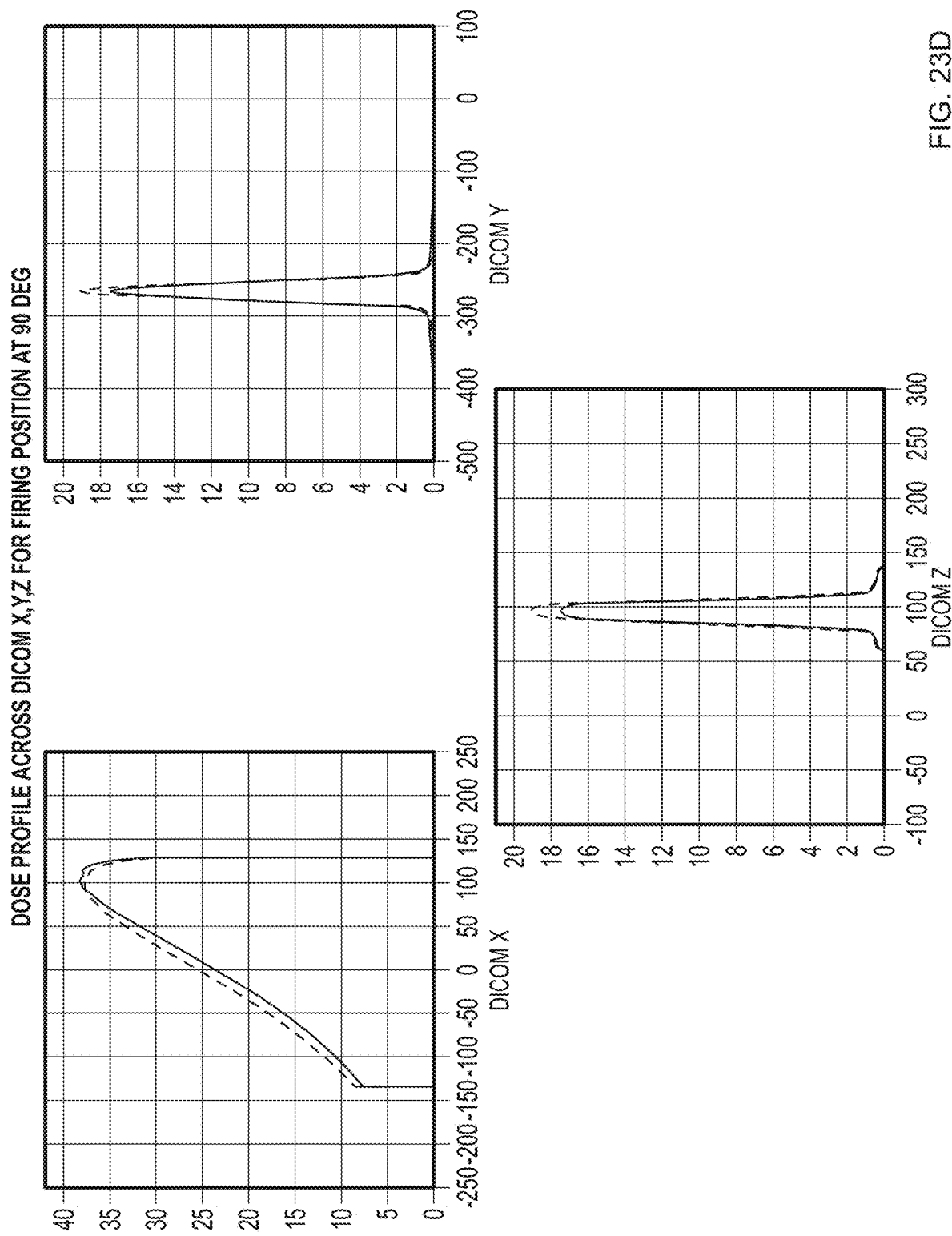
FIG. 23D depicts a dose profile (along the X-, Y-, and Z-axes, from left to right) as viewed the 90 degree firing angle/position before and after a fluence shift.

FIG. 23D shows the dose (along the X-, Y-, and Z-axes) as viewed from the 90 degree firing angle/position before and after the 6 cm fluence shift. As seen in FIG. 23D, the planned fluence and the shifted fluence nearly coincide; the maximum dose value $D_{max}$ match closely. These profiles below show that virtual localization methods described herein accommodate and/or compensate for magnification changes that may result from fluence shift, and as such, appropriately scales the dose such that the planned dose is delivered regardless of changes in depth (i.e., distance from the linac).

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein may include various combinations and/or sub-combinations of the functions, components, and/or features of the different embodiments described.

The invention claimed is:

1. A method for virtual target region localization and radiation delivery, the method comprising:
   acquiring an image of a patient in a treatment position and identifying a patient target region in the acquired image;
   selecting a localization reference point within the acquired image, wherein the localization reference point corresponds with a planned localization reference point;
   calculating a fluence for delivery to the patient target region at each firing position of a therapeutic radiation source by calculating a localization function based on the localization reference point, and applying the localization function to a shift-invariant firing filter derived based on the planned localization reference point; and
   emitting, using the therapeutic radiation source, the delivery fluence to the patient target region.

2. The method of claim 1, wherein applying the localization function to the shift-invariant firing filter comprises convolving the localization function with the shift-invariant firing filter.

3. The method of claim 2, wherein the localization function is one of a delta function, Gaussian function, circular function, and interpolation.

4. The method of claim 3, wherein the Gaussian function is a truncated Gaussian function.

5. The method of claim 3, wherein the interpolation is one of a linear, bi-cubic, spline, or Fourier shift.

6. The method of claim 2, further comprising:
   identifying a second patient target region in the acquired image;
   selecting a second localization reference point for the second patient target region within the acquired image, wherein the second localization reference point corresponds with a second planned localization reference point;
   calculating a second delivery fluence at each firing position of the therapeutic radiation source by calculating a second delta function based on the second localization reference point, and convolving the second delta function with a second shift-invariant firing filter based on the second planned localization reference point; and
   emitting, using the therapeutic radiation source, the second delivery fluence to the second patient target region.

7. The method of claim 2, wherein the localization function is a first localization function ($\delta$), wherein the first shift-invariant firing filter comprises a first set of fluence map filters ($p_1, p_2, \ldots, p_i$) calculated during treatment planning for each firing position (i) of a therapeutic radiation source, and the method comprises calculating a first set of projections of the localization function ($\delta_i$) to each firing position (i), $$\delta_i = \text{proj}_i(\delta)$$

wherein each projection ($\delta_i$) is a 2-D fluence distribution,
wherein calculating the first fluence for delivery comprises calculating a first delivery fluence map ($f_i$) for each firing position (i) of the therapeutic radiation source by convolving each projection in the first set of projections of the first localization function ($\delta_i$) with the corresponding fluence map filter ($p_i$), $$f_i = p_i * \delta_i$$

and
wherein delivering the first fluence comprises moving the therapeutic radiation source to each firing position (i) and emitting radiation according to the first delivery fluence map ($f_i$) to the first patient target region.

8. The method of claim 7, wherein each projection ($\delta_i$) is a m×n matrix, where m is a number of multi-leaf collimator leaves and n is a number selected during treatment planning.

9. The method of claim 8, wherein n is the number of beam stations selected during the treatment planning.

10. The method of claim 7, wherein the first localization function is one of a delta function, Gaussian function, circular function, and interpolation.

11. The method of claim 10, wherein the Gaussian function is a truncated Gaussian function.

12. The method of claim 10, wherein the interpolation is one of a linear, bi-cubic, spline, and Fourier shift.

13. The method of claim 7, wherein the second shift-invariant firing filter comprises a second set of fluence map filters ($p\_2_1, p\_2_2, \ldots, p\_2_i$) calculated during treatment planning for each firing position (i), and the method comprises calculating a second set of projections of the second localization function ($\delta\_2_i$) to each firing position (i), $$\delta\_2_i = \text{proj}_i(\delta\_2)$$

wherein each projection ($\delta\_2_i$) is a 2-D fluence distribution,
wherein calculating the second fluence for delivery comprises calculating a second delivery fluence map ($f\_2_i$) for each firing position (i) by convolving each projection in the second set of projections of the second localization function ($\delta\_2_i$) with the corresponding fluence map filter ($p\_2_i$), $$f\_2_i = p\_2_i * \delta\_2_i$$

and wherein delivering the second calculated fluence comprises moving the therapeutic radiation source to each firing position (i) and emitting radiation according to the second delivery fluence map ($f\_2_i$) to the second patient target region.

14. The method of claim 13, wherein each projection ($\delta\_2_i$) is a m×n matrix.

15. The method of claim 14, where m is a number of multi-leaf collimator leaves and n is a number selected during treatment planning.

16. The method of claim 15, wherein n is the number of beam stations selected during the treatment planning.

17. The method of claim 13, wherein the second localization function is one of a delta function, Gaussian function, circular function, and interpolation.

18. The method of claim 17, wherein the Gaussian function is a truncated Gaussian function.

19. The method of claim 17, wherein the interpolation is one of a linear, bi-cubic, spline, and Fourier shift.

20. The method of claim 7, wherein delivering the calculated fluence comprises segmenting the delivery fluence map ($f_i$, $f\_2_i$) into a plurality of radiation therapy system machine instructions for each firing position.

21. The method of claim 20, wherein the plurality of radiation therapy system machine instructions comprises one or more multi-leaf collimator configurations for each firing position, and wherein emitting radiation fluence further comprises moving leaves of a multi-leaf collimator to the multi-leaf collimator configuration that corresponds to the firing position location of the therapeutic radiation source, and emitting a pulse of radiation.

22. The method of claim 21, wherein the plurality of radiation therapy system machine instructions further comprises therapeutic radiation source pulse parameters for each firing position, and wherein emitting the pulse of radiation comprises emitting radiation having the therapeutic radiation source pulse parameters that correspond to the firing position location of the therapeutic radiation source.

23. The method of claim 20, wherein calculating the delivery fluence map ($f_i$, $f\_2_i$) further comprises convolving each projection in the first or second set of projections with the corresponding shift-invariant fluence map filter, and applying a virtual flattening filter correction factor (FF):

$$(f_i) = FF \cdot (p_i * \delta_i)$$

$$(f\_2_i) = FF \cdot (p\_2_i * \delta\_2_i)$$

wherein the virtual flattening filter correction factor (FF) is a m×n matrix and is an inverse of flatness profile of a radiation beam emitted by the therapeutic radiation source.

24. The method of claim 23, wherein calculating the delivery fluence map ($f_i$, $f\_2_i$) further comprises convolving each projection in the set of projections with the shift-invariant fluence map filter, applying the virtual flattening filter correction factor (FF), and a distance compensation factor $$\left(\frac{d'_i}{d_i}\right)^2:$$

$$(f_i) = \left(\frac{d'_i}{d_i}\right)^2 \cdot FF \cdot (p_i \star \delta_i)$$

$$(f\_2_i) = \left(\frac{d'_i}{d_i}\right)^2 \cdot FF \cdot (p\_2_i \star \delta\_2_i)$$

wherein $d_i$ represents a distance from firing position i to a center of the patient target region defined during treatment planning, and d' represents a distance from firing position i to a center of the patient target region determined at radiation delivery.

25. The method of claim 20, wherein calculating the delivery fluence map ($f_i$, $f\_2_i$) further comprises convolving each projection in the set of projections with the shift-invariant fluence map filter p', $p\_2'$ with a delta function $\delta_i$, $\delta\_2_i$ that have been circularly convolved with a delta function with an angular shift ($\varphi$, $\varphi\_2$) where the patient target region is located off isocenter at a location $\delta_{LOC}$ and $\delta\_2_{LOC}$, $$\delta_i = proj_i(\delta) * \delta_{i,roll}$$

$$p' = \delta(\varphi_{roll}) \circledast p$$

$$\delta_{i,roll} = proj_i(\delta_{LOC}) proj_i(ROT(\delta_{LOC}, \varphi_{roll}))^{-1}$$

$$(f_i) = (p_i' * \delta_i)$$

$$\delta\_2_i = proj_i(\delta\_2) * \delta\_2_{i,roll}$$

$$p\_2' = \delta(\varphi\_2_{roll}) \circledast p\_2$$

$$\delta\_2_{i,roll} = proj_i(\delta\_2_{LOC}) proj_i(ROT(\delta\_2_{LOC}, \varphi\_2_{roll}))^{-1}$$

$$(f\_2_i) = (p\_2_i' * \delta\_2_i).$$

26. The method of claim 1, wherein the acquired image comprises one or more of a positron emission tomography (PET) image, X-ray projection image or images, computed tomography (CT) image, and magnetic resonance imaging (MRI) image.

27. The method of claim 1, further comprising:
identifying a second patient target region in the acquired image;
selecting a second localization reference point for the second patient target region within the acquired image, wherein the second localization reference point corresponds with a second planned localization reference point;
calculating a second delivery fluence at each firing position of the therapeutic radiation source by calculating a second localization function based on the second localization reference point, and applying the second localization function to a second shift-invariant firing filter based on the second planned localization reference point; and
emitting, using the therapeutic radiation source, the second delivery fluence to the second patient target region.

28. The method of claim 27, wherein emitting the first delivery fluence to the first patient target region and emitting the second delivery fluence to the second patient target region occur concurrently.

29. The method of claim 27, wherein emitting the first delivery fluence to the first patient target region and emitting the second delivery fluence to the second patient target region occur sequentially.

30. The method of claim 27, wherein delivering the second calculated fluence comprises segmenting the second calculated fluence into a plurality of radiation therapy system machine instructions for each firing position.

31. The method of claim 27, wherein the first patient target region is in a first treatment area of a patient defined during treatment planning and the second target region is in a second treatment area of the patient defined during treatment planning.

32. The method of claim 31, wherein the first treatment area has an axial length of about 8 cm or less and comprises a first set of axial planes, and the second treatment area has an axial length of about 8 cm or less and does not overlap with the first treatment area, wherein the second treatment area comprises a second set of axial planes.

33. The method of claim 32, wherein a center of the first treatment area and a center of the second treatment area are collinear along an IEC-Y axis and/or co-planar with the IEC-Y axis.

34. The method of claim 31, wherein the first treatment area and the second treatment area overlap.

35. The method of claim 1, wherein delivering the calculated fluence comprises segmenting the calculated fluence into a plurality of radiation therapy system machine instructions for each firing position.

36. The method of claim 1, wherein the localization reference point is a user-selected location within the acquired image.

37. The method of claim 1, wherein the localization reference point corresponds to a treatment plan isocenter defined relative to the patient target region during treatment planning.

38. The method of claim 1, wherein the firing positions of a therapeutic radiation source comprise locations of the therapeutic radiation source relative to a patient platform location.

39. The method of claim 38, wherein the therapeutic radiation source is mounted on a gantry rotatable about a longitudinal axis, and the locations of the therapeutic radiation source are designated by gantry angles about the longitudinal axis.

40. The method of claim 39, wherein the patient platform is movable to different locations along the longitudinal axis.

41. A method for virtual target region localization and radiation delivery, the method comprising:
    acquiring an image of a patient in a treatment position and identifying in the acquired image a patient target region;
    selecting a localization reference point within the acquired image, wherein the localization reference point corresponds with a planned localization reference point;
    calculating a spatial offset based on a shift between the localization reference point and the planned localization reference point;
    shifting a boundary of a planned region of interest based on the spatial offset, wherein the boundary of the planned region of interest surrounds the patient target region;
    acquiring imaging data that has been spatially filtered by the shifted region of interest;
    calculating a fluence for delivery to the patient target region at each firing position of a therapeutic radiation source by calculating a localization function based on the localization reference point, and applying the localization function to a shift-invariant firing filter derived based on the planned localization reference point; and
    emitting, using the therapeutic radiation source, the delivery fluence to the patient target region.

42. The method of claim 41, wherein the boundary of the planned region of interest comprises a spatial filter.

43. The method of claim 41, wherein shifting the boundary of the planned region of interest comprises applying a rotation and a shift to the planned region of interest by a roll correction factor $\varphi$ that represents a rotational translation of the localization reference point relative to the planned localization reference point, and wherein calculating the fluence for delivery comprises circularly convolving the set of firing filters with the roll correction factor $\varphi$.

* * * * *

UNITED STATES PATENT AND TRADEMARK OFFICE
CERTIFICATE OF CORRECTION

PATENT NO. : 12,115,386 B2  Page 1 of 1
APPLICATION NO. : 17/571273
DATED : October 15, 2024
INVENTOR(S) : Yevgen Voronenko et al.

It is certified that error appears in the above-identified patent and that said Letters Patent is hereby corrected as shown below:

In the Claims

At Column 114, Claim number 13, Line number 56, reads:
"$f\_2_i = p\_2_i * \delta\_2_i$"
Should read:
--$f\_2_i = p\_2_i * \delta\_2$--

At Column 116, Claim number 25, Line number 6-22, reads:
"$\delta\ i = proj\ i\ (\delta)\ *(\delta)\ i,roll$
$p' = \delta(\varphi\ roll) \circledast p$
$\delta\ i,roll = proj\ i(\delta\ LOC) proj\ i(ROT(\delta\ LOC, \varphi\ roll))-1$
$(f\ i) = (p\ i' * \delta\ i)$
$\delta\_2\ i = proj\ i\ (\delta\_2) * \delta\_2\ i,roll$
$p\_2' = \delta(\varphi\_2\ roll) \circledast p\_2$
$\delta\_2\ i,roll = proj\ i(\delta\_2\ LOC) proj\ i(ROT(\delta\_2\ LOC, \varphi\ roll))-1$
$f\_2\ i = (p\_2\ i' * \delta\_2\ i)$"
Should read:
--$\delta\ i = proj\ i\ (\delta) * (\delta)\ i,roll$
$p' = \delta(\varphi\ roll) \circledast p$
$\delta\ i,roll = proj\ i(\delta\ LOC) \otimes proj\ i(ROT(\delta\ LOC, \varphi\ roll))-1$
$(f\ i) = (p\ i' * \delta\ i)$
$\delta\_2\ i = proj\ i\ (\delta\_2) * \delta\_2\ i,roll$
$p\_2' = \delta(\varphi\_2\ roll) \circledast p\_2$
$\delta\_2\ i,roll = proj\ i(\delta\_2\ LOC) \otimes proj\ i(ROT(\delta\_2\ LOC, \varphi\ roll))-1$
$f\_2\ i = (p\_2\ i' * \delta\_2\ i)$--

Signed and Sealed this
Twenty-ninth Day of April, 2025

Coke Morgan Stewart
*Acting Director of the United States Patent and Trademark Office*